(12) United States Patent
Klar et al.

(10) Patent No.: US 9,388,140 B2
(45) Date of Patent: Jul. 12, 2016

(54) SUBSTITUTED BENZIMIDAZOLES

(75) Inventors: Ulrich Klar, Berlin (DE); Marcus Koppitz, Berlin (DE); Duy Nguyen, Berlin (DE); Dirk Kosemund, Berlin (DE); Roland Neuhaus, Berlin (DE); Gerhard Siemeister, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 271 days.

(21) Appl. No.: 14/008,981

(22) PCT Filed: Mar. 28, 2012

(86) PCT No.: PCT/EP2012/055562
§ 371 (c)(1),
(2), (4) Date: Jun. 26, 2014

(87) PCT Pub. No.: WO2012/130905
PCT Pub. Date: Oct. 4, 2012

(65) Prior Publication Data
US 2014/0302010 A1    Oct. 9, 2014

(30) Foreign Application Priority Data

Mar. 31, 2011  (EP) .................................... 11160696
Jun. 17, 2011  (EP) .................................... 11170306
Nov. 23, 2011  (EP) .................................... 11190249

(51) Int. Cl.
| | | |
|---|---|---|
| *A61K 31/415* | (2006.01) | |
| *C07D 235/00* | (2006.01) | |
| *C07D 235/18* | (2006.01) | |
| *C07D 231/56* | (2006.01) | |
| *C07D 235/08* | (2006.01) | |
| *C07D 401/04* | (2006.01) | |
| *C07D 403/04* | (2006.01) | |
| *C07D 403/12* | (2006.01) | |
| *C07D 405/12* | (2006.01) | |
| *C07D 413/12* | (2006.01) | |
| *A61K 45/06* | (2006.01) | |
| *A61K 31/4184* | (2006.01) | |
| *A61K 31/4196* | (2006.01) | |
| *A61K 31/422* | (2006.01) | |
| *A61K 31/4439* | (2006.01) | |
| *A61K 31/5377* | (2006.01) | |
| *C07D 401/06* | (2006.01) | |

(52) U.S. Cl.
CPC .......... *C07D 235/08* (2013.01); *A61K 31/4184* (2013.01); *A61K 31/4196* (2013.01); *A61K 31/422* (2013.01); *A61K 31/4439* (2013.01); *A61K 31/5377* (2013.01); *A61K 45/06* (2013.01); *C07D 401/04* (2013.01); *C07D 401/06* (2013.01); *C07D 403/04* (2013.01); *C07D 403/12* (2013.01); *C07D 405/12* (2013.01); *C07D 413/12* (2013.01)

(58) Field of Classification Search
None
See application file for complete search history.

(56) References Cited

U.S. PATENT DOCUMENTS

2002/0165241 A1* 11/2002 Claiborne ............ C07D 401/12
514/263.22

OTHER PUBLICATIONS

Jordan, V. C. Nature Reviews: Drug Discovery, 2, 2003, 205-213.*
Vippagunta, et al. Advanced Drug Delivery Reviews, 48, 2001, 18.*
Hackam, et al. JAMA, 296(14), 2006, 1731-1732.*

* cited by examiner

*Primary Examiner* — Jeffrey S Lundgren
*Assistant Examiner* — Michael Schmitt

(57) ABSTRACT

The present invention relates to substituted benzimidazole compounds of general formula (I) in which $R^3$, $R^5$ and A are as defined in the claims, to methods of preparing said compounds, to pharmaceutical compositions and combinations comprising said compounds and to the use of said compounds for manufacturing a pharmaceutical composition for the treatment or prophylaxis of a disease, in particular of a hyperproliferative and/or angiogenesis disorder, as a sole agent or in combination with other active ingredients.

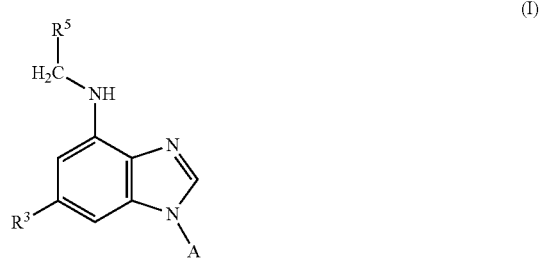

(I)

18 Claims, No Drawings

SUBSTITUTED BENZIMIDAZOLES

The present invention relates to substituted benzimidazole compounds of general formula (I) as described and defined herein, to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

BACKGROUND OF THE INVENTION

The present invention relates to chemical compounds that inhibit Mps-1 (Monopolar Spindle 1) kinase (also known as Tyrosine Threonine Kinase, TTK). Mps-1 is a dual specificity Ser/Thr kinase which plays a key role in the activation of the mitotic checkpoint (also known as spindle checkpoint, spindle assembly checkpoint) thereby ensuring proper chromosome segregation during mitosis [Abrieu A et al., Cell, 2001, 106, 83-93]. Every dividing cell has to ensure equal separation of the replicated chromosomes into the two daughter cells. Upon entry into mitosis, chromosomes are attached at their kinetochores to the microtubules of the spindle apparatus. The mitotic checkpoint is a surveillance mechanism that is active as long as unattached kinetochores are present and prevents mitotic cells from entering anaphase and thereby completing cell division with unattached chromosomes [Suijkerbuijk S J and Kops G J, Biochemica et Biophysica Acta, 2008, 1786, 24-31; Musacchio A and Salmon E D, Nat Rev Mol Cell Biol., 2007, 8, 379-93]. Once all kinetochores are attached in a correct amphitelic, i.e. bipolar, fashion with the mitotic spindle, the checkpoint is satisfied and the cell enters anaphase and proceeds through mitosis. The mitotic checkpoint consists of complex network of a number of essential proteins, including members of the MAD (mitotic arrest deficient, MAD 1-3) and Bub (Budding uninhibited by benzimidazole, Bub 1-3) families, the motor protein CENP-E, Mps-1 kinase as well as other components, many of these being over-expressed in proliferating cells (e.g. cancer cells) and tissues [Yuan B et al., Clinical Cancer Research, 2006, 12, 405-10]. The essential role of Mps-1 kinase activity in mitotic checkpoint signalling has been shown by shRNA-silencing, chemical genetics as well as chemical inhibitors of Mps-1 kinase [Jelluma N et al., PLos ONE, 2008, 3, e2415; Jones M H et al., Current Biology, 2005, 15, 160-65; Dorer R K et al., Current Biology, 2005, 15, 1070-76; Schmidt M et al., EMBO Reports, 2005, 6, 866-72].

There is ample evidence linking reduced but incomplete mitotic checkpoint function with aneuploidy and tumourigenesis [Weaver B A and Cleveland D W, Cancer Research, 2007, 67, 10103-5; King R W, Biochimica et Biophysica Acta, 2008, 1786, 4-14]. In contrast, complete inhibition of the mitotic checkpoint has been recognised to result in severe chromosome missegregation and induction of apoptosis in tumour cells [Kops G J et al., Nature Reviews Cancer, 2005, 5, 773-85; Schmidt M and Medema R H, Cell Cycle, 2006, 5, 159-63; Schmidt M and Bastians H, Drug Resistance Updates, 2007, 10, 162-81]. Therefore, mitotic checkpoint abrogation through pharmacological inhibition of Mps-1 kinase or other components of the mitotic checkpoint represents a new approach for the treatment of proliferative disorders including solid tumours such as carcinomas and sarcomas and leukaemias and lymphoid malignancies or other disorders associated with uncontrolled cellular proliferation.

Established anti-mitotic drugs such as vinca alkaloids, taxanes or epothilones activate the SAC inducing a mitotic arrest either by stabilising or destabilising microtubule dynamics. This arrest prevents separation of sister chromatids to form the two daughter cells. Prolonged arrest in mitosis forces a cell either into mitotic exit without cytokinesis or into mitotic catastrophe leading to cell death.

In contrast, inhibitors of Mps-1 induce a SAC inactivation that accelerates progression of cells through mitosis resulting in severe chromosomal missegregation and finally in cell death.

These findings suggest that Mps-1 inhibitors should be of therapeutic value for the treatment of proliferative disorders associated with enhanced uncontrolled proliferative cellular processes such as, for example, cancer, inflammation, arthritis, viral diseases, neurodegenerative diseases such as Alzheimer's disease, cardiovascular diseases, or fungal diseases in a warm-blooded animal such as man.

Therefore, inhibitors of Mps-1 represent valuable compounds that should complement therapeutic options either as single agents or in combination with other drugs.

Different compounds have been disclosed in prior art which show inhibitory effect on Mps-1 kinase. WO2010/124826A1 discloses substituted imidazoquinoxaline compounds as inhibitors of Mps-1 kinase or TTK. WO2011/026579A1 discloses substituted aminoquinoxalines as Mps-1 inhibitors. WO2011/013729A1 discloses fused imidazole derivatives as Mps-1 inhibitors. WO2011/063908A1, WO2011/064328A1 as well as WO2011063907 A1 disclose triazolopyridine derivates as inhibitors of Mps-1 kinase.

However, benzimidazole derivatives have not been disclosed in the context of Mps-1 kinase inhibitors. Benzimidaole derivates have been disclosed for the treatment or prophylaxis of different diseases:

EP0694535A1 discloses substituted benzimidazoles as tachykinin receptor antagonists. U.S. Pat. No. 5,552,426 discloses substituted benzimidazoles for treating or preventing conditions associated with β-amyloid peptide such as Alzheimer's disease. U.S. Pat. No. 5,990,146 discloses substituted benzimidazoles and their use in inhibiting cellular proliferation and protein kinase enzymatic activity. U.S. Pat. No. 6,369,092B1 discloses a method for inhibiting neoplastic cells and related conditions by exposing them to substituted benzimidazole derivatives. WO1997/12613A1 discloses inter alia substituted benzimidazoles as inhibitors of 15-lipoxygenase. WO1997/25041 discloses substituted benzimidazoles for the treatment of conditions associated with an excess of neuropeptide Y. WO1997/31635 discloses substituted benzimidazoles for the treatment of sleep apnea in a mammal. WO1997/33873 discloses substituted benzimidazoles for the treatment of interstitial cystitis or urethral syndrome in a mammal. WO2001/57020A1 discloses substituted benzimidazoles having activity against mammalian factor Xa. WO2007/112093A2 discloses benzimidazolyl-pyridine compounds for inflammation and immune-related uses. WO2009/000413A1 discloses a copper catalyzed process for the regioselective synthesis of benzimidazoles and azabenzimidazoles. WO2009/039248A2 discloses substituted benzimidazoles and their use for treating a host with a virus from the Flaviviridae family.

However, the state of the art described above does not describe the specifically substituted benzimidazole compounds of general formula (I) of the present invention, or a stereoisomer, a tautomer, an N-oxide, a hydrate, a solvate, or a salt thereof, or a mixture of same, as described and defined herein, and as hereinafter referred to as "compounds of the present invention", or their pharmacological activity.

Furthermore, the state of the art described above does not describe the use of a compound of the present invention as Mps-1 inhibitor.

It has now been found, and this constitutes the basis of the present invention, that said compounds of the present invention have surprising and advantageous properties.

In particular, said compounds of the present invention have surprisingly been found to effectively inhibit Mps-1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1 kinase, such as, for example, hematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynecological tumours, urological tumours including renal, bladder and prostate tumours, skin tumours, and sarcomas, and/or metastases thereof.

SUMMARY OF THE INVENTION

The present invention covers compounds of general formula (I):

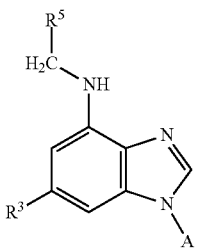

(I)

in which:
A represents

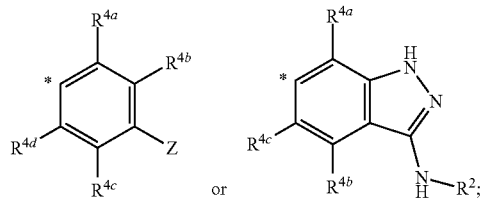

wherein * indicates the point of attachment of said groups with the rest of the molecule;

Z represents a —C(═O)N(H)$R^1$ or —C(═S)N(H)$R^1$ group;

$R^1$ represents a hydrogen atom or a $C_1$-$C_6$-alkyl- or $C_3$-$C_6$-cycloalkyl-group; wherein said $C_1$-$C_6$-alkyl- or $C_3$-$C_6$-cycloalkyl-group is optionally substituted, identically or differently, with 1, 2, 3 or 4 groups selected from: halogen, —OH, —CN, $C_1$-$C_6$-alkyl-, $C_1$-$C_6$-alkoxy-;

$R^2$ represents a hydrogen atom or a $C_1$-$C_6$-alkyl- or $C_3$-$C_6$-cycloalkyl-group; wherein said $C_1$-$C_6$-alkyl- or $C_3$-$C_6$-cycloalkyl-group is optionally substituted, identically or differently, with 1, 2, 3 or 4 groups selected from: halogen, —OH, —CN, $C_1$-$C_6$-alkyl-, $C_1$-$C_6$-alkoxy-;

$R^3$ represents a hydrogen atom or a halogen atom or a —CN, $C_1$-$C_6$-alkyl-, —$(CH_2)_m$—$C_2$-$C_6$-alkenyl, —$(CH_2)_m$—$C_4$-$C_8$-cycloalkenyl, —$(CH_2)_m$—$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, —$C_1$-$C_6$-alkyl-aryl, —$C_1$-$C_6$-alkyl-heteroaryl, heteroaryl-, —$C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —C(═O)$R^6$, —C(═O)N(H)$R^{6a}$, —C(═O)N($R^{6a}$)$R^{6b}$, —CO(═O)—$R^6$, —N($R^{6a}$)$R^{6b}$, —$NO_2$, —N(H)C(═O)$R^6$, —O$R^6$, —S$R^6$, —S(═O)$R^6$, —S(═O)$_2R^6$, —S(═O)(═N$R^{6a}$) $R^{6b}$, —S(═O)$_2$N($R^{6b}$)$R^{6c}$, —S—$(CH_2)_n$—N($R^{6a}$)$R^{6b}$ or —S—$(CH_2)_n$-(3- to 7-membered heterocycloalkyl) group;

said $C_1$-$C_6$-alkyl-, —$(CH_2)_m$—$C_2$-$C_6$-alkenyl, —$(CH_2)_m$—$C_2$-$C_6$-alkynyl, —$(CH_2)_m$—$C_3$-$C_6$-cycloalkyl, aryl-$C_1$-$C_6$-alkyl-, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —$C_1$-$C_6$-alkyl-aryl, —$C_1$-$C_6$-alkyl-heteroaryl or heteroaryl- group being optionally substituted, identically or differently, with 1, 2, 3, 4 or 5 $R^7$ groups;

$R^{4a}$, $R^{4b}$, $R^{4c}$, $R^{4d}$ represent, independently from each other, a hydrogen or halogen atom or a —CN, $C_1$-$C_6$-alkyl-, $C_1$-$C_6$-alkoxy-, halo-$C_1$-$C_6$-alkyl-, halo-$C_1$-$C_6$-alkoxy-, $R^{6a}(R^{6b})N$—$C_1$-$C_6$-alkyl-, H O—$C_1$-$C_6$-alkyl-, NC—$C_1$-$C_6$-alkyl-, $C_1$-$C_6$-alkoxy-$C_1$-$C_6$-alkyl- or halo-$C_1$-$C_6$-alkoxy-$C_1$-$C_6$-alkyl-group;

$R^5$ represents a hydrogen atom or a $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group;

said $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group being optionally substituted, identically or differently, with 1, 2, 3, 4 or 5 $R^8$ groups;

$R^6$, $R^{6a}$, $R^{6b}$, $R^{6c}$,
represent, independently from each other, a hydrogen atom, or a $C_1$-$C_6$-alkyl-, H O—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl- or heteroaryl-$C_1$-$C_6$-alkyl-group;
wherein said $C_3$-$C_6$-cycloalkyl-group is optionally substituted, identically or differently with 1 or 2 groups selected from: halogen, —OH, —CN, $C_1$-$C_6$-alkyl-, HO—$C_1$-$C_6$-alkyl-, $C_1$-$C_6$-alkoxy-, halo-$C_1$-$C_6$-alkyl-, halo-$C_1$-$C_6$-alkoxy-;

$R^7$ represents a hydrogen or halogen atom or a HO—, —CN, $C_1$-$C_6$-alkoxy-, halo-$C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —CO(=O)—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N,S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —SF$_5$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$ or —S(=O)(=N$R^{6c}$)$R^6$ group;
wherein said aryl- or heteroaryl-group is optionally substituted, identically or differently, with 1, 2 or 3 $C_1$-$C_6$-alkyl-groups;
or
when 2 $R^7$ groups are present ortho to each other on an aryl ring, said 2 $R^7$ groups together form a bridge:
*O(CH$_2$)$_2$O*, *O(CH$_2$)O*, *NH(C(=O))NH*, wherein * represent the point of attachment to said aryl ring;

$R^8$ represents a hydrogen or halogen atom or a —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —CO(=O)—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$ $R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$, —S(=O)(=N$R^{6c}$)$R^6$ or —S(=O)$_2$-(3- to 7-membered heterocycloalkyl) group;
wherein said 3- to 7-membered heterocycloalkyl- or heteroaryl-group is optionally substituted, identically or differently, with 1, 2, 3 or 4 $C_1$-$C_6$-alkyl-groups m is an integer of 0, 1, 2, 3, 4, 5 or 6;
n is an integer of 0, 1, 2, 3, 4 or 5; and
X is S, S(=O), S(=O)$_2$, O, N$R^6$, C$R^{6a}$$R^{6b}$, C(=C$R^{6a}$$R^{6b}$), C(=O) or C(OH)($R^{6a}$);
or a stereoisomer, a tautomer, an N-oxide, a hydrate, a solvate, or a salt thereof, or a mixture of same.

The present invention also relates to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom" or "halo-" is to be understood as meaning a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said halo-$C_1$-$C_6$-alkyl group is, for example, —CF$_3$, —CHF$_2$, —CH$_2$F, —CF$_2$CF$_3$ or —CH$_2$CF$_3$.

The term "$C_1$-$C_6$-alkoxy" is to be understood as preferably meaning a linear or branched, saturated, monovalent, hydrocarbon group of formula —O—($C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —OCF$_3$, —OCHF$_2$, —OCH$_2$F, —OCF$_2$CF$_3$, or —OCH$_2$CF$_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —CH$_2$CH$_2$OCF$_3$, —CH$_2$CH$_2$OCHF$_2$, —CH$_2$CH$_2$OCH$_2$F, —CH$_2$CH$_2$OCF$_2$CF$_3$, or —CH$_2$CH$_2$OCH$_2$CF$_3$.

The term "C$_2$-C$_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("C$_2$-C$_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "C$_2$-C$_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("C$_2$-C$_3$-alkynyl"). Said C$_2$-C$_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-inyl, hex-3-inyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-inyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-inyl.

The term "C$_3$-C$_6$-cycloalkyl" is to be understood as meaning a saturated, monovalent, monocyclic hydrocarbon ring which contains 3, 4, 5 or 6 carbon atoms ("C$_3$-C$_6$-cycloalkyl"). Said C$_3$-C$_6$-cycloalkyl group is for example a cyclopropyl, cyclobutyl, cyclopentyl or cyclohexyl ring.

The term "C$_4$-C$_8$-cycloalkenyl" is to be understood as preferably meaning a monovalent, mono- or bicyclic hydrocarbon ring which contains 4, 5, 6, 7 or 8 carbon atoms and one, two, three or four double bonds, in conjugation or not, as the size of said cycloalkenyl ring allows. Said C$_4$-C$_8$-cycloalkenyl group is for example, a monocyclic hydrocarbon ring, e.g. a cyclobutenyl, cyclopentenyl, or cyclohexenyl or a bicyclic hydrocarbon ring, e.g. a cylooctadienyl ring.

The term "3- to 7-membered heterocycloalkyl", is to be understood as meaning a saturated, monovalent, mono- or bicyclic hydrocarbon ring which contains 2, 3, 4, 5, or 6 carbon atoms, and one or more heteroatom-containing groups selected from C(=O), O, S, S(=O), S(=O)$_2$, NR$^a$, in which R$^a$ represents a hydrogen atom, or a C$_1$-C$_6$-alkyl- or halo-C$_1$-C$_6$-alkyl-group; it being possible for said heterocycloalkyl group to be attached to the rest of the molecule via any one of the carbon atoms or, if present, the nitrogen atom.

Particularly, said 3- to 7-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl"), wherein two adjacent atoms of the 3- to 7-membered heterocycloalkyl-group are optionally substituted in such a way, that an aryl- or heteroaryl-group is formed.

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example. Optionally, said heterocycloalkyl can be benzo fused.

Said heterocyclyl can be bicyclic, such as, without being limited thereto, a 5,5-membered ring, e.g. a hexahydrocyclopenta[c]pyrrol-2(1H)-yl) ring, or a 5,6-membered bicyclic ring, e.g. a hexahydropyrrolo[1,2-a]pyrazin-2(1H)-yl ring.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl, or 4H-[1,4]thiazinyl ring, for example, or, it may be benzo-fused, such as, without being limited thereto, a dihydroisoquinolinyl ring, for example.

The term "4- to 8-membered heterocycloalkenyl", is to be understood as meaning an unsaturated, monovalent, mono- or bicyclic hydrocarbon ring which contains 4, 5, 6, 7 or 8 carbon atoms, and one or more heteroatom-containing groups selected from C(=O), O, S, S(=O), S(=O)$_2$, NR$^a$, in which R$^a$ represents a hydrogen atom, or a C$_1$-C$_6$-alkyl- or halo-C$_1$-C$_6$-alkyl-group; it being possible for said heterocycloalkenyl group to be attached to the rest of the molecule via any one of the carbon atoms or, if present, the nitrogen atom. Examples of said heterocycloalkenyl may contain one or more double bonds, e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group, or, it may be benzo fused.

The term "aryl" is to be understood as preferably meaning a monovalent, aromatic or partially aromatic, mono- or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group, wherein two adjacent atoms of the aryl-group are optionally substituted in such a way, that a 3- to 7-membered heterocycloalkyl-group is formed.

The term "heteroaryl" is understood as preferably meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed, wherein two adjacent atoms of the heteroaryl-group are optionally substituted in such a way, that a 3- to 7-membered heterocycloalkyl-group is formed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

In accordance with a first aspect, the present invention is directed to compounds of general formula (I):

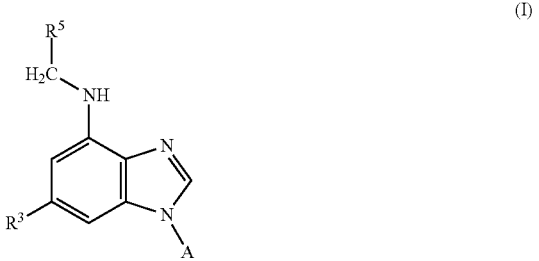

(I)

in which:
A represents

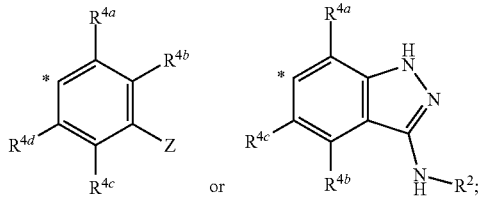

wherein * indicates the point of attachment of said groups with the rest of the molecule;

Z represents a —C(=O)N(H)R$^1$ or —C(=S)N(H)R$^1$ group;

R$^1$ represents a hydrogen atom or a $C_1$-$C_6$-alkyl- or $C_3$-$C_6$-cycloalkyl-group; wherein said $C_1$-$C_6$-alkyl- or $C_3$-$C_6$-cycloalkyl-group is optionally substituted, identically or differently, with 1, 2, 3 or 4 groups selected from: halogen, —OH, —CN, $C_1$-$C_6$-alkyl-, $C_1$-$C_6$-alkoxy-;

R$^2$ represents a hydrogen atom or a $C_1$-$C_6$-alkyl- or $C_3$-$C_6$-cycloalkyl-group; wherein said $C_1$-$C_6$-alkyl- or $C_3$-$C_6$-cycloalkyl-group is optionally substituted, identically or differently, with 1, 2, 3 or 4 groups selected from: halogen, —OH, —CN, $C_1$-$C_6$-alkyl-, $C_1$-$C_6$-alkoxy-;

R$^3$ represents a hydrogen atom or a halogen atom or a —CN, $C_1$-$C_6$-alkyl-, —$(CH_2)_m$—$C_2$-$C_6$-alkenyl, —$(CH_2)_m$—$C_4$-$C_8$-cycloalkenyl, —$(CH_2)_m$—$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, —$C_1$-$C_6$-alkyl-aryl, —$C_1$-$C_6$-alkyl-heteroaryl, heteroaryl-, —$C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —C(=O)R$^6$, —C(=O)N(H)R$^{6a}$, —C(=O)N(R$^{6a}$)R$^{6b}$, —CO(=O)—R$^6$, —N(R$^{6a}$)R$^{6b}$, —NO$_2$, —N(H)C(=O)R$^6$, —OR$^6$, —SR$^6$, —S(=O)R$^6$, —S(=O)$_2$R$^6$, —S(=O)(=NR$^{6a}$)R$^{6b}$, —S(=O)$_2$N(R$^{6b}$)R$^{6c}$, —S—$(CH_2)_n$—N(R$^{6a}$)R$^{6b}$ or —S—$(CH_2)_n$-(3- to 7-membered heterocycloalkyl) group;

said $C_1$-$C_6$-alkyl-, —$(CH_2)_m$—$C_2$-$C_6$-alkenyl, —$(CH_2)_m$—$C_2$-$C_6$-alkynyl, —$(CH_2)_m$—$C_3$-$C_6$-cycloalkyl, aryl-$C_1$-$C_6$-alkyl-, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —$C_1$-$C_6$-alkyl-aryl, —$C_1$-$C_6$-alkyl-heteroaryl or heteroaryl-group being optionally substituted, identically or differently, with 1, 2, 3, 4 or 5 R$^7$ groups;

R$^{4a}$, R$^{4b}$, R$^{4c}$, R$^{4d}$
represent, independently from each other, a hydrogen or halogen atom or a —CN, $C_1$-$C_6$-alkyl-, $C_1$-$C_6$-alkoxy-, halo-$C_1$-$C_6$-alkyl-, halo-$C_1$-$C_6$-alkoxy-, $R^{6a}(R^{6b})$N—$C_1$-$C_6$-alkyl-, H O—$C_1$-$C_6$-alkyl-, NC—$C_1$-$C_6$-alkyl-, $C_1$-$C_6$-alkoxy-$C_1$-$C_6$-alkyl- or halo-$C_1$-$C_6$-alkoxy-$C_1$-$C_6$-alkyl-group;

R$^5$ represents a hydrogen atom or a $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group;

said $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group being optionally substituted, identically or differently, with 1, 2, 3, 4 or 5 R$^8$ groups;

R$^6$, R$^{6a}$, R$^{6b}$, R$^{6c}$,
represent, independently from each other, a hydrogen atom or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl- or heteroaryl-$C_1$-$C_6$-alkyl-group;

wherein said $C_3$-$C_6$-cycloalkyl-group is optionally substituted, identically or differently with 1 or 2 groups selected from: halogen, —OH, —CN, $C_1$-$C_6$-alkyl-, HO—$C_1$-$C_6$-alkyl-, $C_1$-$C_6$-alkoxy-, halo-$C_1$-$C_6$-alkyl-, halo-$C_1$-$C_6$-alkoxy-;

R$^7$ represents a hydrogen or halogen atom or a HO—, —CN, $C_1$-$C_6$-alkoxy-, halo-$C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —CO(=O)—R$^6$, —N(R$^{6a}$)R$^{6b}$, —NO$_2$, —N(H)C(=O)

R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —SF$_5$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$ or —S(=O)(=NR$^{6c}$)R$^6$ group;

wherein said aryl- or heteroaryl-group is optionally substituted, identically or differently, with 1, 2, or 3 C$_1$-C$_6$-alkyl-groups; or when 2 R$^7$ groups are present ortho to each other on an aryl ring, said 2 R$^7$ groups together form a bridge: *O(CH$_2$)$_2$O*, *O(CH$_2$)O*, *NH(C(=O))NH*, wherein * represent the point of attachment to said aryl ring;

R$^8$ represents a hydrogen or halogen atom or a —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl-, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —CO(=O)—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, —S(=O)(=NR$^{6c}$)R$^6$ or —S(=O)$_2$-(3- to 7-membered heterocycloalkyl) group;

wherein said 3- to 7-membered heterocycloalkyl- or heteroaryl-group, is optionally substituted, identically or differently, with 1, 2, 3 or 4 C$_1$-C$_6$-alkyl-groups m is an integer of 0, 1, 2, 3, 4, 5 or 6;

n is an integer of 0, 1, 2, 3, 4 or 5; and

X represents S, S(=O), S(=O)$_2$, O, NR$^6$, CR$^{6a}$R$^{6b}$, C(=CR$^{6a}$R$^{6b}$), C(=O) or C(OH)(R$^{6a}$).

In a preferred embodiment, with respect to compounds of formula (I), supra, A is

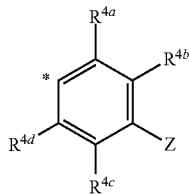

wherein * indicates the point of attachment of said group with the rest of the molecule.

In another preferred embodiment, with respect to compounds of formula (I), supra, A is

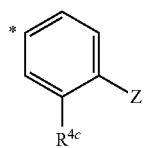

wherein * indicates the point of attachment of said group with the rest of the molecule;

R$^{4c}$ represents a hydrogen or halogen atom or a —CN, C$_1$-C$_6$-alkyl-, C$_1$-C$_6$-alkoxy-, halo-C$_1$-C$_6$-alkyl-, halo-C$_1$-C$_6$-alkoxy-, R$^{6a}$(R$^{6b}$)N—C$_1$-C$_6$-alkyl-, HO—C$_1$-C$_6$-alkyl-, NC—C$_1$-C$_6$-alkyl-, C$_1$-C$_6$-alkoxy-C$_1$-C$_6$-alkyl- or halo-C$_1$-C$_6$-alkoxy-C$_1$-C$_6$-alkyl-group. Preferably R$^{4c}$ is selected from: halo-, —CN, —OH, C$_1$-C$_6$-alkyl-, HO—C$_1$-C$_6$-alkyl-, and C$_1$-C$_6$-alkoxy-.

In another preferred embodiment, with respect to compounds of formula (I), supra, A is

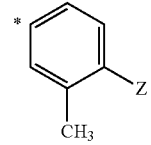

wherein * indicates the point of attachment of said group with the rest of the molecule.

In another preferred embodiment, with respect to compounds of formula (I), supra, R$^1$ represents a C$_1$-C$_6$-alkyl-group;
wherein said C$_1$-C$_6$-alkyl-group is optionally substituted, identically or differently, with 1, 2, 3 or 4 groups selected from: halogen, —OH, —CN, C$_1$-C$_4$-alkoxy-.

In another preferred embodiment, with respect to compounds of formula (I), supra, R$^1$ represents a C$_1$-C$_4$-alkyl-group;
wherein said C$_1$-C$_4$-alkyl-group is optionally substituted, identically or differently, with 1, 2, 3 or 4 groups selected from: halogen, —OH, —CN, C$_1$-C$_3$-alkoxy-.

In another preferred embodiment, with respect to compounds of formula (I), supra, R$^1$ represents a C$_3$-C$_6$-cycloalkyl-group;
wherein said C$_3$-C$_6$-cycloalkyl-group is optionally substituted, identically or differently, with 1, 2, 3 or 4 groups selected from: halogen, —OH, —CN, C$_1$-C$_4$-alkyl-, C$_1$-C$_4$-alkoxy-.

Preferably, the C$_3$-C$_6$-cycloalkyl-group is a substituted or unsubstituted cyclopropyl-group.

In another preferred embodiment, with respect to compounds of formula (I), supra, R$^1$ represents a C$_3$-C$_6$-cycloalkyl-group;
wherein said C$_3$-C$_6$-cycloalkyl-group is optionally substituted, identically or differently, with 1 or 2 groups selected from: halogen, —CN, C$_1$-C$_3$-alkyl-.

Preferably, the C$_3$-C$_6$-cycloalkyl-group is a a substituted or unsubstituted cyclopropyl-group.

In another preferred embodiment, with respect to compounds of formula (I), supra, R$^1$ represents a C$_3$-C$_6$-cycloalkyl-group;
wherein said C$_3$-C$_6$-cycloalkyl-group is optionally substituted with one group selected from: —CN, —CH$_3$.

Preferably, the C$_3$-C$_6$-cycloalkyl-group is a a substituted or unsubstituted cyclopropyl-group.

In another preferred embodiment, with respect to compounds of formula (I), supra, R$^1$ is selected from methyl-, ethyl-, cyclopropyl-,

wherein* indicates the point of attachment of said groups with the rest of the molecule.

Preferably, $R^1$ is a methyl- or ethyl-group.

In another preferred embodiment, with respect to compounds of formula (I), supra,
$R^2$ represents a $C_1$-$C_6$-alkyl-group;
  wherein said $C_1$-$C_6$-alkyl-group is optionally substituted, identically or differently, with 1, 2, 3 or 4 groups selected from: halogen, —OH, —CN, $C_1$-$C_4$-alkoxy-.

In another preferred embodiment, with respect to compounds of formula (I), supra,
$R^2$ represents a $C_1$-$C_4$-alkyl-group;
  wherein said $C_1$-$C_4$-alkyl-group is optionally substituted, identically or differently, with 1, 2, 3 or 4 groups selected from: halogen, —OH, —CN, $C_1$-$C_3$-alkoxy-.

In another preferred embodiment, with respect to compounds of formula (I), supra,
$R^2$ represents a $C_3$-$C_6$-cycloalkyl-group;
  wherein said $C_3$-$C_6$-cycloalkyl-group is optionally substituted, identically or differently, with 1, 2, 3 or 4 groups selected from: halogen, —OH, —CN, $C_1$-$C_4$-alkyl-, $C_1$-$C_4$-alkoxy-.
Preferably, the $C_3$-$C_6$-cycloalkyl-group is a a substituted or unsubstituted cyclopropyl-group.

In another preferred embodiment, with respect to compounds of formula (I), supra,
$R^2$ is selected from hydrogen, methyl-, cyclopropyl-.

In another preferred embodiment, with respect to compounds of formula (I), supra,
$R^3$ represents a hydrogen atom, halogen atom or an aryl-, heteroaryl-, aryl-X— or heteroaryl-X— group;
  said aryl-, aryl-X—, heteroaryl- or heteroaryl-X— group being optionally substituted, identically or differently, with 1, 2 or 3 $R^7$ groups.
  The aryl-group preferably is a substituted or unsubstituted phenyl-group.
  The heteroaryl-group preferably is a substituted or unsubstituted pyridyl or 1-pethylpyrazolyl-group.

In another preferred embodiment, with respect to compounds of formula (I), supra, $R^3$ represents an aryl- or heteroaryl-group; wherein said aryl- or heteroaryl-group is optionally substituted, identically or differently, with 1, 2 or 3 $R^7$ groups. The aryl-group preferably is a phenyl-group. The heteroaryl-group preferably is a substituted or unsubstituted pyridyl- or 1-methylpyrazolyl-group.

In another preferred embodiment, with respect to compounds of formula (I), supra, $R^3$ represents an aryl-X— or heteroaryl-X— group; wherein said aryl-X— or heteroaryl-X— group is optionally substituted, identically or differently, with 1, 2 or 3 $R^7$ groups. The aryl-group preferably is a substituted or unsubstituted phenyl-group.

In another preferred embodiment, with respect to compounds of formula (I), supra, $R^3$ represents an aryl-O— or heteroaryl-O— group; wherein said aryl-O— or heteroaryl-O— group is optionally substituted, identically or differently, with 1, 2 or 3 $R^7$ groups. The aryl-group preferably is a substituted or unsubstituted phenyl-group.

In another preferred embodiment, with respect to compounds of formula (I), supra, $R^3$ represents an aryl-S(=O)$_p$— or heteroaryl-S(=O)$_p$— group; wherein said aryl-S(=O)$_p$ or heteroaryl-S(=O)$_p$— group is optionally substituted, identically or differently, with 1, 2 or 3 $R^7$ groups; wherein p is 0, 1 or 2. The aryl-group preferably is a substituted or unsubstituted phenyl-group.

In another preferred embodiment, with respect to compounds of formula (I), supra, $R^3$ represents an aryl-$NR^6$— or heteroaryl-$NR^6$— group; wherein said aryl-$NR^6$— or heteroaryl-$NR^6$— group is optionally substituted, identically or differently, with 1, 2 or 3 $R^7$ groups. The aryl-group preferably is a substituted or unsubstituted phenyl-group.

In another preferred embodiment, with respect to compounds of formula (I), supra, $R^3$ represents an aryl-NH— or heteroaryl-NH— group; wherein said aryl-NH— or heteroaryl-NH— group is optionally substituted, identically or differently, with 1, 2 or 3 $R^7$ groups. The aryl-group preferably is a substituted or unsubstituted phenyl-group.

In another preferred embodiment, with respect to compounds of formula (I), supra, $R^3$ represents an aryl-$CR^{6a}R^{6b}$— or heteroaryl-$CR^{6a}R^{6b}$— group; wherein said aryl-$CR^{6a}R^{6b}$- or heteroaryl-$CR^{6a}R^{6b}$— group is optionally substituted, identically or differently, with 1, 2 or 3 $R^7$ groups. The aryl-group preferably is a substituted or unsubstituted phenyl-group.

In another preferred embodiment, with respect to compounds of formula (I), supra, $R^3$ represents an aryl-$CH_2$— or heteroaryl-$CH_2$— group; wherein said aryl-$CH_2$— or heteroaryl-$CH_2$— group is optionally substituted, identically or differently, with 1, 2 or 3 $R^7$ groups. The aryl-group preferably is a substituted or unsubstituted phenyl-group.

In another preferred embodiment, with respect to compounds of formula (I), supra, $R^3$ represents an aryl-$CH_2$— or heteroaryl-$CH_2$— group; wherein said aryl-$CH_2$— or heteroaryl-$CH_2$— group is optionally substituted, identically or differently, with 1, 2 or 3 $R^7$ groups. The aryl-group preferably is a substituted or unsubstituted phenyl-group.

In another preferred embodiment, with respect to compounds of formula (I), supra, $R^3$ represents an aryl-C(=O)— or heteroaryl-C(=O)— group; wherein said aryl-C(=O)— or heteroaryl-C(=O)— group is optionally substituted, identically or differently, with 1, 2 or 3 $R^7$ groups. The aryl-group preferably is a substituted or unsubstituted phenyl-group.

In another preferred embodiment, with respect to compounds of formula (I), supra, $R^3$ represents an aryl-C(OH)($R^{6a}$)— or heteroaryl-C(OH)($R^{6a}$)— group; wherein said aryl-C(OH)($R^{6a}$)— or heteroaryl-C(OH)($R^{6a}$)— group is optionally substituted, identically or differently, with 1, 2 or 3 $R^7$ groups. The aryl-group preferably is a substituted or unsubstituted phenyl-group.

In another preferred embodiment, with respect to compounds of formula (I), supra, $R^3$ represents an aryl-C(=$CR^{6a}R^{6b}$)— or heteroaryl-C(=$CR^{6a}R^{6b}$) group; wherein said aryl-C(=$CR^{6a}R^{6b}$) or heteroaryl-C(=$CR^{6a}R^{6b}$) group is optionally substituted, identically or differently, with 1, 2 or 3 $R^7$ groups. The aryl-group preferably is a substituted or unsubstituted phenyl-group.

In another preferred embodiment, with respect to compounds of formula (I), supra, $R^3$ is selected from:

H, Br,

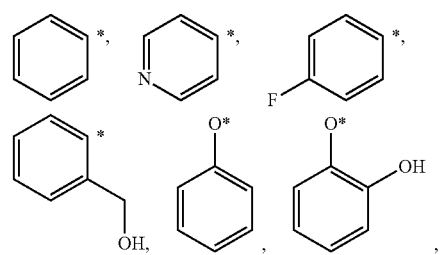

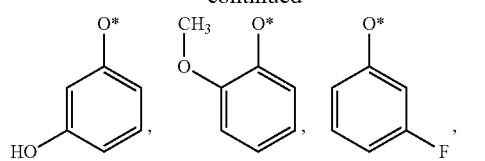
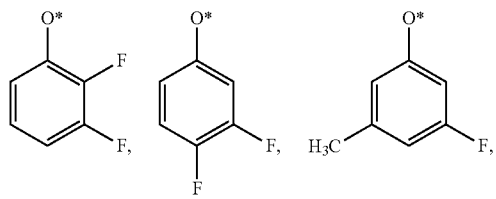
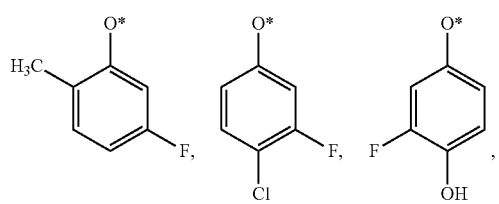
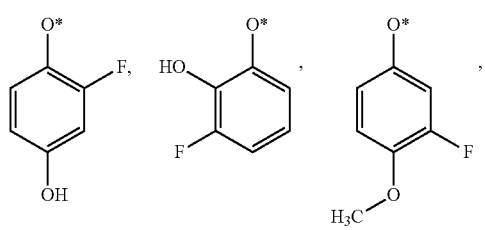
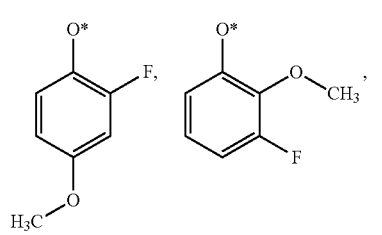
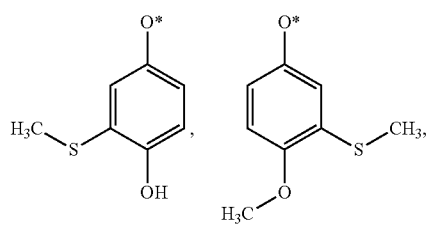
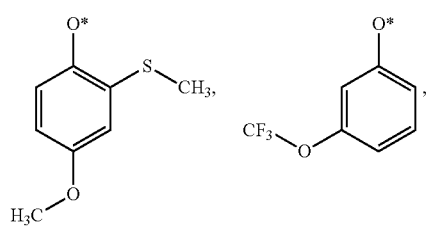
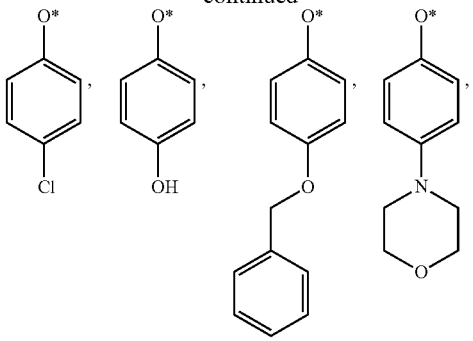
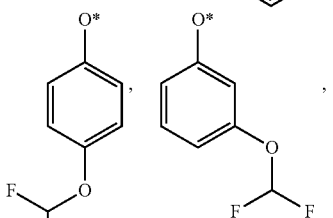
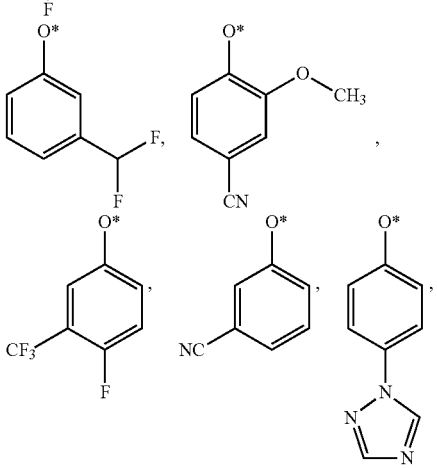
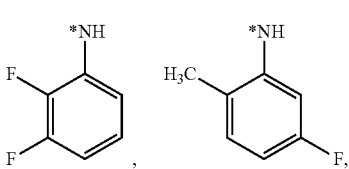
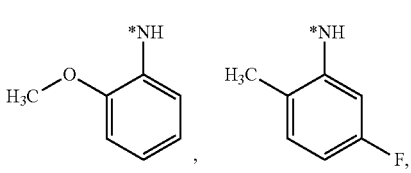
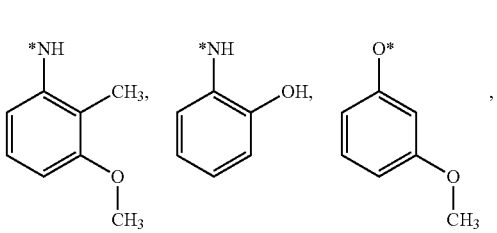

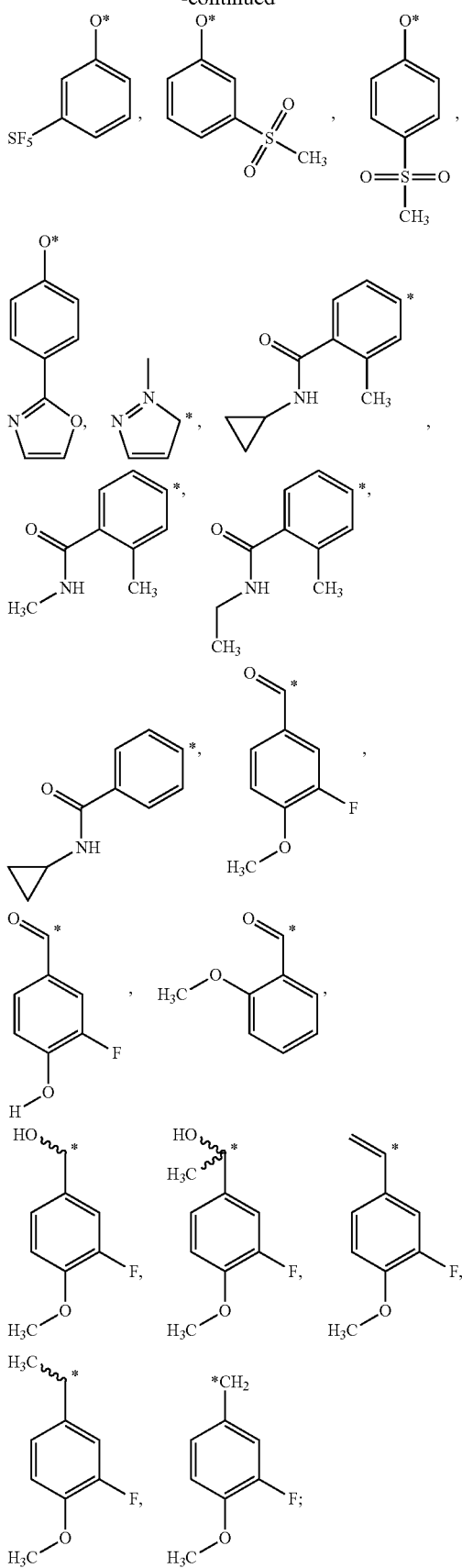

wherein * indicates the point of attachment of said groups with the rest of the molecule.

In another preferred embodiment, with respect to compounds of formula (I), supra, $R^{4a}$, $R^{4b}$, $R^{4c}$, and $R^{4d}$ are selected, independently from each other, from hydrogen, halogen, —OH, —CN, $C_1$-$C_6$-alkyl-, $C_1$-$C_6$-alkoxy-, halo-$C_1$-$C_6$-alkyl-, halo-$C_1$-$C_6$-alkoxy-, HO—$C_1$-$C_6$-alkyl-.

In another preferred embodiment of the present invention $R^{4a}$ and $R^{4d}$ represent, independently from each other, a hydrogen or halogen atom, or a $C_1$-$C_6$-alkyl-, $C_1$-$C_6$-alkoxy-, or a halo-$C_1$-$C_6$-alkyl-group.

In another preferred embodiment of the present invention $R^{4a}$ and $R^{4d}$ represent hydrogen.

In another preferred embodiment of the present invention $R^{4b}$ and $R^{4c}$ represent independently from each other, a hydrogen or halogen atom, or a —CN, —OH, $C_1$-$C_6$-alkyl-, $C_1$-$C_6$-alkoxy- or HO—$C_1$-$C_6$-alkyl-group.

In another preferred embodiment of the present invention $R^{4b}$ and $R^{4c}$ represent independently from each other, a hydrogen or halogen atom, or a —CN, —OH, $C_1$-$C_6$-alkyl-, $C_1$-$C_6$-alkoxy- or HO—$C_1$-$C_6$-alkyl-group; with the proviso that at least one of the groups $R^{4b}$ and $R^{4c}$ is not a hydrogen atom.

In another preferred embodiment of the present invention $R^{4b}$ and $R^{4c}$ represent independently from each other, a hydrogen atom, a $C_1$-$C_6$-alkyl- or a HO—$C_1$-$C_6$-alkyl-group.

In another preferred embodiment of the present invention $R^{4b}$ and $R^{4c}$ represent independently from each other, a hydrogen atom or a $C_1$-$C_6$-alkyl-group.

In another preferred embodiment of the present invention $R^{4b}$ and $R^{4c}$ represent independently from each other, a hydrogen atom, a $C_1$-$C_3$-alkyl- or a HO—$C_1$-$C_3$-alkyl-group; with the proviso that at least one of the groups $R^{4b}$ and $R^{4c}$ is not a hydrogen atom.

In another preferred embodiment of the present invention one of the groups $R^{4b}$ and $R^{4c}$ represents a hydrogen atom while the other one represents a group selected from: halo-, —CN, —OH, $C_1$-$C_6$-alkyl-, $C_1$-$C_6$-alkoxy-, halo-$C_1$-$C_6$-alkyl-, halo-$C_1$-$C_6$-alkoxy-, $R^{6a}(R^{6b})N$—$C_1$-$C_6$-alkyl-, HO—$C_1$-$C_6$-alkyl-, NC—$C_1$-$C_6$-alkyl-, $C_1$-$C_6$-alkoxy-$C_1$-$C_6$-alkyl-, and halo-$C_1$-$C_6$-alkoxy-$C_1$-$C_6$-alkyl-.

In another preferred embodiment of the present invention one of the groups $R^{4b}$ and $R^{4c}$ represents a hydrogen atom while the other one represents a group selected from: halo-, —CN, —OH, $C_1$-$C_6$-alkyl-, HO—$C_1$-$C_6$-alkyl-, and $C_1$-$C_6$-alkoxy-.

In another preferred embodiment of the present invention either: $R^{4b}$=—$CH_3$ and $R^{4c}$=hydrogen;
or: $R^{4b}$=hydrogen and $R^{4c}$=—$CH_3$.

In another preferred embodiment, with respect to compounds of formula (I), supra,
$R^5$ represents —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group;
said —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, —$C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group is optionally substituted, identically or differently, with 1, 2, 3, 4 or 5 $R^8$ groups.

In another preferred embodiment, with respect to compounds of formula (I), supra, $R^5$ represents a $C_1$-$C_6$-alkyl-, —$(CH_2)_m$-(3- to 7-membered heterocycloalkyl) or halo-$C_1$-$C_6$-alkyl-group;
said $C_1$-$C_6$-alkyl-, —$(CH_2)_m$-(3- to 7-membered heterocycloalkyl) or halo-$C_1$-$C_6$-alkyl-group is optionally substituted, identically or differently, with 1, 2, 3, 4 or 5 $R^8$ groups. Preferably, the 3- to 7-membered heterocycloalkyl-group is a tetrahydropyranyl-group. Preferably, m is either 0 or 1. Preferably, the 3- to 7-membered heterocycloalkyl-group is a tetrahydropyranyl-group. Preferably, m is either 0 or 1.

In another preferred embodiment, with respect to compounds of formula (I), supra, $R^5$ represents a $C_1$-$C_6$-alkyl-, —$(CH_2)_m$-(3- to 7-membered heterocycloalkyl) or halo-$C_1$-$C_6$-alkyl-group. Preferably, the 3- to 7-membered heterocycloalkyl-group is a tetrahydropyranyl-group. Preferably, m is either 0 or 1.

In another preferred embodiment, with respect to compounds of formula I, supra, $R^5$ is selected from:

H, $(CH_3)_2CH$—, $CHF_2$—, $CF_3$—, $CF_3$—$CH_2$—, $CF_3$—$CH_2$—$CH_2$—, $CF_3$—$CH(OH)$—, $HO$—$CH_2$—$HO$—$C(CH_3)_2$—, $HO$—$C(CH_3)_2CH_2$—, $HO$—$CH_2$—$CH(OH)$—, $H_3C$—$O$—$CH_2$—, $H_2N$—$CH_2$—$CH_2$—$H_2N$—$C(CH_3)_2$—, $(CH_3)_2N$—$CH_2$—, $(CH_3)_2N$—$CH_2$—$CH_2$—, $(CH_3)_2N$—$CH_2$—$CH_2$—$CH_2$—$(CH_3)_2N$—$C(CH_3)_2$—, $H_3C$—$S(\!=\!O)_2$—$CH_2$—, $H_3C$—$S(\!=\!O)_2$—$CH_2$—$CH_2$—, $HO$—$S(\!=\!O)_2$—$CH_2$—$HO$—$S(\!=\!O)_2$—$CH_2$—$CH_2$—, $NC$—$CH_2$—, $H_3C$—$C(\!=\!O)$—$N(H)$—$CH_2$, $H_3C$—$C(\!=\!O)$—$N(H)$—$CH_2$—$CH_2$—$H_2N$—$C(\!=\!O)$—$CH_2$—, $(CH_3)_2N$—$C(\!=\!O)$—$CH_2$—, $H_3C$—$N(H)$—$C(\!=\!O)$—$N(CH_3)$—$CH_2$—$CH_2$—,

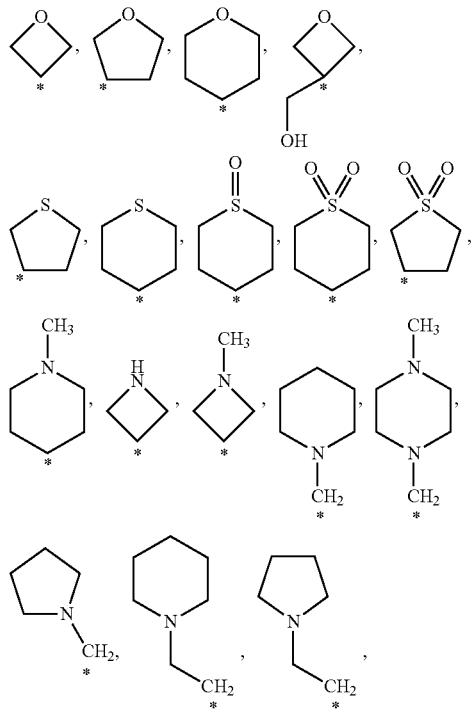

wherein * indicates the point of attachment of said groups with the rest of the molecule.

In another preferred embodiment, with respect to compounds of formula (I), supra, $R^5$ represents a group selected from:

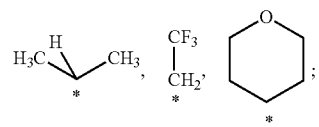

wherein * indicates the point of attachment of said group with the rest of the molecule.

In another preferred embodiment, with respect to compounds of formula (I), supra, $R^6$, $R^{6a}$, $R^{6b}$, and ROC represent, independently from each other, a hydrogen atom, or a $C_1$-$C_6$-alkyl-, $C_3$-$C_6$-cycloalkyl- or aryl-$C_1$-$C_6$-alkyl-group.

In another preferred embodiment, with respect to compounds of formula (I), supra, $R^6$, $R^{6a}$, $R^{6b}$, and $R^{6c}$ represent, independently from each other, a hydrogen atom, or a $C_1$-$C_6$-alkyl-group.

$R^7$ represents a hydrogen or halogen atom, or a HO—, —CN, $C_1$-$C_6$-alkoxy-, halo-$C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —$C(\!=\!O)R^6$, —$C(\!=\!O)N(H)R^{6a}$, —$C(\!=\!O)N(R^{6a})R^{6b}$, —$CO(\!=\!O)$—$R^6$, —$N(R^{6a})R^{6b}$, —$NO_2$, —$N(H)C(\!=\!O)R^6$, —$N(R^{6c})C(\!=\!O)R^6$, —$N(H)C(\!=\!O)N(R^{6a})R^{6b}$, —$N(R^{6c})C(\!=\!O)N(R^{6a})R^{6b}$, —$N(H)C(\!=\!O)OR^6$, —$N(R^{6c})C(\!=\!O)OR^6$, —$N(H)S(\!=\!O)R^6$, —$N(R^{6c})S(\!=\!O)R^6$, —$N(H)S(\!=\!O)_2R^6$, —$N(R^{6c})S(\!=\!O)_2R^6$, —$N\!=\!S(\!=\!O)(R^{6a})R^{6b}$, —$OR^6$, —$O(C\!=\!O)R^6$, —$O(C\!=\!O)N(R^{6a})R^{6b}$, —$O(C\!=\!O)OR^6$, —$SR^6$, —$SF_5$, —S(=O)R⁶, —S(=O)N(H)R⁶, —S(=O)N(R⁶ᵃ)R⁶ᵇ, —S(=O)₂R⁶, —S(=O)₂N(H)R⁶, —S(=O)₂N(R⁶ᵃ)R⁶ᵇ or —S(=O)(=NR⁶ᶜ)R⁶ group;
wherein said aryl- or heteroaryl-group is optionally substituted, identically or differently, with 1, 2 or 3 $C_1$-$C_6$-alkyl-groups;
or
when 2 R⁷ groups are present ortho- to each other on an aryl ring, said 2 R⁷ groups together form a bridge: *O(CH₂)₂O*, *O(CH₂)O*, *NH(C(=O))NH*, wherein * represent the point of attachment to said aryl ring.

In another preferred embodiment, with respect to compounds of formula (I), supra, R⁷ represents a hydrogen or halogen atom, or a HO—, —CN, $C_1$-$C_6$-alkoxy-, halo-$C_1$-$C_6$-alkoxy-, $C_1$-$C_6$-alkyl-, halo-$C_1$-$C_6$-alkyl-, HO—$C_1$-$C_6$-alkyl-, H₂N—$C_1$-$C_6$-alkyl-, $C_2$-$C_6$-alkenyl, 3- to 7-membered heterocycloalkyl-, heteroaryl-, —C(=O)N(H)R⁶ᵃ, —N(R⁶ᵃ)R⁶ᵇ, —N(H)C(=O)R⁶, —OR⁶, —SR⁶, —SF₅ or —S(=O)₂R⁶ group.

In another preferred embodiment, with respect to compounds of formula (I), supra, R⁷ represents a halogen atom, or a HO—, —CN, $C_1$-$C_6$-alkoxy-, halo-$C_1$-$C_6$-alkoxy-, $C_1$-$C_6$-alkyl-, HO—$C_1$-$C_6$-alkyl-, 3- to 7-membered heterocycloalkyl-, heteroaryl-, —C(=O)N(H)R⁶ᵃ, —OR⁶, —SR⁶, —SF₅ or —S(=O)₂R⁶ group.

In another preferred embodiment, with respect to compounds of formula (I), supra,
R⁸ represents a halogen atom or a —CN, —OH, $C_1$-$C_6$-alkoxy-, $C_1$-$C_6$-alkyl-, HO—$C_1$-$C_6$-alkyl, —C(=O)N (R⁶ᵃ)R⁶ᵇ, —N(R⁶ᵃ)R⁶ᵇ, —N(H)C(=O)R⁶, —N(R⁶ᶜ)C (=O)N(R⁶ᵃ)R⁶ᵇ, —S(=O)₂R⁶ or —S(=O)₂OH group.

In a preferred embodiment, the invention relates to compounds of formula (I), supra, wherein X is S.
In another preferred embodiment, with respect to compounds of formula (I), supra, X is S(=O).
In another preferred embodiment, with respect to compounds of formula (I), supra, X is S(=O)₂.
In another preferred embodiment, with respect to compounds of formula (I), supra, X is O.
In another preferred embodiment, with respect to compounds of formula (I), supra, X is NR⁶. Preferably, X is NH or N(CH₃). Most preferably, X is NH.
In another preferred embodiment, with respect to compounds of formula (I), supra, X is CR⁶ᵃR⁶ᵇ. Preferably, X is CH₂ or C(H)(CH₃).
In another preferred embodiment, with respect to compounds of formula (I), supra, X is C(=CR⁶ᵃR⁶ᵇ). Preferably, X is C(=CH₂).
In another preferred embodiment, with respect to compounds of formula (I), supra, X is C(=O).
In another preferred embodiment, with respect to compounds of formula (I), supra, X is C(OH)(R⁶ᵃ). Preferably, X is C(OH)(H) or C(OH)(CH₃).
In another preferred embodiment, with respect to compounds of formula (I), supra, Z represents a —C(=O)N(H)R¹ group.
In another preferred embodiment, with respect to compounds of formula (I), supra, n is 1.
In another preferred embodiment, with respect to compounds of formula (I), supra, m is 0 or 1.

It is to be understood that the present invention relates also to any combination of the preferred embodiments described above. Some examples of combinations are given hereinafter. However, the invention is not limited to these combinations.

In a preferred embodiment the present invention is related to compounds of formula (I):

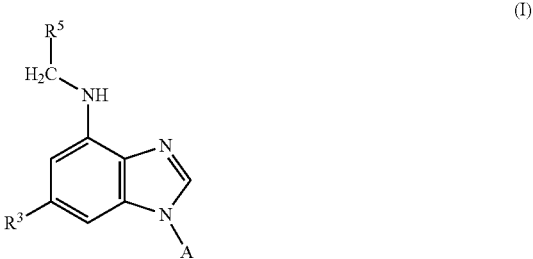

(I)

in which:
A represents

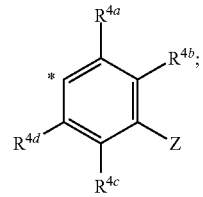

wherein * indicates the point of attachment of said group with the rest of the molecule;
Z represents a —C(=O)N(H)R¹ group;
R¹ represents a hydrogen atom or a $C_1$-$C_6$-alkyl- or $C_3$-$C_6$-cycloalkyl-group;
wherein said $C_1$-$C_6$-alkyl- or $C_3$-$C_6$-cycloalkyl-group is optionally substituted, identically or differently, with 1, 2, 3 or 4 groups selected from: halogen, —OH, —CN, $C_1$-$C_6$-alkyl-, $C_1$-$C_6$-alkoxy-;
R³ represents a hydrogen atom or a halogen atom or a —CN, $C_1$-$C_6$-alkyl-, —(CH₂)ₘ—$C_2$-$C_6$-alkenyl, —(CH₂)ₘ—$C_4$-$C_8$-cycloalkenyl, —(CH₂)ₘ—$C_2$-$C_6$-alkynyl, —(CH₂)ₘ—$C_3$-$C_6$-cycloalkyl, —(CH₂)ₘ-(3- to 7-membered heterocycloalkyl), —(CH₂)ₘ-(4- to 8-membered heterocycloalkenyl), aryl-$C_1$-$C_6$-alkyl-, heteroaryl-$C_1$-$C_6$-alkyl-, halo-$C_1$-$C_6$-alkyl-, R⁶ᵃ(R⁶ᵇ)N—$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, —$C_1$-$C_6$-alkyl-aryl, —$C_1$-$C_6$-alkyl-heteroaryl, heteroaryl-, —$C_1$-$C_6$-alkyl-X—, —X—(CH₂)ₘ—$C_2$-$C_6$-alkenyl, —X—(CH₂)ₘ—$C_4$-$C_8$-cycloalkenyl, —X—(CH₂)ₘ—$C_2$-$C_6$-alkynyl, —X—(CH₂)ₘ—$C_3$-$C_6$-cycloalkyl, —X—(CH₂)ₘ-(3- to 7-membered heterocycloalkyl), —X—(CH₂)ₘ-(4- to 8-membered heterocycloalkenyl), aryl-X—, heteroaryl-X—, —C(=O)R⁶, —C(=O)N(H)R⁶ᵃ, —C(=O)N(R⁶ᵃ)R⁶ᵇ, —CO(=O)—R⁶, —N(R⁶ᵃ)R⁶ᵇ, —NO₂, —N(H)C(=O)R⁶, —OR⁶, —SR⁶, —S(=O)R⁶, —S(=O)₂R⁶, —S(=O)(=NR⁶ᵃ)R⁶ᵇ, —S(=O)₂N(R⁶ᵇ)R⁶ᶜ, —S—(CH₂)ₙ—N(R⁶ᵃ)R⁶ᵇ or —S—(CH₂)ₙ-(3- to 7-membered heterocycloalkyl) group;
said $C_1$-$C_6$-alkyl-, —(CH₂)ₘ—$C_2$-$C_6$-alkenyl, —(CH₂)ₘ—$C_2$-$C_6$-alkynyl, —(CH₂)ₘ—$C_3$-$C_6$-cycloalkyl, aryl-$C_1$-$C_6$-alkyl-, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—(CH₂)ₘ—$C_2$-$C_6$-alkenyl, —X—(CH₂)ₘ—$C_4$-$C_8$-cycloalkenyl, —X—(CH₂)ₘ—$C_2$-$C_6$-alkynyl, —X—(CH₂)ₘ—$C_3$-$C_6$-cycloalkyl, —X—(CH₂)ₘ-(3- to 7-membered heterocycloalkyl), —X—(CH₂)ₘ-(4- to 8-membered heterocycloalkenyl), aryl-X—, heteroaryl-X—, —$C_1$-$C_6$-alkyl-aryl, —$C_1$-$C_6$-alkyl-heteroaryl or heteroaryl-group being optionally substituted, identically or differently, with 1, 2, 3, 4 or 5 $R^7$ groups;

$R^{4a}$ and $R^{4d}$ represent a hydrogen atom;

one of the groups $R^{4b}$ and $R^{4c}$ represents a hydrogen atom while the other one represents a group selected from: halo-, —CN, —OH, $C_1$-$C_6$-alkyl-, HO—$C_1$-$C_6$-alkyl-, and $C_1$-$C_6$-alkoxy-;

$R^5$ represents a hydrogen atom or a $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group;

said $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group being optionally substituted, identically or differently, with 1, 2, 3, 4 or 5 $R^8$ groups;

$R^6$, $R^{6a}$, $R^{6b}$, $R^{6c}$ represent, independently from each other, a hydrogen atom or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl- or heteroaryl-$C_1$-$C_6$-alkyl-group;

$R^7$ represents a hydrogen or halogen atom or a HO—, —CN, $C_1$-$C_6$-alkoxy-, halo-$C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(═O)$R^6$, —C(═O)N(H)$R^{6a}$, —C(═O)N($R^{6a}$)$R^{6b}$, —CO(═O)—$R^6$, —N($R^{6a}$)$R^{6b}$, —$NO_2$, —N(H)C(═O)$R^6$, —N($R^{6c}$)C(═O)$R^6$, —N(H)C(═O)N($R^{6a}$)$R^{6b}$, —N($R^{6c}$)C(═O)N($R^{6a}$)$R^{6b}$, —N(H)C(═O)$OR^6$, —N($R^{6c}$)C(═O)$OR^6$, —N(H)S(═O)$R^6$, —N($R^{6c}$)S(═O)$R^6$, —N(H)S(═O)$_2R^6$, —N($R^{6c}$)S(═O)$_2R^6$, —N═S(═O)($R^{6a}$)$R^{6b}$, —$OR^6$, —O(C═O)$R^6$, —O(C═O)N($R^{6a}$)$R^{6b}$, —O(C═O)$OR^6$, —$SR^6$, —$SF_5$, —S(═O)$R^6$, —S(═O)N(H)$R^6$, —S(═O)N($R^{6a}$)$R^{6b}$, —S(═O)$_2R^6$, —S(═O)$_2$N(H)$R^6$, —S(═O)$_2$N($R^{6a}$)$R^{6b}$, —S(═O)(═$NR^{6c}$)$R^6$ group;

wherein said aryl- or heteroaryl-group is optionally substituted, identically or differently, with 1, 2 or 3 $C_1$-$C_6$-alkyl-groups;

$R^8$ represents a hydrogen or halogen atom or a —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(═O)$R^6$, —C(═O)N(H)$R^{6a}$, —C(═O)N($R^{6a}$)$R^{6b}$, —CO(═O)—$R^6$, —N($R^{6a}$)$R^{6b}$, —$NO_2$, —N(H)C(═O)$R^6$, —N($R^{6c}$)C(═O)$R^6$, —N(H)C(═O)N($R^{6a}$)$R^{6b}$, —N($R^{6c}$)C(═O)N($R^{6a}$)$R^{6b}$, —N(H)C(═O)$OR^6$, —N($R^{6c}$)C(═O)$OR^6$, —N(H)S(═O)$R^6$, —N($R^{6c}$)S(═O)$_2R^6$, —N(H)S(═O)$_2R^6$, —N($R^{6c}$)S(═O)$_2R^6$, —N═S(═O)($R^{6a}$)$R^{6b}$, —$OR^6$, —O(C═O)$R^6$, —O(C═O)N($R^{6a}$)$R^{6b}$, —O(C═O)$OR^6$, —$SR^6$, —S(═O)$R^6$, —S(═O)N(H)$R^6$, —S(═O)N($R^{6a}$)$R^{6b}$, —S(═O)$_2R^6$, —S(═O)$_2$N(H)$R^6$, —S(═O)$_2$N($R^{6a}$)$R^{6b}$, —S(═O)(═$NR^{6c}$)$R^6$ or —S(═O)$_2$-(3- to 7-membered heterocycloalkyl) group;

wherein said 3- to 7-membered heterocycloalkyl- or heteroaryl-group, is optionally substituted, identically or differently, with 1, 2, 3 or 4 $C_1$-$C_6$-alkyl-groups;

m is 0 or 1;

n is an integer of 0, 1, 2, 3, 4 or 5; and

X is S, S(═O), S(═O)$_2$, O, $NR^6$, $CR^{6a}R^{6b}$, C(═$CR^{6a}R^{6b}$), C(═O) or C(OH)($R^{6a}$);

or a stereoisomer, a tautomer, an N-oxide, a hydrate, a solvate, or a salt thereof, or a mixture of same.

In another preferred embodiment the present invention is related to compounds of formula (I):

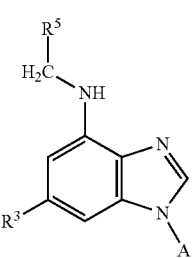

(I)

in which:

A represents

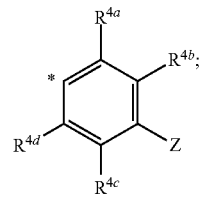

wherein * indicates the point of attachment of said group with the rest of the molecule;

Z represents a —C(═O)N(H)$R^1$ group;

$R^1$ represents a hydrogen atom or a $C_1$-$C_6$-alkyl- or $C_3$-$C_6$-cycloalkyl-group;

wherein said $C_1$-$C_6$-alkyl- or $C_3$-$C_6$-cycloalkyl-group is optionally substituted, identically or differently, with 1, 2, 3 or 4 groups selected from: halogen, —OH, —CN, $C_1$-$C_6$-alkyl-, $C_1$-$C_6$-alkoxy-;

$R^3$ represents a hydrogen atom, a halogen atom, an aryl-, —$C_1$-$C_6$-alkyl-aryl, —$C_1$-$C_6$-alkyl-heteroaryl, heteroaryl-, aryl-X— or heteroaryl-X— group; said aryl-, —$C_1$-$C_6$-alkyl-aryl, —$C_1$-$C_6$-alkyl-heteroaryl, heteroaryl-, aryl-X— or heteroaryl-X— group being optionally substituted, identically or differently, with 1, 2, 3, 4 or 5 $R^7$ groups;

$R^{4a}$ and $R^{4d}$ represent a hydrogen atom;

one of the groups $R^{4b}$ and $R^{4c}$ represents a hydrogen atom while the other one represents a group selected from: halo-, —CN, —OH, $C_1$-$C_6$-alkyl-, HO—$C_1$-$C_6$-alkyl-, and $C_1$-$C_6$-alkoxy-;

$R^5$ represents a hydrogen atom or a $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group;

said $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group being optionally substituted, identically or differently, with 1, 2, 3, 4 or 5 $R^8$ groups;

$R^6$, $R^{6a}$, $R^{6b}$, $R^{6c}$ represent, independently from each other, a hydrogen atom or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl- or heteroaryl-$C_1$-$C_6$-alkyl-group;

$R^7$ represents a hydrogen or halogen atom or a HO—, —CN, $C_1$-$C_6$-alkoxy-, halo-$C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —CO(=O)—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —SF$_5$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$ or —S(=O)(=N$R^{6c}$)$R^6$ group;

wherein said aryl- or heteroaryl-group is optionally substituted, identically or differently, with 1, 2 or 3 $C_1$-$C_6$-alkyl-groups;

$R^8$ represents a hydrogen or halogen atom, or a —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —CO(=O)—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$, —S(=O)(=N$R^{6c}$)$R^6$ or —S(=O)$_2$-(3- to 7-membered heterocycloalkyl) group;

wherein said 3- to 7-membered heterocycloalkyl- or heteroaryl-group, is optionally substituted, identically or differently, with 1, 2, 3 or 4 $C_1$-$C_6$-alkyl-groups;

m is 0 or 1;

n is an integer of 0, 1, 2, 3, 4 or 5; and

X is S, S(=O), S(=O)$_2$, O, N$R^6$, C$R^{6a}R^{6b}$, C(=C$R^{6a}R^{6b}$), C(=O) or C(OH)($R^{6a}$);

or a stereoisomer, a tautomer, an N-oxide, a hydrate, a solvate, or a salt thereof, or a mixture of same.

In another preferred embodiment the present invention is related to compounds of formula (I):

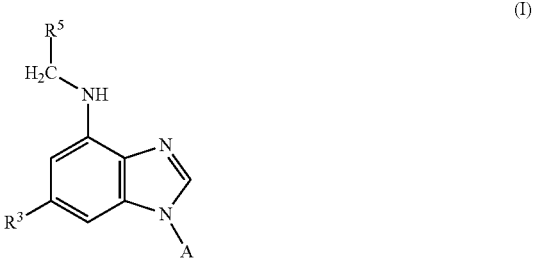

(I)

in which:

A represents

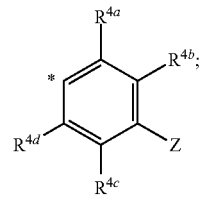

wherein * indicates the point of attachment of said group with the rest of the molecule;

Z represents a —C(=O)N(H)$R^1$ group;

$R^1$ represents a hydrogen atom or a $C_1$-$C_6$-alkyl- or $C_3$-$C_6$-cycloalkyl-group; wherein said $C_1$-$C_6$-alkyl- or $C_3$-$C_6$-cycloalkyl-group is optionally substituted, identically or differently, with 1, 2, 3 or 4 groups selected from: halogen, OH, —CN, $C_1$-$C_6$-alkyl-, $C_1$-$C_6$-alkoxy-;

$R^3$ represents a hydrogen atom or a halogen atom or a —CN, $C_1$-$C_6$-alkyl-, —$(CH_2)_m$—$C_2$-$C_6$-alkenyl, —$(CH_2)_m$—$C_4$-$C_8$-cycloalkenyl, —$(CH_2)_m$—$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, —$C_1$-$C_6$-alkyl-aryl, —$C_1$-$C_6$-alkyl-heteroaryl, heteroaryl-, —$C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —C(=O)$R^6$, —C(=O)N(H)$R^{6a}$, —C(=O)N($R^{6a}$)$R^{6b}$, —CO(=O)—$R^6$, —N($R^{6a}$)$R^{6b}$, —NO$_2$, —N(H)C(=O)$R^6$, —O$R^6$, —S$R^6$, —S(=O)$R^6$, —S(=O)$_2R^6$, —S(=O)(=N$R^{6a}$)$R^{6b}$, —S(=O)$_2$N($R^{6b}$)$R^{6c}$, —S—$(CH_2)_n$—N($R^{6a}$)$R^{6b}$ or —S—$(CH_2)_n$-(3- to 7-membered heterocycloalkyl) group;

said $C_1$-$C_6$-alkyl-, —$(CH_2)_m$—$C_2$-$C_6$-alkenyl, —$(CH_2)_m$—$C_2$-$C_6$-alkynyl, —$(CH_2)_m$—$C_3$-$C_6$-cycloalkyl, aryl-$C_1$-$C_6$-alkyl-, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—$(CH_2)_m$—$C_2$-$C_6$-alkenyl, —X—(CH$_2$)$_m$—C$_4$-C$_8$-cycloalkenyl, —X—(CH$_2$)$_m$—C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C$_1$-C$_6$-alkyl-aryl, —C$_1$-C$_6$-alkyl-heteroaryl, heteroaryl-group optionally being substituted, identically or differently, with 1, 2, 3, 4 or 5 R$^7$ groups;

R$^{4a}$, R$^{4b}$, R$^{4c}$, R$^{4d}$
are selected, independently from each other, from hydrogen, halogen, —CN, C$_1$-C$_6$-alkyl-, C$_1$-C$_6$-alkoxy-, halo-C$_1$-C$_6$-alkyl-, halo-C$_1$-C$_6$-alkoxy-;

R$^5$ represents a hydrogen atom or a C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_4$-C$_8$-cycloalkenyl-, aryl- or heteroaryl-group;
wherein said C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_4$-C$_8$-cycloalkenyl-, aryl- or heteroaryl-group is optionally substituted, identically or differently, with 1, 2, 3, 4 or 5 R$^8$ groups;

R$^6$, R$^{6a}$, R$^{6b}$, R$^{6c}$
represent, independently from each other, a hydrogen atom or a C$_1$-C$_6$-alkyl-, HO—C$_1$-C$_6$-alkyl-, C$_3$-C$_6$-cycloalkyl-, C$_2$-C$_6$-alkenyl-, 3- to 7-membered heterocycloalkyl-, aryl-, heteroaryl-, aryl-C$_1$-C$_6$-alkyl- or heteroaryl-C$_1$-C$_6$-alkyl-group;

R$^7$ represents a hydrogen or halogen atom or a HO—, —CN, C$_1$-C$_6$-alkoxy-, halo-C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl-, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —CO(=O)—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —SF$_5$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$ or —S(=O)(=NR$^{6c}$)R$^6$ group;
wherein said aryl- or heteroaryl-group is optionally substituted, identically or differently, with 1, 2 or 3 C$_1$-C$_6$-alkyl-groups;

R$^8$ represents a hydrogen or halogen atom or a —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl-, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —CO(=O)—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6b}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, —S(=O)(=NR$^{6c}$)R$^6$ or —S(=O)$_2$-(3- to 7-membered heterocycloalkyl) group;
wherein said 3- to 7-membered heterocycloalkyl- or heteroaryl-group is optionally substituted, identically or differently, with 1, 2, 3, or 4 C$_1$-C$_6$-alkyl-groups;

m is 0 or 1;
n is an integer of 0, 1, 2, 3, 4, or 5; and
X is S, S(=O), S(=O)$_2$, O, NR$^6$, CR$^{6a}$R$^{6b}$, C(=CR$^{6a}$R$^{6b}$), C(=O) or C(OH)(R$^{6a}$);

or a stereoisomer, a tautomer, an N-oxide, a hydrate, a solvate, or a salt thereof, or a mixture of same.

In another preferred embodiment the present invention is related to compounds of formula (I):

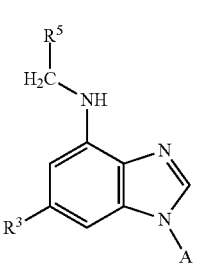

(I)

in which:
A represents

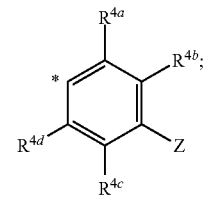

wherein * indicates the point of attachment of said group with the rest of the molecule;
Z represents a —C(=O)N(H)R$^1$ or —C(=S)N(H)R$^1$ group;
R$^1$ is selected from methyl-, ethyl-, cyclopropyl-,

wherein * indicates the point of attachment of said groups with the rest of the molecule;
R$^3$ represents a hydrogen atom or a halogen atom or a —CN, C$_1$-C$_6$-alkyl-, —(CH$_2$)$_m$—C$_2$-C$_6$-alkenyl, —(CH$_2$)$_m$—C$_4$-C$_8$-cycloalkenyl, —(CH$_2$)$_m$—C$_2$-C$_6$-alkynyl, —(CH$_2$)$_m$—C$_3$-C$_6$-cycloalkyl, —(CH$_2$)$_m$-(3- to 7-membered heterocycloalkyl), —(CH$_2$)$_m$-(4- to 8-membered heterocycloalkenyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$- cycloalkenyl-, $C_2$-$C_6$-alkynyl-, aryl-, —$C_1$-$C_6$-alkyl-aryl, —$C_1$-$C_6$-alkyl-heteroaryl, heteroaryl-, —$C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —C(=O)$R^6$, —C(=O)N(H)$R^{6a}$, —C(=O)N($R^{6a}$)$R^{6b}$, —CO(=O)—$R^6$, —N($R^{6a}$)$R^{6b}$, —$NO_2$, —N(H)C(=O)$R^6$, —O$R^6$, —S$R^6$, —S(=O)$R^6$, —S(=O)$_2R^6$, —S(=O)(=N$R^{6a}$)$R^{6b}$, —S(=O)$_2$N($R^{6b}$)$R^{6c}$, —S—$(CH_2)_n$—N($R^{6a}$)$R^{6b}$, or —S—$(CH_2)_n$-(3- to 7-membered heterocycloalkyl) group;

said $C_1$-$C_6$-alkyl-, —$(CH_2)_m$—$C_2$-$C_6$-alkenyl, —$(CH_2)_m$—$C_2$-$C_6$-alkynyl, —$(CH_2)_m$—$C_3$-$C_6$-cycloalkyl, aryl-$C_1$-$C_6$-alkyl-, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —$C_1$-$C_6$-alkyl-aryl, —$C_1$-$C_6$-alkyl-heteroaryl, heteroaryl-group optionally being substituted, identically or differently, with 1, 2, 3, 4 or 5 $R^7$ groups;

$R^{4a}$, $R^{4b}$, $R^{4c}$, $R^{4d}$
are selected, independently from each other, from: hydrogen, halogen, —CN, $C_1$-$C_6$-alkyl-, $C_1$-$C_6$-alkoxy-, halo-$C_1$-$C_6$-alkyl-, halo-$C_1$-$C_6$-alkoxy-;

$R^5$ represents a hydrogen atom or a $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group;
wherein said $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group is optionally substituted, identically or differently, with 1, 2, 3, 4 or 5 $R^8$ groups;

$R^6$, $R^{6a}$, $R^{6b}$, $R^{6c}$
represent, independently from each other, a hydrogen atom, or a $C_1$-$C_6$-alkyl-, H O—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl- or heteroaryl-$C_1$-$C_6$-alkyl-group;

$R^7$ represents a hydrogen or halogen atom or a HO—, —CN, $C_1$-$C_6$-alkoxy-, halo-$C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-$C_2$-$C_6$-alkenyl-, $C_2$-$C_6$-alkynyl-, 3- to 7-membered heterocycloalkyl-, aryl-heteroaryl-, —C(=O)$R^6$, —C(=O)N(H)$R^{6a}$, —C(=O)N($R^{6a}$)$R^{6b}$, —CO(=O)—$R^6$, —N($R^{6a}$)$R^{6b}$, —$NO_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —$SF_5$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$ or —S(=O)(=N$R^{6c}$)$R^6$ group;
wherein said aryl- or heteroaryl-group is optionally substituted, identically or differently, with 1, 2 or 3 $C_1$-$C_6$-alkyl-groups;

$R^8$ represents a hydrogen or halogen atom or a —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —$NO_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2 R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$, —S(=O)(=N$R^{6c}$)$R^6$ or —S(=O)$_2$-(3- to 7-membered heterocycloalkyl) group;
wherein said 3- to 7-membered heterocycloalkyl- or heteroaryl-group is optionally substituted, identically or differently, with 1, 2, 3 or 4 $C_1$-$C_6$-alkyl-groups;

m is 0 or 1;
n is an integer of 0, 1, 2, 3, 4, or 5; and
X is S, S(=O), S(=O)$_2$, O, N$R^6$, C$R^{6a}R^{6b}$, C(=C$R^{6a}R^{6b}$), C(=O) or C(OH)($R^{6a}$);
or a stereoisomer, a tautomer, an N-oxide, a hydrate, a solvate, or a salt thereof, or a mixture of same.

In another preferred embodiment the present invention is related to compounds of formula (I):

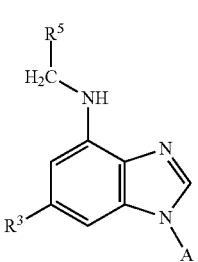

(I)

in which:
A represents a

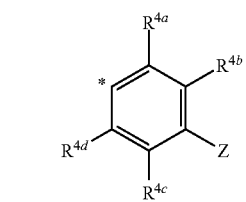

-group;

wherein * indicates the point of attachment of said group with the rest of the molecule;

Z is selected from —C(═O)N(H)R$^1$ or —C(═S)N(H)R$^1$;

R$^1$ represents a C$_3$-C$_6$-cycloalkyl-group; wherein said C$_3$-C$_6$-cycloalkyl-group is optionally substituted, identically or differently, with 1 or 2 groups selected from: halogen, OH, —CN, C$_1$-C$_6$-alkyl-, C$_1$-C$_6$-alkoxy-;

R$^3$ represents a hydrogen atom or a halogen atom, or a —CN, C$_1$-C$_6$-alkyl-, —(CH$_2$)$_m$—C$_2$-C$_6$-alkenyl, —(CH$_2$)$_m$—C$_4$-C$_8$-cycloalkenyl, —(CH$_2$)$_m$—C$_2$-C$_6$-alkynyl, —(CH$_2$)$_m$—C$_3$-C$_6$-cycloalkyl, —(CH$_2$)$_m$-(3- to 7-membered heterocycloalkyl), —(CH$_2$)$_m$-(4- to 8-membered heterocycloalkenyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl-, —C$_1$-C$_6$-alkyl-aryl, —C$_1$-C$_6$-alkyl-heteroaryl, heteroaryl-, —C$_1$-C$_6$-alkyl-X—, —X—(CH$_2$)$_m$—C$_2$-C$_6$-alkenyl, —X—(CH$_2$)$_m$—C$_4$-C$_8$-cycloalkenyl, —X—(CH$_2$)$_m$—C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C(═O)R$^6$, —C(═O)N(H)R$^{6a}$, —C(═O)N(R$^{6a}$)R$^{6b}$, —CO(═O)—R$^6$, —N(R$^{6a}$)R$^{6b}$, —NO$_2$, —N(H)C(═O)R$^6$, —OR$^6$, —SR$^6$, —S(═O)R$^6$, —S(═O)$_2$R$^6$, —S(═O)(═NR$^{6a}$)R$^{6b}$, —S(═O)$_2$N(R$^{6b}$)R$^{6c}$, —S—(CH$_2$)$_n$—N(R$^{6a}$)R$^{6b}$ or —S—(CH$_2$)$_n$-(3- to 7-membered heterocycloalkyl) group;

said C$_1$-C$_6$-alkyl-, —(CH$_2$)$_m$—C$_2$-C$_6$-alkenyl, —(CH$_2$)$_m$—C$_2$-C$_6$-alkynyl, —(CH$_2$)$_m$—C$_3$-C$_6$-cycloalkyl, aryl-C$_1$-C$_6$-alkyl-, heteroaryl-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl-, C$_1$-C$_6$-alkyl-X—, —X—(CH$_2$)$_m$—C$_2$-C$_6$-alkenyl, —X—(CH$_2$)$_m$—C$_4$-C$_8$-cycloalkenyl, —X—(CH$_2$)$_m$—C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C$_1$-C$_6$-alkyl-aryl, —C$_1$-C$_6$-alkyl-heteroaryl, heteroaryl-group optionally being substituted, identically or differently, with 1, 2, 3, 4 or 5 R$^7$ groups;

R$^{4a}$ and R$^{4d}$ represent a hydrogen atom;

R$^{4b}$ and R$^{4c}$ are selected, independently from each other, from hydrogen, halogen, —CN, —C$_1$-C$_6$-alkyl-, —C$_1$-C$_6$-alkoxy-, halo-C$_1$-C$_6$-alkyl-, halo-C$_1$-C$_6$-alkoxy-;

R$^5$ represents a hydrogen atom or a C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_4$-C$_8$-cycloalkenyl-, aryl- or heteroaryl-group;

wherein said C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_4$-C$_8$-cycloalkenyl-, aryl- or heteroaryl-group is optionally substituted, identically or differently, with 1, 2, 3, 4 or 5 R$^8$ groups;

R$^6$, R$^{6a}$, R$^{6b}$, R$^{6c}$ represent, independently from each other, a hydrogen atom, or a C$_1$-C$_6$-alkyl-, H O—C$_1$-C$_6$-alkyl-, C$_3$-C$_6$-cycloalkyl-, C$_2$-C$_6$-alkenyl-, 3- to 7-membered heterocycloalkyl-, aryl-, heteroaryl-, aryl-C$_1$-C$_6$-alkyl- or heteroaryl-C$_1$-C$_6$-alkyl-group;

R$^7$ represents a hydrogen or halogen atom or a HO—, —CN, C$_1$-C$_6$-alkoxy-, halo-C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl-, 3- to 7-membered heterocycloalkyl-, aryl-, heteroaryl-, —C(═O)R$^6$, —C(═O)N(H)R$^{6a}$, —C(═O)N(R$^{6a}$)R$^{6b}$, —CO(═O)—R$^6$, —N(R$^{6a}$)R$^{6b}$, —NO$_2$, —N(H)C(═O)R$^6$, —N(R$^{6c}$)C(═O)R$^6$, —N(H)C(═O)N(R$^{6a}$)R$^{6b}$, —N(R$^{6c}$)C(═O)N(R$^{6a}$)R$^{6b}$, —N(H)C(═O)OR$^6$, —N(R$^{6c}$)C(═O)OR$^6$, —N(H)S(═O)R$^6$, —N(R$^{6c}$)S(═O)R$^6$, —N(H)S(═O)$_2$R$^6$, —N(R$^{6c}$)S(═O)$_2$R$^6$, —N═S(═O)(R$^{6a}$)R$^{6b}$, —OR$^6$, —O(C═O)R$^6$, —O(C═O)N(R$^{6a}$)R$^{6b}$, —O(C═O)OR$^6$, —SR$^6$, —SF$_5$, —S(═O)R$^6$, —S(═O)N(H)R$^6$, —S(═O)N(R$^{6a}$)R$^{6b}$, —S(═O)$_2$R$^6$, —S(═O)$_2$N(H)R$^6$, —S(═O)$_2$N(R$^{6a}$)R$^{6b}$ or —S(═O)(═NR$^{6c}$)R$^6$ group;

wherein said aryl- or heteroaryl-group is optionally substituted, identically or differently, with 1, 2 or 3 C$_1$-C$_6$-alkyl-groups;

R$^8$ represents a hydrogen or halogen atom or a —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl-, 3- to 7-membered heterocycloalkyl-, aryl-, heteroaryl-, —C(═O)R$^6$, —C(═O)N(H)R$^{6a}$, —C(═O)N(R$^{6a}$)R$^{6b}$, —CO(═O)—R$^6$, —N(R$^{6a}$)R$^{6b}$, —NO$_2$, —N(H)C(═O)R$^6$, —N(R$^{6c}$)C(═O)R$^6$, —N(H)C(═O)N(R$^{6a}$)R$^{6b}$, —N(R$^{6c}$)C(═O)N(R$^{6a}$)R$^{6b}$, —N(H)C(═O)OR$^6$, —N(R$^{6c}$)C(═O)OR$^6$, —N(H)S(═O)R$^6$, —N(R$^{6c}$)S(═O)R$^6$, —N(H)S(═O)$_2$R$^6$, —N(R$^{6c}$)S(═O)$_2$ R$^6$, —N═S(═O)(R$^{6a}$)R$^{6b}$, —OR$^6$, —O(C═O)R$^6$, —O(C═O)N(R$^{6a}$)R$^{6b}$, —O(C═O)OR$^6$, —SR$^6$, —S(═O)R$^6$, —S(═O)N(H)R$^6$, —S(═O)N(R$^{6a}$)R$^{6b}$, —S(═O)$_2$R$^6$, —S(═O)$_2$N(H)R$^6$, —S(═O)$_2$N(R$^{6a}$)R$^{6b}$, —S(═O)(═NR$^{6c}$)R$^6$ or —S(═O)$_2$-(3- to 7-membered heterocycloalkyl) group;

wherein said 3- to 7-membered heterocycloalkyl- or heteroaryl-group is optionally substituted, identically or differently, with 1, 2, 3 or 4 C$_1$-C$_6$-alkyl-groups;

m is 0 or 1;

n is an integer of 0, 1, 2, 3, 4, or 5; and

X is S, S(═O), S(═O)$_2$, O, NR$^6$, CR$^{6a}$R$^{6b}$, C(═CR$^{6a}$R$^{6b}$), C(═O) or C(OH)(R$^{6a}$);

or a stereoisomer, a tautomer, an N-oxide, a hydrate, a solvate, or a salt thereof, or a mixture of same.

In another preferred embodiment the present invention is related to compounds of formula (I):

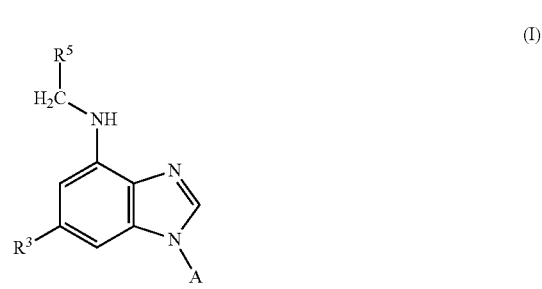

in which:

A represents

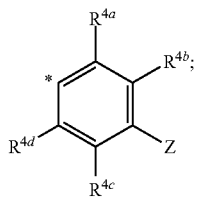

wherein * indicates the point of attachment of said group with the rest of the molecule;

Z represents a —C(=O)N(H)R$^1$ or —C(=S)N(H)R$^1$ group;

R$^1$ represents a hydrogen atom or a C$_1$-C$_6$-alkyl- or C$_3$-C$_6$-cycloalkyl-group; wherein said C$_1$-C$_6$-alkyl- or C$_3$-C$_6$-cycloalkyl-group is optionally substituted, identically or differently, with 1, 2, 3, or 4 groups selected from: halogen, —OH, —CN, C$_1$-C$_6$-alkyl-, C$_1$-C$_6$-alkoxy-;

R$^2$ represents a hydrogen atom or a C$_1$-C$_6$-alkyl- or C$_3$-C$_6$-cycloalkyl-group; wherein said C$_1$-C$_6$-alkyl- or C$_3$-C$_6$-cycloalkyl-group is optionally substituted, identically or differently, with 1, 2, 3 or 4 groups selected from: halogen, —OH, —CN, C$_1$-C$_6$-alkyl-, C$_1$-C$_6$-alkoxy-;

R$^3$ represents an aryl-X— or heteroaryl-X— group; wherein said aryl-X— or heteroaryl-X— group is optionally substituted, identically or differently, with 1, 2, 3, 4 or 5 R$^7$ groups;

R$^{4a}$, R$^{4b}$, R$^{4c}$, R$^{4d}$
are selected, independently from each other, from hydrogen, halogen, —CN, C$_1$-C$_6$-alkyl-, C$_1$-C$_6$-alkoxy-, halo-C$_1$-C$_6$-alkyl-, halo-C$_1$-C$_6$-alkoxy-;

R$^5$ represents a hydrogen atom or a C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_4$-C$_8$-cycloalkenyl-, aryl- or heteroaryl-group;

wherein said C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3to 7-membered heterocycloalkyl-, C$_4$-C$_8$-cycloalkenyl-, aryl- or heteroaryl-group is optionally substituted, identically or differently, with 1, 2, 3, 4 or 5 R$^8$ groups;

R$^6$, R$^{6a}$, R$^{6b}$, R$^{6c}$
represent, independently from each other, a hydrogen atom or a C$_1$-C$_6$-alkyl-, HO—C$_1$-C$_6$-alkyl-, C$_3$-C$_6$-cycloalkyl-, C$_2$-C$_6$-alkenyl-, 3- to 7-membered heterocycloalkyl-, aryl-, heteroaryl-, aryl-C$_1$-C$_6$-alkyl- or heteroaryl-C$_1$-C$_6$-alkyl-group;

R$^7$ represents a hydrogen or halogen atom or a HO—, —CN, C$_1$-C$_6$-alkoxy-, halo-C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl-, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —CO(=O)—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —SF$_5$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$ or —S(=O)(=NR$^{6c}$)R$^6$ group;

wherein said aryl- or heteroaryl-group is optionally substituted, identically or differently, with 1, 2 or 3 C$_1$-C$_6$-alkyl-groups;

R$^8$ represents a hydrogen or halogen atom, or a —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl-, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —CO(=O)—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O) OR$^6$, —N(H)S(=O)R$^6$, —N(R$^{6c}$)S(=O)R$^6$, —N(H)S(=O)$_2$R$^6$, —N(R$^{6c}$)S(=O)$_2$ R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, —S(=O)(=NR$^{6c}$)R$^6$ or —S(=O)$_2$-(3- to 7-membered heterocycloalkyl) group;

wherein said 3- to 7-membered heterocycloalkyl- or heteroaryl-group is optionally substituted, identically or differently, with 1, 2, 3 or 4 C$_1$-C$_6$-alkyl-groups;

m is 0 or 1;

n is an integer of 0, 1, 2, 3, 4, or 5; and

X is S, S(=O), S(=O)$_2$, O, NR$^6$, CR$^{6a}$R$^{6b}$, C(=CR$^{6a}$R$^{6b}$), C(=O) or C(OH)(R$^{6a}$);

or a stereoisomer, a tautomer, an N-oxide, a hydrate, a solvate, or a salt thereof, or a mixture of same.

In another preferred embodiment the present invention is related to compounds of formula (I):

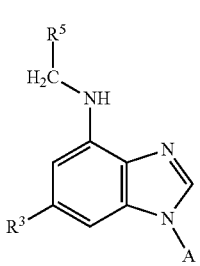

(I)

in which:

A represents

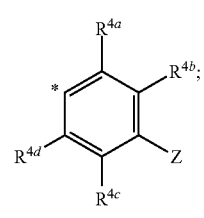

wherein * indicates the point of attachment of said group with the rest of the molecule;

Z represents a —C(=O)N(H)R$^1$ group;

R$^1$ represents a C$_1$-C$_3$-alkyl- or C$_3$-C$_6$-cycloalkyl-group;
wherein said C$_1$-C$_3$-alkyl-group is optionally substituted, identically or differently, with 1, 2 or 3 groups selected from: halogen, OH, —CN, C$_1$-C$_3$-alkoxy-;
wherein said C$_3$-C$_6$-cycloalkyl-group is optionally substituted, identically or differently, with 1, 2 or 3 groups selected from: halogen, OH, —CN, C$_1$-C$_3$-alkyl-, C$_1$-C$_3$-alkoxy-;

R$^3$ represents a hydrogen atom or a halogen atom, or an aryl-, heteroaryl-, aryl-X— or heteroaryl-X— group;
said aryl-, heteroaryl-, aryl-X— or heteroaryl-X— group being optionally substituted, identically or differently, with 1 or 2 R$^7$ groups;

R$^{4a}$ and R$^{4d}$ represent a hydrogen atom;

one of the groups R$^{4b}$ and R$^{4c}$ represents a hydrogen atom while the other one represents a group selected from: halo-, —CN, —OH, C$_1$-C$_6$-alkyl-, C$_1$-C$_6$-alkoxy-, halo-C$_1$-C$_6$-alkyl-, halo-C$_1$-C$_6$-alkoxy-, R$^{6a}$(R$^{6b}$)N—C$_1$-C$_6$-alkyl-, HO—C$_1$-C$_6$-alkyl-, NC—C$_1$-C$_6$-alkyl-, C$_1$-C$_6$-alkoxy-C$_1$-C$_6$-alkyl-, and halo-C$_1$-C$_6$-alkoxy-C$_1$-C$_6$-alkyl-;

R$^5$ represents a C$_1$-C$_6$-alkyl-, —(CH$_2$)$_m$-(3- to 7-membered heterocycloalkyl) or halo-C$_1$-C$_6$-alkyl-group;
said C$_1$-C$_6$-alkyl-, —(CH$_2$)$_m$-(3- to 7-membered heterocycloalkyl) or halo-C$_1$-C$_6$-alkyl-group is optionally substituted, identically or differently, with 1, 2, 3, 4 or 5 R$^8$ groups;

R$^6$, R$^{6a}$, R$^{6b}$, R$^{6c}$
represent, independently from each other, a hydrogen atom or a C$_1$-C$_6$-alkyl-, C$_3$-C$_6$-cycloalkyl- or aryl-C$_1$-C$_6$-alkyl-group;

R$^7$ represents a hydrogen or halogen atom or a HO—, —CN, C$_1$-C$_6$-alkoxy-, halo-C$_1$-C$_6$-alkoxy-, C$_1$-C$_6$-alkyl-, HO—C$_1$-C$_6$-alkyl-, 3- to 7-membered heterocycloalkyl-, aryl-, heteroaryl-, —C(=O)N(H)R$^{6a}$, —OR$^6$, —SR$^6$, —SF$_5$ or —S(=O)$_2$R$^6$ group;
wherein said aryl- or heteroaryl-group is optionally substituted, identically or differently, with 1, 2, or 3 C$_1$-C$_6$-alkyl-groups;

R$^8$ represents a hydrogen or halogen atom or a —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-,
C$_2$-C$_6$-alkynyl-, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —CO(=O)—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, —S(=O)(=NR$^{6c}$)R$^6$ or —S(=O)$_2$-(3- to 7-membered heterocycloalkyl) group;
wherein said 3- to 7-membered heterocycloalkyl- or heteroaryl-group, is optionally substituted, identically or differently, with 1, 2, 3 or 4 C$_1$-C$_6$-alkyl-groups;

m is an integer of 0 or 1;
n is an integer of 0, 1, 2, 3, 4 or 5; and
X is O, NR$^6$, CR$^{6a}$R$^{6b}$, C(=CR$^{6a}$R$^{6b}$), C(=O) or C(OH)(R$^{6a}$);

or a stereoisomer, a tautomer, an N-oxide, a hydrate, a solvate, or a salt thereof, or a mixture of same.

In another preferred embodiment the present invention is related to compounds of formula (I):

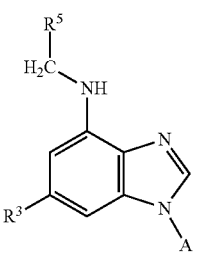

(I)

in which:

A represents

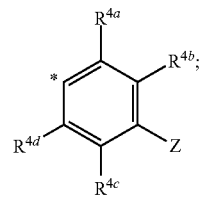

wherein * indicates the point of attachment of said groups with the rest of the molecule;

Z represents a —C(=O)N(H)R$^1$ group;

R$^1$ represents a C$_1$-C$_2$-alkyl- or C$_3$-C$_6$-cycloalkyl-group;
wherein said C$_1$-C$_3$-alkyl-group is optionally substituted with one —CN group; wherein said C$_3$-C$_6$-cycloalkyl-group is optionally substituted with one group selected from: —CN, —CH$_3$;

R$^3$ represents a hydrogen atom or a halogen atom or an aryl-, heteroaryl-, aryl-X— or heteroaryl-X— group;
said aryl-, heteroaryl-, aryl-X— or heteroaryl-X— group being optionally substituted, identically or differently, with 1 or 2 R$^7$ groups;

R$^{4a}$ and R$^{4d}$ represent a hydrogen atom;
one of the groups R$^{4b}$ and R$^{4c}$ represents a hydrogen atom while the other one represents a methyl group;

R$^5$ represents a C$_1$-C$_6$-alkyl-, —(CH$_2$)$_m$-(3- to 7-membered heterocycloalkyl) or halo-C$_1$-C$_6$-alkyl-group;

R$^6$, R$^{6a}$, R$^{6b}$, R$^{6c}$
represent, independently from each other, a hydrogen atom, or a C$_1$-C$_3$-alkyl-, C$_3$-C$_6$-cycloalkyl- or aryl-C$_1$-C$_3$-alkyl-group;

R$^7$ represents a hydrogen or halogen atom, or a HO—, —CN, —CH$_3$, C$_1$-C$_3$-alkoxy-, halo-C$_1$-C$_3$-alkoxy-, HO—C$_1$-C$_3$-alkyl-, 3- to 7-membered heterocycloalkyl-, aryl-, heteroaryl-, —C(=O)N(H)R$^{6a}$, —OR$^6$, —SR$^6$, —SF$_5$ or —S(=O)$_2$R$^6$ group;

m is an integer of 0 or 1;
X is O, NR$^6$, CR$^{6a}$R$^{6b}$, C(=CR$^{6a}$R$^{6b}$), C(=O) or C(OH)(R$^{6a}$);

or a stereoisomer, a tautomer, an N-oxide, a hydrate, a solvate, or a salt thereof, or a mixture of same.

It is to be understood that the present invention relates to any sub-combination within any embodiment of the present invention of compounds of general formula (I), supra.

In an embodiment of the above-mentioned aspects, the invention relates to compounds of formula (I), according to any of the above-mentioned embodiments, in the form of or a stereoisomer, a tautomer, an N-oxide, a hydrate, a solvate, or a salt thereof, or a mixture of same.

More particularly still, the present invention covers compounds of general formula (I) which are disclosed in the Experimental Section of this text, infra.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers.

Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

1H-tautomer    2H-tautomer    4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

Furthermore, the present invention includes all possible crystalline forms, or polymorphs, of the compounds of the present invention, either as single polymorphs, or as a mixture of more than one polymorph, in any ratio.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

In an embodiment of the above-mentioned aspects, the invention relates to compounds of formula (I), according to any of the above-mentioned embodiments, in the form of or a stereoisomer, a tautomer, an N-oxide, a hydrate, a solvate, or a salt thereof, or a mixture of same.

The compounds of the present invention have surprisingly been found to effectively inhibit Mps-1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1 kinase, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Therefore, the compounds of formula (I), supra, are expected to be valuable as therapeutic agents.

Accordingly, in another embodiment, the present invention is directed to a compound of general formula (I), supra, or a stereoisomer, a tautomer, an N-oxide, a hydrate, a solvate, or a salt thereof, particularly a pharmaceutically acceptable salt thereof, or a mixture of same, for use in the treatment or prophylaxis of a disease.

In another embodiment, the present invention provides a method of treating disorders associated with enhanced uncontrolled proliferative cellular processes in a patient in need of such treatment, comprising administering to the patient an effective amount of a compound of formula (I).

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The terms "cell proliferative disorder" or "disorder associated with enhanced uncontrolled proliferative cellular processes" include disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

In another embodiment, the present invention is directed to a compound of general formula (I), or a stereoisomer, a tautomer, an N-oxide, a hydrate, a solvate, or a salt thereof, particularly a pharmaceutically acceptable salt thereof, or a mixture of same, for use in the treatment or prophylaxis of a disease, wherein said disease is a disease of uncontrolled cell growth, proliferation and/or survival, an inappropriate cellular immune response, or an inappropriate cellular inflammatory response, particularly in which the uncontrolled cell growth, proliferation and/or survival, inappropriate cellular immune response, or inappropriate cellular inflammatory response is mediated by the mitogen-activated protein kinase (MEK-ERK) pathway, more particularly in which the disease of uncontrolled cell growth, proliferation and/or survival, inappropriate cellular immune response, or inappropriate cellular inflammatory response is a haematological tumour, a solid tumour and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The present invention also relates to useful forms of the compounds as disclosed herein, such as metabolites, hydrates, solvates, prodrugs, salts, in particular pharmaceutically acceptable salts, in vivo hydrolysable esters, and co-precipitates.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovakbase, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Compounds of formula (I) may be administered as the sole pharmaceutical agent or in combination with one or more additional therapeutic agents where the combination causes no unacceptable adverse effects. This combination therapy includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In another aspect, the invention provides a pharmaceutical composition comprising a compound of general formula (I), or a stereoisomer, a tautomer, an N-oxide, a hydrate, a solvate, or a salt thereof, particularly a pharmaceutically acceptable salt thereof, or a mixture of same, and a pharmaceutically acceptable diluent or carrier.

Preferably, the pharmaceutical composition comprises:
one or more compounds of general formula (I), or a stereoisomer, a tautomer, an N-oxide, a hydrate, a solvate, or a salt thereof, particularly a pharmaceutically acceptable salt thereof, or a mixture of same; and
one or more agents selected from: a taxane, such as Docetaxel, Paclitaxel, or Taxol; an epothilone, such as Ixabepilone, Patupilone, or Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2'-deoxyadenosine; Thioguanine; an anti-androgen, such as Flutamide, Cyproterone acetate, or Bicalutamide; Bortezomib; a platinum derivative, such as Cisplatin, or Carboplatin; Chlorambucil; Methotrexate; and Rituximab.

In still another aspect, the invention provides a process for preparing a pharmaceutical composition. The process includes the step of combining at least one compound of formula (I) as defined above with at least one pharmaceutically acceptable carrier, and bringing the resulting combination into a suitable administration form.

In still another aspect, the invention provides use of a compound of formula (I) as defined above for manufacturing a pharmaceutical composition for the treatment or prevention of a cell proliferative disorder. In certain embodiments, the cell proliferative disorder is cancer.

The active component of formula (I) can act systemically and/or locally. For this purpose, it can be applied in a suitable manner, for example orally, parenterally, pulmonally, nasally, sublingually, lingually, buccally, rectally, transdermally, conjunctivally, otically, or as an implant or stent.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Regardless of the route of administration selected, the compounds of the invention, which may be used in a suitable hydrated form, and/or the pharmaceutical compositions of the present invention, are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient.

In accordance with another aspect, the present invention covers methods of preparing compounds of the present invention, said methods comprising the steps as described in the Experimental Section herein.

In accordance with another aspect, the present invention also relates to methods of preparing a compound of general formula (I), supra.

In accordance with a first embodiment, the present invention relates to a method of preparing a compound of general formula (I), the method comprises the step of allowing an intermediate compound of general formula (II):

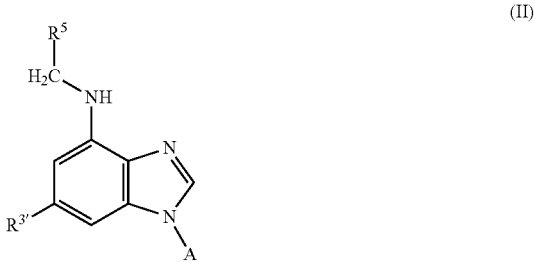

in which $R^5$ and A are as defined for general formula (I), supra, and $R^{3'}$ is a halogen atom, to react with a compound of general formula (IIa):

in which $R^3$ is as defined for general formula (I), supra, and Y is a substituent which is displaced in a coupling reaction, such as a hydrogen atom, or a boronic acid group, or a boronic ester group, for example, thereby giving, upon optional deprotection, a compound of general formula (I):

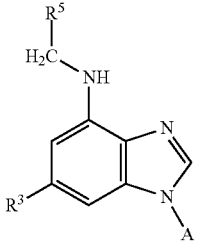
(I)

in which $R^3$, $R^5$ and A are as defined for general formula (I), supra.

In accordance with a second embodiment, the present invention also relates to a method of preparing a compound of general formula (I), supra, said method comprising the step of allowing an intermediate compound of general formula (IV):

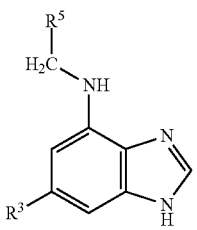
(IV)

in which $R^3$ and $R^5$ are as defined for general formula (I) supra to react with a compound of general formula (IVa):

A—Y    (IVa)

in which A is as defined for general formula I supra, and Y is a substituent which is displaced in a coupling reaction, such as for a boronic acid group, or a boronic ester group, for example, thereby giving, upon optional deprotection, a compound of general formula (I):

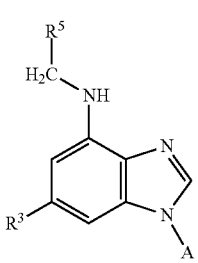
(I)

in which $R^3$, $R^5$ and A are as defined for general formula (I), supra.

In accordance with a further aspect, the present invention covers intermediate compounds which are useful in the preparation of compounds of the present invention of general formula (I), particularly in the methods described herein.

In particular, the present invention covers compounds of general formula (II):

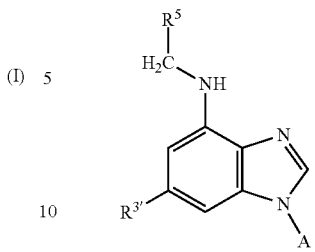
(II)

in which $R^5$ and A are as defined for general formula (I), supra, and $R^{3'}$ is a halogen atom.

The present invention also covers compounds of general formula (IV):

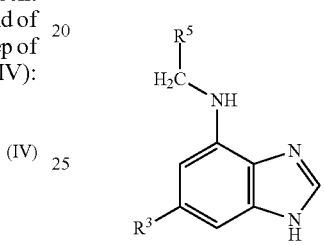
(IV)

in which $R^3$ and $R^5$ are as defined for general formula (I), supra.

Experimental Section

As mentioned supra, another aspect of the present invention is a method which may be used for preparing the compounds according to the present invention.

The following Table lists the abbreviations used in this paragraph, and in the Examples section. NMR peak forms are stated as they appear in the spectra, possible higher order effects have not been considered.

Names of compounds were generated using the Autonom 2000 add-in of ISIS/Draw [MDL Information Systems Inc. (Elsevier MDL)] or the ICS naming tool 12.01 of ACD labs. In some cases generally accepted names of commercially available reagents were used.

| Abbreviation | Meaning |
|---|---|
| Ac | Acetyl |
| br | Broad |
| c- | cyclo- |
| d | Doublet |
| dd | doublet of doublets |
| DCE | Dichloroethane |
| DCM | Dichloromethane |
| DIPEA | N,N-diisopropylethylamine |
| DMAP | 4-Dimethylaminopyridine |
| DMF | N,N-dimethylformamide |
| DMSO | dimethyl sulfoxide |
| DIPEA | N,N-Diisopropylethylamine |
| dppf | 1,1'-bis(di-phenylphosphino)ferrocene |
| EDC | N-[3-(dimethylamino)propyl]-N'-ethylcarbodiimide |
| eq | Equivalent |
| ESI | electrospray ionisation |
| EtOAc | ethyl acetate |
| m | multiplet |
| MS | mass spectrometry |
| MW | molecular weight |
| NMP | N-methylpyrrolidinone |
| NMR | nuclear magnetic resonance spectroscopy: chemical shifts (δ) are given in ppm. |

| Abbreviation | Meaning |
|---|---|
| HATU | 2-(1H-7-Azabenzotriazol-1-yl)--1,1,3,3-tetramethyl uronium hexafluorophosphate Methanaminium |
| HCl | hydrochloric acid |
| MPLC | middle performance liquid chromatography |
| MS | mass spectrometry |
| NMR | nuclear magnetic resonance spectroscopy: chemical shifts (δ) are given in ppm. The chemical shifts were corrected by setting the DMSO signal to 2.50 ppm using unless otherwise stated. |
| Pd(dppf)Cl$_2$ | 1,1'-bis(diphenylphosphino)ferrocenedichloropalladium(II) |
| P(oTol)$_3$ | tri-o-tolylphosphine |
| q | quartet |
| rt | room temperature |
| RT | retention time in minutes |
| s | singlet |
| sept | septet |
| t | triplet |
| TEA | triethylamine |
| TFA | trifluoroacetic acid |
| THF | tetrahydrofuran |
| UPLC | ultra performance liquid chromatography |

Other abbreviations have their meanings customary per se to the skilled person. The various aspects of the invention described in this application are illustrated by the following examples which are not meant to limit the invention in any way.

The Scheme and procedures described below illustrate general synthetic routes to the compounds of general formula (I) of the invention and are not intended to be limiting. It is clear to the person skilled in the art that the order of transformations as exemplified in the Scheme can be modified in various ways. The order of transformations exemplified in the Scheme is therefore not intended to be limiting. In addition, interconversion of any of the substituents, $R^3$, $R^{3'}$, $R^5$, A or A' can be achieved before and/or after the exemplified transformations. Examples for such interconversions can be transformation of $R^{3'}$ to $R^3$ or A' to A. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3$^{rd}$ edition, Wiley 1999). Specific examples are described in the subsequent paragraphs. Further, it is possible that two or more successive steps may be performed without work-up being performed between said steps, e.g. a "one-pot" reaction, as is well-known to the person skilled in the art.

Synthesis of Compounds of General Formula (I) of the Present Invention

Compounds of general formula (I) can be synthesized as depicted in the Scheme, with $R^3$, $R^5$, and A having the meaning as given for general formula (I), supra, and $R^{3'}$ representing a group $R^3$ or a leaving group.

The Scheme exemplifies routes that allow variations for $R^3$, $R^{3'}$, $R^5$, A and A' during the synthesis. Group A can be introduced directly, or by a group A' containing functional moieties that can be converted to generate group A.

However, also other routes were used for synthesis of the target compounds. Compounds of formula (XI) and (XII) may be commercially available or can be synthesized according to procedures known to persons skilled in the art.

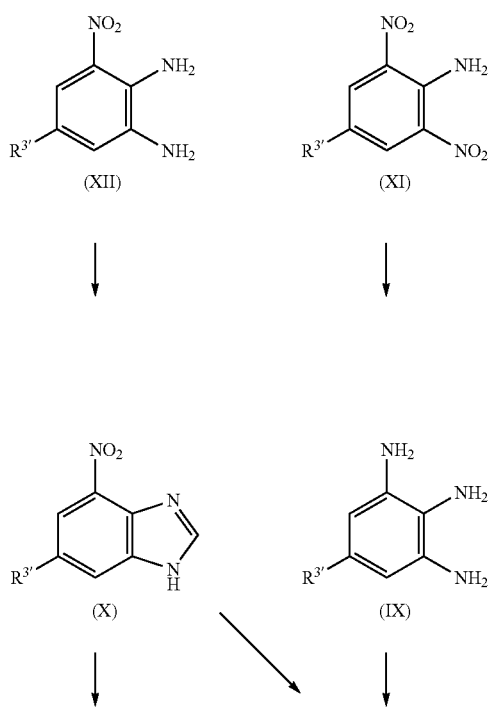

Scheme

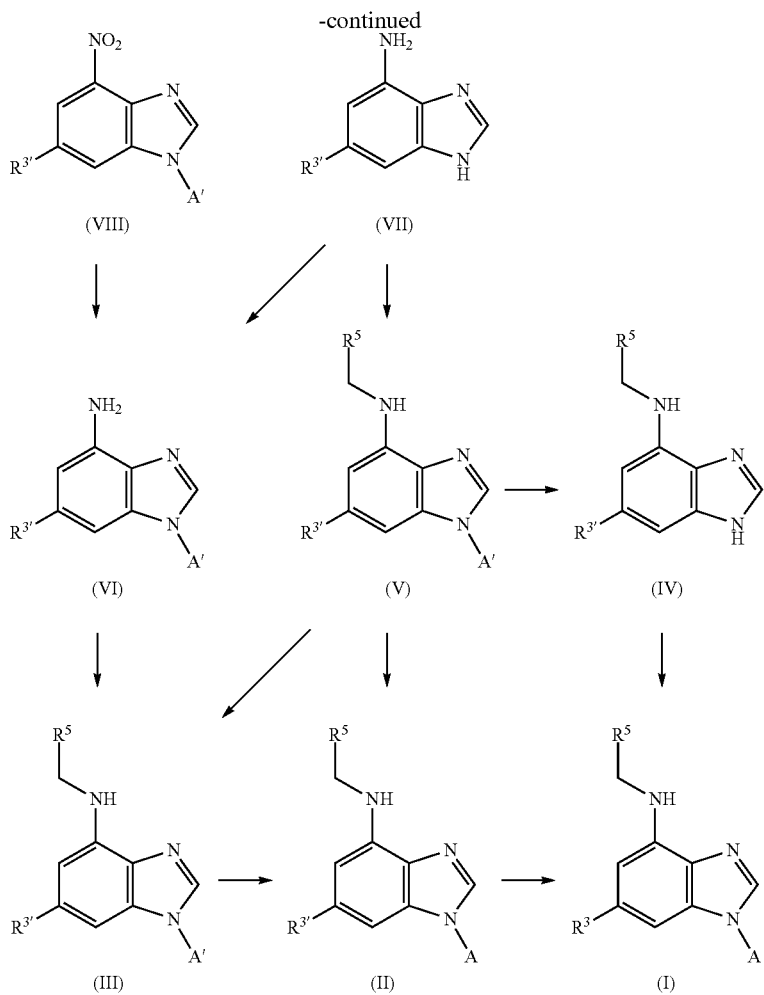

A typical reaction to introduce the CH$_2$R$^5$—group to compounds of formula (VI) or (VII) is a reductive amination reaction using an aldehyde of formula O=CHR$^5$, a reducing agent, for example sodium tris(acetato-kappaO)(hydrido)borate or sodium cyanoborohydride, and a suitable solvent like, for example acetic acid, at reaction temperatures ranging from room temperature to the boiling point of the solvent.

Compounds of general formula (I), (II) or (VIII) can be obtained from compounds of general formula (IV), (V) or (X) via a coupling reaction between a reagent of formula Y-A or Y-A', in which A and A' are defined supra and Y represents a suitable functional group by which the groups A or A' can be transferred to the benzimidazole nitrogen atom of compounds of formula (IV), (V) or (X). Said coupling reactions are performed in the presence of suitable catalysts, such as, for example, copper based catalysts like copper(II)diacetate. Examples of suitable functional groups for Y include boronic acids, A-B(OH)$_2$, A'-B(OH)$_2$, or boronic esters, A-B(OC$_1$-C$_6$-alkyl)$_2$, or A'-B(OC$_1$-C$_6$-alkyl)$_2$.

In the case R$^{3'}$ represents a leaving group such as for example a chlorine, bromine or iodine atom or a triflate- or nonaflate-group, this group can be substituted by nucleophiles like primary or secondary amines, alkoxides, thiolates or carbon anion bearing groups to add secondary or tertiary amines, ethers, thioethers or carbon attached groups. The reactions are performed in inert solvents like for example tetrahydrofuran or dimethyl sulfoxide to give compounds of general formula (I) or (IV). The substitution reactions can also be performed in the presense of a catalyst, for example, copper based catalysts like copper(I)chloride. Optionally, suitable ligands like N,N-dimethylglycine or phenyl hydrogen pyrrolidin-2-ylphosphonate can be added. Such substitution ractions can also be performed at other intermediate compound like compounds of formula (II), (III), (V), (VI), (VII), (VIII), (IX), (X), (XI) or (XII).

In the case R$^{3'}$ represents a leaving group such as for example a chlorine, bromine or iodine atom or a triflate- or nonaflate-group, these groups can be converted in coupling reactions using compounds of general formula R$^3$—Y in which Y represents a suitable functional group like for example boronic acids, R$^3$—B(OH)$_2$, or boronic esters, R$^3$—B(OC$_1$-C$_6$-alkyl)$_2$ in the presence of suitable catalysts, such as, for example, palladium based catalysts like, for example, Palladium (II) acetate, tetrakis(triphenylphosphine) palladium (0), bis(triphenylphosphine)palladium (II) chloride or (1,1,-bis(diphenylphosphino) ferrocene)-dichloropalladium (II) and optionally suitable additives such as, for example, phosphines like, for example, P(oTol)$_3$ or triphenylphosphine and, and optionally with a suitable base, such as, for example, potassium carbonate, sodium 2-methylpropan-2-olate, tetrabutylammonium fluoride or tribasic potassium phosphate in a suitable solvent, such as, for example, tetrahydrofuran.

Examples of such coupling reactions may be found in the textbook entitled "Metal-Catalyzed Cross-Coupling Reactions", Armin de Meijere (Editor), Francois Diederich (Editor) September 2004, Wiley Interscience ISBN: 978-3-527-30518-6.

Residues in compounds of formulas (I), (II), (III), (IV), (V), (VI), (VII), (VIII) or (IX) can be optionally modified. For example, thioethers can be oxidized using oxidation reagents like 3-chlorobenzenecarboperoxoic acid, oxone or dimethyldioxirane in inert solvents like for example dichloromethane or acetone, respectively. Depending on the stoichiometric ratio of oxidation reagent to the afore mentioned compounds sulfoxides or sulfones or mixtures thereof will be obtained.

In general, all compounds of formula (I), (II), (III), (IV), (V), (VI), (VII), (VIII) and (X) can comprise mixtures with their corresponding tautomeric form in the five membered nitrogen containing ring. The tautomeric forms can be used as a mixture or can be separated by methods known to persons skilled in the art.

Residues in compounds of formulas (I), (II), (III), (IV), (V), (VI), (VII), (VIII), (IX), (X), (XI) or (XII) can be optionally modified. For example, thioethers can be oxidized using oxidation reagents like for example 3-chlorobenzenecarboperoxoic acid, oxone or dimethyldioxirane in inert solvents like for example dichloromethane or acetone, respectively. Depending on the stoichiometric ratio of oxidation reagent to the afore mentioned compounds sulfoxides or sulfones or mixtures thereof will be obtained.

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be removed by stirring using a suitable solvent. In some cases, the compounds may be purified by chromatography, particularly flash chromatography, using for example pre-packed silica gel cartridges, e.g. from Separtis such as Isolute® Flash silica gel or Isolute® Flash NH2 silica gel in combination with a suitable chromatographic system such as a Flashmaster II (Separtis) or an Isolera system (Biotage) and eluents such as, for example, gradients of hexane/EtOAc or DCM/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluants such as, for example, gradients of water and acetonitrile which may contain additives such as trifluoroacetic acid, formic acid or aqueous ammonia.

EXAMPLES

Analytical UPLC-MS was performed as follows:
Method A: System: UPLC Acquity (Waters) with PDA Detector and Waters ZQ mass spectrometer; Column: Acquity BEH C18 1.7 μm 2.1×50 mm; Temperature: 60° C.; Solvent A: Water+0.1% formic acid; Solvent B: acetonitrile; Gradient: 99% A→1% A (1.6 min)→1% A (0.4 min); Flow: 0.8 mL/min; Injection Volume: 1.0 μl (0.1 mg-1 mg/mL sample concentration); Detection: PDA scan range 210-400 nm—Fixed and ESI (+), scan range 170-800 m/z Intermediate Example 1-1

Preparation of 4-(4-nitro-benzoimidazol-1-yl)-benzonitrile

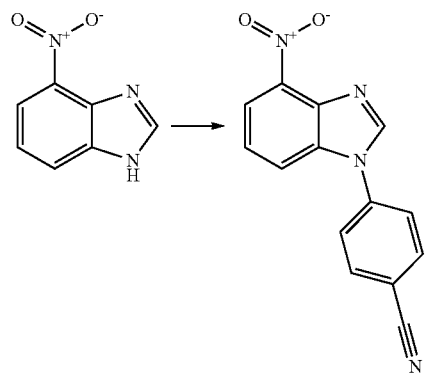 [SMILES: O=[N+]([O-])c1cccc2[nH]cnc12 ; N#Cc1ccc(-n2cnc3c([N+](=O)[O-])cccc32)cc1]

To a stirred suspension of sodium hydride (665 mg, 16.64 mmol) in DMF (90 mL) at rt was added 4-nitro-1H-benzimidazole (2714 mg, 16.64 mmol) in several portions. After stirring for 1 h, 4-fluorobenzonitrile (1350 mg, 11.146 mmol) was added and the mixture was stirred for 15 h at 130° C. After cooling, water was added, the precipitate was filtered off, washed with water and dried to yield 4-(4-nitro-benzoimidazol-1-yl)-benzonitrile (2.47 g, 47.76%).

$^1$H-NMR (300 MHz, $d_6$-DMSO): δ=8.92 (1H), 8.16-8.11 (3H), 8.08 (1H), 7.97 (1H), 7.95 (1H), 7.53 (1H) ppm.

Intermediate Example 2-1

Preparation of 4-(4-amino-1H-benzimidazol-1-yl)benzonitrile

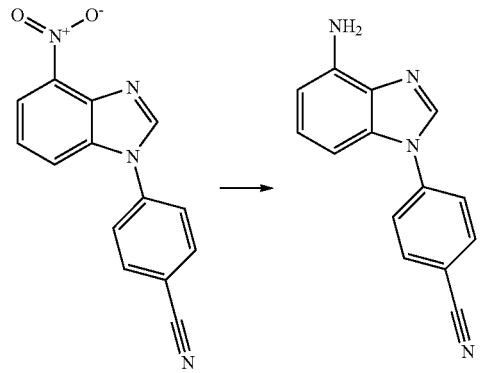 [SMILES: N#Cc1ccc(-n2cnc3c([N+](=O)[O-])cccc32)cc1 ; N#Cc1ccc(-n2cnc3c(N)cccc32)cc1]

To a stirred solution of 4-(4-nitro-1H-benzimidazol-1-yl)benzonitrile (1.2 g, 4.54 mmol) in ethanol (100 mL) at rt was added Pd/C 10% (96 mg) in one portion and the mixture was stirred under a hydrogen atmosphere at normal pressure for 26 h. The suspension was filtered, and the solution was evaporated. Purification of the residue by flash chromatography yielded 4-(4-amino-1H-benzimidazol-1-yl)benzonitrile (0.45 g, 42.3%).

$^1$H-NMR (300 MHz, d$_6$-DMSO): δ=8.43 (1H), 8.05 (2H), 7.87 (2H), 7.01 (1H), 6.82 (1H), 6.46 (1H), 5.45 (2H) ppm. UPLC-MS: RT=0.86 min; m/z 235.3 [MH$^+$]; required MW=234.3.

Intermediate Example 3-1

Preparation of 4-{4-[(2-methylpropyl)amino]-1H-benzimidazol-1-yl}benzonitrile

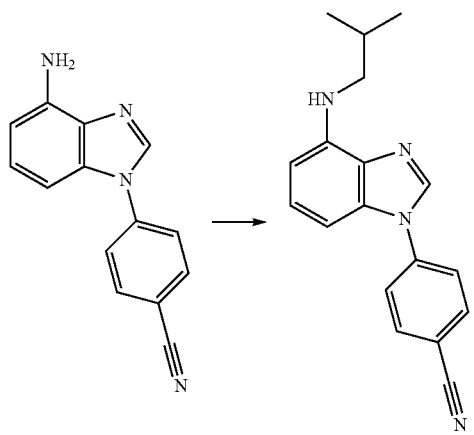 [SMILES: N#Cc1ccc(-n2cnc3c(N)cccc32)cc1 ; CC(C)CNc1cccc2c1ncn2-c1ccc(C#N)cc1]

To a stirred solution of 4-(4-amino-1H-benzimidazol-1-yl)benzonitrile (246 mg, 1.05 mmol) in dichloromethane (10 mL) at rt was added sodium triacetoxy borohydride (311 mg, 1.47 mmol, 1.4 eq), isobutyraldehyde (91 mg, 1.26 mmol, 1.2 eq) and acetic acid (63 m g, 1.05 mmol, 1 eq) and the mixture was stirred for 2 h. The mixture was poured on water and extracted with DCM. After evaporation of the organic phase, purification of the residue by flash chromatography yielded 190 mg 4-{4-[(2-methylpropyl)amino]-1H-benzimidazol-1-yl}benzonitrile (62.3%).

$^1$H-NMR (300 MHz, d$_6$-DMSO): δ=8.43 (1H), 8.05 (2H), 7.87 (2H), 7.07 (1H), 6.82 (1H), 6.36 (1H), 5.73 (1H), 3.06 (2H), 1.93 (1H), 0.90 (6H) ppm. UPLC-MS: RT=1.34 min; m/z (ES+) 291.4 [MH$^+$]; required MW=290.4

Intermediate Example 3-2

Preparation of 4-[4-(isobutylamino)-6-phenyl-1H-benzimidazol-1-yl]benzonitrile

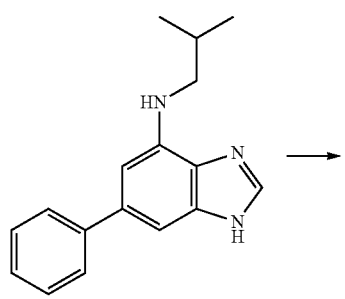

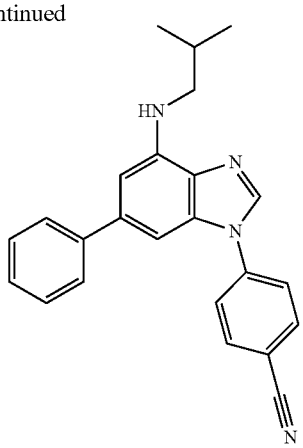

To a suspension of 15.1 mg sodium hydride (60%) in N,N-dimethylformamide were added 100 mg (377 μmol)N-isobutyl-6-phenyl-1H-benzimidazol-4-amine in portions over 1 hour at 23° C. followed by 38.8 mg 4-fluorobenzonitrile. The mixture was heated at 130° C. for 16 hours. Brine was added and the mixture extracted with ethyl acetate. The organic layer was dried over sodium sulfate. After filtration and removal of the solvent the residue was purified by chromatography to give 68.0 mg (47%) of the title compound.

$^1$H-NMR (DMSO-d6): δ=0.98 (6H), 2.03 (1H), 3.19 (2H), 5.84 (1H), 6.63 (1H), 7.03 (1H), 7.33 (1H), 7.43 (2H), 7.65 (2H), 7.98 (2H), 8.09 (2H), 8.48 (1H) ppm.

Intermediate Example 4-1

Preparation of 4-{4-[(2-methylpropyl)amino]-1H-benzimidazol-1-yl}benzoic acid

To a stirred solution of 4-{4-[(2-methylpropyl)amino]-1H-benzimidazol-1-yl}benzonitrile (220 mg, 0.758 mmol) in ethanol (14 m L) at rt was added sodium hydroxide (7 N aqueous solution, 14 mL) in one portion. After stirring at 90° C. for 24 h, the mixture is cooled to rt and acidified with citric acid (10% aqueous solution). The precipitate was filtered, and the remaining solid was washed and dried to yield 4-{4-[(2-methylpropyl)amino]-1H-benzimidazol-1-yl}benzoic acid as a white solid (215 mg, 91.7%).

$^1$H-NMR (300 MHz, d$_6$-DMSO): δ=8.40 (1H), 8.11 (2H), 7.76 (2H), 7.06 (1H), 6.82 (1H), 6.35 (1H), 5.71 (1H), 3.06

(2H), 1.93 (1H), 0.91 (6H) ppm. UPLC-MS: RT=1.27 min; m/z 310.4 [MH⁺]; required MW=309.4.

Intermediate Example 4-2

Preparation of 4-[4-(isobutylamino)-6-phenyl-1H-benzimidazol-1-yl]benzoic acid

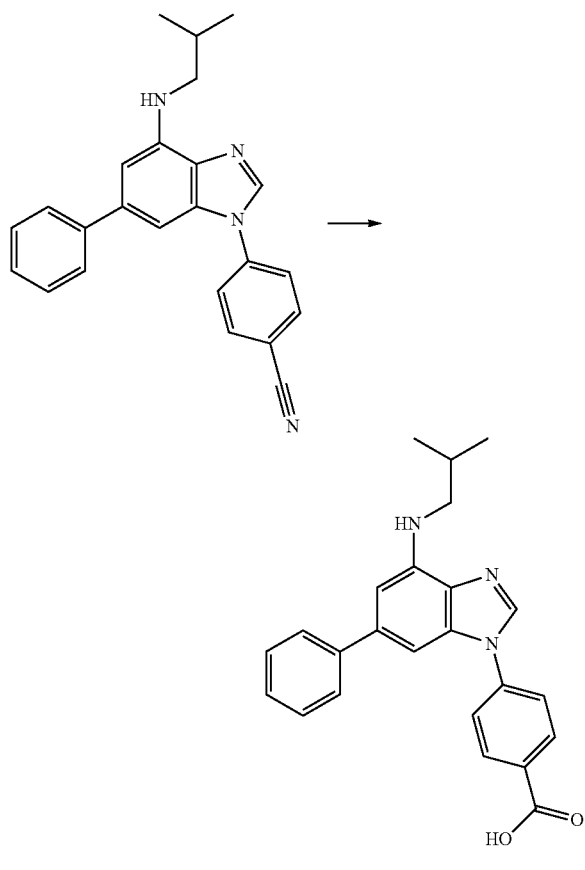

30.0 mg (103 μmol) 4-[4-(isobutylamino)-6-phenyl-1H-benzimidazol-1-yl] benzonitrile which was prepared according to intermediate example 3-2 were transformed in analogy to intermediate example 4-1 to give after working up and purification 28.0 mg (88%) of the title compound.

$^1$H-NMR (DMSO-d6): δ=0.91 (6H), 1.93 (1H), 3.05 (2H), 5.71 (1H), 6.35 (1H), 6.82 (1H), 7.06 (1H), 7.76 (2H), 8.11 (2H), 8.40 (1H), 13.12 (1H) ppm.

Intermediate Example 5-1

Preparation of 5-bromobenzene-1,2,3-triamine

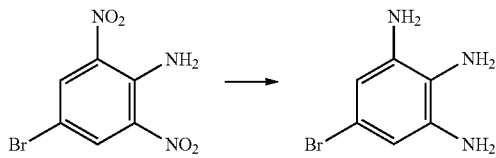 [SMILES: Nc1c([N+](=O)[O-])cc(Br)cc1[N+](=O)[O-] ; Nc1cc(Br)cc(N)c1N]

To a stirred suspension of 4-bromo-2,6-dinitroaniline (110 g, 420 mmol) in HCl conc (2200 mL) at −20° C. was added tin(II)chloride dihydrate (568 g, 2519 mmol, 6 eq) in one portion under cooling. After stirring overnight ar rt, water (1000 mL) was added to the suspension, and the pH was adjusted to 10 using sodium hydroxide (50% aqueous solution). After extraction with ethyl acetate (3×2000 mL), the organic phase was washed with saturated sodium chloride solution, dried over sodium sulphate and evaporated in vacuo to yield 81.5 g 5-bromobenzene-1,2,3-triamine (96.1%).

$^1$H-NMR (300 MHz, d₆-DMSO): δ=6.05 (2H), 4.49 (4H), 3.76 (2H) ppm.

Intermediate Example 5-2

Preparation of biphenyl-3,4,5-triamine

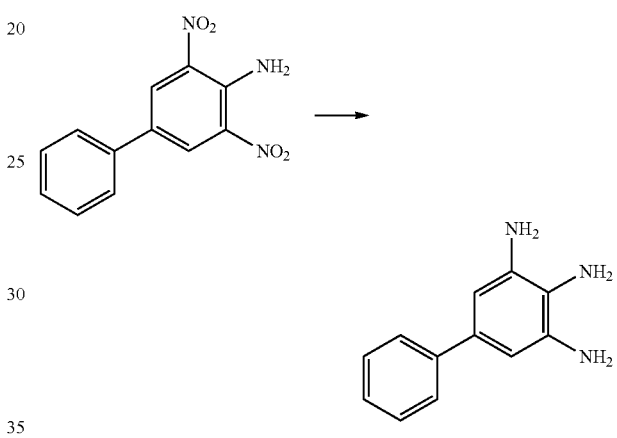

To a solution of 80 mg (309 μmol) 3,5-dinitrobiphenyl-4-amine in a mixture of 34 mL ethanol and 10 mL THF were added 6.6 mg palladium on charcoal (10%) and the mixture was stirred under an atmosphere of hydrogen for 26 hours at 23° C. After filtration and removal of the solvent the residue was purified by chromatography to yield 50 mg (81%) of the title compound.

$^1$H-NMR (DMSO-d6D): δ=3.89 (2H), 4.37 (4H), 6.26 (2H), 7.14 (1H), 7.29 (2H), 7.38 (2H) ppm.

Intermediate Example 6-1

Preparation of 6-bromo-1H-benzimidazol-4-amine

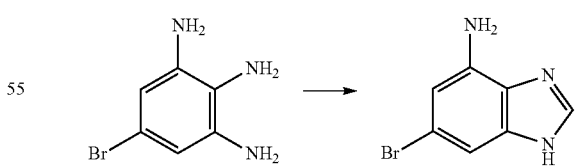

To a stirred suspension of 5-bromobenzene-1,2,3-triamine (81.5 g, 403 mmol) in HCl conc (2400 mL) at rt was added formic acid (46 mL, 1210 mmol, 3 eq). After stirring at reflux for 90 min, water (500 mL) was added to the suspension, and the pH was adjusted to 8 using ammonia (33% aqueous solution). After extraction with ethyl acetate (3×1000 mL), the organic phase was washed with saturated sodium chloride solution, dried over sodium sulphate and evaporated in vaccuo. The crude product was trituarated with diethyl ether (200 mL), filtered and dried to yield 82.3 g 6-bromo-1H-benzimidazol-4-amine (96.3%).

¹H-NMR (300 MHz, d₆-DMSO): δ=12.15 (1H), 7.97 (1H), 6.46 (1H), 5.49 (2H) ppm.

Intermediate Example 7-1

Preparation of tert-butyl 4-amino-6-bromo-1H-benzimidazole-1-carboxylate

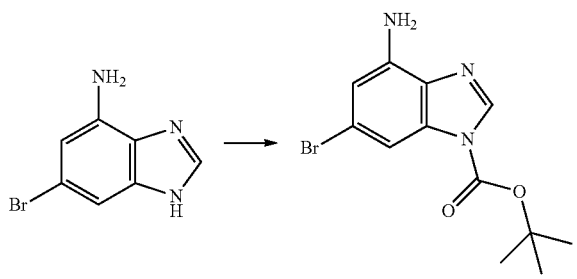 [SMILES: Nc1cc(Br)cc2[nH]cnc12 ; CC(C)(C)OC(=O)n1cnc2c(N)cc(Br)cc21]

To a stirred suspension of 6-bromo-1H-benzimidazol-4-amine (10.27 g, 48.43 mmol) in DCM at 0° C. was added TEA (13.5 mL, 96.86 mmol), DMAP (592 mg, 4.84 mmol) and dropwise a solution of di-tert-butyl dicarbonate (11.63 g, 53.27 mmol, 1.1 eq) in DCM. After stirring for 1 h at 0° C., the clear solution is stirred for 72 h at rt. After evaporation, the product is triturated with ethanol and hexane to yield 14.89 g tert-butyl 4-amino-6-bromo-1H-benzimidazole-1-carboxylate (95.84%).

¹H-NMR (300 MHz, d₆-DMSO): δ=8.37 (1H), 7.16 (1H), 6.64 (1H), 5.84 (2H), 1.59 (6H) ppm. UPLC-MS: RT=1.28 min; m/z 313.2 [MH⁺]; required MW=312.2.

Intermediate Example 8-1

Preparation of tert-butyl 6-bromo-4-[(3,3,3-trifluoropropyl)amino]-1H-benzimidazole-1-carboxylate

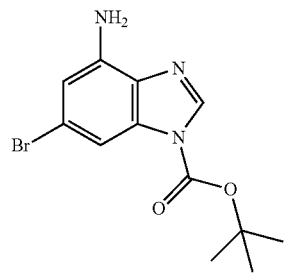

-continued

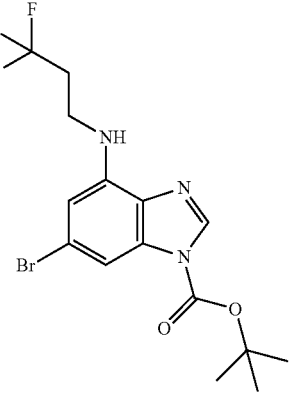

To a stirred solution of tert-butyl 4-amino-6-bromo-1H-benzimidazole-1-carboxylate (5.85 g, 18.74 mmol) in DCE (1000 mL) at rt was added 3,3,3-trifluoropropanal (6.30 g, 56.22 mmol, 3 eq), sodium triacetoxy borohydride (19.86 g, 93.70 mmol, 5 eq) and acetic acid (21.5 mL, 374.79 mmol, 20 eq) and the mixture was stirred for 2 h. Water and DCM was added, and the organic phase was separated and washed with water After addition of DCM (100 mL), the organic phase was washed with water and evaporated to yield 7.63 g tert-butyl 6-bromo-4-[(3,3,3-trifluoropropyl)amino]-1H-benzimidazole-1-carboxylate (81.79%).

¹H-NMR (300 MHz, d₆-DMSO): δ=8.43 (1H), 7.25 (1H), 6.59 (1H), 6.37 (1H), 3.48 (2H), 2.58 (2H), 1.59 (6H) ppm.

Intermediate Example 9-1

Preparation of 6-bromo-N-(3,3,3-trifluoropropyl)-1H-benzimidazol-4-amine

Method A

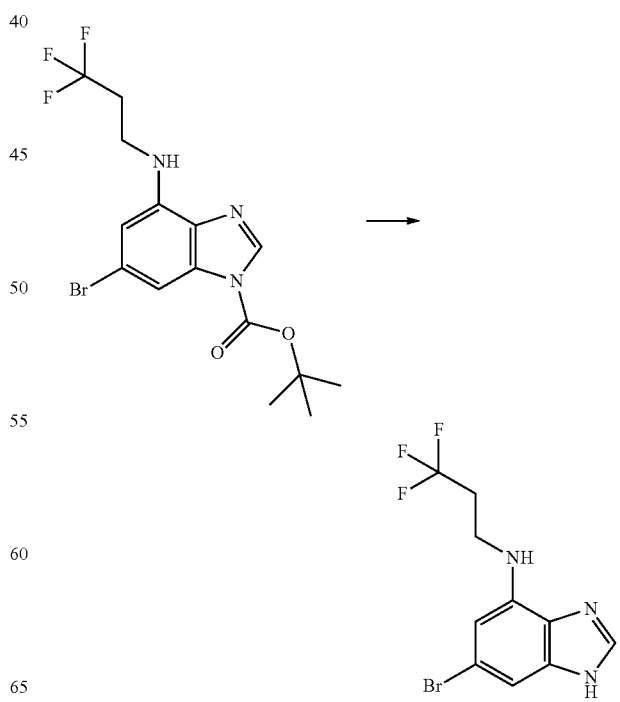

To a stirred solution of intermediate tert-butyl 6-bromo-4-[(3,3,3-trifluoropropyl)amino]-1H-benzimidazole-1-carboxylate (7.63 g, 18.69 mmol) in DCM (200 mL) at -rt was added water (20 mL) and TFA (200 mL). After stirring for 2 h, the solution was concentrated, ethyl acetate was added and the organic phase was washed with sodium carbonate solution and water. Evaporation of the yielded 5.17 g 6-bromo-N-(3,3,3-trifluoropropyl)-1H-benzimidazol-4-amine (89.8%).

$^1$H-NMR (300 MHz, d$_6$-DMSO): δ=12.39 (1H), 7.99 (1H), 6.90 (1H), 6.34 (1H), 6.03 (1H), 3.47 (2H), 2.58 (2H) ppm. UPLC-MS: RT=0.96 min; m/z 309.1 [MH$^+$]; required MW=308.1.

Intermediate Example 9-2

Preparation of 6-bromo-N-isobutyl-1H-benzimidazol-4-amine

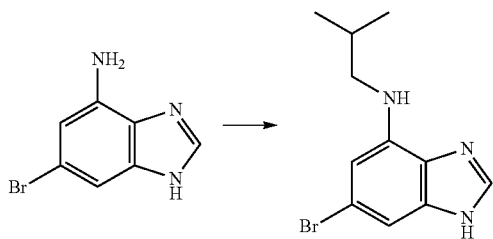

500 mg (1.60 mmol) 6-bromo-1H-benzimidazol-4-amine which was prepared according to intermediate example 6-1 were transformed in analogy to intermediate example 8-1 using 2-methylpropanal to give after working up and purification 242.6 mg (51%) of the title compound.

$^1$H-NMR (DMSO-d6): δ=0.90 (6H), 1.89 (1H), 2.98 (2H), 5.78 (1H), 6.27 (1H), 6.82 (1H), 7.97 (1H), 12.24 (1H) ppm.

Method B

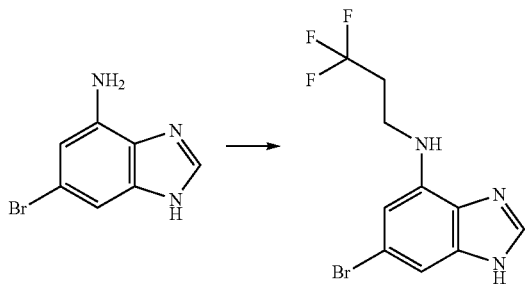 [SMILES: Nc1cc(Br)cc2[nH]cnc12 ; FC(F)(F)CCNc1cc(Br)cc2[nH]cnc12]

A mixture comprising 3.00 g (14.1 mmol) 6-bromo-1H-benzimidazol-4-amine which was prepared according to intermediate example 2-2, 1.59 g 3,3,3-trifluoropropanal, 2.5 mL acetic acid and 9.00 g sodium tris(acetato-kappaO)(hydrido)borate was stirred at 23° C. for 2.5 hours. After storage at 5° C. overnight, 476 mg 3,3,3-trifluoropropanal were added and stirring continued at 23° C. for 2 hours. The mixture was cooled to 3° C., poured into a 2M aqueous ammonia and extracted with dichloromethane. The organic layer was washed with saturated sodium hydrogencarbonate solution, brine and dried over sodium sulfate. After filtration and removal of the solvent the residue was purified by chromatography to give 2.91 g (67%) of the title compound.

Intermediate Example 10-1

Preparation of 4-(4-amino-6-bromo-1H-benzimidazol-1-yl)-N-cyclopropyl-2-methylbenzamide

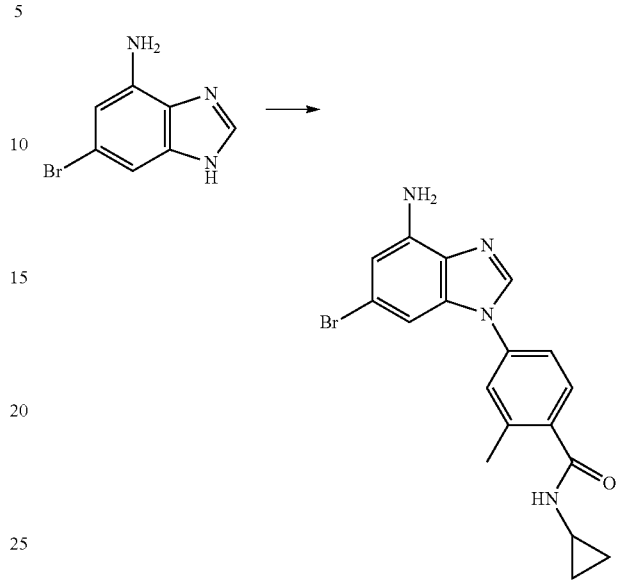

To a stirred solution of [4-(cyclopropylcarbamoyl)-3-methylphenyl]boronic acid (13.95 g, 63.68 mmol) in DCM (160 mL) at rt was added under a nitrogen atmosphere 6-bromo-1H-benzimidazol-4-amine (6.75 g, 31.84 mmol), copper(II) acetate (11.57 g, 63.68 mmol), pyridine N-oxide (3.33 g, 35.02 mmol) and pyridine (7.55 g, 95.53 mmol). After stirring overnight at rt, the mixture was stirred at 40° C. for 3 days. Filtration through ALLOX, extraction with water and evaporation of the organic phase gave the crude product, which was purified by flash chromatography to yield 6 g 4-(4-amino-6-bromo-1H-benzimidazol-1-yl)-N-cyclopropyl-2-methylbenzamide (50%).

$^1$H-NMR (300 MHz, d$_6$-DMSO, main isomer): δ=8.39 (1H), 8.33 (1H), 7.52-7.46 (3H), 6.83 (1H), 6.61 (1H), 5.79 (2H), 2.86 (1H), 2.42 (3H), 0.70 (2H), 0.55 (2H) ppm. UPLC-MS: RT=0.96 min; m/z 386.3 [MH$^+$]; required MW=385.3.

Intermediate Example 11-1

Preparation of 4-{6-bromo-4-[(3,3,3-trifluoropropyl)amino]-1H-benzimidazol-1-yl}-N-cyclopropyl-2-methylbenzamide Method A

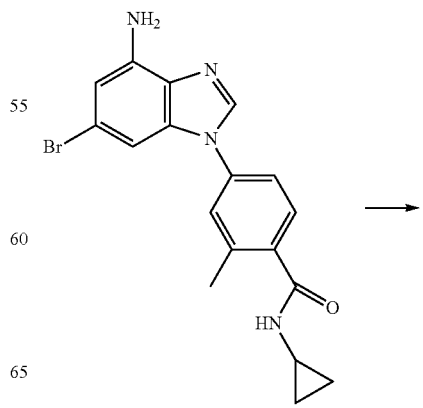

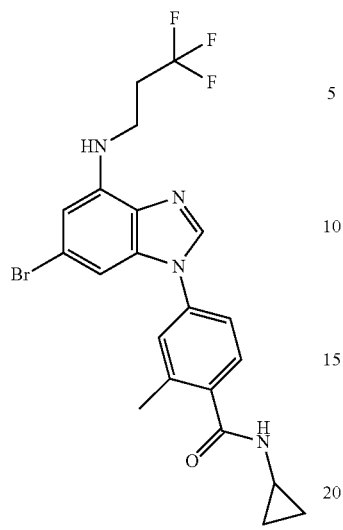

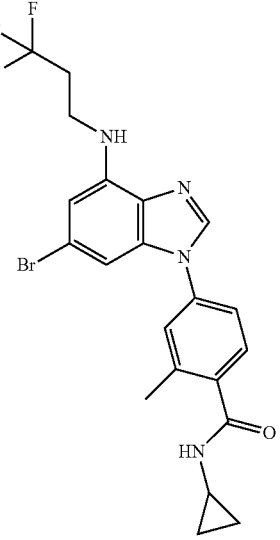

To a stirred solution of 4-(4-amino-6-bromo-1H-benzimidazol-1-yl)-N-cyclopropyl-2-methylbenzamide (5.00 g, 12.98 mmol) in DCE at rt was added 3,3,3-trifluoropropanal (4.36 g, 38.93 mmol, 3 eq), sodium triacetoxy borohydride (13.75 g, 64.89 mmol, 5 eq) and acetic acid (14.9 mL, 259.56 mmol, 20 eq) and the mixture was stirred for overnight. Water and DCM was added, and the organic phase was separated and washed with water After addition of DCM, the organic phase was washed with water and evaporated to yield 4-{6-bromo-4-[(3,3,3-trifluoropropyl)amino]-1H-benzimidazol-1-yl}-N-cyclopropyl-2-methylbenzamide (50%).

$^1$H-NMR (300 MHz, d$_6$-DMSO): δ=8.39 (1H), 8.37 (1H), 7.52 (1H), 7.49 (2H), 6.91 (1H), 6.53 (1H), 6.32 (1H), 3.57 (2H), 2.85 (1H), 2.64 (2H), 2.42 (3H), 0.71 (2H), 055 (2H) ppm.

To a solution of 751 mg [4-(cyclopropylcarbamoyl)-3-methylphenyl]boronic acid in 68.6 mL dichloromethane were added 528 mg (1.71 mmol) 6-bromo-N-(3,3,3-trifluoropropyl)-1H-benzimidazol-4-amine which was prepared according to intermediate example 1b, 623 mg copper(II)diacetate, 179 mg pyridine 1-oxide and 416 µL pyridine. The mixture was stirred at 23° C. for two days. Water was added and the mixture was extracted with dichloromethane and methanol. The organic layer was washed with water and dried over sodium sulfate. After filtration and removal of the solvent the residue was purified by chromatography to give 188 mg (22%) of the title compound.

Intermediate Example 12-1

Preparation of 6-bromo-N-(tetrahydro-2H-pyran-4-ylmethyl)-1H-benzimidazol-4-amine

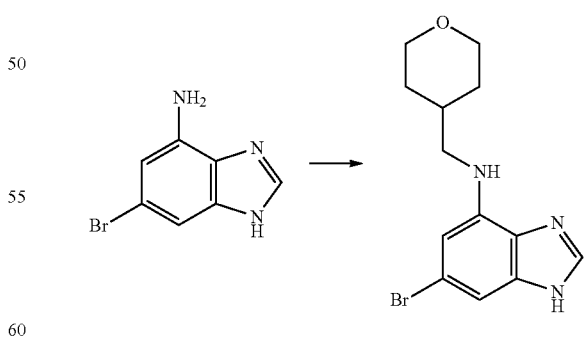

3.00 g mg (14.1 mmol) 6-bromo-1H-benzimidazol-4-amine which was prepared according to intermediate example 6-1 were transformed in analogy to intermediate example 11-1, method A using tetrahydro-2H-pyran-4-carbaldehyde to give after working up and purification 2.65 g (60%) of the title compound.

Method B

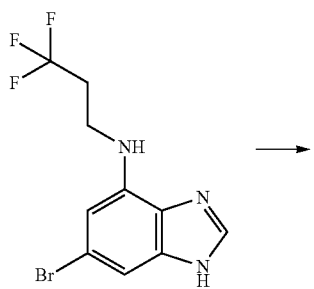

¹H-NMR (DMSO-d6): δ=1.09-1.31 (2H), 1.61 (2H), 1.84 (1H), 3.09 (2H), 3.23 (2H), 3.81 (2H), 5.67+5.86 (1H), 6.30+6.34 (1H), 6.80+6.99 (1H), 7.95+8.06 (1H), 12.12+12.24 (1H) ppm.

Intermediate Example 13-1

Preparation of 4-{6-bromo-4-[(tetrahydro-2H-pyran-4-ylmethyl)amino]-1H-benzimidazol-1-yl}-N-cyclopropyl-2-methylbenzamide

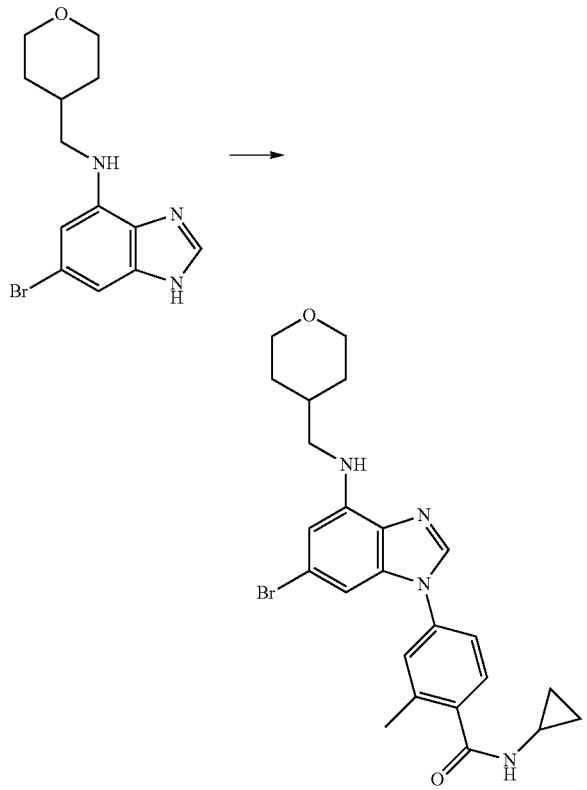

1.00 g (3.22 mmol) 6-bromo-N-(tetrahydro-2H-pyran-4-ylmethyl)-1H-benzimidazol-4-amine which was prepared according to intermediate example 12-1 were transformed in analogy to intermediate example 11-1, Method B to give after working up and purification 824 mg (53%) of the title compound.

¹H-NMR (DMSO-d6): δ=0.51 (2H), 0.67 (2H), 1.20 (2H), 1.62 (2H), 1.87 (1H), 2.38 (3H), 2.82 (1H), 3.15 (2H), 3.23 (2H), 3.82 (2H), 6.17 (1H), 6.46 (1H), 6.80 (1H), 7.43-7.50 (3H), 8.31 (1H), 8.36 (1H) ppm.

Intermediate Example 14-1

Preparation of [4-(cyclopropylcarbamoyl)-3-methylphenyl]boronic acid

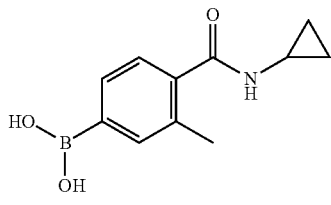 [SMILES: Cc1cc(B(O)O)ccc1C(=O)NC1CC1]

Step A

Preparation of 4-bromo-N-cyclopropyl-2-methylbenzamide

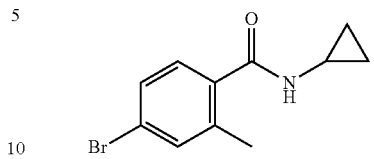

To a stirred solution of 4-bromo-2-methylbenzoic acid (300 g, 1.4 mol) in DCM (8.4 L) at rt was added cyclopropanamine (79.64 g, 1.4 mol) and EDC (320.9 g, 1.67 mol) in one portion. After stirring overnight, the solution was washed with water and the aqueous phase was reextracted with DCM. The combined organic phases were dried over sodium sulfate, filtered and evaporated. The remaining solid was triturated with diisopropyl ether, filtered, washed and dried in vaccuo to yield 260 g (73.4%) 4-bromo-N-cyclopropyl-2-methylbenzamide.

¹H-NMR (300 MHz, CDCl₃): δ=7.34 (s, 1H), 7.27 (d, 1H), 7.14 (d, 1H), 5.96 (bs, 1H), 2.85 (m, 1H), 2.38 (s, 3H), 0.85 (m, 2H), 0.59 (m, 2H) ppm.

Step B

Preparation of N-cyclopropyl-2-methyl-4-(4,4,5,5-tetramethyl-1,3,2-dioxaborolan-2-yl)benzamide

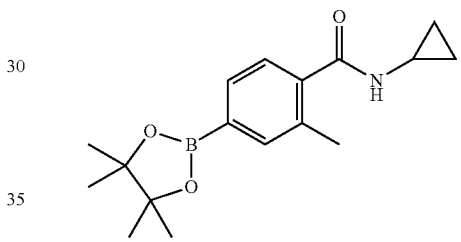

To a solution of 4-bromo-N-cyclopropyl-2-methylbenzamide (260 g, 1.02 mol) in dioxane (2 L) at rt was added bis-(pinacolato)-diboron (390 g, 1.53 mol), 2-dicyclohexylphosphino-2',4',6'-triisopropylbiphenyl (19.5 g, 40.9 mmol), potassium acetate (150.6 g, 1.53 mol) and tris-(dibenzylidenaceton)-dipalladium(0) (9.37 g, 10.2 mmol) and the mixture was refluxed for 6 h, After cooling to rt, water (3 L) and ethyl acetate (5 L) was added and the mixture stirred for 15 min. The organic phase was washed with water, dried over sodium sulfate filtered and evaporated. Flash chromatography (ethyl acetate/hexane) yielded 308 g (56.3%) N-cyclopropyl-2-methyl-4-(4,4,5,5-tetramethyl-1,3,2-dioxaborolan-2-yl)benzamide.

¹H-NMR (300 MHz, CDCl₃): δ=7.63 (s, 1H), 7.60 (d, 1H), 7.28 (d, 1H), 5.94 (bs, 1H), 2.87 (m, 1H), 2.41 (s, 3H), 1.33 (s, 6H), 0.85 (m, 2H), 0.59 (m, 2H) ppm.

Step C

Preparation of [4-(cyclopropylcarbamoyl)-3-methylphenyl]boronic acid

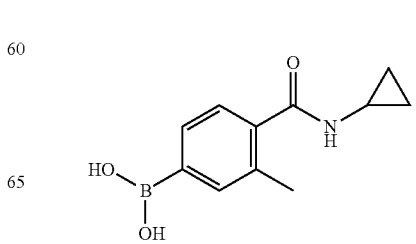

To a solution of N-cyclopropyl-2-methyl-4-(4,4,5,5-tetramethyl-1,3,2-dioxaborolan-2-yl)benzamide (20.2 g, 67.13 mol) in acetone (300 mL) at rt was added sodium periodate (43.1 g, 201.40 mot) and ammonium acetate (134.26 mol, 134 mL 1M aqueous solution) and the mixture was stirred for 3 h. More water was added (120 mL), and the mixture was stirred at 40° C. for 2 h more. After addition of 4 N HCl (32 mL), the organic phase was removed in vaccuo and the reminder was extracted with ethyl actate. The organic phase was washed with saturated sodium chloride solution, filtered through a Whatman filter and evaporated. The residue was redissolved in toluene and evaporated (two times) to yield 14.59 g (94.3%) [4-(cyclopropylcarbamoyl)-3-methylphenyl]boronic acid.

$^1$H-NMR (300 MHz, d$_6$-DMSO): δ=8.21 (1H), 8.04 (2H), 7.56 (2H), 7.17 (1H), 2.77 (1H), 2.25 (3H), 0.62 (2H), 0.47 (2H) ppm.

Intermediate Example 15-1

Preparation of
N-isobutyl-6-phenyl-1H-benzimidazol-4-amine

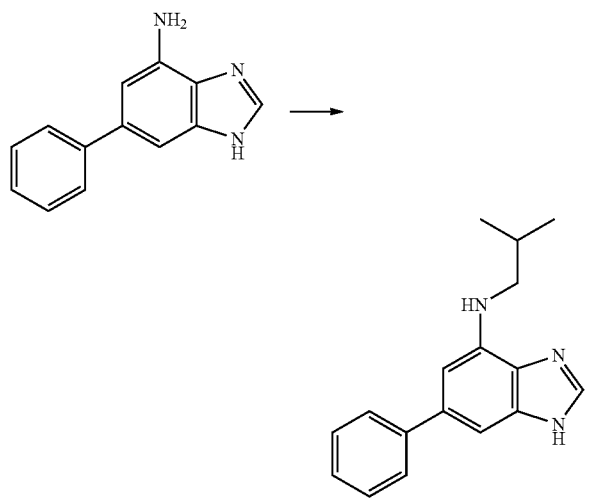

458 mg (2.19 mmol) 6-phenyl-1H-benzimidazol-4-amine which was prepared according to intermediate example 16-1 were transformed in analogy to intermediate example 8-1 using 2-methylpropanal to give after working up and purification 397 mg (91%) of the title compound.

$^1$H-NMR (DMSO-d6): δ=0.94 (6H), 1.95 (1H), 3.09 (2H), 5.49 (1H), 6.45 (1H), 6.92 (1H), 7.26 (1H), 7.39 (2H), 7.59 (2H), 8.00 (1H), 12.20 (1H) ppm.

Intermediate Example 16-1

Preparation of 6-phenyl-1H-benzimidazol-4-amine

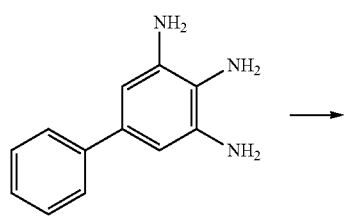

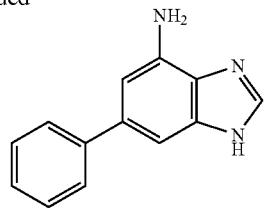

800 mg (4.02 mmol) biphenyl-3,4,5-triamine which was prepared according to intermediate example 5-2 were transformed in analogy to intermediate example 6-1 to give after working up and purification 517 mg (60%) of the title compound.

$^1$H-NMR (DMSO-d6): δ=5.33 (2H), 6.62 (1H), 6.92 (1H), 7.25 (1H), 7.38 (2H), 7.54 (2H), 8.00 (1H), 12.15 (1H) ppm.

Intermediate Example 17-1

Preparation of 3,5-dinotrobiphenyl-4-amine

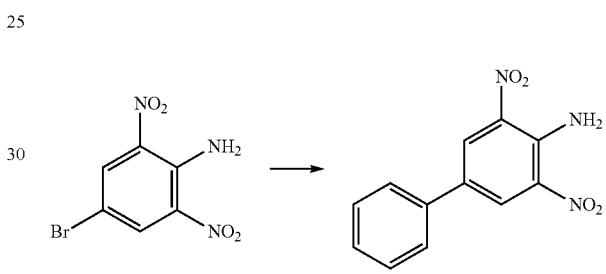

A mixture comprising 1.0 g (3.82 mmol) 4-bromo-2,6-dinitroaniline, 20 mL THF, 931 mg phenylboronic acid, 935 mg (1,1,-bis(diphenylphosphino)ferrocene)-dichloropalladium (II) and a solution of 633 mg potassium carbonate in 4.6 mL water was heated under reflux for 6 hours. The solvent was removed and the residue purified by chromatography to give 962 mg (97%) of the title compound.

$^1$H-NMR (DMSO-d6): δ=7.37 (1H), 7.46 (2H), 7.71 (2H), 8.35 (2H), 8.67 (2H) ppm.

Intermediate Example 18-1

Preparation of 4-bromo-2,6-dinitroaniline

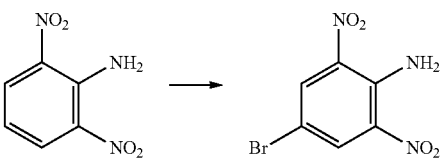 [SMILES: Nc1c([N+](=O)[O-])cccc1[N+](=O)[O-] ; Nc1c([N+](=O)[O-])cc(Br)cc1[N+](=O)[O-]]

A mixture comprising 247.5 g (1.35 mol) 2,6-dinitroaniline, 2.5 L acetic acid and 250 mL bromine was heated to 100° C. for a few minutes. After cooling, the formed crystals were filtered and washed with n-hexane to give 304 g (86%) of the title compound.

$^1$H-NMR (DMSO-d6): δ=8.32 (2H), 8.53 (2H) ppm.

Example 1

Preparation of N-cyclopropyl-4-{4-[(2-methylpropyl)amino]-1H-benzimidazol-1-yl}benzamide

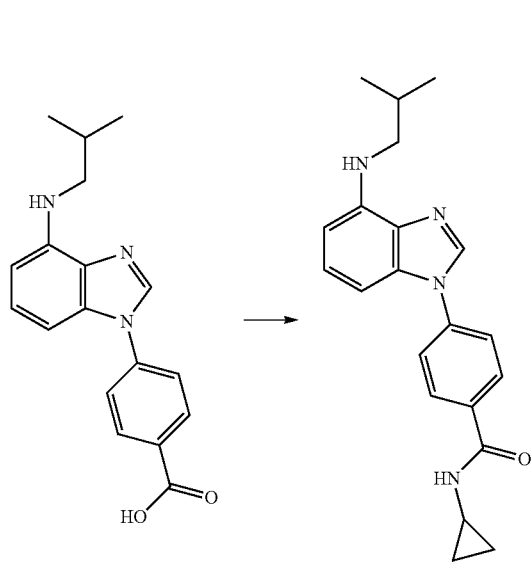 [SMILES: CC(C)CNc1cccc2c1ncn2-c1ccc(C(=O)O)cc1 ; CC(C)CNc1cccc2c1ncn2-c1ccc(C(=O)NC2CC2)cc1]

To a stirred solution of 4-{4-[(2-methylpropyl)amino]-1H-benzimidazol-1-yl}benzoic acid (63 mg, 0.2 mmol) which was prepared according to intermediate example 4-1 in THF (5 mL), at rt was added HATU (85 mg, 0.22 mmol), DIPEA (29 mg, 0.22 mmol) and cyclopropylamine (12.8 mg, 0.22 mg) in one portion. After stirring for 4 h, the solution was evaporated and the remaining solid was purified by flash chromatography to yield N-cyclopropyl-4-{4-[(2-methylpropyl)amino]-1H-benzimidazol-1-yl}benzamide as an off-white solid (24 mg, 33.8%).

$^1$H-NMR (300 MHz, $d_6$-DMSO): δ=8.54 (1H), 8.37 (1H), 8.00 (2H), 7.71 (2H), 7.06 (1H), 6.78 (1H), 6.34 (1H), 5.70 (1H), 3.06 (2H), 2.85 (1H), 1.94 (1H), 0.91 (6H), 0.68 (2H), 0.57 (2H) ppm. UPLC-MS: RT=1.29 min; m/z 349.5 [MH$^+$]; required MW=348.5.

Example 2

Preparation of N-cyclopropyl-2-methyl-4-{6-(pyridin-4-yl)-4-[(3,3,3-trifluoropropyl)amino]-1H-benzimidazol-1-yl}benzamide

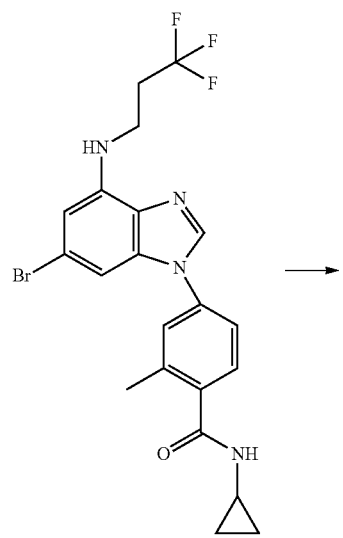

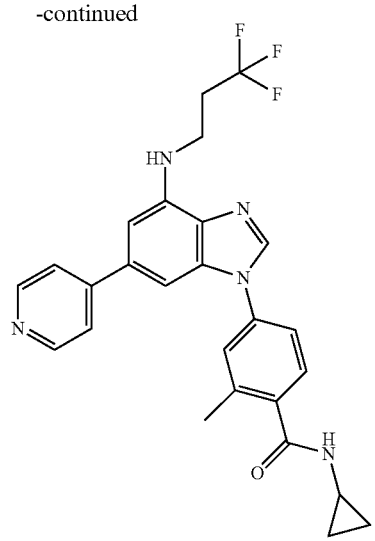

To a stirred solution of 4-{6-bromo-4-[(3,3,3-trifluoropropyl)amino]-1H-benzimidazol-1-yl}-N-cyclopropyl-2-methylbenzamide (30.8 mg, 0.05 mmol) in NMP (2 mL) was subsequently added 24.58 mg pyridin-4-ylboronic acid (0.2 mmol, 4 eq), 12.3 mg Pd(dppf)Cl$_2$ (0.015 mmol, 0.3 eq) and aqueous potassium carbonate solution (1M, 150 μL) in one portion at rt. After heating for 40 min at 140° C. in a microwave oven, the mixture was filtered an subjected to preparative HPLC to yield 6.77 mg (27.95%) N-cyclopropyl-2-methyl-4-{6-(pyridin-4-yl)-4-[(3,3,3-trifluoropropyl)amino]-1H-benzimidazol-1-yl}benzamide.

$^1$H-NMR (300 MHz, $d_6$-DMSO): δ=8.56 (2H), 8.41 (2H), 7.67 (2H), 7.56 (2H), 7.48 (1H), 7.09 (1H), 6.73 (1H), 6.14 (1H), 3.63 (2H), 2.82 (1H), 2.67 (2H), 2.40 (3H), 0.66 (2H), 0.51 (2H) ppm. UPLC-MS: RT=0.90 min; m/z 480.5 [MH$^+$]; required MW=479.5.

Example 3

Preparation of N-Cyclopropyl-4-{6-[(5-fluoro-2-methylphenyl)amino]-4-[(3,3,3-trifluoropropyl)amino]-1H-benzimidazol-1-yl}-2-methylbenzamide

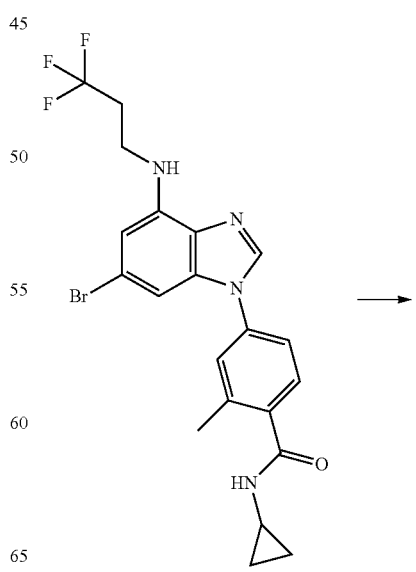

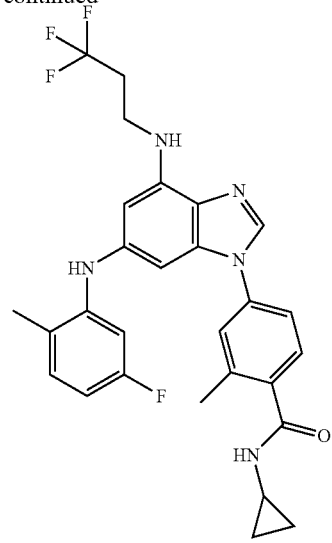

A mixture comprising 89.5 mg (186 μmol) 4-{6-bromo-4-[(3,3,3-trifluoropropyl)amino]-1H-benzimidazol-1-yl}-N-cyclopropyl-2-methylbenzamide which was prepared according to intermediate example 11-1, 0.3 mL dimethyl sulfoxide, 1.2 mL toluene, 69.5 mg 1,1'-binaphthalene-2,2'-diylbis(diphenylphosphine), 34.1 mg tris(dibenzylideneacetone)dipalladium (0), 5-fluoro-2-methylaniline and 62.5 mg sodium 2-methylpropan-2-olate were heated to 100° C. under microwave irradiation for 5 minutes. The reaction mixture was poured into water and extracted with ethyl acetate. The combined organic phases were dried over sodium sulfate. After filtration and removal of solvent the residue was purified by chromatography to give 51.7 mg (50%) of the title compound.

$^1$H-NMR (CDCl$_3$): δ=0.64 (2H), 0.91 (2H), 2.23 (3H), 2.46-2.60 (2H), 2.52 (3H), 2.93 (1H), 3.61 (2H), 5.07 (1H), 5.46 (1H), 5.92 (1H), 6.19 (1H), 6.51 (1H), 6.58 (1H), 6.89 (1H), 7.08 (1H), 7.30 (1H), 7.33 (1H), 7.48 (1H), 7.85 (1H) ppm.

Example 4

Preparation of N-cyclopropyl-4-{6-(3-fluorophenoxy)-4-[(3,3,3-trifluoropropyl)amino]-1H-benzimidazol-1-yl}-2-methylbenzamide

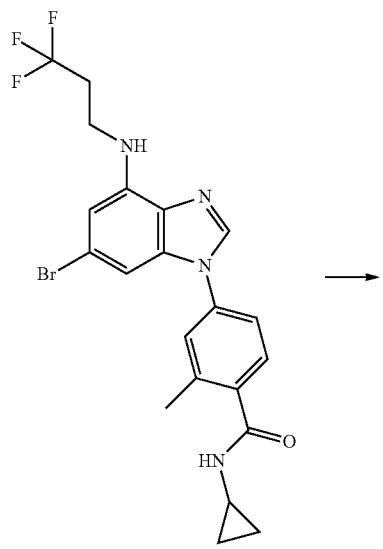

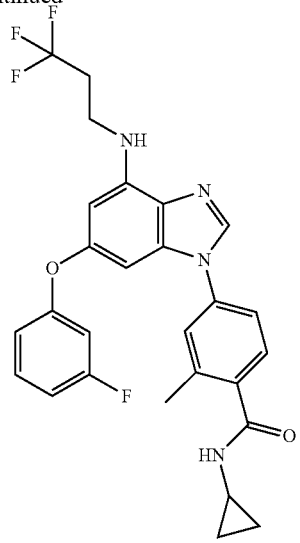

A mixture comprising 63 mg (131 μmol) 4-{6-bromo-4-[(3,3,3-trifluoropropyl)amino]-1H-benzimidazol-1-yl}-N-cyclopropyl-2-methylbenzamide which was prepared according to intermediate example 11-1, 14.7 mg 3-fluorophenol 85.3 mg caesium carbonate, 2.7 mg N,N-dimethylglycine, 5.2 mg copper(I)chloride and 0.5 mL 1,4-dioxane was heated at 110° C. using microwave irradiation for 2.5 hour. 0.5 mL 1,4-dioxane and 2.7 mg N,N-dimethylglycine were added and the mixture was heated at 110° C. using microwave irradiation for 1 hour. The mixture war poured into water and extracted with ethyl acetate. The organic layer was dried over sodium sulfate. After filtration and removal of the solvent the residue war purified by chromatography to give 2.9 mg (4%) of the title compound.

$^1$H-NMR (DMSO-d6): δ=0.49 (2H), 0.653 (2H), 2.35 (3H), 2.49-2.66 (2H), 2.80 (1H), 3.50 (2H), 6.15 (1H), 6.22 (1H), 6.42 (1H), 6.75-6.89 (3H), 7.31 (1H), 7.39-7.43 (2H), 7.46 (1H), 8.29-8.34 (2H) ppm.

Example 5

Preparation of N-cyclopropyl-4-{6-[(2,3-difluorophenyl)amino]-4-[(3,3,3-trifluoropropyl)amino]-1H-benzimidazol-1-yl}-2-methylbenzamide

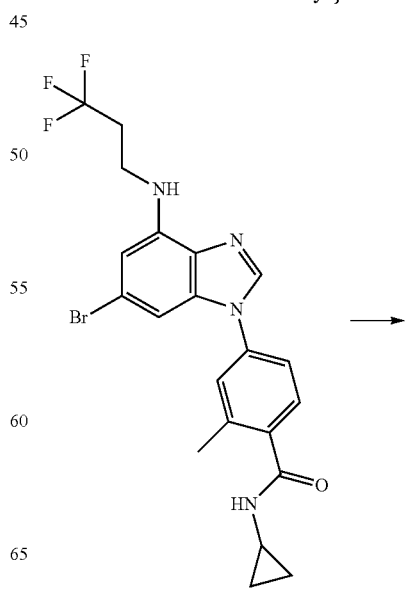

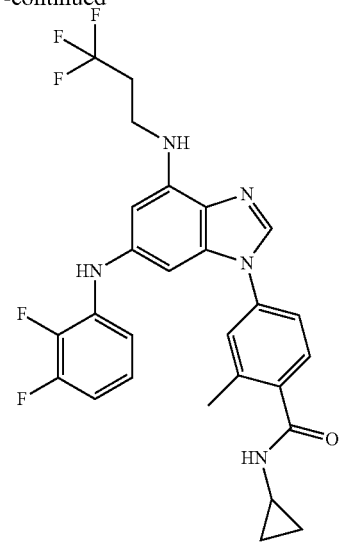

89.5 mg (186 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 3 using 2,3-difluoroaniline to give after working up and purification 12 mg (12%) of the title compound.

$^1$H-NMR (CDCl$_3$): δ=0.64 (2H), 0.91 (2H), 2.44-2.63 (2H), 2.52 (3H), 2.93 (1H), 3.61 (2H), 5.13 (1H), 5.91 (2H), 6.25 (1H), 6.57-6.69 (2H), 6.88 (1H), 6.97 (1H), 7.29 (1H), 7.32 (1H), 7.48 (1H), 7.86 (1H) ppm.

Example 6

Preparation of 4-{6-bromo-4-[(2-methylpropyl)amino]-1H-benzimidazol-1-yl}-N-cyclopropylbenzamide

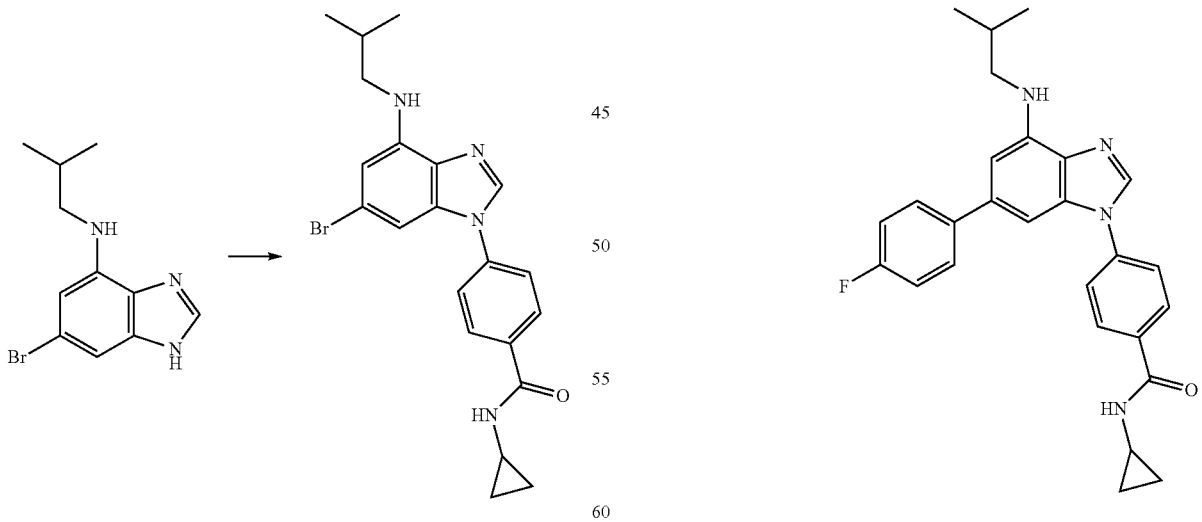

254 mg (947 μmol) 6-bromo-N-isobutyl-1H-benzimidazol-4-amine which was prepared according to intermediate example 9-2 were transformed in analogy to intermediate example 10-1 using [4-(cyclopropylcarbamoyl)phenyl]boronic acid to give after working up and purification 64.2 mg (15%) of the title compound.

$^1$H-NMR (DMSO-d6): δ=0.56 (2H), 0.69 (2H), 0.90 (6H), 1.92 (1H), 2.84 (1H), 3.05 (2H), 6.13 (1H), 6.44 (1H), 6.86 (1H), 7.69 (2H), 7.99 (2H), 8.38 (1H), 8.56 (1H) ppm.

Example 7

Preparation of N-cyclopropyl-4-{6-(4-fluorophenyl)-4-[(2-methylpropyl)amino]-1H-benzimidazol-1-yl}benzamide

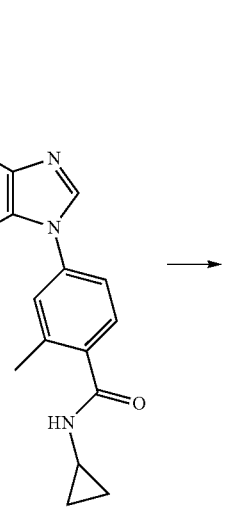

43 mg (101 μmol) 4-{6-bromo-4-[(2-methylpropyl)amino]-1H-benzimidazol-1-yl}-N-cyclopropylbenzamide which was prepared according to example 6 were transformed in analogy to example 2 using (4-fluorophenyl)boronic acid to give after working up and purification 24.4 mg (51%) of the title compound.

¹H-NMR (DMSO-d6): δ=0.56 (2H), 0.69 (2H), 0.94 (6H), 1.99 (1H), 2.85 (1H), 3.15 (2H), 5.83 (1H), 6.55 (1H), 6.93 (1H), 7.21 (2H), 7.65 (2H), 7.78 (2H), 8.01 (2H), 8.40 (1H), 8.55 (1H) ppm.

¹H-NMR (DMSO-d6): δ=0.56 (2H), 0.69 (2H), 0.94 (6H), 1.99 (1H), 2.85 (1H), 3.15 (2H), 5.82 (1H), 6.58 (1H), 6.95 (1H), 7.29 (1H), 7.39 (2H), 7.61 (2H), 7.78 (2H), 8.01 (2H), 8.40 (1H), 8.55 (1H) ppm.

Example 8

Preparation of N-cyclopropyl-4-{4-[(2-methylpropyl)amino]-6-phenyl-1H-benzimidazol-1-yl}benzamide Example 9

Preparation of N-cyclopropyl-4-{6-(3-fluorophenoxy)-4-[(tetrahydro-2H-pyran-4-ylmethyl)amino]-1H-benzimidazol-1-yl}-2-methylbenzamide

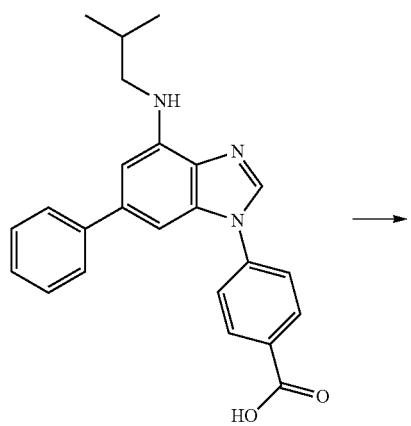

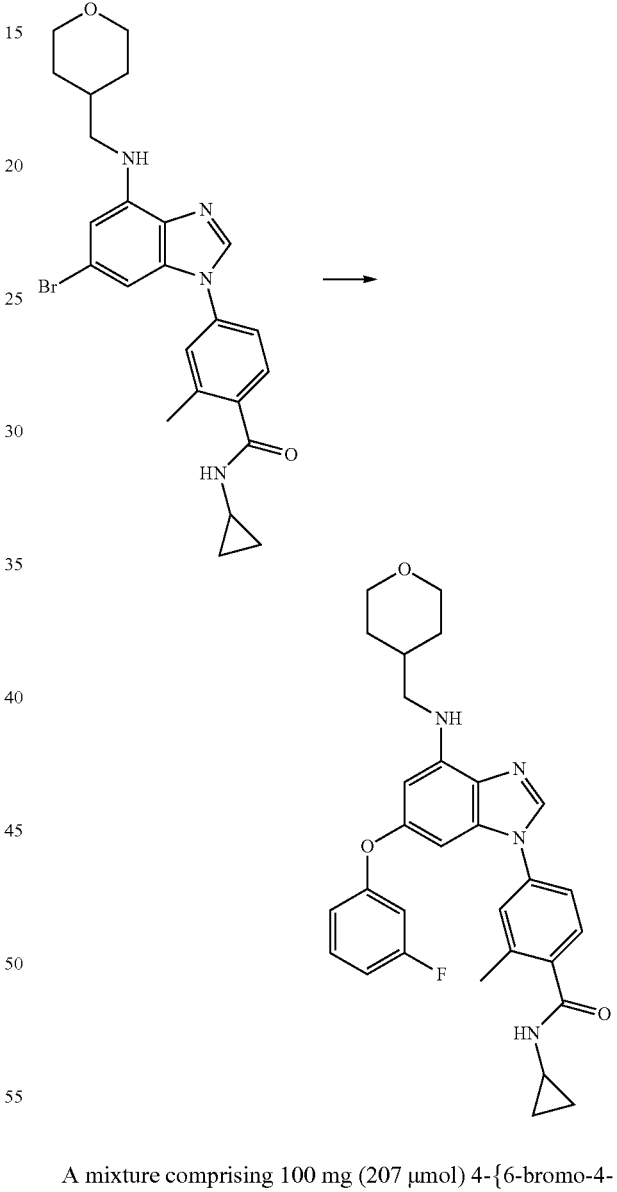

To a solution of 44 mg (114 μmol) 4-[4-(isobutylamino)-6-phenyl-1H-benzimidazol-1-yl]benzoic acid which was prepared according to intermediate example 4-2 in 2.8 mL THF were added 47.7 mg HATU, 22 μL N,N-diisopropylethylamine and the mixture was stirred at 23° C. for 20 hours. The solvent was removed and the residue purified by chromatography to give 41.0 mg (85%) of the title compound.

A mixture comprising 100 mg (207 μmol) 4-{6-bromo-4-[(tetrahydro-2H-pyran-4-ylmethyl)amino]-1H-benzimidazol-1-yl}-N-cyclopropyl-2-methylbenzamide which was prepared according to intermediate example 13-1, 116 mg 3-fluorophenol 337 mg caesium carbonate, 9.4 mg (RS)-phenyl hydrogen pyrrolidin-2-ylphosphonate, 8.2 mg copper (I)chloride and 1.6 mL 1,4-dioxane was heated at 110° C. using microwave irradiation for 1 hour and at 140° C. for 2 hours. The mixture war poured into water and extracted with a mixture of ethyl acetate and methanol. The organic layer was dried over sodium sulfate. After filtration and removal of the solvent the residue war purified by chromatography to give 50.1 mg (47%) of the title compound.

¹H-NMR (DMSO-d6): δ=0.48 (2H), 0.65 (2H), 1.17 (2H), 1.58 (2H), 1.85 (1H), 2.34 (3H), 2.79 (1H), 3.11 (2H), 3.21 (2H), 3.80 (2H), 6.08-6.15 (2H), 6.35 (1H), 6.77 (2H), 6.84 (1H), 7.31 (1H), 7.41 (2H), 7.45 (1H), 8.30 (1H), 8.32 (1H) ppm.

Example 10

4-{6-(3-Fluorophenoxy)-4-[(3,3,3-trifluoropropyl) amino]-1H-benzimidazol-1-yl}-N,2-dimethylbenzamide

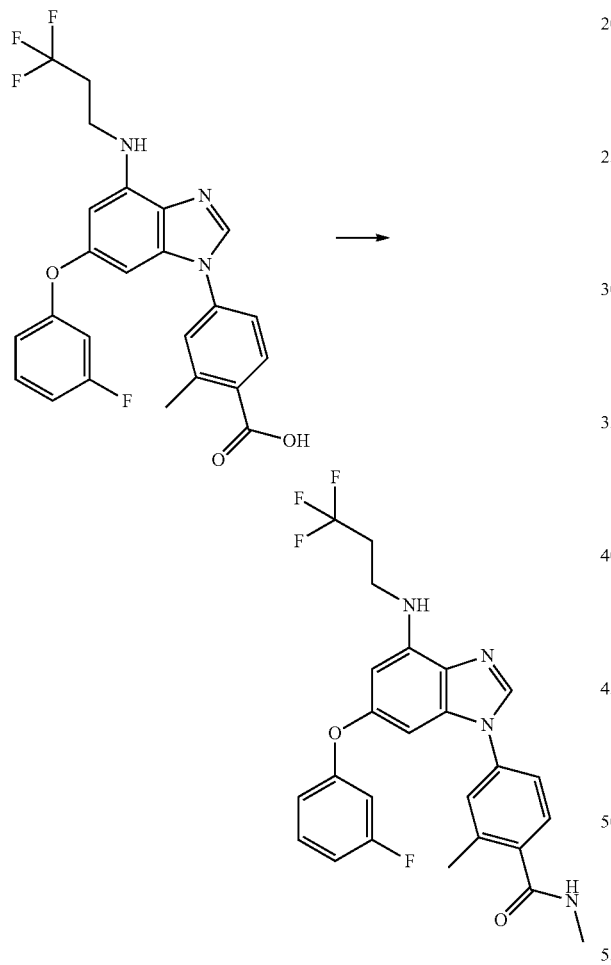

¹H-NMR (CDCl₃): δ=2.42-2.62 (2H), 2.52 (3H), 3.02 (3H), 3.59 (2H), 5.16 (1H), 5.82 (1H), 6.20 (1H), 6.52 (1H), 6.64-6.81 (3H), 7.19-7.37 (3H), 7.50 (1H), 7.91 (1H) ppm.

Example 10a

4-{6-(3-Fluorophenoxy)-4-[(3,3,3-trifluoropropyl) amino]-1H-benzimidazol-1-yl}-2-methylbenzoic acid

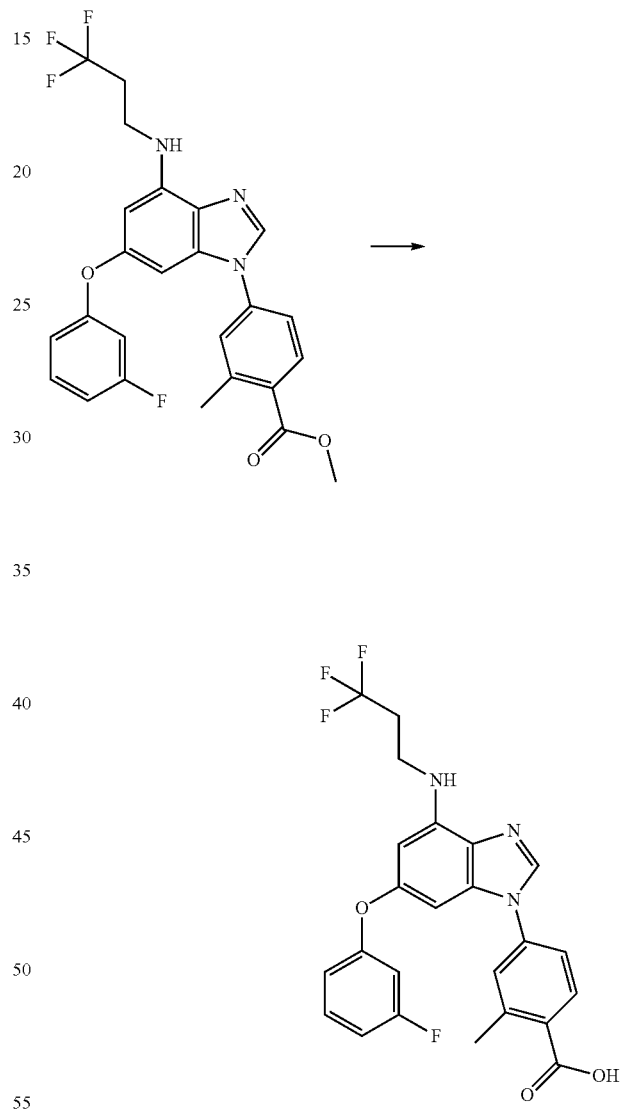

A mixture comprising 20 mg (42 μmol) 4-{6-(3-fluorophenoxy)-4-[(3,3,3-trifluoropropyl)amino]-1H-benzimidazol-1-yl}-2-methylbenzoic acid which was prepared according to intermediate example 10a, 31.7 μL methanamine solution in tetrahydrofuran (2M), 24.1 mg N-[(dimethylamino)(3H-[1,2,3]triazolo[4,5-b]pyridin-3-yloxy)methylene]-N-methyl-methanaminium hexafluorophosphate, 7.7 mg N,N-dimethylpyridin-4-amine and 0.5 mL N,N-dimethylformamide was stirred at 23° C. overnight. The solvent was removed and the residue purified by chromatography to give 12.8 mg (59%) of the title compound.

To a solution of 275 mg (564 μmol) methyl 4-{6-(3-fluorophenoxy)-4-[(3,3,3-trifluoropropyl)amino]-1H-benzimidazol-1-yl}-2-methylbenzoate which was prepared according to intermediate example 10b in 12 mL tetrahydrofurane and 4 mL methanol were added 2.8 mL of a 1M aqueous lithium hydroxide solution and the mixture was stirred at 23° C. overnight. Water was added, the mixture was acidified by the addition of a 1M hydrochloric acid and extracted with dichloromethane and methanol. The organic layer was washed with brine and dried over sodium sulfate. After filtration and removal of solvent the residue was purified by chromatography to give 246 mg (88%) of the title compound.

Example 10b

Methyl 4-{6-(3-fluorophenoxy)-4-[(3,3,3-trifluoropropyl)amino]-1H-benzimidazol-1-yl}-2-methylbenzoate

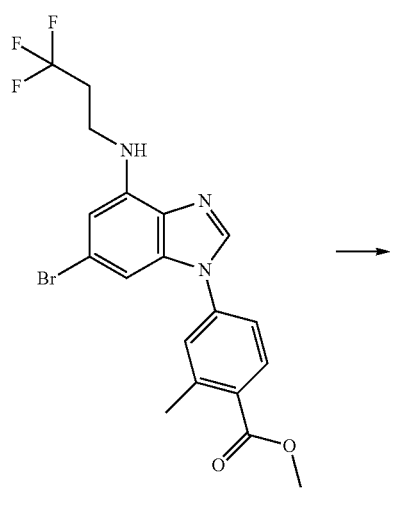

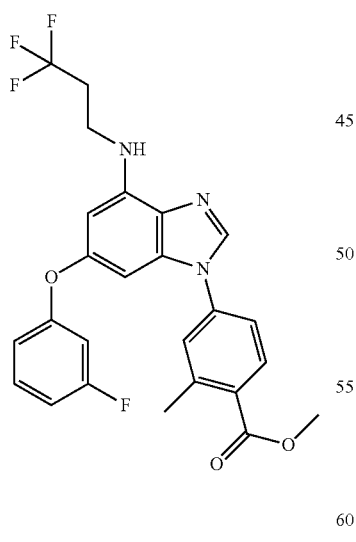

550 mg (1.21 mmol) methyl 4-{6-bromo-4-[(3,3,3-trifluoropropyl)amino]-1H-benzimidazol-1-yl}-2-methylbenzoate which was prepared according to intermediate example 10c were transformed in analogy to example 4 to give after working up and purification 290 mg (49%) of the title compound.

Example 10c

Methyl 4-{6-bromo-4-[(3,3,3-trifluoropropyl)amino]-1H-benzimidazol-1-yl}-2-methylbenzoate

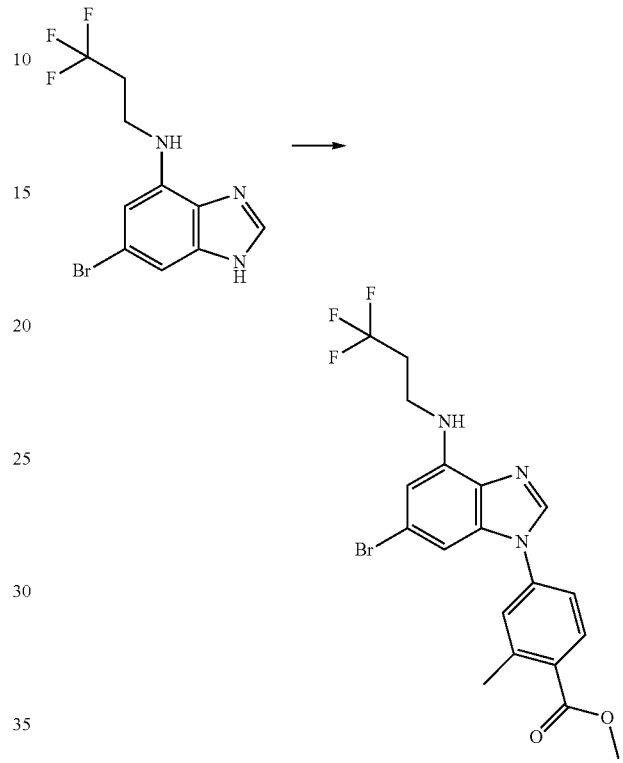

2.50 g (8.11 mmol) 6-bromo-N-(3,3,3-trifluoropropyl)-1H-benzimidazol-4-amine which was prepared according to intermediate example 10d were transformed in analogy to intermediate example 10-1 using [4-(methoxycarbonyl)-3-methylphenyl]boronic acid to give after working up and purification 1.41 g (36%) of the title compound.

Example 10d

6-Bromo-N-(3,3,3-trifluoropropyl)-1H-benzimidazol-4-amine methyl

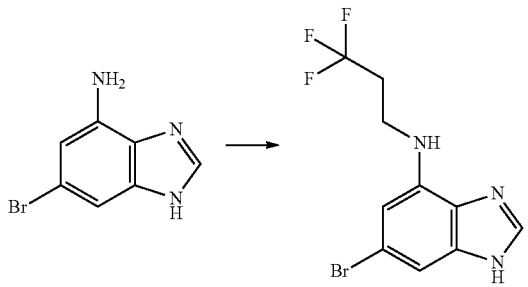 [SMILES: Nc1cc(Br)cc2[nH]cnc12 ; FC(F)(F)CCNc1cc(Br)cc2[nH]cnc12]

5.00 g (23.6 mmol) 6-bromo-1H-benzimidazol-4-amine which was prepared according to intermediate example 6-1 were transformed in analogy to intermediate example 3-1 using 3,3,3-trifluoropropanal to give after working up and purification 5.36 g (74%) of the title compound.

Example 11

N-ethyl-4-{6-(3-fluorophenoxy)-4-[(3,3,3-trifluoropropyl)amino]-1H-benzimidazol-1-yl}-2-methylbenzamide

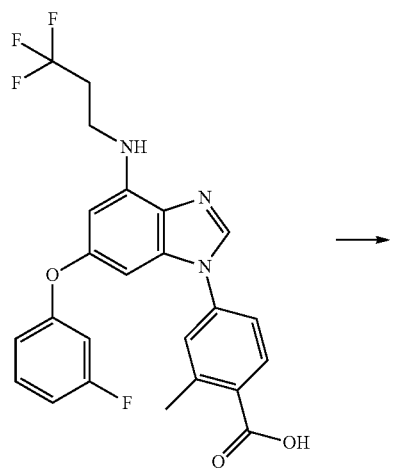

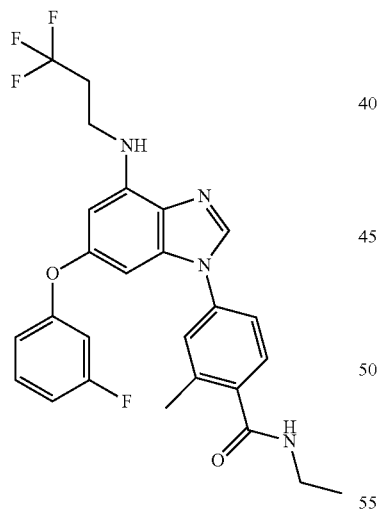

20 mg (42 µmol) 4-{6-(3-fluorophenoxy)-4-[(3,3,3-trifluoropropyl)amino]-1H-benzimidazol-1-yl}-2-methylbenzoic acid which was prepared according to intermediate example 10a were transformed in analogy to example 10 using ethanamine to give after working up and purification 12.9 mg (58%) of the title compound.

$^{1}$H-NMR (CDCl$_3$): δ=1.27 (3H), 2.43-2.59 (2H), 2.52 (3H), 3.51 (2H), 3.59 (2H), 5.16 (1H), 5.75 (1H), 6.20 (1H), 6.52 (1H), 6.66-6.80 (3H), 7.20-7.35 (3H), 7.51 (1H), 7.91 (1H) ppm.

Example 12

4-{6-(3-Fluorophenoxy)-4-[(3,3,3-trifluoropropyl)amino]-1H-benzimidazol-1-yl}-2-methyl-N-(1-methylcyclopropyl)benzamide

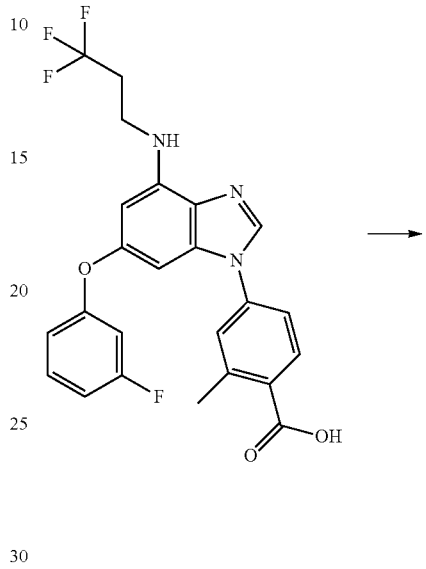

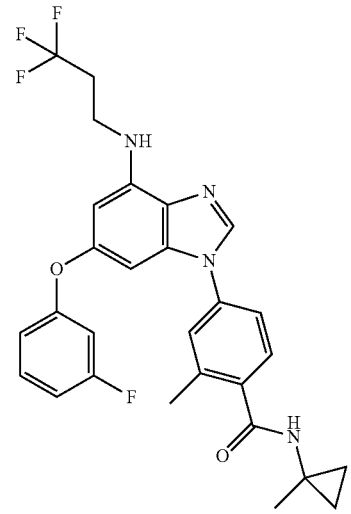

20 mg (42 µmol) 4-{6-(3-fluorophenoxy)-4-[(3,3,3-trifluoropropyl)amino]-1H-benzimidazol-1-yl}-2-methylbenzoic acid which was prepared according to intermediate example 10a were transformed in analogy to example 10 using 1-methylcyclopropanaminium chloride to give after working up and purification 8.8 mg (38%) of the title compound.

$^{1}$H-NMR (CDCl$_3$): δ=0.77 (2H), 0.87 (2H), 1.52 (3H), 2.43-2.59 (2H), 2.49 (3H), 3.59 (2H), 5.17 (1H), 6.07 (1H), 6.20 (1H), 6.50 (1H), 6.65-6.82 (3H), 7.20-7.33 (3H), 7.45 (1H), 7.90 (1H) ppm.

Example 13

N-(1-cyanocyclopropyl)-4-{6-(3-fluorophenoxy)-4-[(3,3,3-trifluoropropyl)amino]-1H-benzimidazol-1-yl}-2-methylbenzamide

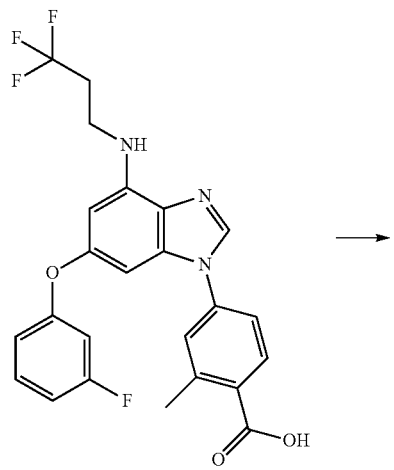

30 mg (63 μmol) 4-{6-(3-fluorophenoxy)-4-[(3,3,3-trifluoropropyl)amino]-1H-benzimidazol-1-yl}-2-methylbenzoic acid which was prepared according to intermediate example 10a were transformed in analogy to example 10 using 1-cyanocyclopropanaminium chloride to give after working up and purification 6.85 mg (19%) of the title compound.

$^1$H-NMR (CDCl$_3$): δ=1.39 (2H), 1.68 (2H), 2.44-2.59 (2H), 2.54 (3H), 3.59 (2H), 5.17 (1H), 6.20 (1H), 6.34 (1H), 6.51 (1H), 6.66-6.80 (3H), 7.20-7.37 (3H), 7.49 (1H), 7.91 (1H) ppm.

Example 14

N-cyclopropyl-4-{6-(2,3-difluorophenoxy)-4-[(3,3,3-trifluoropropyl)amino]-1H-benzimidazol-1-yl}-2-methylbenzamide

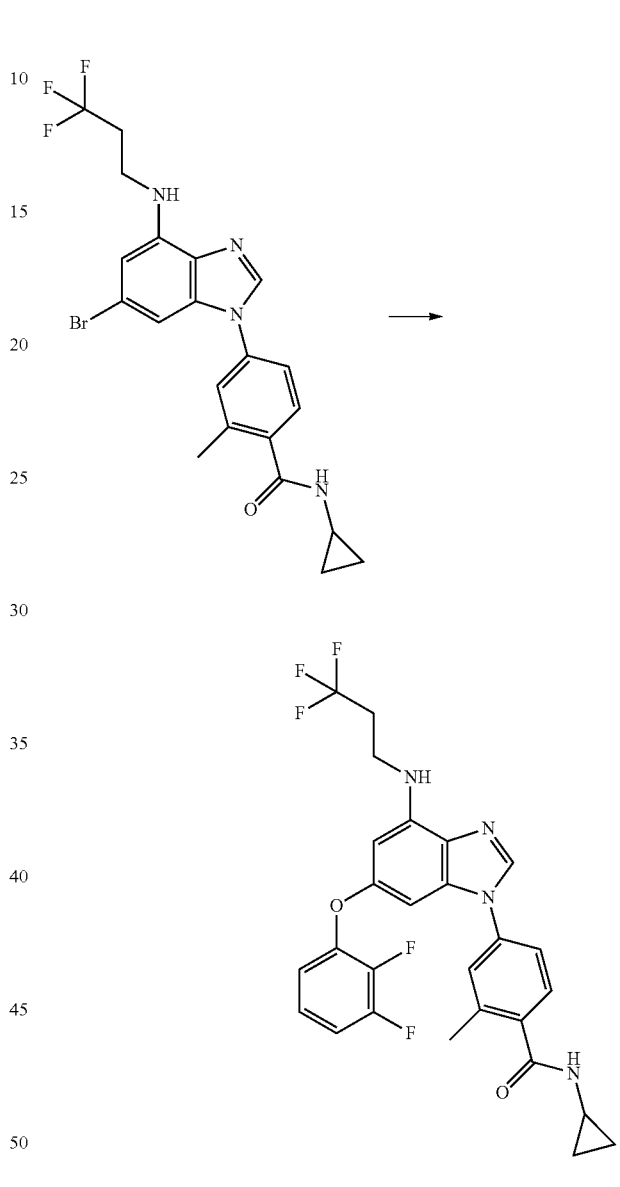

A mixture comprising 50 mg (104 μmol) 4-{6-bromo-4-[(3,3,3-trifluoropropyl)amino]-1H-benzimidazol-1-yl}-N-cyclopropyl-2-methylbenzamide which was prepared according to intermediate example 11-1, 67.6 mg 2,3-difluorophenol, 169 mg caesium carbonate, 4.72 mg (RS) phenyl hydrogen pyrrolidin-2-ylphosphonate, 4.11 mg copper(I) chloride and 0.8 mL 1,4-dioxane was heated at 130° C. using microwave irradiation for 1 hour. 270 mg 2,3-difluorophenol, 677 mg caesium carbonate, and 0.8 mL 1,4-dioxane were and reaction was continued at 150° C. and 160° C. for 1 hour each using microwave irradiation. The mixture was poured into water and extracted with ethyl acetate and methanol. The organic layer was dried over sodium sulfate. After filtration and removal of the solvent the residue war purified by chromatography to give 4.6 mg (8%) of the title compound.

¹H-NMR (CDCl₃): δ=0.63 (2H), 0.91 (2H), 2.43-2.59 (2H), 2.50 (3H), 2.92 (1H), 3.59 (2H), 5.17 (1H), 5.91 (1H), 6.21 (1H), 6.44 (1H), 6.75 (1H), 6.85-7.02 (2H), 7.29 (2H), 7.47 (1H), 7.88 (1H) ppm.

Example 15

N-cyclopropyl-4-{6-(3-fluoro-5-methylphenoxy)-4-[(tetrahydro-2H-pyran-4-ylmethyl)amino]-1H-benzimidazol-1-yl}-2-methylbenzamide

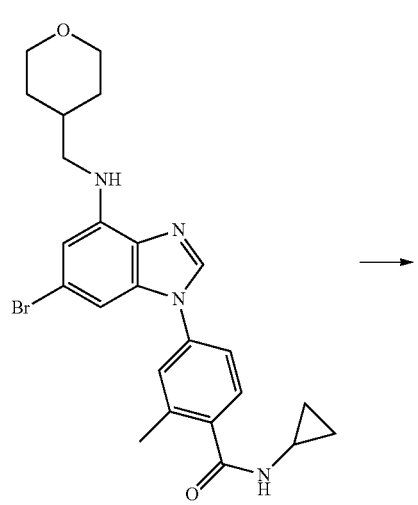

→

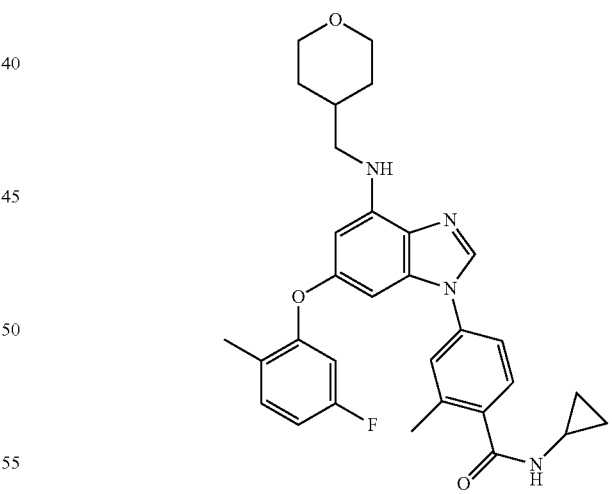

50 mg (103 μmol) 4-{6-bromo-4-[(tetrahydro-2H-pyran-4-ylmethyl)amino]-1H-benzimidazol-1-yl}-N-cyclopropyl-2-methylbenzamide which was prepared according to intermediate example 13-1 were transformed in analogy to example 14 using 3-fluoro-5-methylphenol to give after working up and purification 13.9 mg (24%) of the title compound.

¹H-NMR (DMSO-d6): δ=0.49 (2H), 0.65 (2H), 1.18 (2H), 1.58 (2H), 1.85 (1H), 2.21 (3H), 2.35 (3H), 2.80 (1H), 3.11 (2H), 3.21 (2H), 3.80 (2H), 6.08 (1H), 6.10 (1H), 6.35 (1H), 6.56 (1H), 6.60 (1H), 6.68 (1H), 7.42 (2H), 7.46 (1H), 8.29 (1H), 8.31 (1H) ppm.

Example 16

N-cyclopropyl-4-{6-(5-fluoro-2-methylphenoxy)-4-[(tetrahydro-2H-pyran-4-ylmethyl)amino]-1H-benzimidazol-1-yl}-2-methylbenzamide

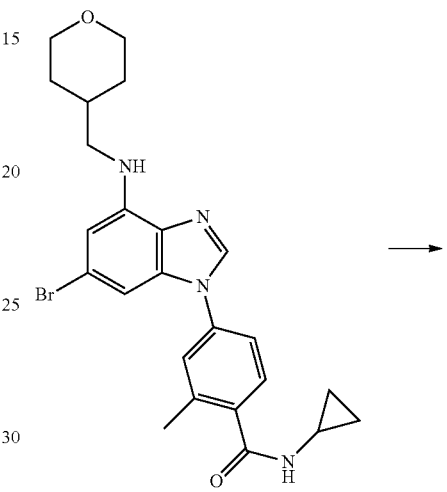

→

50 mg (103 μmol) 4-{6-bromo-4-[(tetrahydro-2H-pyran-4-ylmethyl)amino]-1H-benzimidazol-1-yl}-N-cyclopropyl-2-methylbenzamide which was prepared according to intermediate example 13-1 were transformed in analogy to example 14 using 5-fluoro-2-methylphenol to give after working up and purification 13.8 mg (24%) of the title compound.

¹H-NMR (DMSO-d6): δ=0.49 (2H), 0.65 (2H), 1.18 (2H), 1.58 (2H), 1.84 (1H), 2.16 (3H), 2.34 (3H), 2.80 (1H), 3.11

(2H), 3.21 (2H), 3.80 (2H), 6.04-6.10 (2H), 6.23 (1H), 6.58 (1H), 6.81 (1H), 7.25 (1H), 7.37-7.45 (3H), 8.27 (1H), 8.31 (1H) ppm.

Example 17

N-cyclopropyl-4-{6-(3,4-difluorophenoxy)-4-[(tetrahydro-2H-pyran-4-ylmethyl)amino]-1H-benzimidazol-1-yl}-2-methylbenzamide

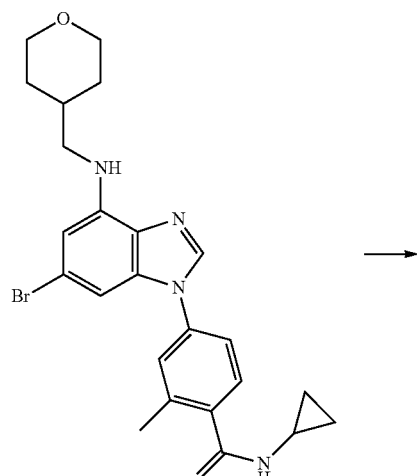

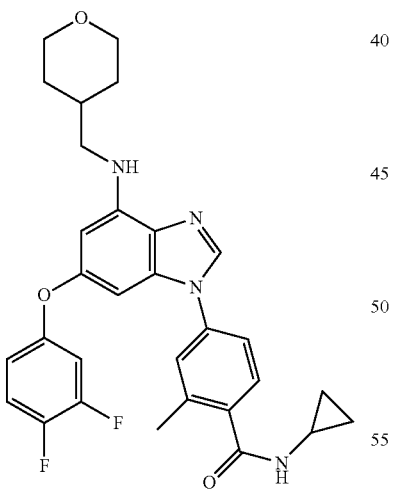

50 mg (103 µmol) 4-{6-bromo-4-[(tetrahydro-2H-pyran-4-ylmethyl)amino]-1H-benzimidazol-1-yl}-N-cyclopropyl-2-methylbenzamide which was prepared according to intermediate example 13-1 were transformed in analogy to example 14 using 3,4-difluorophenol to give after working up and purification 13.7 mg (24%) of the title compound.

$^1$H-NMR (DMSO-d6): δ=0.49 (2H), 0.65 (2H), 1.18 (2H), 1.59 (2H), 1.84 (1H), 2.35 (3H), 2.80 (1H), 3.11 (2H), 3.21 (2H), 3.80 (2H), 6.10 (2H), 6.33 (1H), 6.78 (1H), 7.07 (1H), 7.34 (1H), 7.41 (2H), 7.45 (1H), 8.29 (1H), 8.32 (1H) ppm.

Example 18

4-{6-(4-Chlorophenoxy)-4-[(3,3,3-trifluoropropyl)amino]-1H-benzimidazol-1-yl}-N-cyclopropyl-2-methylbenzamide

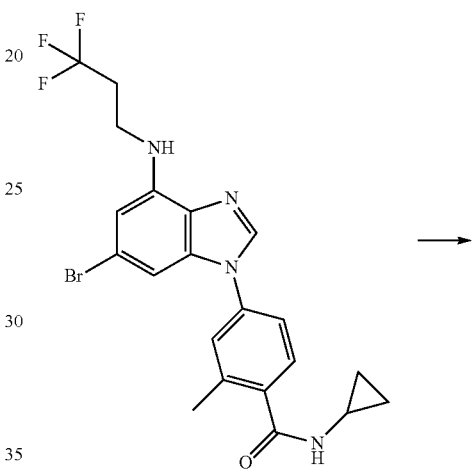

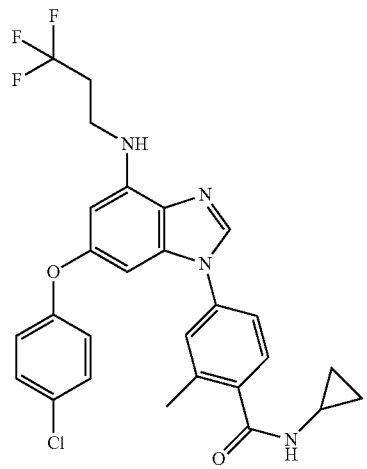

75 mg (156 µmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 14 using 4-chlorophenol to give after working up and purification 11.3 mg (13%) of the title compound.

¹H-NMR (CDCl₃): δ=0.67 (2H), 0.95 (2H), 2.49-2.60 (2H), 2.55 (3H), 2.97 (1H), 3.63 (2H), 5.19 (1H), 5.96 (1H), 6.22 (1H), 6.49 (1H), 6.97 (2H), 7.27-7.36 (4H), 7.51 (1H), 7.93 (1H) ppm.

Example 19

N-cyclopropyl-4-{6-[(5-fluoro-2-methylphenyl)amino]-4-[(tetrahydro-2H-pyran-4-ylmethyl)amino]-1H-benzimidazol-1-yl}-2-methylbenzamide

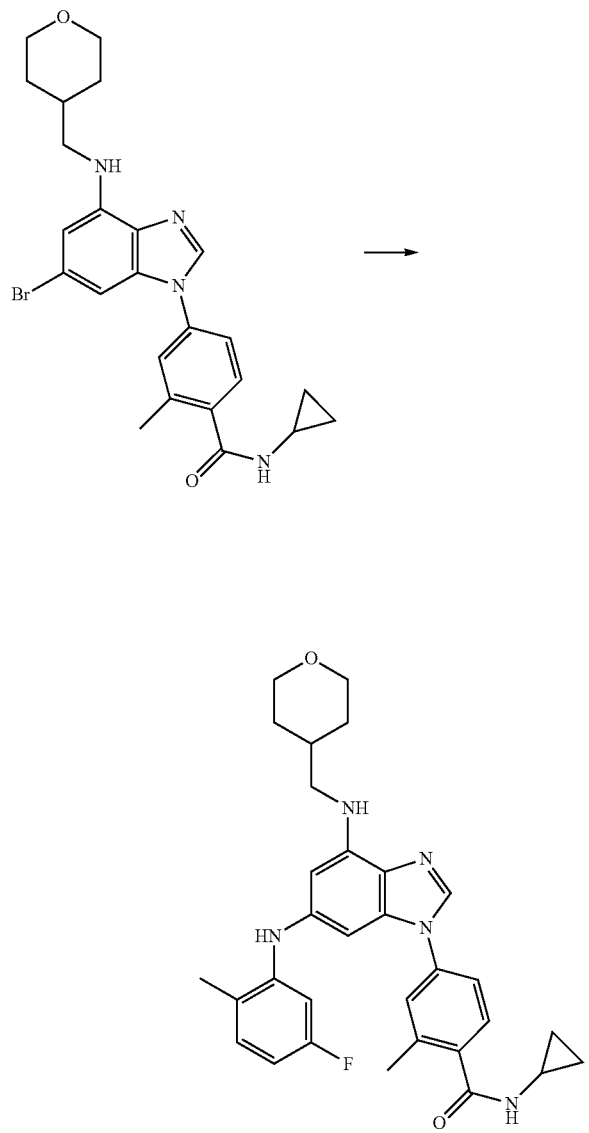

50 mg (103 µmol) 4-{6-bromo-4-[(tetrahydro-2H-pyran-4-ylmethyl)amino]-1H-benzimidazol-1-yl}-N-cyclopropyl-2-methylbenzamide which was prepared according to intermediate example 13-1 were transformed in analogy to example 3 to give after working up and purification 11.4 mg (20%) of the title compound.

¹H-NMR (DMSO-d6): δ=0.50 (2H), 0.66 (2H), 1.20 (2H), 1.61 (2H), 1.89 (1H), 2.15 (3H), 2.36 (3H), 2.80 (1H), 3.09 (2H), 3.23 (2H), 3.83 (2H), 5.82 (1H), 6.17 (1H), 6.43 (1H), 6.48 (1H), 6.84 (1H), 7.07 (1H), 7.24 (1H), 7.38-7.47 (3H), 8.15 (1H), 8.33 (1H) ppm.

Example 20

N-cyclopropyl-4-{6-[2-(hydroxymethyl)phenyl]-4-[(tetrahydro-2H-pyran-4-ylmethyl)amino]-1H-benzimidazol-1-yl}-2-methylbenzamide

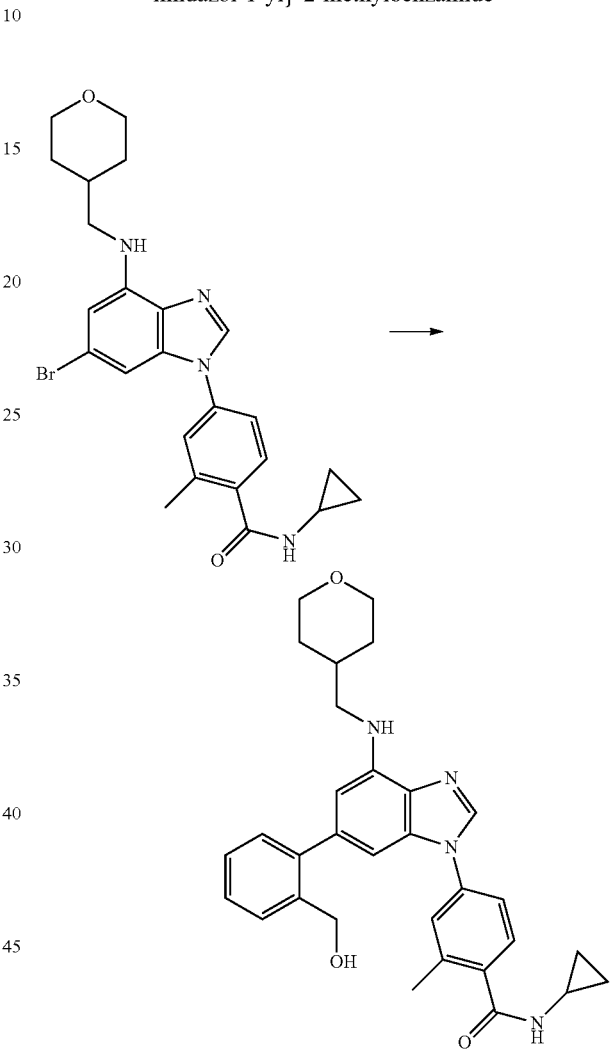

A mixture comprising 50 mg (103 µmol) 4-{6-bromo-4-[(tetrahydro-2H-pyran-4-ylmethyl)amino]-1H-benzimidazol-1-yl}-N-cyclopropyl-2-methylbenzamide which was prepared according to intermediate example 13-1, 31.4 mg [2-(hydroxymethyl)phenyl]boronic acid, 1.25 mL n-propanol, 155 µL of an aqueous 2M potassium carbonate solution, 0.1 mL 1-methyl-2-pyrrolidon, 5.4 mg triphenylphosphine, and 14.6 mg bis(triphenylphosphine)palladium(II) chloride was stirred at 120° C. for 2 hours under microwave irradiation. The solution was cooled, water added and extracted with ethylacetate and methanol. The organic phase was washed with brine and dried over sodium sulfate. After filtration and removal of solvent the residue was purified by chromatography to give 22 mg (37%) of the title compound.

¹H-NMR (DMSO-d6): δ=0.49 (2H), 0.65 (2H), 1.21 (2H), 1.63 (2H), 1.90 (1H), 2.37 (3H), 2.80 (1H), 3.13 (2H), 3.17 (2H), 3.22 (2H), 3.81 (2H), 5.04 (1H), 5.85 (1H), 6.35 (1H), 6.71 (1H), 7.21-7.28 (2H), 7.31 (1H), 7.43 (1H), 7.47-7.53 (3H), 8.32 (1H), 8.34 (1H) ppm.

Example 21

N-cyclopropyl-4-{6-[2-(hydroxymethyl)phenyl]-4-[(3,3,3-trifluoropropyl)amino]-1H-benzimidazol-1-yl}-2-methylbenzamide

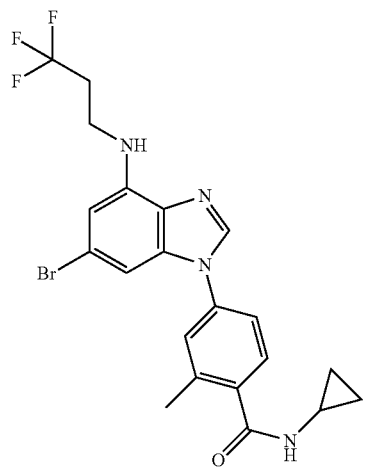

50 mg (104 µmol) 4-{6-bromo-4-[(3,3,3-trifluoropropyl)amino]-1H-benzimidazol-1-yl}-N-cyclopropyl-2-methyl-benzamide which was prepared according to intermediate example 11-1 were transformed in analogy to example 20 to give after working up and purification 20.4 mg (37%) of the title compound.

$^1$H-NMR (CDCl$_3$): δ=0.63 (2H), 0.90 (2H), 1.78 (1H), 2.47-2.60 (2H), 2.51 (3H), 2.92 (1H), 3.65 (2H), 4.65 (2H), 5.12 (1H), 5.93 (1H), 6.47 (1H), 6.88 (1H), 7.32-7.42 (5H), 7.47 (1H), 7.54 (1H), 7.94 (1H) ppm.

Example 22

4-{6-(4-Chloro-3-fluorophenoxy)-4-[(tetrahydro-2H-pyran-4-ylmethyl)amino]-1H-benzimidazol-1-yl}-N-cyclopropyl-2-methylbenzamide

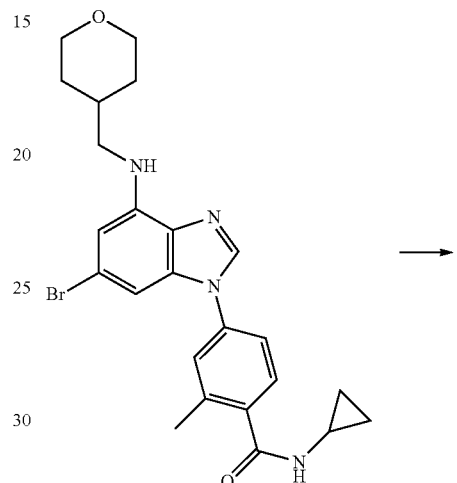

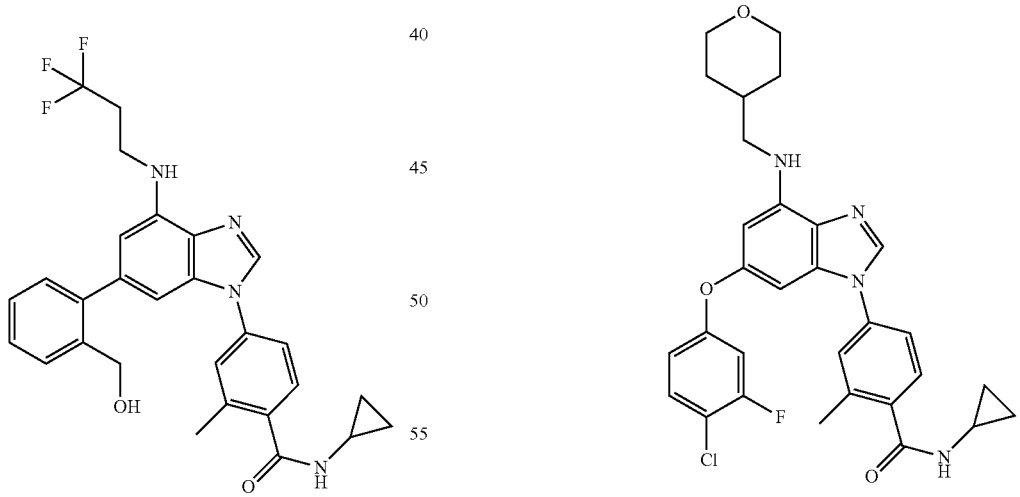

50 mg (103 µmol) 4-{6-bromo-4-[(tetrahydro-2H-pyran-4-ylmethyl)amino]-1H-benzimidazol-1-yl}-N-cyclopropyl-2-methylbenzamide which was prepared according to intermediate example 13-1 were transformed in analogy to example 14 using 4-chloro-3-fluorophenol to give after working up and purification 13.8 mg (23%) of the title compound.

$^1$H-NMR (DMSO-d6): δ=0.49 (2H), 0.65 (2H), 1.18 (2H), 1.59 (2H), 1.85 (1H), 2.35 (3H), 2.80 (1H), 3.12 (2H), 3.21

(2H), 3.80 (2H), 6.09-6.15 (2H), 6.39 (1H), 6.79 (1H), 7.02 (1H), 7.41-7.49 (4H), 8.29-8.33 (2H) ppm.

Example 23

4-{6-(4-Chlorophenoxy)-4-[(tetrahydro-2H-pyran-4-ylmethyl)amino]-1H-benzimidazol-1-yl}-N-cyclopropyl-2-methylbenzamide

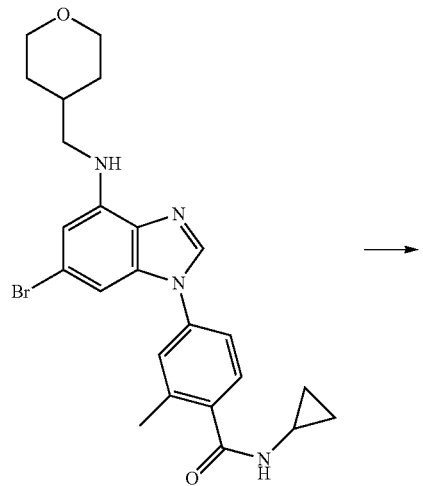

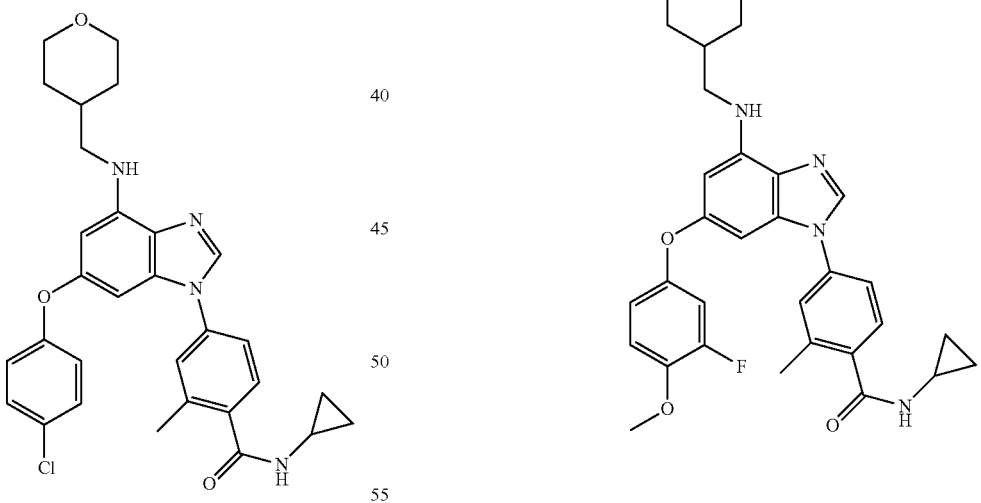

50 mg (103 µmol) 4-{6-bromo-4-[(tetrahydro-2H-pyran-4-ylmethyl)amino]-1H-benzimidazol-1-yl}-N-cyclopropyl-2-methylbenzamide which was prepared according to intermediate example 13-1 were transformed in analogy to example 14 using 4-chlorophenol to give after working up and purification 13.1 mg (23%) of the title compound.

$^1$H-NMR (DMSO-d6): δ=0.49 (2H), 0.65 (2H), 1.18 (2H), 1.59 (2H), 1.84 (1H), 2.35 (3H), 2.80 (1H), 3.11 (2H), 3.21

(2H), 3.80 (2H), 6.06-6.11 (2H), 6.31 (1H), 6.96 (2H), 7.33 (2H), 7.40 (2H), 7.44 (1H), 8.28 (1H), 8.31 (1H) ppm.

Example 24

N-cyclopropyl-4-{6-(2-fluoro-4-methoxyphenoxy)-4-[(tetrahydro-2H-pyran-4-ylmethyl)amino]-1H-benzimidazol-1-yl}-2-methylbenzamide

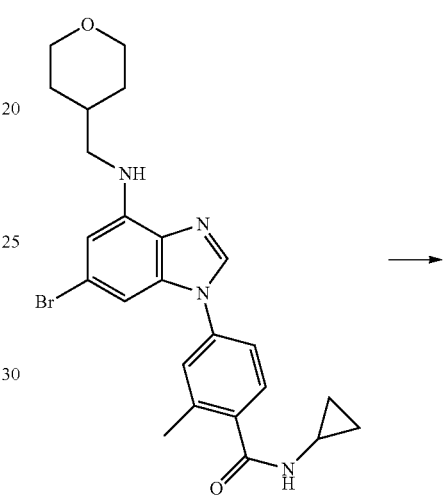

50 mg (103 µmol) 4-{6-bromo-4-[(tetrahydro-2H-pyran-4-ylmethyl)amino]-1H-benzimidazol-1-yl}-N-cyclopropyl-2-methylbenzamide which was prepared according to intermediate example 13-1 were transformed in analogy to example 14 using 2-fluoro-4-methoxyphenol to give after working up and purification 14.1 mg (24%) of the title compound.

$^1$H-NMR (DMSO-d6): δ=0.49 (2H), 0.65 (2H), 1.18 (2H), 1.58 (2H), 1.84 (1H), 2.33 (3H), 2.80 (1H), 3.10 (2H), 3.22

(2H), 3.72 (3H), 3.81 (2H), 6.05 (2H), 6.10 (1H), 6.72 (1H), 6.96 (1H), 7.09 (1H), 7.34 (1H), 7.37-7.43 (2H), 8.21 (1H), 8.33 (1H) ppm.

(2H), 3.80 (2H), 6.10-6.16 (2H), 6.35 (1H), 6.83 (1H), 7.06-7.16 (2H), 7.41 (2H), 7.44 (1H), 8.29 (1H), 8.32 (1H) ppm.

Example 25

N-cyclopropyl-4-{6-(2,3-difluorophenoxy)-4-[(tetrahydro-2H-pyran-4-ylmethyl)amino]-1H-benzimidazol-1-yl}-2-methylbenzamide

Example 26

N-cyclopropyl-4-{6-(3-fluoro-5-methylphenoxy)-4-[(3,3,3-trifluoropropyl)amino]-1H-benzimidazol-1-yl}-2-methylbenzamide

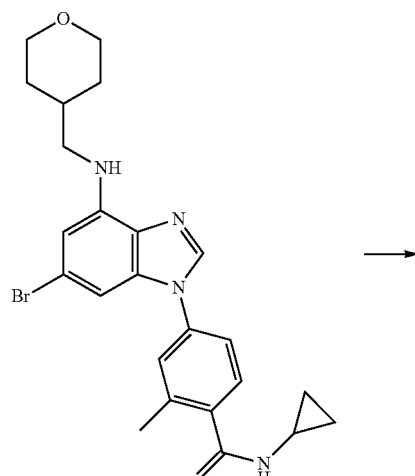

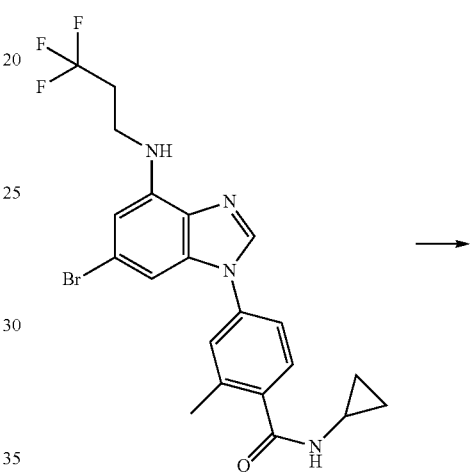

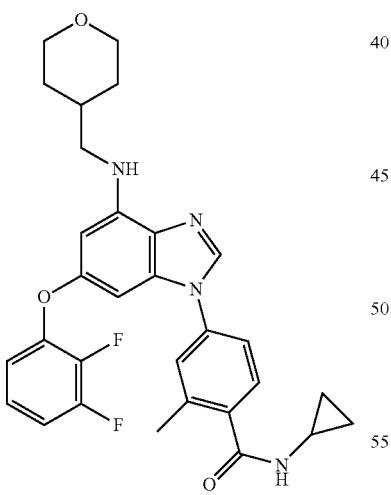

50 mg (103 μmol) 4-{6-bromo-4-[(tetrahydro-2H-pyran-4-ylmethyl)amino]-1H-benzimidazol-1-yl}-N-cyclopropyl-2-methylbenzamide which was prepared according to intermediate example 13-1 were transformed in analogy to example 14 give after working up and purification 6.9 mg (11%) of the title compound.

¹H-NMR (DMSO-d6): δ=0.49 (2H), 0.65 (2H), 1.18 (2H), 1.58 (2H), 1.84 (1H), 2.34 (3H), 2.80 (1H), 3.12 (2H), 3.21

50 mg (104 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 14 using 3-fluoro-5-methylphenol to give after working up and purification 6.0 mg (10%) of the title compound.

¹H-NMR (CDCl₃): δ=0.63 (2H), 0.91 (2H), 2.29 (3H), 2.42-2.59 (2H), 2.51 (3H), 2.92 (1H), 3.59 (2H), 5.14 (1H), 5.89 (1H), 6.19 (1H), 6.46-6.63 (4H), 7.25-7.35 (2H), 7.47 (1H), 7.89 (1H) ppm.

Example 27

N-cyclopropyl-4-{6-(3,4-difluorophenoxy)-4-[(3,3,3-trifluoropropyl)amino]-1H-benzimidazol-1-yl}-2-methylbenzamide

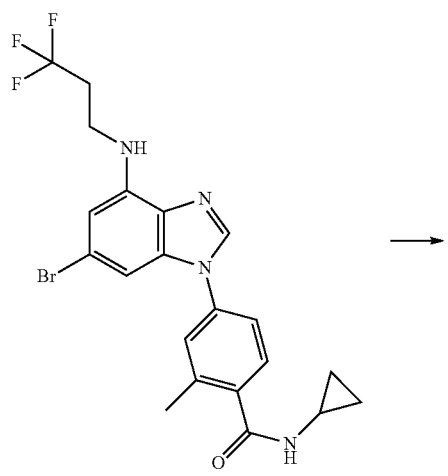

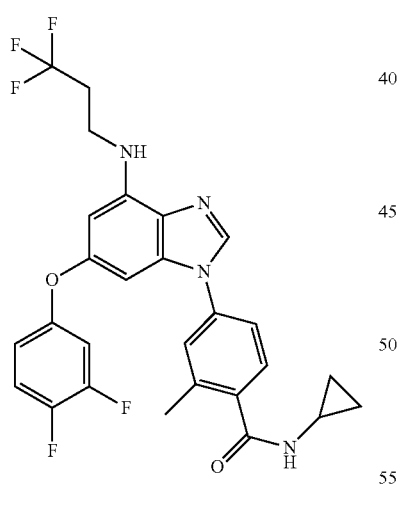

50 mg (104 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 14 using 3,4-difluorophenol to give after working up and purification 11 mg (19%) of the title compound.

¹H-NMR (CDCl₃): δ=0.63 (2H), 0.91 (2H), 2.43-2.58 (2H), 2.51 (3H), 2.92 (1H), 3.59 (2H), 5.16 (1H), 5.90 (1H), 6.16 (1H), 6.44 (1H), 6.71 (1H), 6.81 (1H), 7.08 (1H), 7.24-7.36 (2H), 7.47 (1H), 7.89 (1H) ppm.

Example 28

4-{6-(4-Chloro-3-fluorophenoxy)-4-[(3,3,3-trifluoropropyl)amino]-1H-benzimidazol-1-yl}-N-cyclopropyl-2-methylbenzamide

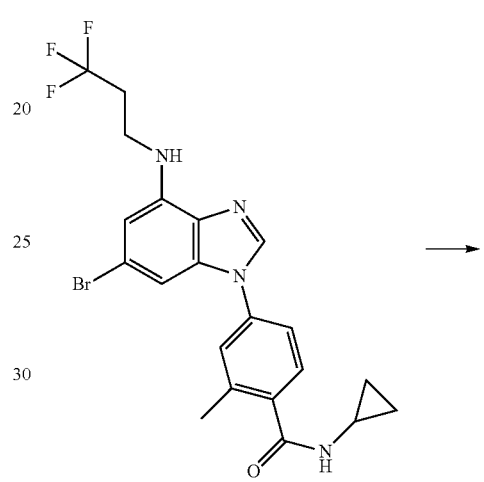

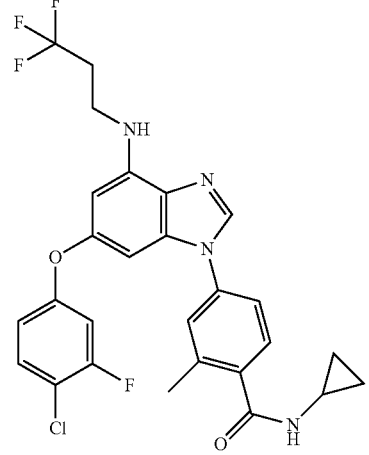

50 mg (104 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 14 using 4-chloro-3-fluorophenol to give after working up and purification 8.4 mg (14%) of the title compound.

¹H-NMR (CDCl₃): δ=0.63 (2H), 0.91 (2H), 2.41-2.59 (2H), 2.52 (3H), 2.92 (1H), 3.59 (2H), 5.17 (1H), 5.90 (1H), 6.17 (1H), 6.48 (1H), 6.71-6.81 (2H), 7.24-7.35 (3H), 7.48 (1H), 7.90 (1H) ppm.

Example 29

N-cyclopropyl-4-{6-(2-fluoro-4-methoxyphenoxy)-4-[(3,3,3-trifluoropropyl)amino]-1H-benzimidazol-1-yl}-2-methylbenzamide

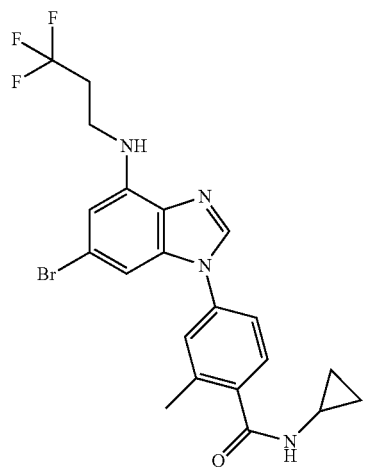
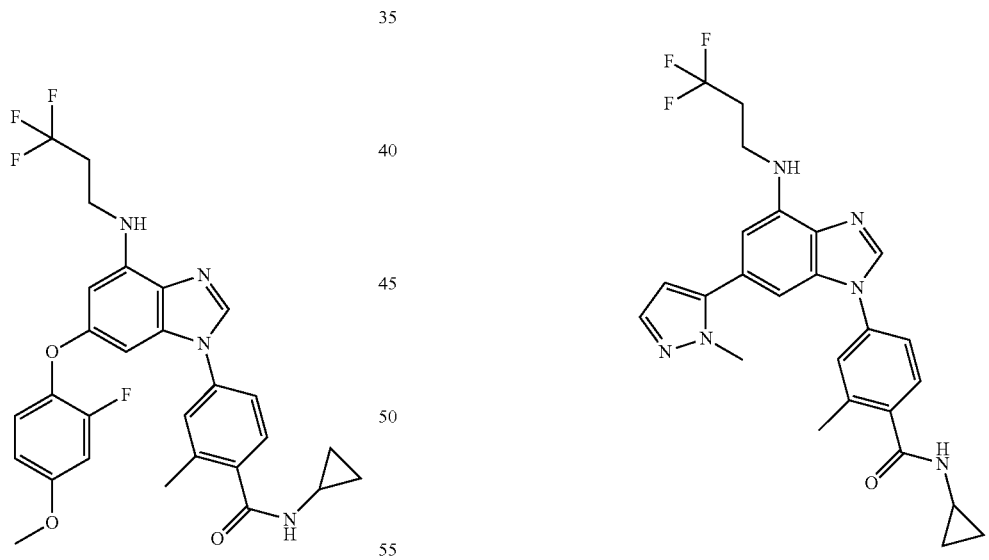

5.92 (1H), 6.19 (1H), 6.29 (1H), 6.63 (1H), 6.74 (1H), 7.02 (1H), 7.21-7.30 (2H), 7.45 (1H), 7.83 (1H) ppm.

Example 30

N-cyclopropyl-2-methyl-4-{6-(1-methyl-1H-pyrazol-5-yl)-4-[(3,3,3-trifluoropropyl)amino]-1H-benzimidazol-1-yl}benzamide 50 mg (104 µmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 14 using 2-fluoro-4-methoxyphenol to give after working up and purification 10.5 mg (18%) of the title compound.

¹H-NMR (CDCl₃): δ=0.64 (2H), 0.91 (2H), 2.42-2.58 (2H), 2.49 (3H), 2.92 (1H), 3.59 (2H), 3.80 (3H), 5.10 (1H), 20 mg (45 µmol) 2-methyl-4-{6-(1-methyl-1H-pyrazol-5-yl)-4-[(3,3,3-trifluoropropyl)amino]-1H-benzimidazol-1-yl}benzoic acid which was prepared according to intermediate example 30a were transformed in analogy to example 10 using cyclopropanamine to give after working up and purification 20.0 mg (87%) of the title compound.

¹H-NMR (DMSO-d6): δ=0.51 (2H), 0.66 (2H), 2.38 (3H), 2.63 (2H), 2.82 (1H), 3.59 (2H), 3.81 (3H), 6.14 (1H), 6.33

(1H), 6.46 (1H), 6.85 (1H), 7.40 (1H), 7.45 (1H), 7.48-7.56 (2H), 8.36 (1H), 8.41 (1H) ppm.

Example 30a

2-Methyl-4-{6-(1-methyl-1H-pyrazol-5-yl)-4-[(3,3,3-trifluoropropyl)amino]-1H-benzimidazol-1-yl}benzoic acid

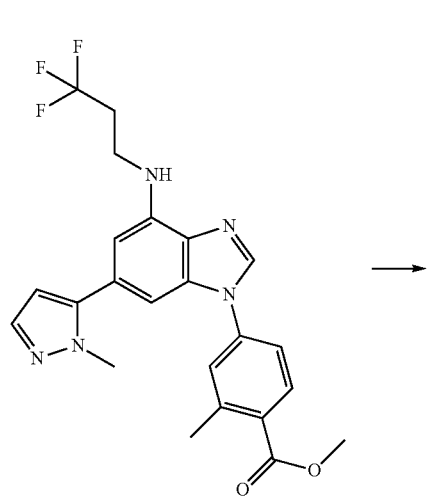

200.5 mg (max. 438 μmol) methyl 2-methyl-4-{6-(1-methyl-1H-pyrazol-5-yl)-4-[(3,3,3-trifluoropropyl)amino]-1H-benzimidazol-1-yl}benzoate which was prepared according to intermediate example 30b were transformed in analogy to intermediate example 11a to give after working up and purification 65.4 mg (34%) of the title compound.

Example 30b

Methyl 2-methyl-4-{6-(1-methyl-1H-pyrazol-5-yl)-4-[(3,3,3-trifluoropropyl)amino]-1H-benzimidazol-1-yl}benzoate

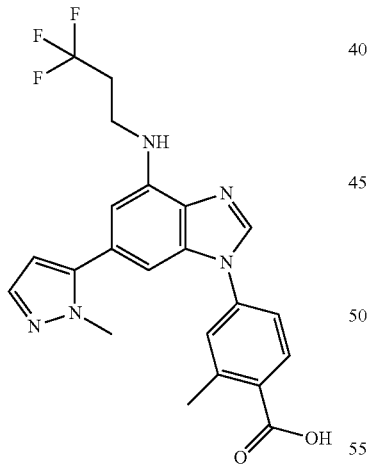

200 mg (438 μmol) methyl 4-{6-bromo-4-[(3,3,3-trifluoropropyl)amino]-1H-benzimidazol-1-yl}-2-methylbenzoate which was prepared according to intermediate example 10c were transformed in analogy to example 20 using 1-methyl-5-(4,4,5,5-tetramethyl-1,3,2-dioxaborolan-2-yl)-1H-pyrazole to give after working up the title compound as crude product that was used without further purification.

Example 31

N-ethyl-2-methyl-4-{6-(1-methyl-1H-pyrazol-5-yl)-4-[(3,3,3-trifluoropropyl)amino]-1H-benzimidazol-1-yl}benzamide

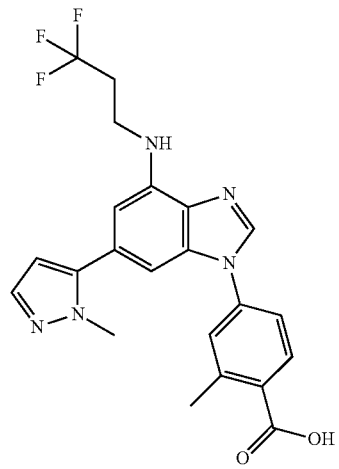

20 mg (45 µmol) 2-methyl-4-{6-(1-methyl-1H-pyrazol-5-yl)-4-[(3,3,3-trifluoropropyl)amino]-1H-benzimidazol-1-yl}benzoic acid which was prepared according to intermediate example 30a were transformed in analogy to example 10 using ethanamine to give after working up and purification 18.3 mg (82%) of the title compound.

$^1$H-NMR (DMSO-d6): δ=1.10 (3H), 2.40 (3H), 2.63 (2H), 3.24 (2H), 3.60 (2H), 3.82 (3H), 6.14 (1H), 6.33 (1H), 6.4 (1H), 6.86 (1H), 7.40 (1H), 7.47 (1H), 7.50-7.56 (2H), 8.31 (1H), 8.42 (1H) ppm.

Example 32

N,2-dimethyl-4-{6-(1-methyl-1H-pyrazol-5-yl)-4-[(3,3,3-trifluoropropyl)amino]-1H-benzimidazol-1-yl}benzamide

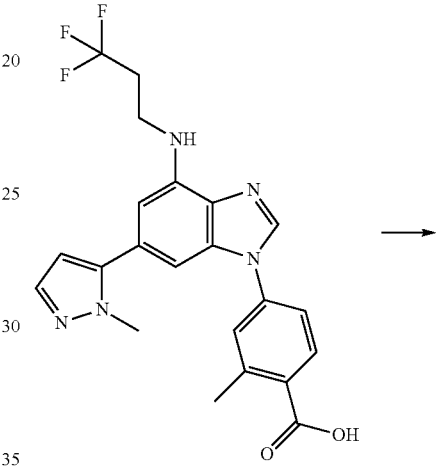

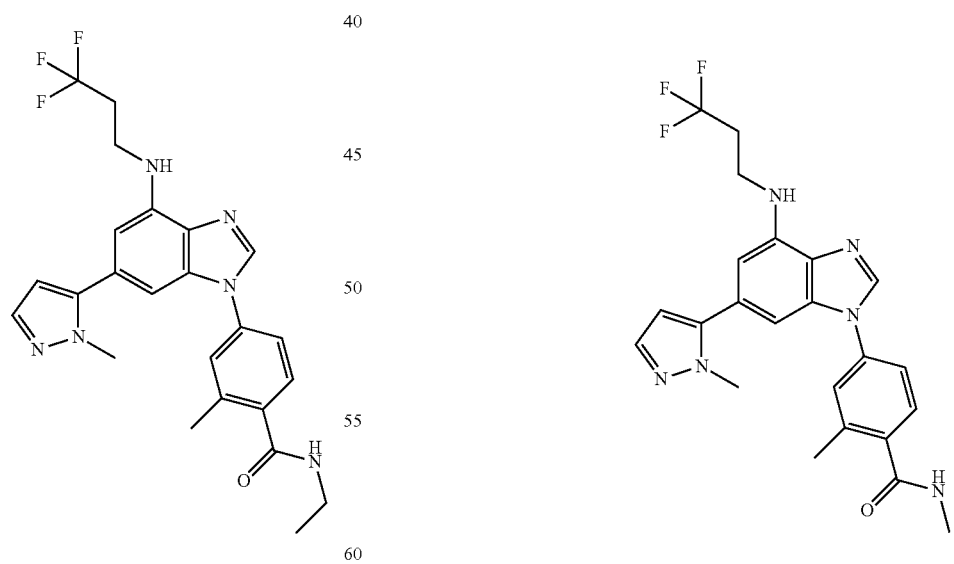

20 mg (45 µmol) 2-methyl-4-{6-(1-methyl-1H-pyrazol-5-yl)-4-[(3,3,3-trifluoropropyl)amino]-1H-benzimidazol-1-yl}benzoic acid which was prepared according to intermediate example 30a were transformed in analogy to example 10 to give after working up and purification 12.1 mg (56%) of the title compound.

¹H-NMR (DMSO-d6): δ=2.40 (3H), 2.63 (2H), 2.75 (3H), 3.59 (2H), 3.81 (3H), 6.15 (1H), 6.34 (1H), 6.47 (1H), 6.86 (1H), 7.40 (1H), 7.48-7.56 (3H), 8.25 (1H), 8.42 (1H) ppm.

Example 33

N-cyclopropyl-4-{6-(3-fluoro-4-methoxyphenoxy)-4-[(3,3,3-trifluoropropyl)amino]-1H-benzimidazol-1-yl}-2-methylbenzamide

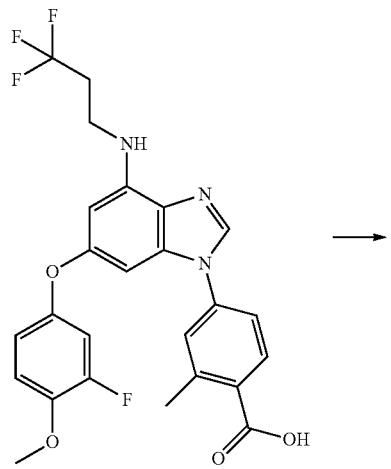

→

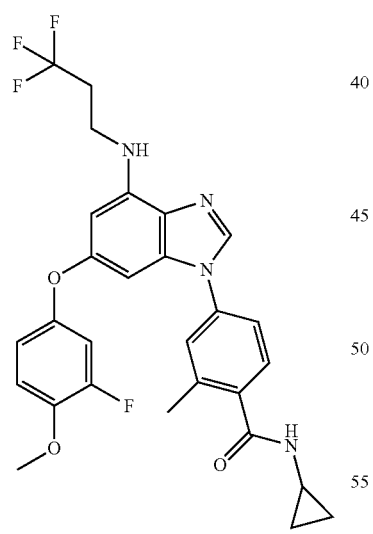

20 mg (40 μmol) 4-{6-(3-fluoro-4-methoxyphenoxy)-4-[(3,3,3-trifluoropropyl)amino]-1H-benzimidazol-1-yl}-2-methylbenzoic acid which was prepared according to intermediate example 33a were transformed in analogy to example 10 using cyclopropanamine to give after working up and purification 13.6 mg (60%) of the title compound.

¹H-NMR (CDCl₃): δ=0.63 (2H), 0.90 (2H), 2.43-2.58 (2H), 2.50 (3H), 2.92 (1H), 3.59 (2H), 3.87 (3H), 5.14 (1H), 5.93 (1H), 6.17 (1H), 6.39 (1H), 6.74 (1H), 6.80 (1H), 6.90 (1H), 7.23-7.33 (2H), 7.46 (1H), 7.86 (1H) ppm.

Example 33a

4-{6-(3-Fluoro-4-methoxyphenoxy)-4-[(3,3,3-trifluoropropyl)amino]-1H-benzimidazol-1-yl}-2-methylbenzoic acid

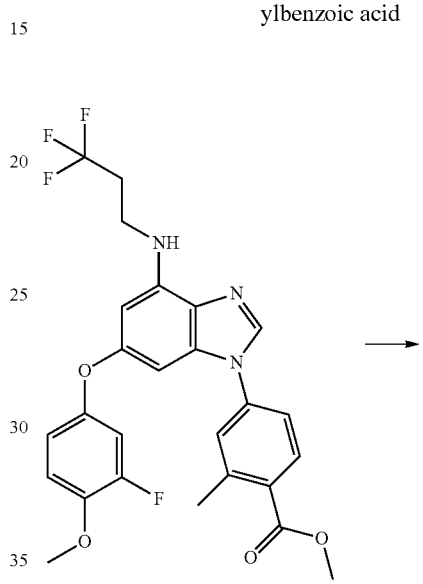

→

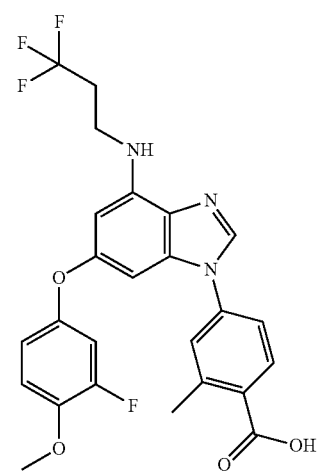

226.8 mg (max. 438 μmol) methyl 4-{6-(3-fluoro-4-methoxyphenoxy)-4-[(3,3,3-trifluoropropyl)amino]-1H-benzimidazol-1-yl}-2-methylbenzoate which was prepared according to intermediate example 33b were transformed in analogy

Example 33b

Methyl 4-{6-(3-fluoro-4-methoxyphenoxy)-4-[(3,3,3-trifluoropropyl)amino]-1H-benzimidazol-1-yl}-2-methylbenzoate

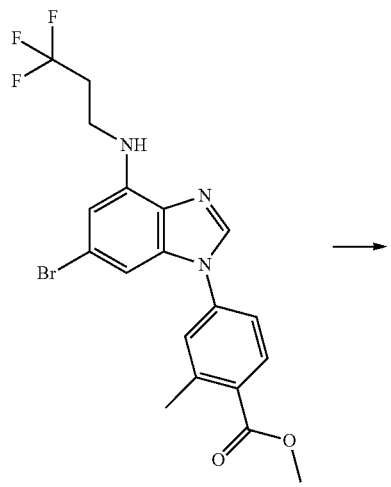

200 mg (438 μmol) methyl 4-{6-bromo-4-[(3,3,3-trifluoropropyl)amino]-1H-benzimidazol-1-yl}-2-methylbenzoate which was prepared according to intermediate example 10c were transformed in analogy to example 4 using 3-fluoro-4-methoxyphenol to give the title compound as crude product that was used without further purification.

Example 34

N-ethyl-4-{6-(3-fluoro-4-methoxyphenoxy)-4-[(3,3,3-trifluoropropyl)amino]-1H-benzimidazol-1-yl}-2-methylbenzamide

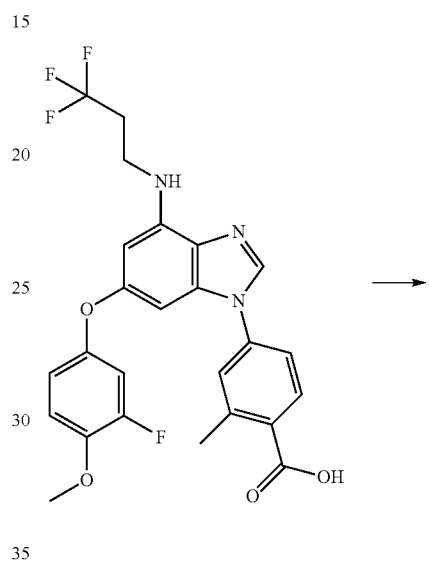

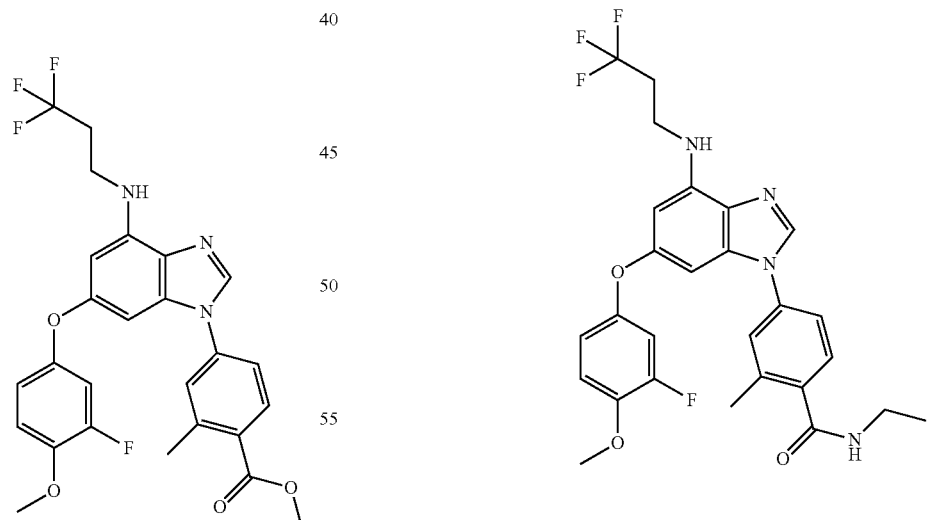

20 mg (40 μmol) 4-{6-(3-fluoro-4-methoxyphenoxy)-4-[(3,3,3-trifluoropropyl)amino]-1H-benzimidazol-1-yl}-2-methylbenzoic acid which was prepared according to intermediate example 33a were transformed in analogy to example 10 using ethanamine to give after working up and purification 14.5 mg (65%) of the title compound.

$^1$H-NMR (CDCl$_3$): δ=1.27 (3H), 2.43-2.58 (2H), 2.51 (3H), 3.51 (2H), 3.59 (2H), 3.87 (3H), 5.14 (1H), 5.78 (1H), 6.17 (1H), 6.41 (1H), 6.74 (1H), 6.80 (1H), 6.90 (1H), 7.27 (1H), 7.29 (1H), 7.49 (1H), 7.87 (1H) ppm.

Example 35

4-{6-(3-Fluoro-4-methoxyphenoxy)-4-[(3,3,3-trifluoropropyl)amino]-1H-benzimidazol-1-yl}-N,2-dimethylbenzamide

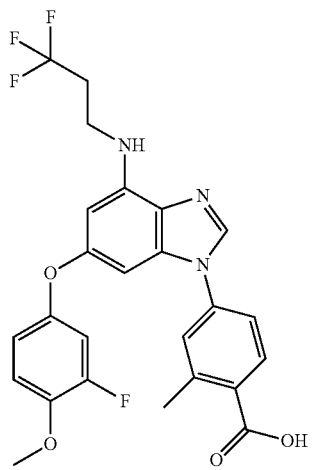

20 mg (40 μmol) 4-{6-(3-fluoro-4-methoxyphenoxy)-4-[(3,3,3-trifluoropropyl)amino]-1H-benzimidazol-1-yl}-2-methylbenzoic acid which was prepared according to intermediate example 33a were transformed in analogy to example 10 to give after working up and purification 10.4 mg (51%) of the title compound.

$^1$H-NMR (CDCl$_3$): δ=2.45-2.59 (2H), 2.51 (3H), 3.03 (3H), 3.57 (2H), 3.87 (3H), 5.49 (1H), 5.86 (1H), 6.19 (1H), 6.37 (1H), 6.74 (1H), 6.80 (1H), 6.90 (1H), 7.24-7.32 (2H), 7.51 (1H), 8.05 (1H) ppm.

Example 36

N-cyclopropyl-4-{6-(2,3-difluorophenoxy)-4-[(3,3,3-trifluoropropyl)amino]-1H-benzimidazol-1-yl}benzamide

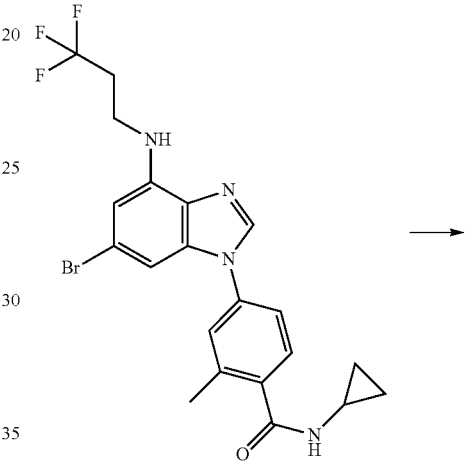

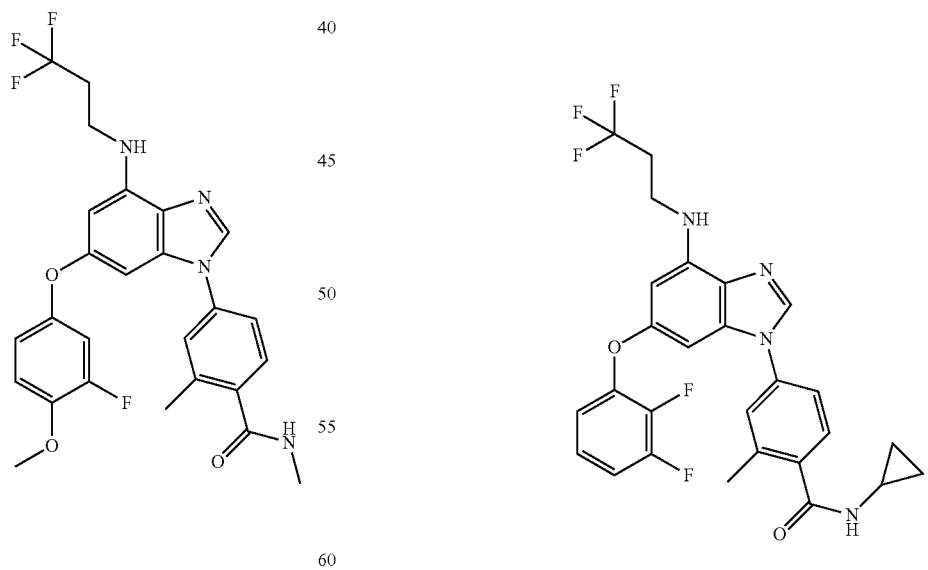

50 mg (107 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 14 using 2,3-difluorophenol to give after working up and purification 4.8 mg (8%) of the title compound.

¹H-NMR (CDCl₃): δ=0.65 (2H), 0.91 (2H), 2.43-2.59 (2H), 2.93 (1H), 3.59 (2H), 5.20 (1H), 6.22 (1H), 6.27 (1H), 6.48 (1H), 6.75 (1H), 6.86-7.01 (2H), 7.51 (2H), 7.90 (2H), 7.94 (1H) ppm.

¹H-NMR (CDCl₃): δ=0.65 (2H), 0.91 (2H), 2.50 (2H), 2.93 (1H), 3.59 (2H), 5.15 (1H), 6.22 (2H), 6.51 (1H), 7.00 (2H), 7.06 (1H), 7.31 (2H), 7.51 (2H), 7.87 (1H), 7.91 (2H) ppm.

Example 37

N-cyclopropyl-4-{6-phenoxy-4-[(3,3,3-trifluoropropyl)amino]-1H-benzimidazol-1-yl}benzamide

Example 38

N-cyclopropyl-4-{6-(3-fluoro-4-methoxyphenoxy)-4-[(3,3,3-trifluoropropyl)amino]-1H-benzimidazol-1-yl}benzamide

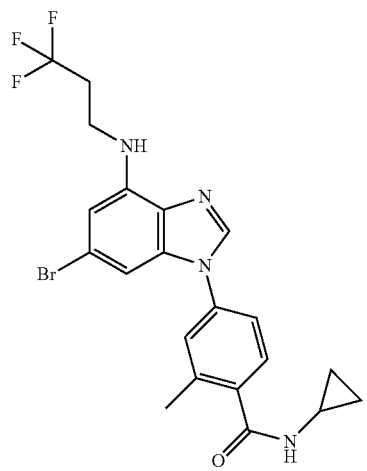

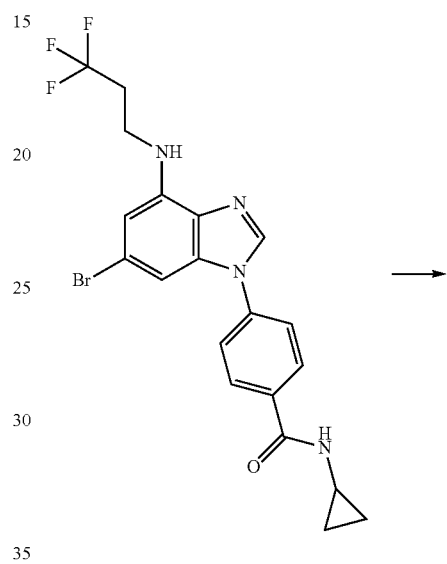

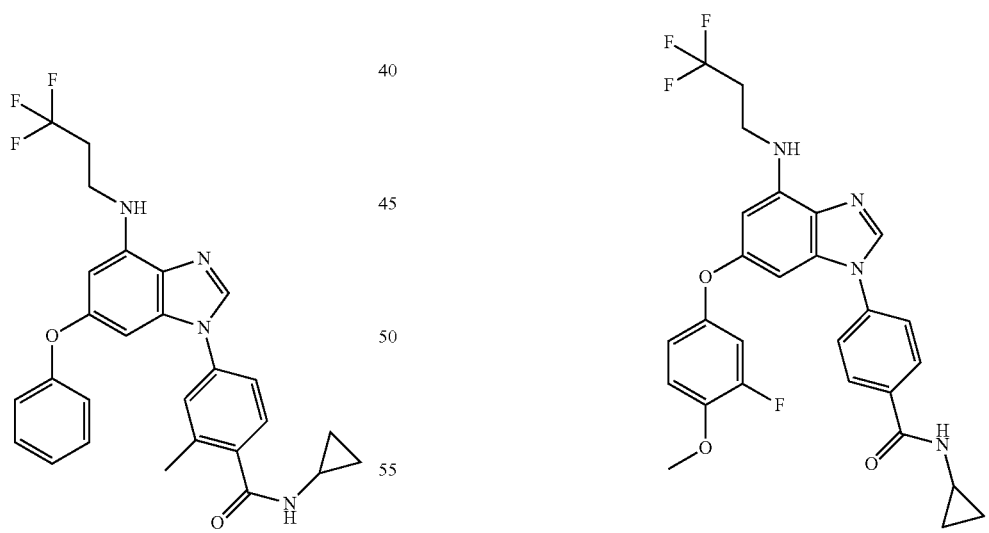

50 mg (107 μmol) 4-{6-bromo-4-[(3,3,3-trifluoropropyl)amino]-1H-benzimidazol-1-yl}-N-cyclopropyl-2-methyl-benzamide which was prepared according to intermediate example 11-1 were transformed in analogy to example 14 using phenol to give after working up and purification 2.1 mg (4%) of the title compound.

50 mg (107 μmol) 4-{6-bromo-4-[(3,3,3-trifluoropropyl)amino]-1H-benzimidazol-1-yl}-N-cyclopropylbenzamide which was prepared according to intermediate example 38a were transformed in analogy to example 4 using 3-fluoro-4-methoxyphenol to give after working up and purification 17.2 mg (29%) of the title compound.

¹H-NMR (CDCl₃): δ=0.65 (2H), 0.91 (2H), 2.43-2.59 (2H), 2.93 (1H), 3.59 (2H), 3.87 (3H), 5.16 (1H), 6.18 (1H), 6.29 (1H), 6.42 (1H), 6.74 (1H), 6.80 (1H), 6.90 (1H), 7.50 (2H), 7.90 (2H), 7.93 (1H) ppm.

Example 38a

4-{6-Bromo-4-[(3,3,3-trifluoropropyl)amino]-1H-benzimidazol-1-yl}-N-cyclopropylbenzamide

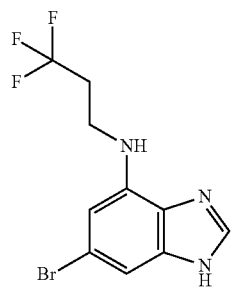

700 mg (2.27 mmol) 6-bromo-N-(3,3,3-trifluoropropyl)-1H-benzimidazol-4-amine which was prepared according to intermediate example 10d were transformed in analogy to intermediate example 11-1 using [4-(cyclopropylcarbamoyl) phenyl]boronic acid to give after working up and purification 377 mg (30%) of the title compound.

Example 39

4-{6-(2-Methoxyphenoxy)-4-[(3,3,3-trifluoropropyl) amino]-1H-benzimidazol-1-yl}-N, 2-dimethylbenzamide

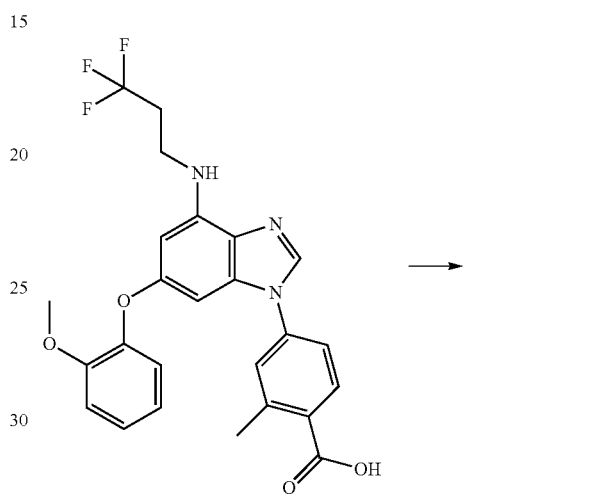

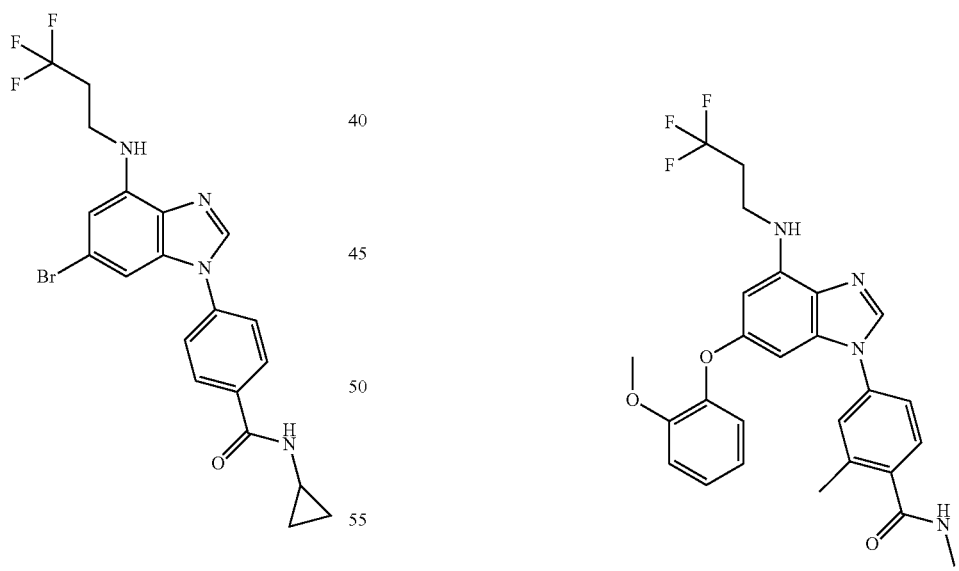

40 mg (82 µmol) 4-{6-(2-methoxyphenoxy)-4-[(3,3,3-trifluoropropyl)amino]-1H-benzimidazol-1-yl}-2-methylbenzoic acid which was prepared according to intermediate example 39a were transformed in analogy to example 10 to give after working up and purification 40 mg (93%) of the title compound.

$^1$H-NMR (DMSO-d6): δ=2.34 (3H), 2.51-2.63 (2H), 2.72 (3H), 3.48 (2H), 3.72 (3H), 6.05 (1H), 6.11 (1H), 6.15 (1H), 6.87 (1H), 6.95 (1H), 7.09 (2H), 7.35 (1H), 7.39 (1H), 7.43 (1H), 8.22 (1H), 8.24 (1H) ppm.

intermediate example 10a to give after working up and purification 222 mg (63%) of the title compound.

Example 39a

4-{6-(2-Methoxyphenoxy)-4-[(3,3,3-trifluoropropyl)amino]-1H-benzimidazol-1-yl}-2-methylbenzoic acid

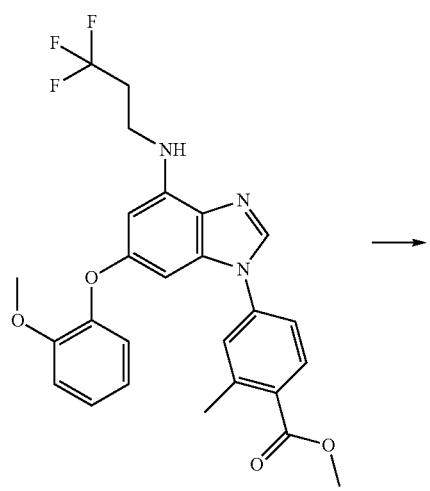

Example 39b

Methyl 4-{6-(2-methoxyphenoxy)-4-[(3,3,3-trifluoropropyl)amino]-1H-benzimidazol-1-yl}-2-methylbenzoate

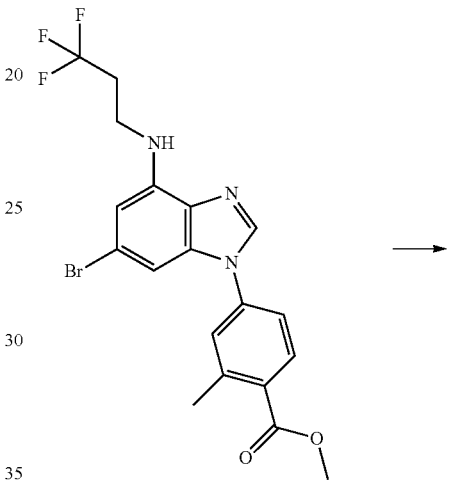

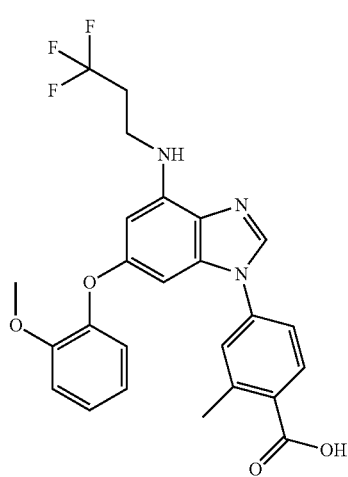

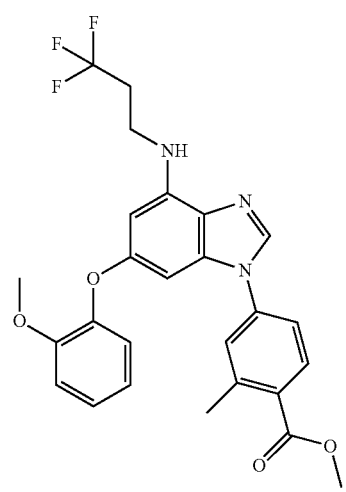

361 mg (max. 723 μmol) methyl 4-{6-(2-methoxyphenoxy)-4-[(3,3,3-trifluoropropyl)amino]-1H-benzimidazol-1-yl}-2-methylbenzoate which was prepared according to intermediate example 39b were transformed in analogy to 330 mg (723 μmol) methyl 4-{6-bromo-4-[(3,3,3-trifluoropropyl)amino]-1H-benzimidazol-1-yl}-2-methylbenzoate which was prepared according to intermediate example 10c were transformed in analogy to example 4 using 2-methoxyphenol to give after working up the title compound as crude product that was used without further purification.

Example 40

N-ethyl-4-{6-(2-methoxyphenoxy)-4-[(3,3,3-trifluoropropyl)amino]-1H-benzimidazol-1-yl}-2-methylbenzamide

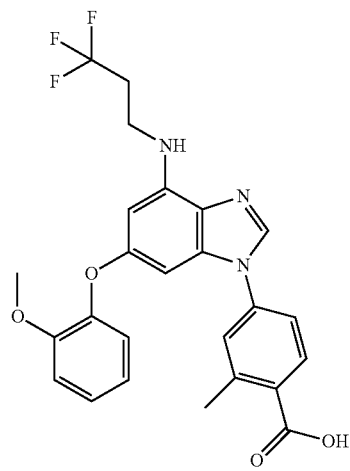

Example 41

N-cyclopropyl-4-{6-(2-methoxyphenoxy)-4-[(3,3,3-trifluoropropyl)amino]-1H-benzimidazol-1-yl}-2-methylbenzamide

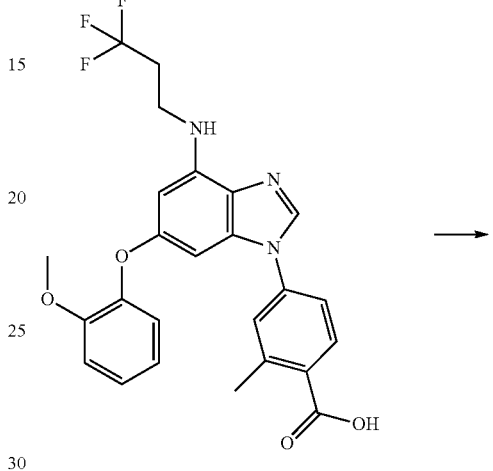

6.15 (1H), 6.88 (1H), 6.95 (1H), 7.06-7.11 (2H), 7.33-7.44 (3H), 8.23 (1H), 8.28 (1H) ppm.

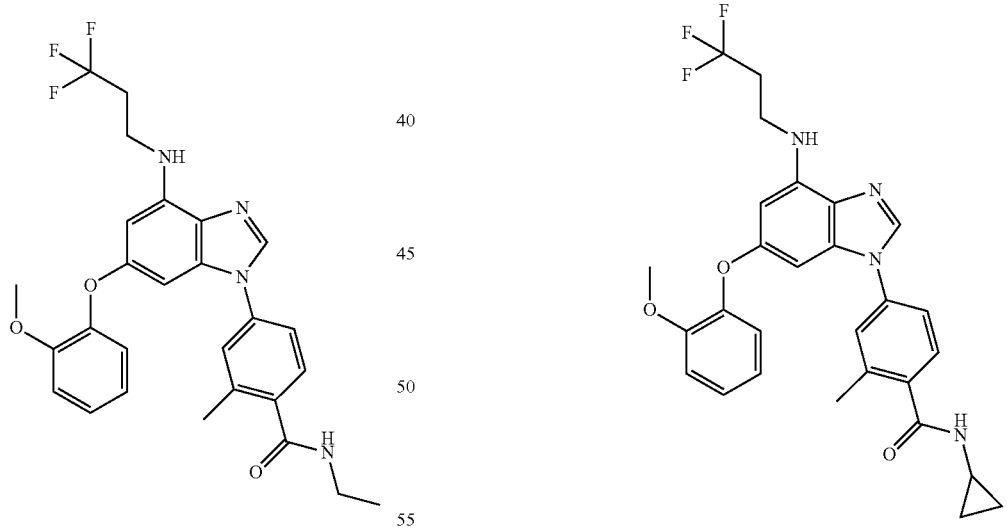

40 mg (82 μmol) 4-{6-(2-methoxyphenoxy)-4-[(3,3,3-trifluoropropyl)amino]-1H-benzimidazol-1-yl}-2-methylbenzoic acid which was prepared according to intermediate example 39a were transformed in analogy to example 10 using ethanamine to give after working up and purification 37 mg (83%) of the title compound.

$^1$H-NMR (DMSO-d6): δ=1.08 (3H), 2.34 (3H), 2.51-2.64 (2H), 3.22 (2H), 3.48 (2H), 3.72 (3H), 6.06 (1H), 6.11 (1H), 40 mg (82 μmol) 4-{6-(2-methoxyphenoxy)-4-[(3,3,3-trifluoropropyl)amino]-1H-benzimidazol-1-yl}-2-methylbenzoic acid which was prepared according to intermediate example 39a were transformed in analogy to example 10 using cyclopropanamine to give after working up and purification 31.6 mg (69%) of the title compound.

$^1$H-NMR (DMSO-d6): δ=0.49 (2H), 0.65 (2H), 2.32 (3H), 2.51-2.63 (2H), 2.80 (1H), 3.48 (2H), 3.72 (3H), 6.06 (1H), 6.11 (1H), 6.13 (1H), 6.87 (1H), 6.95 (1H), 7.06-7.11 (2H), 7.33 (1H), 7.38 (1H), 7.39 (1H), 8.23 (1H), 8.32 (1H) ppm.

Example 42

4-{6-(3-Fluoro-4-methoxyphenoxy)-4-[(tetrahydro-2H-pyran-4-ylmethyl)amino]-1H-benzimidazol-1-yl}-N,2-dimethylbenzamide

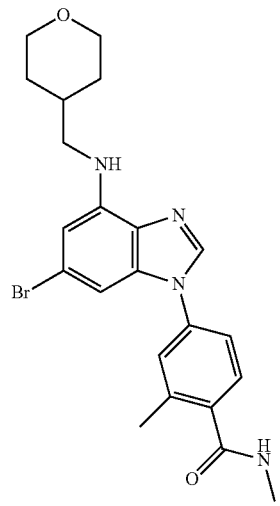

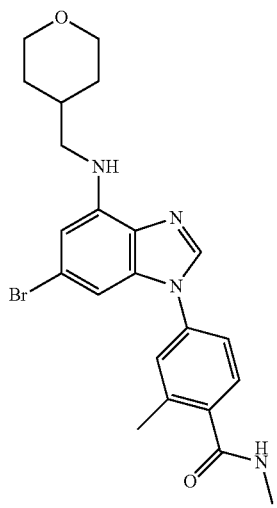

55 mg (120 μmol) 4-{6-bromo-4-[(tetrahydro-2H-pyran-4-ylmethyl)amino]-1H-benzimidazol-1-yl}-N,2-dimethylbenzamide which was prepared according to intermediate example 42a were transformed in analogy to example 4 using 3-fluoro-4-methoxyphenol to give after working up and purification 42.4 mg (65%) of the title compound.

$^1$H-NMR (CD$_3$OD): δ=1.36 (2H), 1.74 (2H), 1.93 (1H), 2.44 (3H), 2.89 (3H), 3.12 (2H), 3.40 (2H), 3.81 (3H), 3.94 (2H), 6.14 (1H), 6.29 (1H), 6.73 (1H), 6.77 (1H), 7.01 (1H), 7.37 (1H), 7.41 (1H), 7.50 (1H), 8.16 (1H) ppm.

Example 42a

4-{6-Bromo-4-[(tetrahydro-2H-pyran-4-ylmethyl)amino]-1H-benzimidazol-1-yl}-N,2-dimethylbenzamide

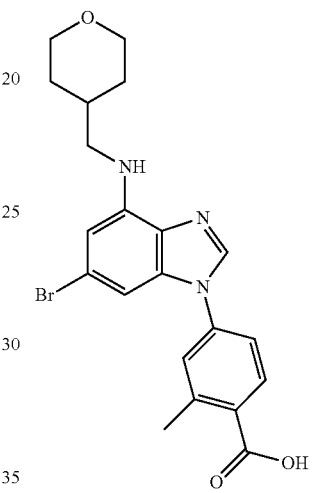

416.5 mg (937 μmol) 4-{6-bromo-4-[(tetrahydro-2H-pyran-4-ylmethyl)amino]-1H-benzimidazol-1-yl}-2-methylbenzoic acid which was prepared according to intermediate example 42b were transformed in analogy to intermediate example 10 to give after working up and purification 327 mg (69%) of the title compound.

example 42c were transformed in analogy to example 10a to give after working up and purification 1.25 g (82%) of the title compound.

Example 42b

4-{6-Bromo-4-[(tetrahydro-2H-pyran-4-ylmethyl) amino]-1H-benzimidazol-1-yl}-2-methylbenzoic acid

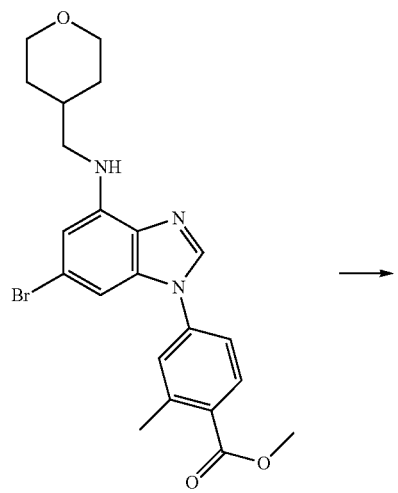

Example 42c

Methyl 4-{6-bromo-4-[(tetrahydro-2H-pyran-4-ylmethyl)amino]-1H-benzimidazol-1-yl}-2-methylbenzoate e

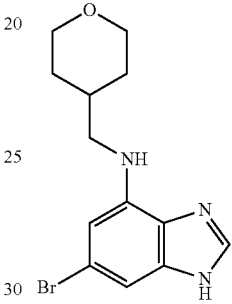

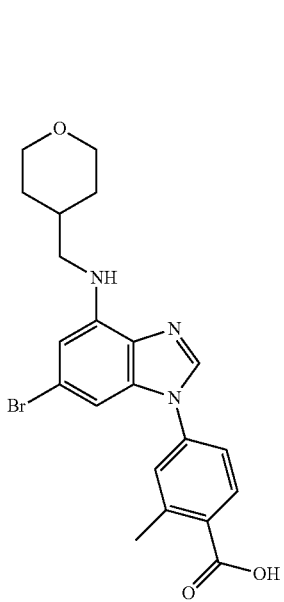

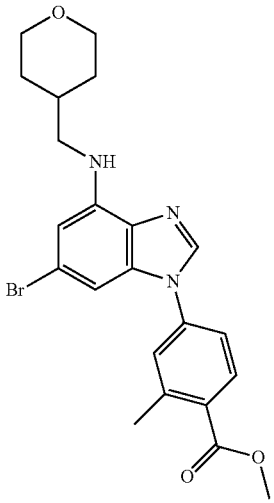

1.5 g (3.27 mmol) methyl 4-{6-bromo-4-[(tetrahydro-2H-pyran-4-ylmethyl)amino]-1H-benzimidazol-1-yl}-2-methylbenzoate which was prepared according to intermediate 3.0 g (9.67 mmol) 6-bromo-N-(tetrahydro-2H-pyran-4-ylmethyl)-1H-benzimidazol-4-amine which was prepared according to intermediate example 12-1 were transformed in analogy to intermediate example 11-1 using [4-(methoxycarbonyl)-3-methylphenyl]boronic acid to give after working up and purification 1.50 g (30%) of the title compound.

Example 43

N-ethyl-4-{6-(3-fluoro-4-methoxyphenoxy)-4-[(tetrahydro-2H-pyran-4-ylmethyl)amino]-1H-benzimidazol-1-yl}-2-methylbenzamide

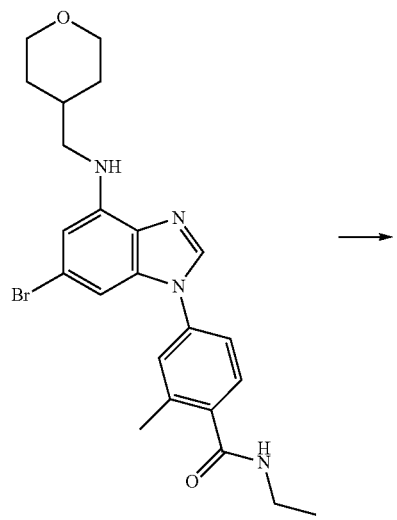

100 mg (212 µmol) 4-{6-bromo-4-[(tetrahydro-2H-pyran-4-ylmethyl)amino]-1H-benzimidazol-1-yl}-N-ethyl-2-methylbenzamide which was prepared according to intermediate example 43a were transformed in analogy to example 4 using 3-fluoro-4-methoxyphenol to give after working up and purification 33.4 mg (28%) of the title compound.

$^1$H-NMR (CDCl$_3$): δ=1.27 (3H), 1.40 (2H), 1.78 (2H), 1.97 (1H), 2.51 (3H), 3.16 (2H), 3.40 (2H), 3.51 (2H), 3.87 (3H), 4.00 (2H), 5.40 (1H), 5.78 (1H), 6.17 (1H), 6.32 (1H), 6.75 (1H), 6.81 (1H), 6.90 (1H), 7.30 (2H), 7.50 (1H), 7.96 (1H) ppm.

Example 43a

4-{6-bromo-4-[(tetrahydro-2H-pyran-4-ylmethyl)amino]-1H-benzimidazol-1-yl}-N-ethyl-2-methylbenzamide

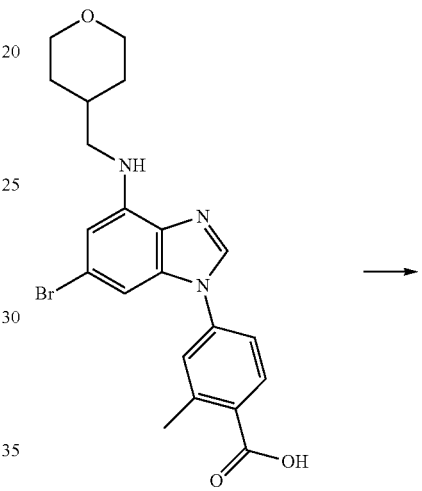

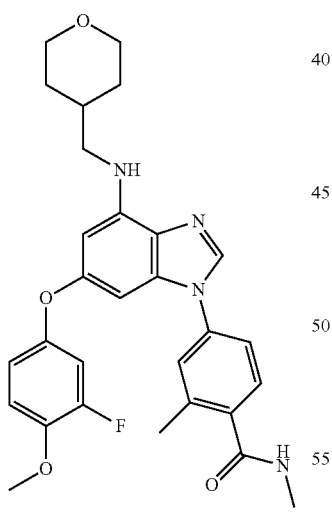

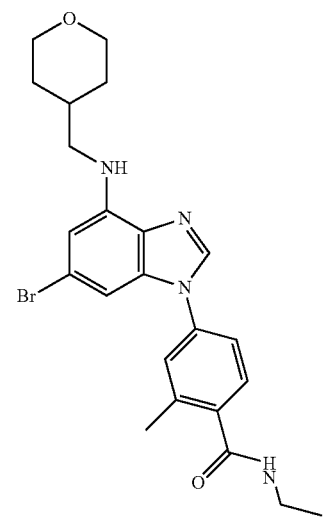

416.5 mg (937 µmol) 4-{6-bromo-4-[(tetrahydro-2H-pyran-4-ylmethyl)amino]-1H-benzimidazol-1-yl}-2-methylbenzoic acid which was prepared according to intermediate example 42b were transformed in analogy to intermediate example 10 using ethanamine to give after working up and purification 393 mg (80%) of the title compound.

Example 44

N-cyclopropyl-4-{6-(3-fluoro-4-methoxyphenoxy)-4-[(tetrahydro-2H-pyran-4-ylmethyl)amino]-1H-benzimidazol-1-yl}-2-methylbenzamide

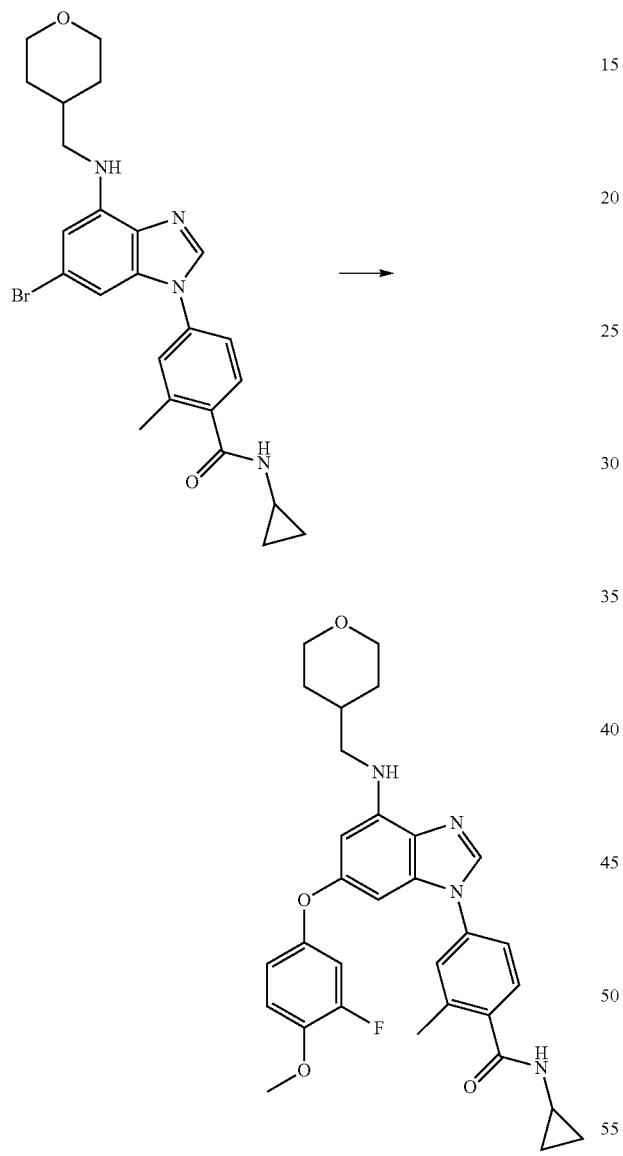

100 mg (207 μmol) 4-{6-bromo-4-[(tetrahydro-2H-pyran-4-ylmethyl)amino]-1H-benzimidazol-1-yl}-N-cyclopropyl-2-methylbenzamide which was prepared according to intermediate example 13-1 were transformed in analogy to example 14 using 3-fluoro-4-methoxyphenol to give after working up and purification 29.0 mg (24%) of the title compound.

$^1$H-NMR (CDCl$_3$): δ=0.62 (2H), 0.91 (2H), 1.40 (2H), 1.77 (2H), 1.95 (1H), 2.50 (3H), 2.91 (1H), 3.15 (2H), 3.39 (2H), 3.86 (3H), 3.99 (2H), 5.29 (1H), 5.94 (1H), 6.16 (1H), 6.31 (1H), 6.68-6.97 (3H), 7.26 (2H), 7.46 (1H), 7.92 (1H) ppm.

Example 45

4-{6-[4-(Benzyloxy)phenoxy]-4-[(3,3,3-trifluoropropyl)amino]-1H-benzimidazol-1-yl}-N-cyclopropyl-2-methylbenzamide

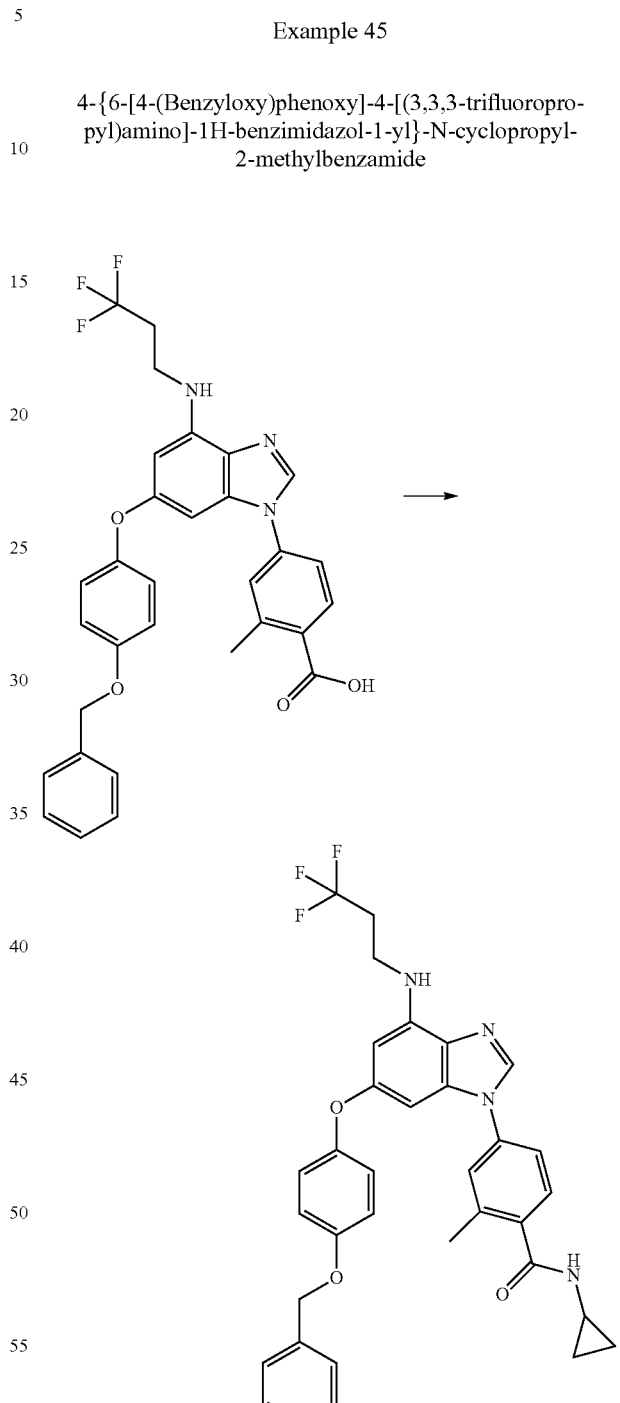

31 mg (55 μmol) 4-{6-[4-(benzyloxy)phenoxy]-4-[(3,3,3-trifluoropropyl)amino]-1H-benzimidazol-1-yl}-2-methylbenzoic acid which was prepared according to intermediate example 45a were transformed in analogy to example 10 using cyclopropanamine to give after working up and purification 26.3 mg (75%) of the title compound.

¹H-NMR (CDCl₃): δ=0.63 (2H), 0.91 (2H), 2.42-2.57 (2H), 2.49 (3H), 2.92 (1H), 3.58 (2H), 5.04 (2H), 5.09 (1H), 5.92 (1H), 6.18 (1H), 6.38 (1H), 6.90-7.01 (4H), 7.23-7.47 (8H), 7.85 (1H) ppm.

Example 45a

4-{6-[4-(Benzyloxy)phenoxy]-4-[(3,3,3-trifluoropropyl)amino]-1H-benzimidazol-1-yl}-2-methylbenzoic acid intermediate example 10a to give after working up and purification 99 mg (40%) of the title compound.

Example 45b

Methyl 4-{6-[4-(benzyloxy)phenoxy]-4-[(3,3,3-trifluoropropyl)amino]-1H-benzimidazol-1-yl}-2-methylbenzoate

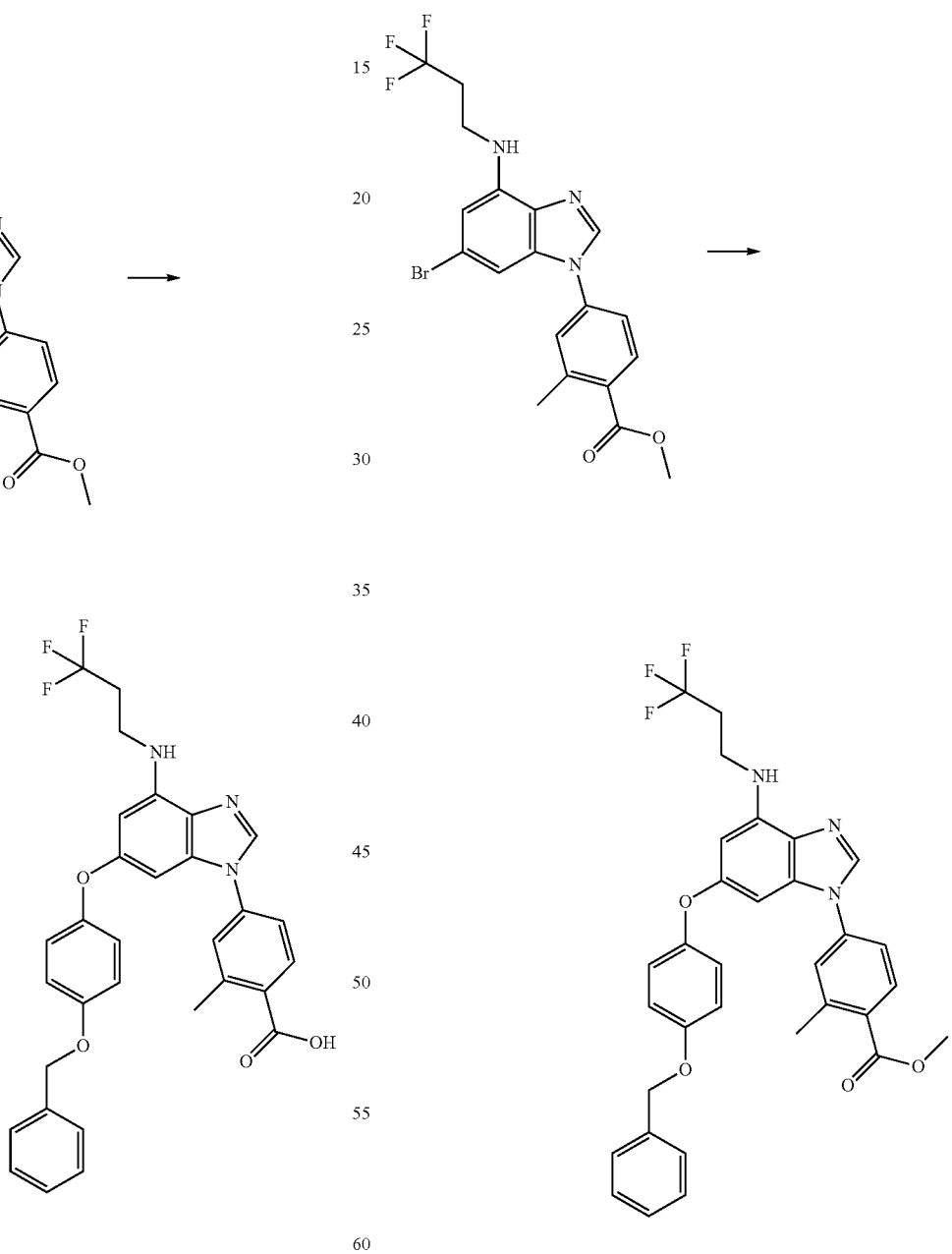

252 mg (max. 438 μmol) methyl 4-{6-[4-(benzyloxy)phenoxy]-4-[(3,3,3-trifluoropropyl)amino]-1H-benzimidazol-1-yl}-2-methylbenzoate which was prepared according to intermediate example 45b were transformed in analogy to 200 mg (438 μmol) methyl 4-{6-bromo-4-[(3,3,3-trifluoropropyl)amino]-1H-benzimidazol-1-yl}-2-methylbenzoate which was prepared according to intermediate example 10c were transformed in analogy to example 4 using 4-(benzyloxy)phenol to give after working up the title compound as crude product that was used without further purification.

Example 46

4-{6-[4-(Benzyloxy)phenoxy]-4-[(3,3,3-trifluoropropyl)amino]-1H-benzimidazol-1-yl}-N-ethyl-2-methylbenzamide

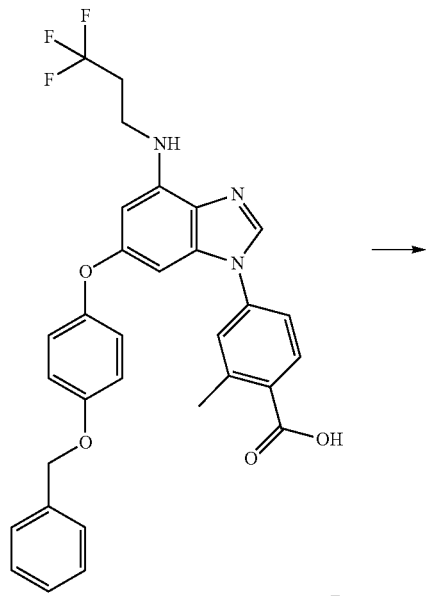

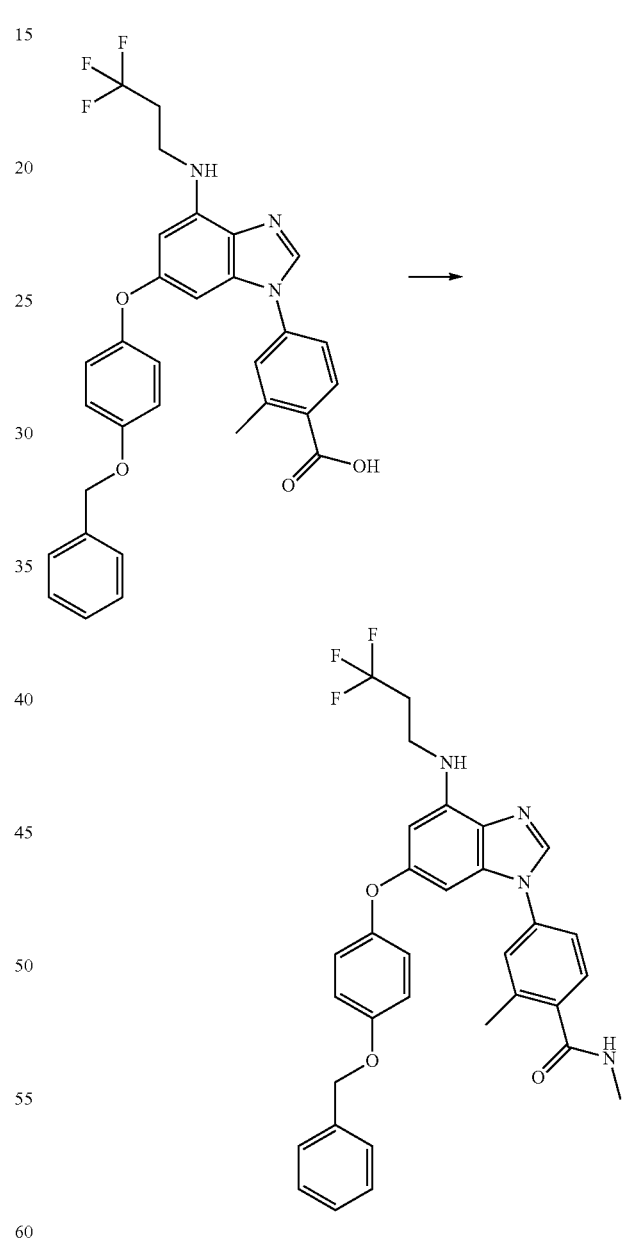

31 mg (55 μmol) 4-{6-[4-(benzyloxy)phenoxy]-4-[(3,3,3-trifluoropropyl)amino]-1H-benzimidazol-1-yl}-2-methylbenzoic acid which was prepared according to intermediate example 45a were transformed in analogy to example 10 using ethanamine to give after working up and purification 24.8 mg (73%) of the title compound.

$^1$H-NMR (CDCl$_3$): δ=1.27 (3H), 2.42-2.58 (2H), 2.50 (3H), 3.51 (2H), 3.58 (2H), 5.04 (2H), 5.10 (1H), 5.78 (1H), 6.18 (1H), 6.39 (1H), 6.90-7.00 (4H), 7.24-7.46 (7H), 7.48 (1H), 7.86 (1H) ppm.

Example 47

4-{6-[4-(Benzyloxy)phenoxy]-4-[(3,3,3-trifluoropropyl)amino]-1H-benzimidazol-1-yl}-N,2-dimethylbenzamide 31 mg (55 μmol) 4-{6-[4-(benzyloxy)phenoxy]-4-[(3,3,3-trifluoropropyl)amino]-1H-benzimidazol-1-yl}-2-methylbenzoic acid which was prepared according to intermediate example 45a were transformed in analogy to example 10 to give after working up and purification 22.3 mg (70%) of the title compound.

¹H-NMR (CDCl₃): δ=2.42-2.58 (2H), 2.50 (3H), 3.03 (3H), 3.58 (2H), 5.04 (2H), 5.10 (1H), 5.79 (1H), 6.18 (1H), 6.39 (1H), 6.90-7.00 (4H), 7.25-7.46 (7H), 7.49 (1H), 7.86 (1H) ppm.

¹H-NMR (DMSO-d6): δ=2.35 (3H), 2.52-2.64 (2H), 2.73 (3H), 3.49 (2H), 6.07 (1H), 6.11 (1H), 6.19 (1H), 6.70 (2H), 6.84 (2H), 7.36 (1H), 7.41 (1H), 7.44 (1H), 8.22 (1H), 8.24 (1H), 9.20 (1H) ppm.

Example 48

4-{6-(4-Hydroxyphenoxy)-4-[(3,3,3-trifluoropropyl)amino]-1H-benzimidazol-1-yl}-N,2-dimethylbenzamide

Example 49

N-ethyl-4-{6-(4-hydroxyphenoxy)-4-[(3,3,3-trifluoropropyl)amino]-1H-benzimidazol-1-yl}-2-methylbenzamide

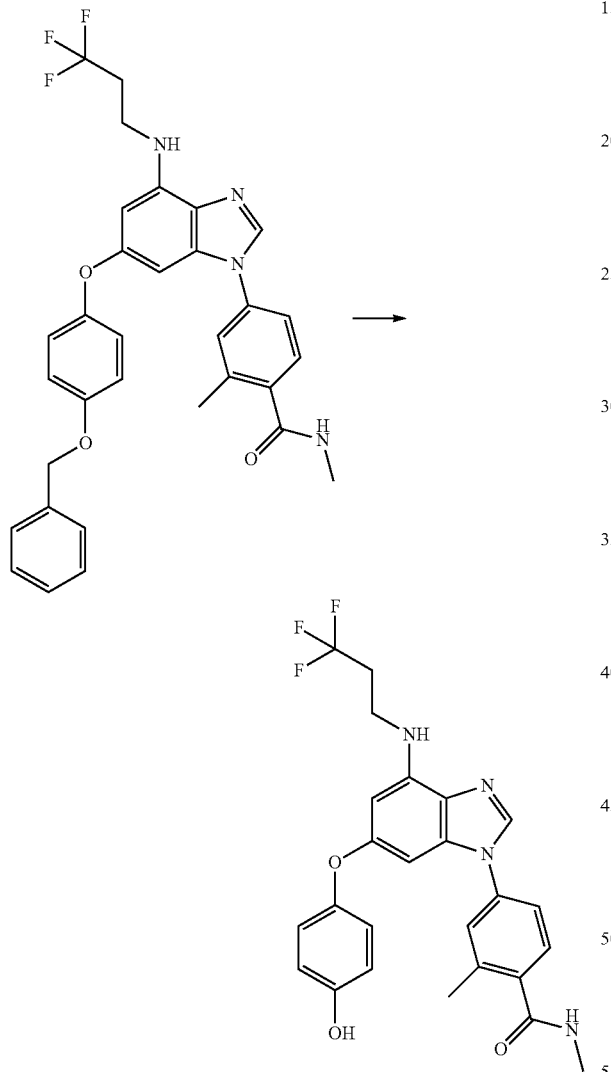

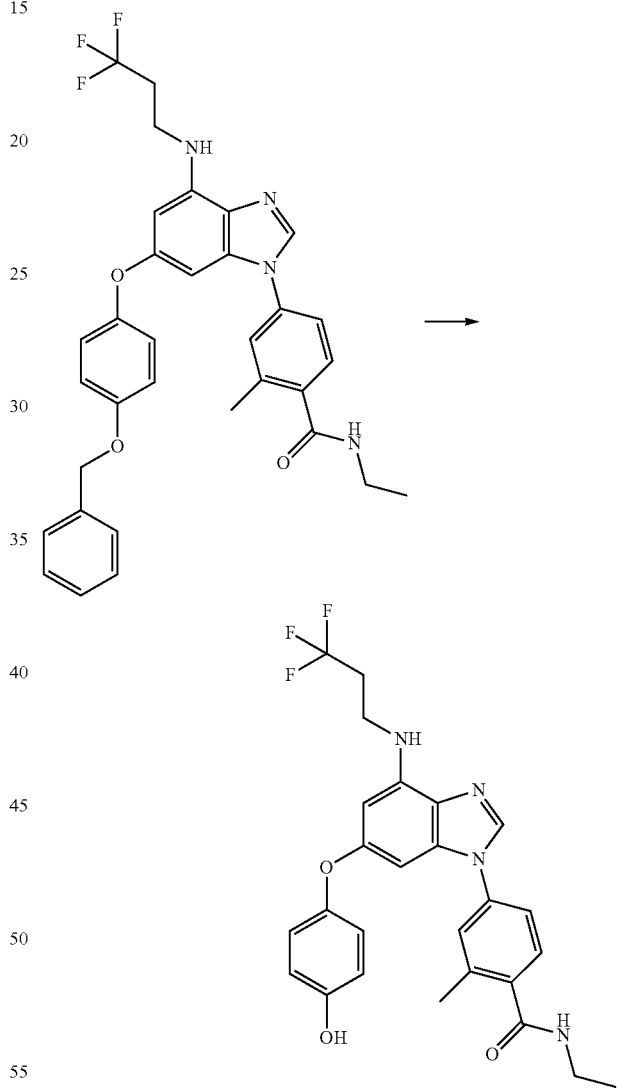

To a solution of 17.2 mg (30 µmol) 4-{6-[4-(Benzyloxy)phenoxy]-4-[(3,3,3-trifluoropropyl)amino]-1H-benzimidazol-1-yl}-N,2-dimethylbenzamide which was prepared according to example 47 in 0.7 mL ethanol were added 3.19 mg palladium on charcoal (10%) and the mixture was vigorously stirred under an atmosphere of hydrogen for 2 hours at 23° C. After filtration and removal of the solvent the residue was purified by chromatography to give 8.2 mg (54%) of the title compound.

19.5 mg (33 µmol) 4-{6-[4-(Benzyloxy)phenoxy]-4-[(3,3,3-trifluoropropyl)amino]-1H-benzimidazol-1-yl}-N-ethyl-2-methylbenzamide which was prepared according to example 46 were transformed in analogy to example 48 to give after working up and purification 8.3 mg (60%) of the title compound.

¹H-NMR (DMSO-d6): δ=1.08 (3H), 2.35 (3H), 2.52-2.64 (2H), 3.22 (2H), 3.49 (2H), 6.07 (1H), 6.11 (1H), 6.19 (1H), 6.70 (2H), 6.84 (2H), 7.36 (1H), 7.41 (1H), 7.42 (1H), 8.23 (1H), 8.29 (1H), 9.20 (1H) ppm.

Example 50

N-cyclopropyl-4-{6-(4-hydroxyphenoxy)-4-[(3,3,3-trifluoropropyl)amino]-1H-benzimidazol-1-yl}-2-methylbenzamide

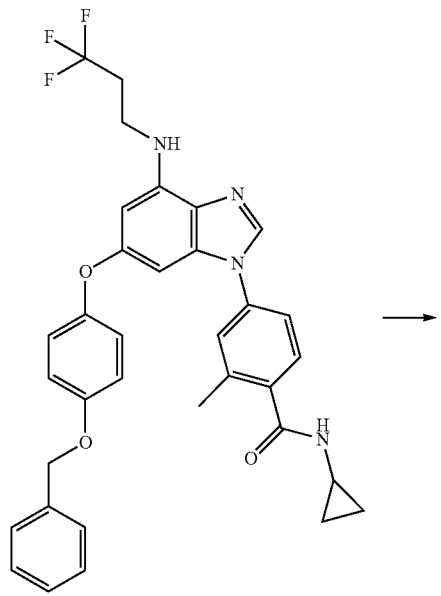

20.4 mg (34 μmol) 4-{6-[4-(Benzyloxy)phenoxy]-4-[(3,3,3-trifluoropropyl)amino]-1H-benzimidazol-1-yl}-N-cyclopropyl-2-methylbenzamide which was prepared according to example 45 were transformed in analogy to example 48 to give after working up and purification 11.2 mg (61%) of the title compound.

$^1$H-NMR (DMSO-d6): δ=0.49 (2H), 0.65 (2H), 2.33 (3H), 2.52-2.64 (2H), 2.80 (1H), 3.49 (2H), 6.07 (1H), 6.11 (1H), 6.17 (1H), 6.69 (2H), 6.84 (2H), 7.33-7.43 (3H), 8.22 (1H), 8.33 (1H), 9.20 (1H) ppm.

Example 51

4,4'-{4-[(3,3,3-Trifluoropropyl)amino]-1H-benzimidazole-1,6-diyl}bis(N-cyclopropyl-2-methylbenzamide)

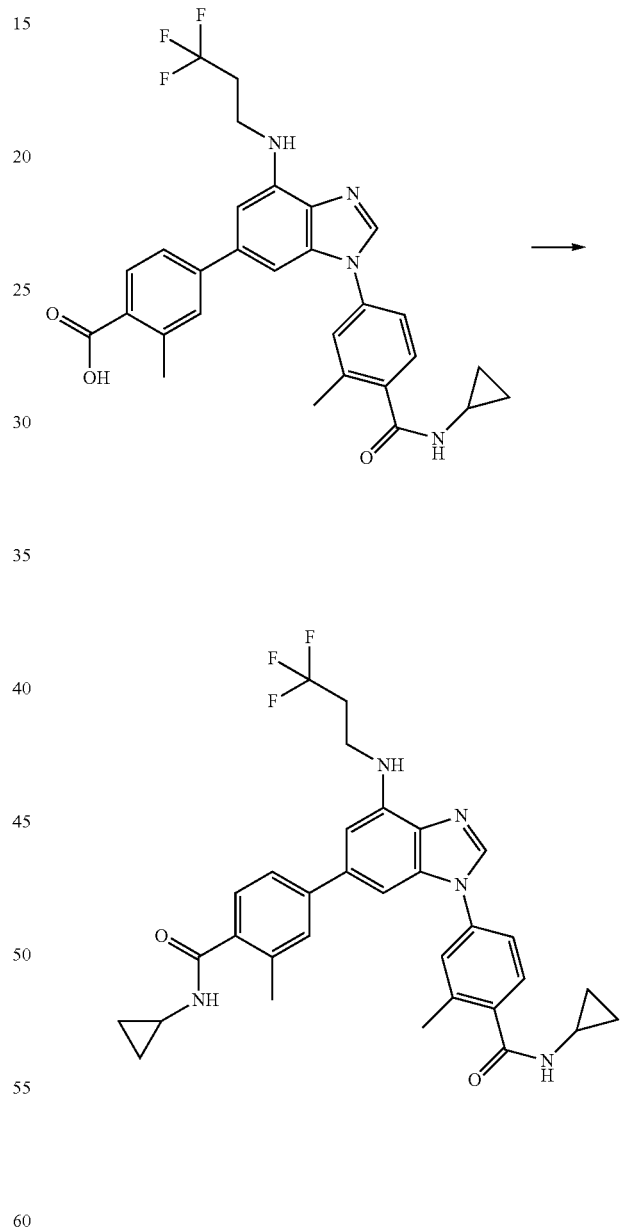

20 mg (37 μmol) 4-{1-[4-(cyclopropylcarbamoyl)-3-methylphenyl]-4-[(3,3,3-trifluoropropyl)amino]-1H-benzimidazol-6-yl}-2-methylbenzoic acid which was prepared according to intermediate example 51a were transformed in analogy to example 10 using cyclopropanamine to give after working up and purification 10.9 mg (48%) of the title compound.

¹H-NMR (DMSO-d6): δ=0.50 (4H), 0.66 (4H), 2.35 (3H), 2.39 (3H), 2.59-2.71 (2H), 2.81 (2H), 3.61 (2H), 6.05 (1H), 6.60 (1H), 6.96 (1H), 7.30 (1H), 7.43-7.56 (5H), 8.21 (1H), 8.36 (1H), 8.37 (1H) ppm.

Example 51a

4-{1-[4-(Cyclopropylcarbamoyl)-3-methylphenyl]-4-[(3,3,3-trifluoropropyl)amino]-1H-benzimidazol-6-yl}-2-methylbenzoic acid analogy to intermediate example 11a to give after working up and purification 95 mg (49%) of the title compound.

Example 51b

Methyl 4-{1-[4-(cyclopropylcarbamoyl)-3-methylphenyl]-4-[(3,3,3-trifluoropropyl)amino]-1H-benzimidazol-6-yl}-2-methylbenzoate

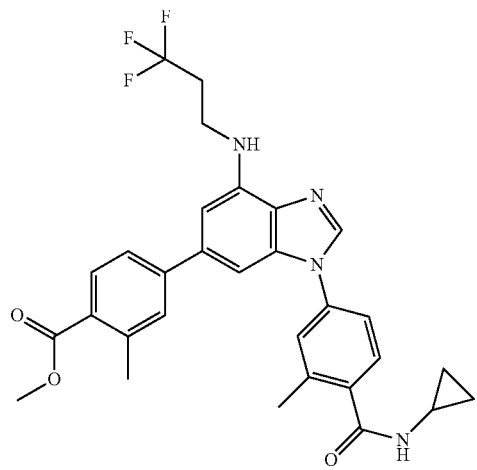

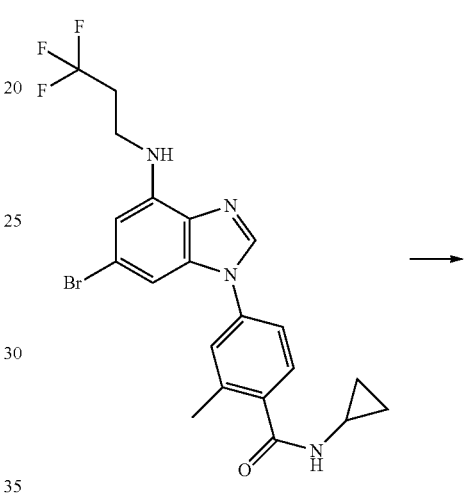

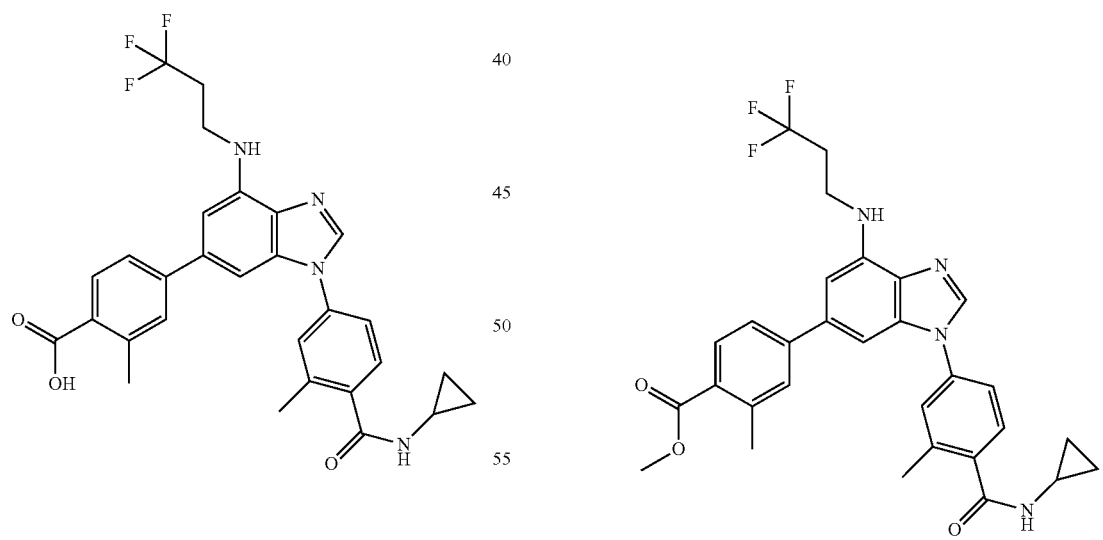

187 mg (340 µmol) methyl 4-{1-[4-(cyclopropylcarbamoyl)-3-methylphenyl]-4-[(3,3,3-trifluoropropyl)amino]-1H-benzimidazol-6-yl}-2-methylbenzoate which was prepared according to intermediate example 51b were transformed in 200 mg (416 µmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 20 using [4-(methoxycarbonyl)-3-methylphenyl]boronic acid to give after working up and purification 192 mg (84%) of the title compound.

6.04 (1H), 6.62 (1H), 6.97 (1H), 7.34 (1H), 7.44-7.56 (5H), 8.09 (1H), 8.36 (1H), 8.37 (1H) ppm.

Example 52

4-{1-[4-(Cyclopropylcarbamoyl)-3-methylphenyl]-4-[(3,3,3-trifluoropropyl)amino]-1H-benzimidazol-6-yl}-N,2-dimethylbenzamide

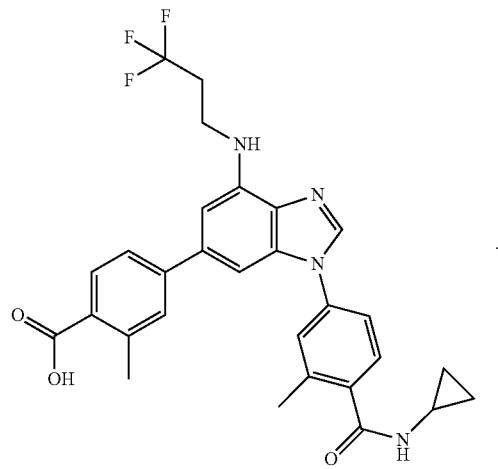

→

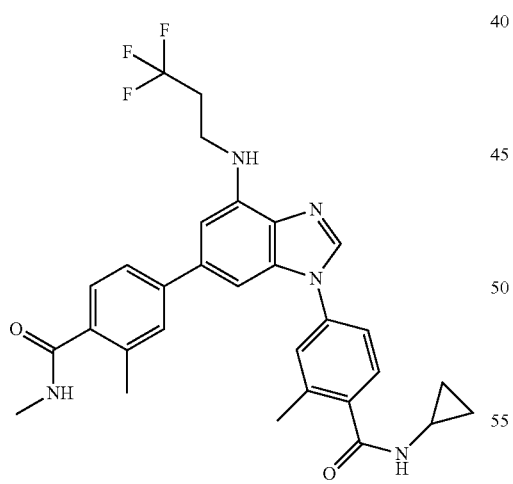

20 mg (37 μmol) 4-{1-[4-(cyclopropylcarbamoyl)-3-methylphenyl]-4-[(3,3,3-trifluoropropyl)amino]-1H-benzimidazol-6-yl}-2-methylbenzoic acid which was prepared according to intermediate example 51a were transformed in analogy to example 10 to give after working up and purification 16.2 mg (75%) of the title compound.

¹H-NMR (DMSO-d6): δ=0.52 (2H), 0.67 (2H), 2.36 (3H), 2.40 (3H), 2.60-2.70 (2H), 2.73 (3H), 2.83 (1H), 3.63 (2H),

Example 53

4-{1-[4-(Cyclopropylcarbamoyl)-3-methylphenyl]-4-[(3,3,3-trifluoropropyl)amino]-1H-benzimidazol-6-yl}-N-ethyl-2-methylbenzamide

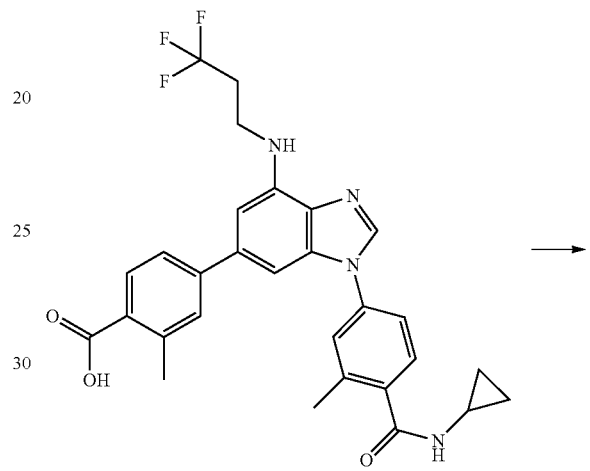

→

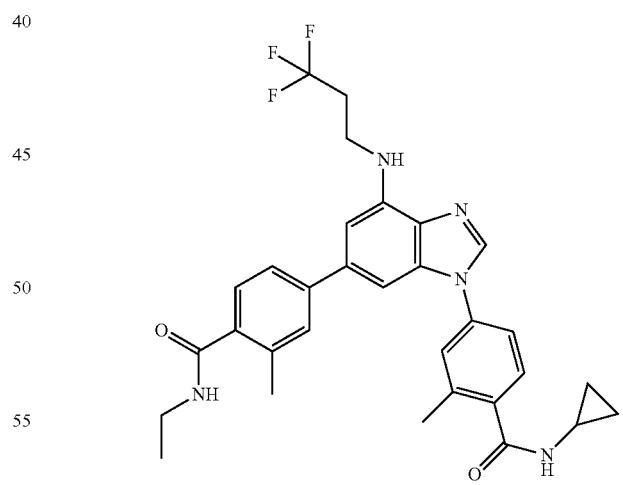

20 mg (37 μmol) 4-{1-[4-(cyclopropylcarbamoyl)-3-methylphenyl]-4-[(3,3,3-trifluoropropyl)amino]-1H-benzimidazol-6-yl}-2-methylbenzoic acid which was prepared according to intermediate example 51a were transformed in analogy to example 10 using ethanamine to give after working up and purification 11.5 mg (52%) of the title compound.

¹H-NMR (DMSO-d6D): δ=0.52 (2H), 0.67 (2H), 1.09 (3H), 2.36 (3H), 2.40 (3H), 2.60-2.72 (2H), 2.83 (1H), 3.22

(2H), 3.63 (2H), 6.05 (1H), 6.62 (1H), 6.97 (1H), 7.32 (1H), 7.44-7.56 (5H), 8.16 (1H), 8.36 (1H), 8.37 (1H) ppm.

Example 54

N-cyclopropyl-4-{6-(2-hydroxyphenoxy)-4-[(3,3,3-trifluoropropyl)amino]-1H-benzimidazol-1-yl}-2-methylbenzamide

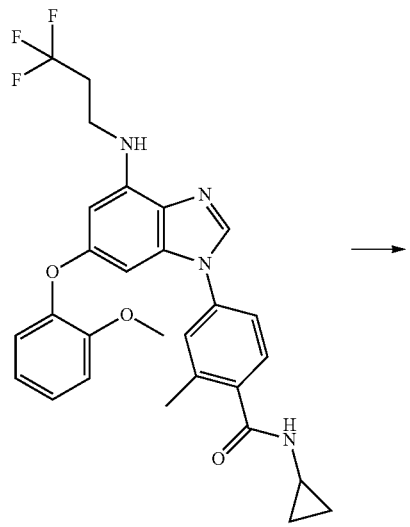

→

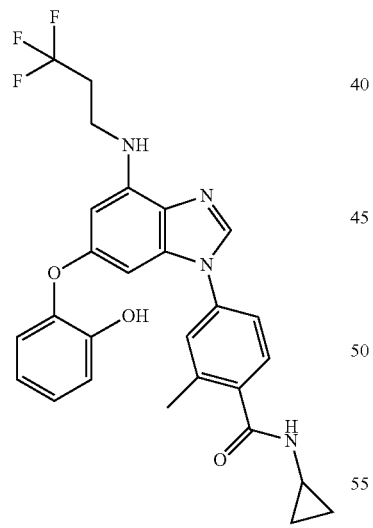

To a solution of 26 mg (50 µmol)N-cyclopropyl-4-{6-(2-methoxyphenoxy)-4-[(3,3,3-trifluoropropyl)amino]-1H-benzimidazol-1-yl}-2-methylbenzamide which was prepared according to example 41 in 3.9 mL dichloromethane were added 297 µL of a 2M boron tribromide solution in dichloromethane and the mixture was stirred at 23° C. overnight. Methanol was added and solvents were removed. The residue was purified by chromatography to give 12.1 mg (45%) of the title compound.

$^1$H-NMR (DMSO-d6): δ=0.48 (2H), 0.65 (2H), 2.32 (3H), 2.49-2.66 (2H), 2.79 (1H), 3.49 (2H), 6.06-6.17 (3H), 6.72 (1H), 6.83-6.98 (3H), 7.30-7.43 (3H), 8.22 (1H), 8.34 (1H), 9.35 (1H) ppm.

Example 55

N-ethyl-4-{6-(2-hydroxyphenoxy)-4-[(3,3,3-trifluoropropyl)amino]-1H-benzimidazol-1-yl}-2-methylbenzamide

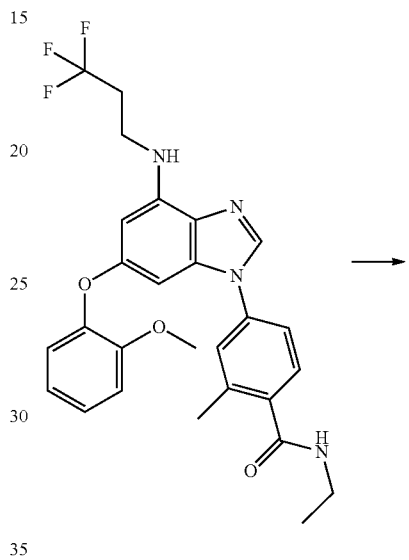

→

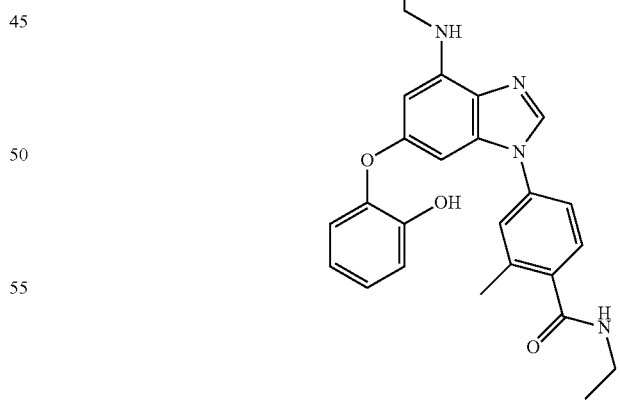

31 mg (60 µmol)N-ethyl-4-{6-(2-methoxyphenoxy)-4-[(3,3,3-trifluoropropyl)amino]-1H-benzimidazol-1-yl}-2-methylbenzamide which was prepared according to example 40 were transformed in analogy to example 54 to give after working up and purification 19.2 mg (60%) of the title compound.

¹H-NMR (DMSO-d6): δ=1.08 (3H), 2.33 (3H), 2.49-2.66 (2H), 3.22 (2H), 3.49 (2H), 6.03-6.30 (3H), 6.72 (1H), 6.84-7.01 (3H), 7.33-7.45 (3H), 8.28-8.38 (2H), 9.37 (1H) ppm.

¹H-NMR (DMSO-d6): δ=2.34 (3H), 2.52-2.64 (2H), 2.72 (3H), 3.49 (2H), 6.08 (1H), 6.10 (1H), 6.17 (1H), 6.72 (1H), 6.87-6.96 (3H), 7.34 (1H), 7.39 (1H), 7.43 (1H), 8.19-8.25 (2H), 9.36 (1H) ppm.

Example 56

4-{6-(2-hydroxyphenoxy)-4-[(3,3,3-trifluoropropyl)amino]-1H-benzimidazol-1-yl}-N,2-dimethylbenzamide Example 57

N-cyclopropyl-4-{6-(3-fluoro-2-methoxyphenoxy)-4-[(3,3,3-trifluoropropyl)amino]-1H-benzimidazol-1-yl}-2-methylbenzamide

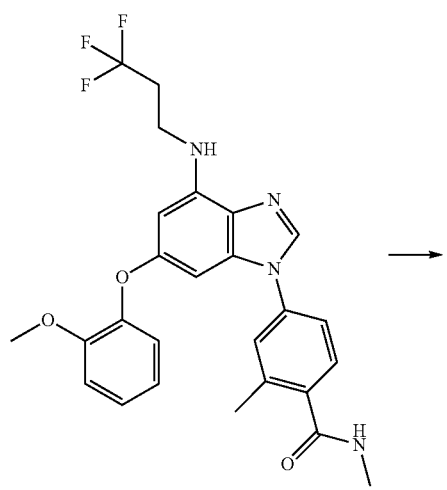

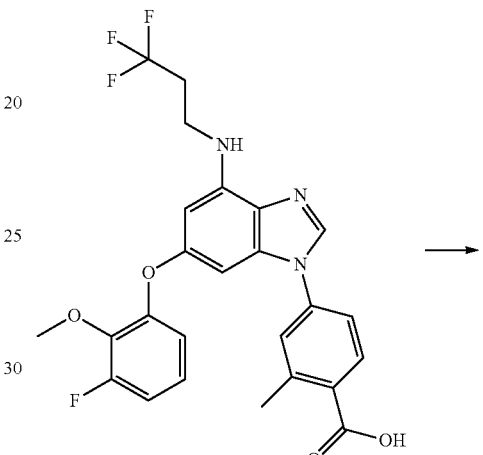

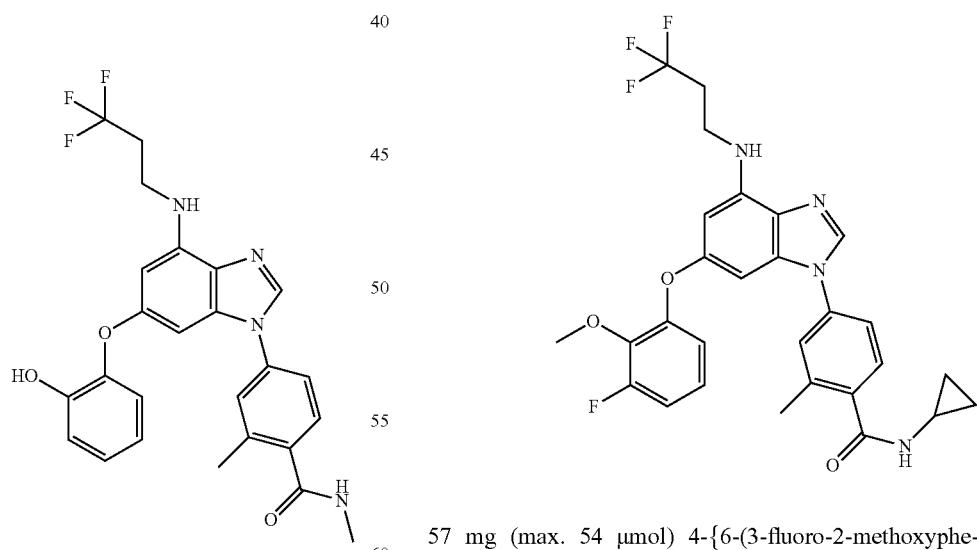

32 mg (64 µmol) 4-{6-(2-methoxyphenoxy)-4-[(3,3,3-trifluoropropyl)amino]-1H-benzimidazol-1-yl}-N,2-dimethylbenzamide which was prepared according to example 39 were transformed in analogy to example 54 to give after working up and purification 56.9 mg (70%) of the title compound.

57 mg (max. 54 µmol) 4-{6-(3-fluoro-2-methoxyphenoxy)-4-[(3,3,3-trifluoropropyl)amino]-1H-benzimidazol-1-yl}-2-methylbenzoic acid which was prepared according to intermediate example 57a were transformed in analogy to example 10 using cyclopropanamine to give after working up and purification 16.1 mg (50%) of the title compound.

¹H-NMR (CDCl₃): δ=0.63 (2H), 0.91 (2H), 2.41-2.62 (2H), 2.50 (3H), 2.92 (1H), 3.59 (1H), 3.95 (3H), 5.23 (1H), 5.90 (1H), 6.21 (1H), 6.39 (1H), 6.71 (1H), 6.79-7.00 (2H), 7.21-7.36 (3H), 7.46 (1H), 7.89 (1H) ppm.

Example 57a

4-{6-(3-fluoro-2-methoxyphenoxy)-4-[(3,3,3-trifluoropropyl)amino]-1H-benzimidazol-1-yl}-2-methylbenzoic acid

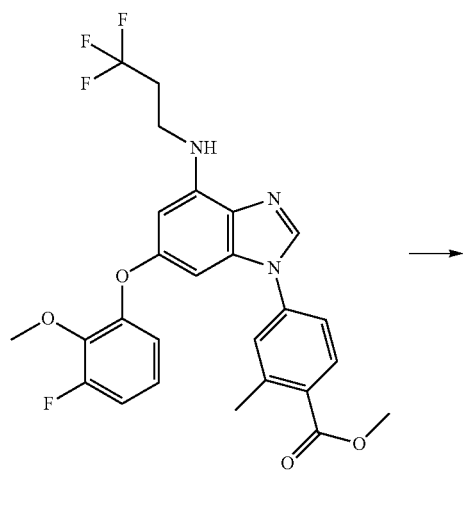

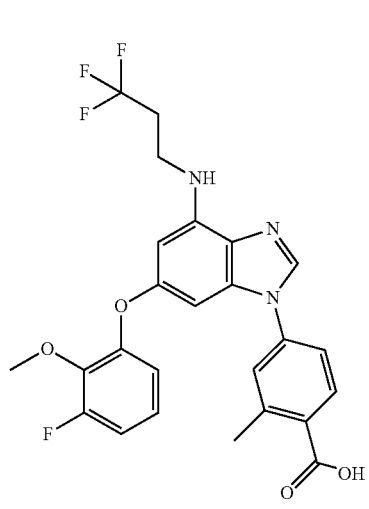

intermediate example 10a to give after working up the title compound as crude product that was used without further purification.

Example 57b methyl 4-{6-(3-fluoro-2-methoxyphenoxy)-4-[(3,3,3-trifluoropropyl)amino]-1H-benzimidazol-1-yl}-2-methylbenzoate

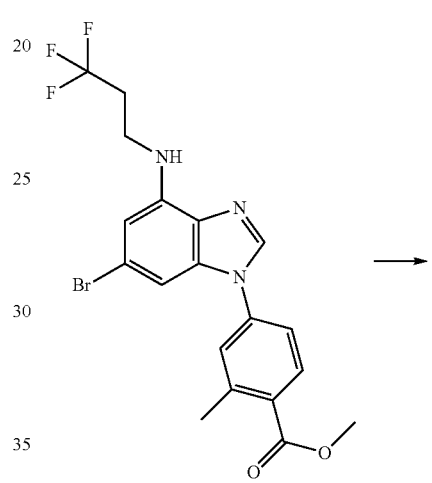

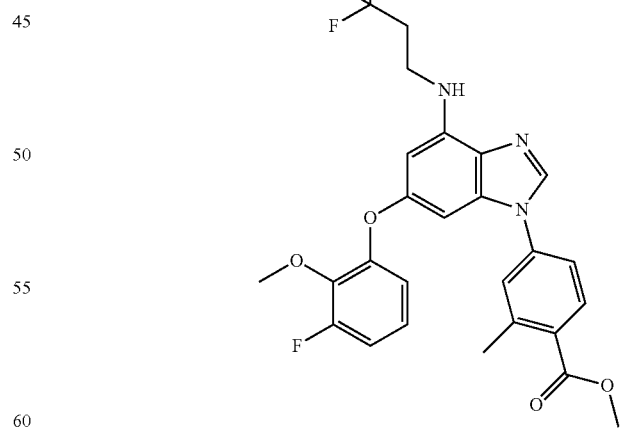

56 mg (max 54 µmol) methyl 4-{6-(3-fluoro-2-methoxyphenoxy)-4-[(3,3,3-trifluoropropyl)amino]-1H-benzimidazol-1-yl}-2-methylbenzoate which was prepared according to intermediate example 57b were transformed in analogy to 50 mg (110 µmol) methyl 4-{6-bromo-4-[(3,3,3-trifluoropropyl)amino]-1H-benzimidazol-1-yl}-2-methylbenzoate which was prepared according to intermediate example 10c were transformed in analogy to example 4 using 3-fluoro-2- methoxyphenol to give after working up the title compound as crude product that was used without further purification.

Example 59

N-cyclopropyl-2-methyl-4-{6-[3-(trifluoromethoxy)phenoxy]-4-[(3,3,3-trifluoropropyl)amino]-1H-benzimidazol-1-yl}benzamide

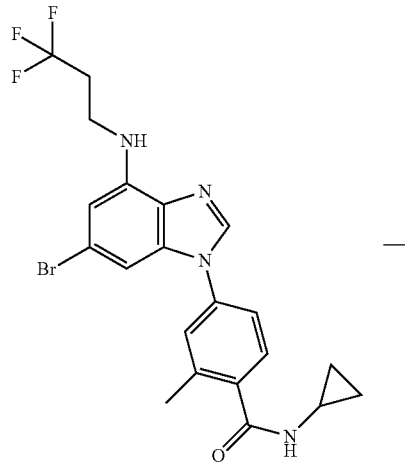

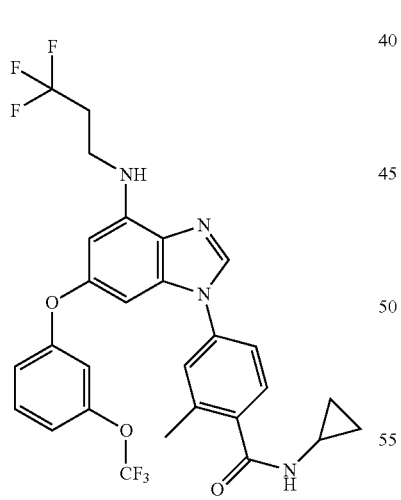

40 mg (83 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using 3-(trifluoromethoxy)phenol to give after working up and purification 16.8 mg (33%) of the title compound.

$^1$H-NMR (DMSO-d6): δ=0.49 (2H), 0.65 (2H), 2.34 (3H), 2.49-2.68 (2H), 2.79 (1H), 3.49 (2H), 6.15 (1H), 6.28 (1H), 6.45 (1H), 6.90-7.04 (3H), 7.37-7.49 (4H), 8.31-8.36 (2H) ppm.

Example 60

N-cyclopropyl-2-methyl-4-{6-[4-(morpholin-4-yl)phenoxy]-4-[(3,3,3-trifluoropropyl)amino]-1H-benzimidazol-1-yl}benzamide

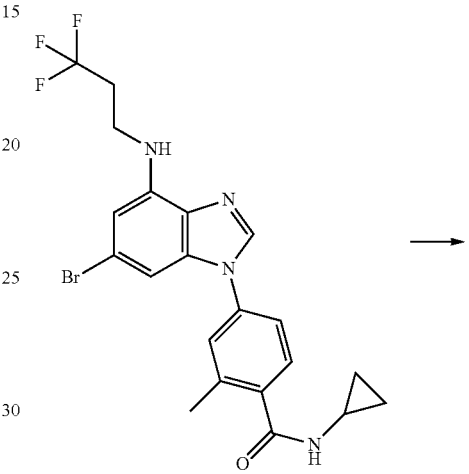

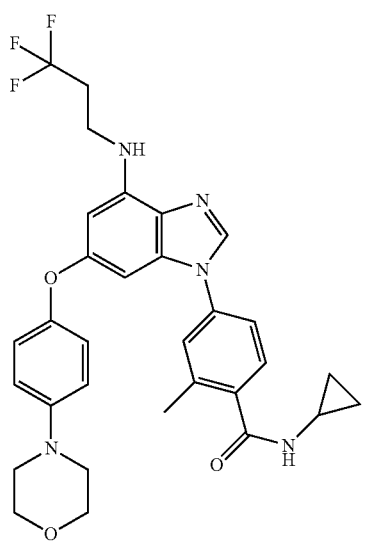

40 mg (83 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using 4-(morpholin-4-yl)phenol to give after working up and purification 5.5 mg (11%) of the title compound.

¹H-NMR (DMSO-d6): δ=0.49 (2H), 0.65 (2H), 2.33 (3H), 2.49-2.6 (2H), 2.79 (1H), 2.99 (4H), 3.48 (2H), 3.68 (4H), 6.08 (1H), 6.14 (1H), 6.21 (1H), 6.89 (4H), 7.33-7.44 (3H), 8.24 (1H), 8.34 (1H) ppm.

Example 61

N-cyclopropyl-4-{6-[4-(difluoromethoxy)phenoxy]-4-[(3,3,3-trifluoropropyl)amino]-1H-benzimidazol-1-yl}-2-methylbenzamide

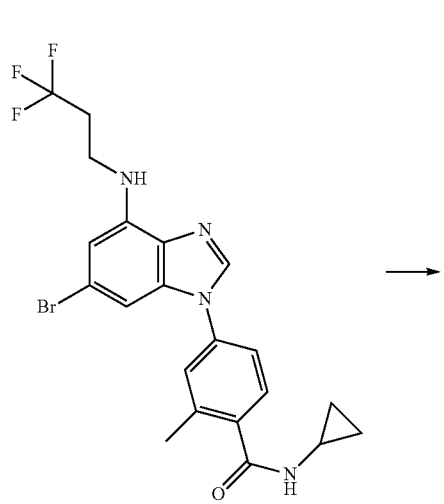

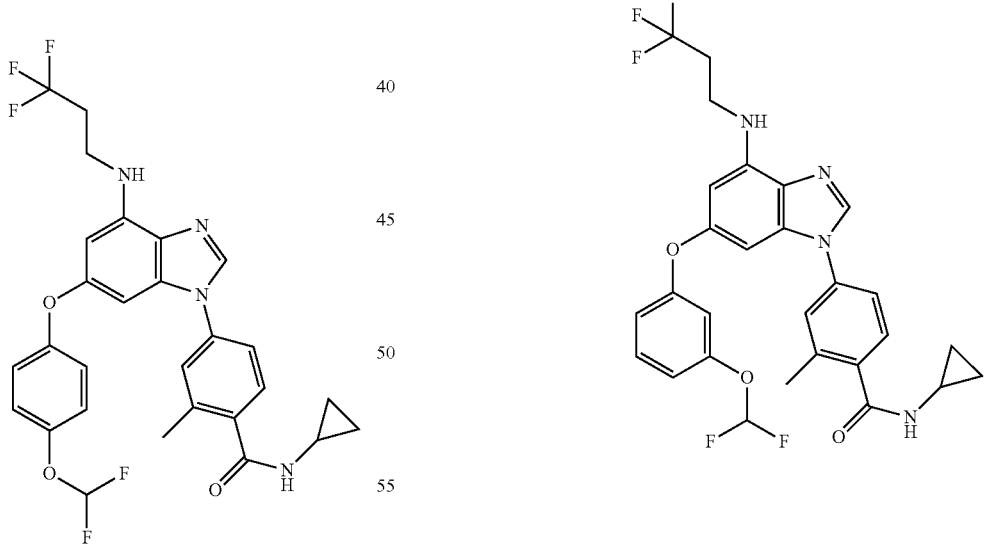

40 mg (83 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using 4-(difluoromethoxy)phenol to give after working up and purification 13.6 mg (28%) of the title compound.

¹H-NMR (DMSO-d6): δ=0.49 (2H), 0.65 (2H), 2.34 (3H), 2.51-2.65 (2H), 2.80 (1H), 3.50 (2H), 6.13 (1H), 6.20 (1H), 6.35 (1H), 7.00 (2H), 7.09 (1H), 7.11 (2H), 7.41 (2H), 7.44 (1H), 8.30 (1H), 8.32 (1H) ppm.

Example 62

N-cyclopropyl-4-{6-[3-(difluoromethoxy)phenoxy]-4-[(3,3,3-trifluoropropyl)amino]-1H-benzimidazol-1-yl}-2-methylbenzamide

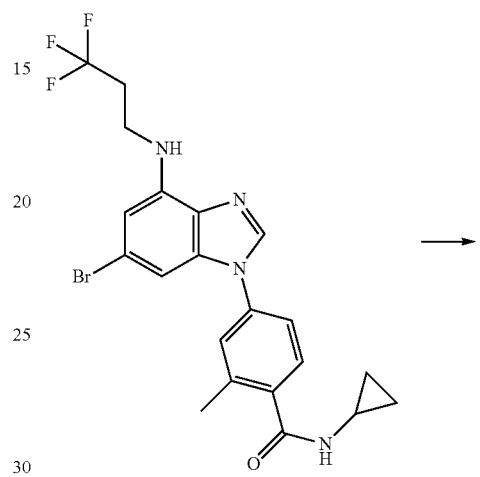

40 mg (83 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using 3-(difluoromethoxy)phenol to give after working up and purification 12.6 mg (26%) of the title compound.

¹H-NMR (DMSO-d6): δ=0.49 (2H), 0.65 (2H), 2.35 (3H), 2.49-2.646 (2H), 2.80 (1H), 3.50 (2H), 6.15 (1H), 6.23 (1H), 6.41 (1H), 6.75-6.85 (3H), 7.19 (1H), 7.32 (1H), 7.41 (2H), 7.45 (1H), 8.29-8.35 (2H) ppm.

6.25 (1H), 6.54 (1H), 6.72-6.80 (2H), 6.93 (1H), 7.12 (1H), 7.21 (1H), 7.41 (2H), 7.45 (1H), 8.13 (1H), 8.34 (1H) ppm.

Example 63

N-cyclopropyl-4-{6-[(2-methoxyphenyl)amino]-4-[(3,3,3-trifluoropropyl)amino]-1H-benzimidazol-1-yl}-2-methylbenzamide Example 64

N-cyclopropyl-2-methyl-4-{6-[3-(methylsulfonyl)phenoxy]-4-[(3,3,3-trifluoropropyl)amino]-1H-benzimidazol-1-yl}benzamide

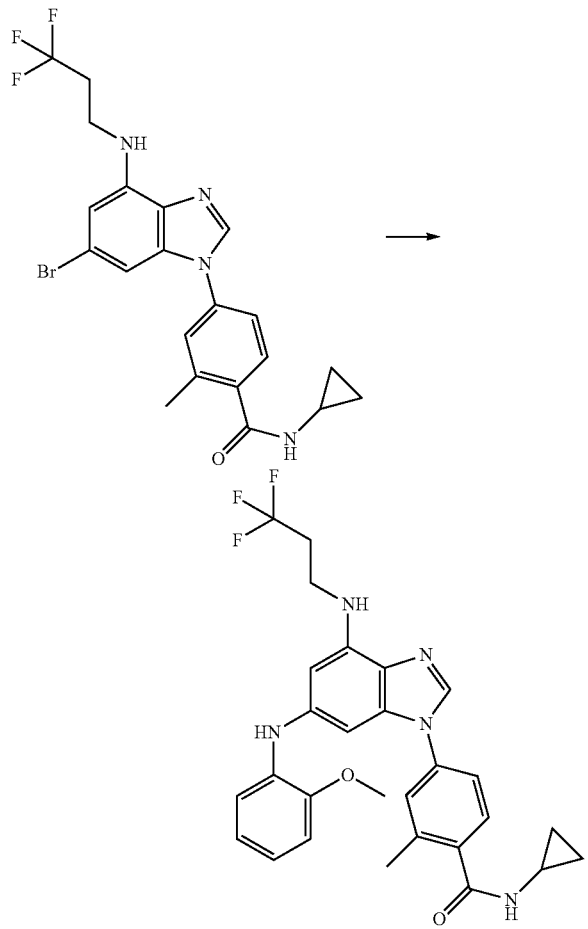

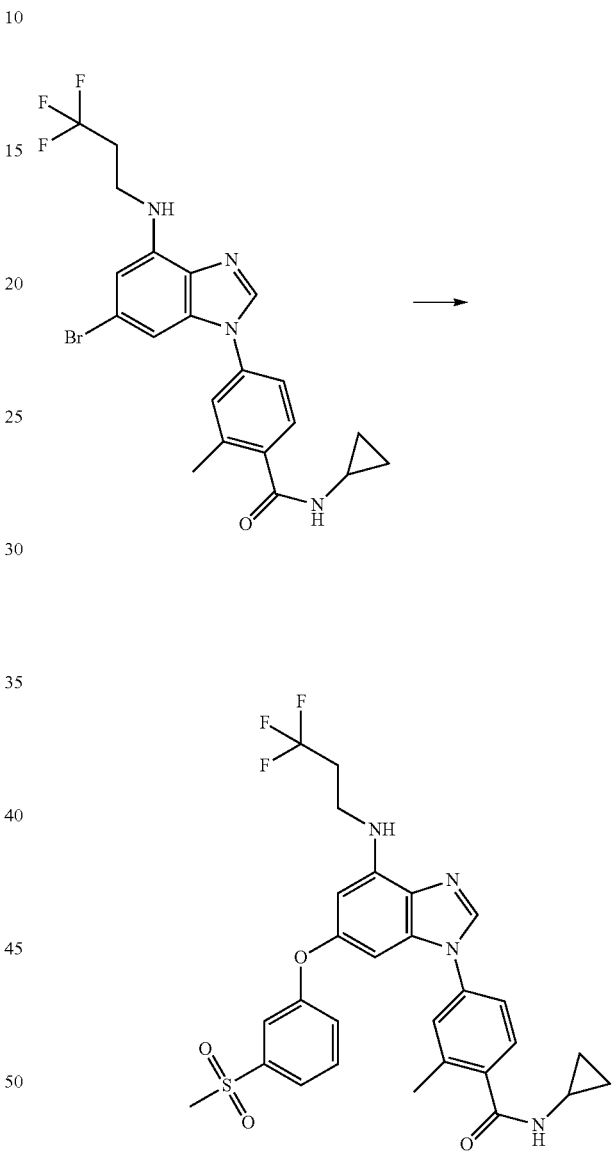

100 mg (208 µmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 3 using 2-methoxyaniline to give after working up and purification 59 mg (54%) of the title compound.

$^1$H-NMR (DMSO-d6): δ=0.50 (2H), 0.65 (2H), 2.36 (3H), 2.53-2.69 (2H), 2.81 (1H), 3.47 (2H), 3.78 (3H), 5.86 (1H), 40 mg (83 µmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using 3-(methylsulfonyl)phenol to give after working up and purification 3.4 mg (7%) of the title compound.

$^1$H-NMR (DMSO-d6): δ=0.48 (2H), 0.65 (2H), 2.35 (3H), 2.52-2.65 (2H), 2.80 (1H), 3.16 (3H), 3.51 (2H), 6.19 (1H), 6.28 (1H), 6.47 (1H), 7.30 (1H), 7.39-7.45 (3H), 7.47 (1H), 7.55-7.59 (2H), 8.31 (1H), 8.35 (1H) ppm.

Example 65

N-cyclopropyl-4-{6-[(3-methoxy-2-methylphenyl)amino]-4-[(3,3,3-trifluoropropyl)amino]-1H-benzimidazol-1-yl}-2-methylbenzamide

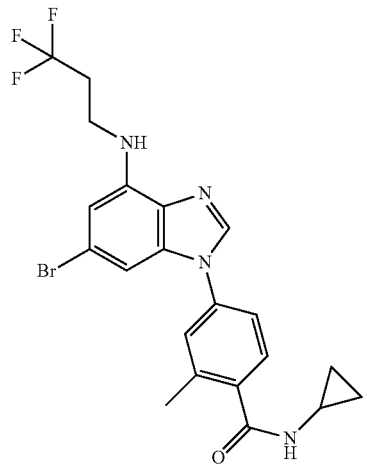

100 mg (208 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 3 using 3-methoxy-2-methylaniline to give after working up and purification 28.6 mg (24%) of the title compound.

¹H-NMR (DMSO-d6): δ=0.49 (2H), 0.65 (2H), 2.00 (3H), 2.34 (3H), 2.51-2.69 (2H), 2.80 (1H), 3.45 (2H), 3.72 (3H), 5.85 (1H), 6.08 (1H), 6.27 (1H), 6.53 (1H), 6.79 (1H), 6.97 (1H), 7.23 (1H), 7.32-7.45 (3H), 8.09 (1H), 8.34 (1H) ppm.

Example 66

4-{6-(2,3-difluorophenoxy)-4-[(3,3,3-trifluoropropyl)amino]-1H-benzimidazol-1-yl}-N-ethyl-2-methylbenzamide 50 mg (107 μmol) 4-{6-bromo-4-[(3,3,3-trifluoropropyl)amino]-1H-benzimidazol-1-yl}-N-ethyl-2-methylbenzamide which was prepared according to intermediate example 66a were transformed in analogy to example 4 using 2,3-difluorophenol to give after working up and purification 18.5 mg (32%) of the title compound.

¹H-NMR (DMSO-d6): δ=1.08 (3H), 2.36 (3H), 2.58 (2H), 3.22 (2H), 3.50 (2H), 6.18 (1H), 6.28 (1H), 6.43 (1H), 6.84 (1H), 7.04-7.18 (2H), 7.41-7.48 (3H), 8.30 (1H), 8.34 (1H) ppm.

were transformed in analogy to example 10 using ethanamine to give after working up and purification 623 mg (96%) of the title compound.

Example 66a

4-{6-bromo-4-[(3,3,3-trifluoropropyl)amino]-1H-benzimidazol-1-yl}-N-ethyl-2-methylbenzamide

Example 66b

4-{6-bromo-4-[(3,3,3-trifluoropropyl)amino]-1H-benzimidazol-1-yl}-2-methylbenzoic acid

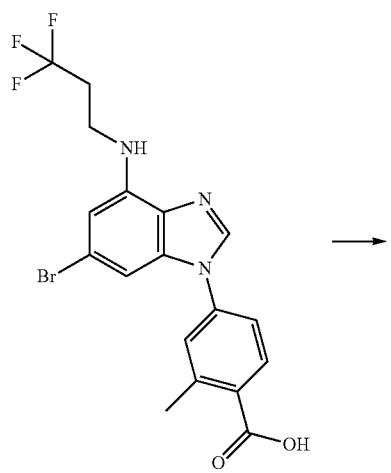

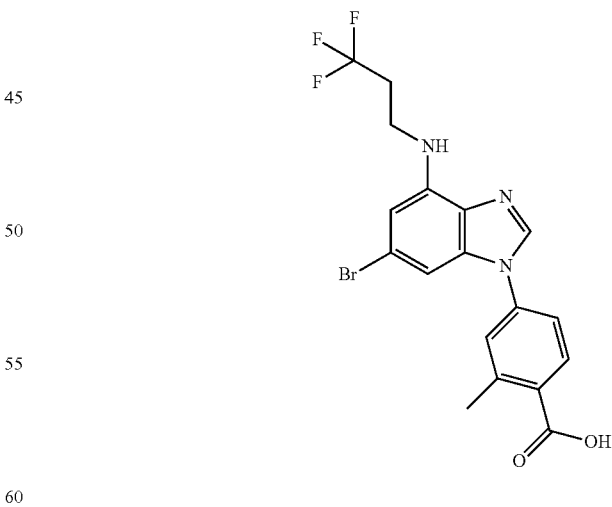

610 mg (1.38 mmol) 4-{6-bromo-4-[(3,3,3-trifluoropropyl)amino]-1H-benzimidazol-1-yl}-2-methylbenzoic acid which was prepared according to intermediate example 66b 1.24 mg (2.72 mmol) methyl 4-{6-bromo-4-[(3,3,3-trifluoropropyl)amino]-1H-benzimidazol-1-yl}-2-methylbenzoate which was prepared according to intermediate example 10c were transformed in analogy to intermediate example 10a to give after working up 1.17 g (97%) of the title compound.

$^1$H-NMR (DMSO-d6): δ=2.36 (3H), 2.58 (2H), 2.73 (3H), 3.50 (2H), 6.18 (1H), 6.28 (1H), 6.44 (1H), 6.83 (1H), 7.04-7.17 (2H), 7.39-7.50 (3H), 8.23 (1H), 8.34 (1H) ppm.

Example 67

4-{6-(2,3-difluorophenoxy)-4-[(3,3,3-trifluoropropyl)amino]-1H-benzimidazol-1-yl}-N,2-dimethylbenzamide Example 67a 4-{6-bromo-4-[(3,3,3-trifluoropropyl)amino]-1H-benzimidazol-1-yl}-N,2-dimethylbenzamide

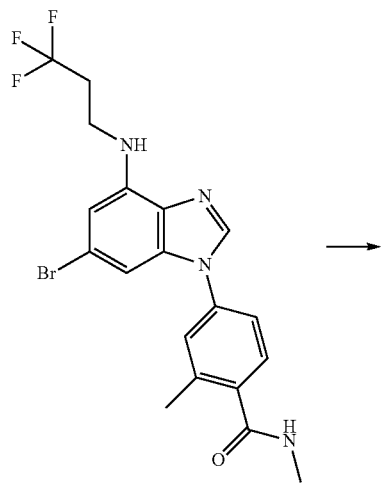

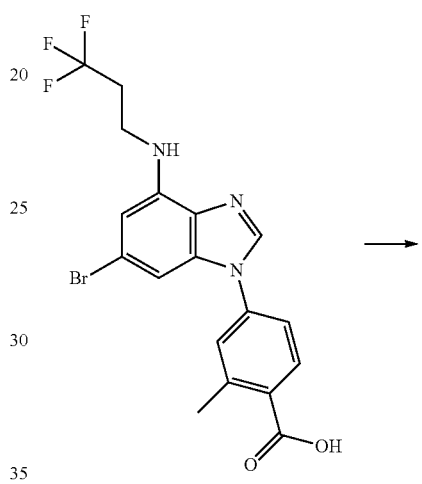

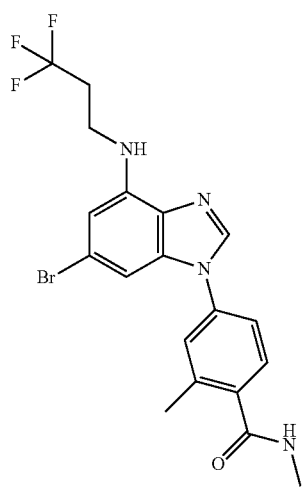

50 mg (110 μmol) 4-{6-bromo-4-[(3,3,3-trifluoropropyl)amino]-1H-benzimidazol-1-yl}-N,2-dimethylbenzamide which was prepared according to intermediate example 67a were transformed in analogy to example 4 using 2,3-difluorophenol to give after working up and purification 13.1 mg (22%) of the title compound.

550 mg (1.24 mmol) 4-{6-bromo-4-[(3,3,3-trifluoropropyl)amino]-1H-benzimidazol-1-yl}-2-methylbenzoic acid which was prepared according to intermediate example 66b were transformed in analogy to example 10 to give after working up and purification 566 mg (99%) of the title compound.

¹H-NMR (DMSO-d6): δ=2.36 (3H), 2.58 (2H), 2.73 (3H), 3.50 (2H), 3.67 (3H), 6.13 (1H), 6.18 (1H), 6.38 (1H), 6.49-6.55 (2H), 6.61 (1H), 7.18 (1H), 7.40 (1H), 7.43-7.47 (2H), 8.21 (1H), 8.31 (1H) ppm.

Example 68

4-{6-(3-methoxyphenoxy)-4-[(3,3,3-trifluoropropyl)amino]-1H-benzimidazol-1-yl}-N,2-dimethylbenzamide Example 69

N-ethyl-4-{6-(3-methoxyphenoxy)-4-[(3,3,3-trifluoropropyl)amino]-1H-benzimidazol-1-yl}-2-methylbenzamide

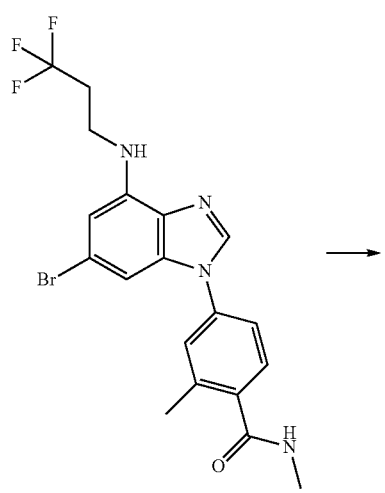

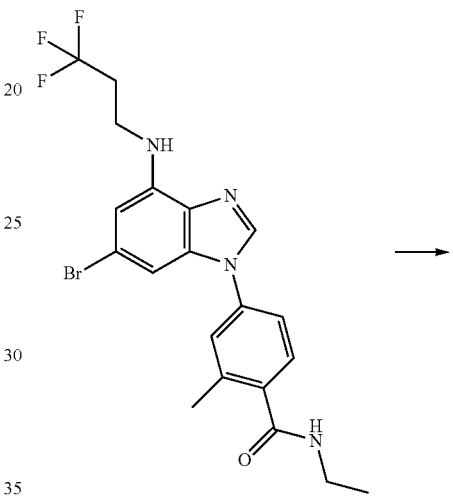

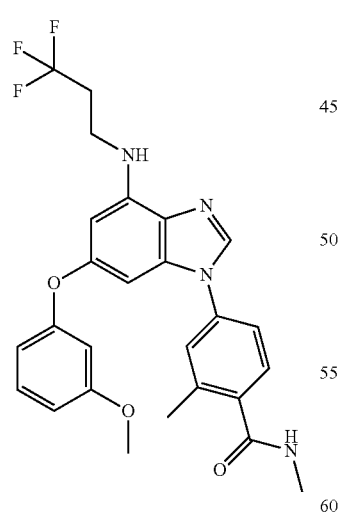

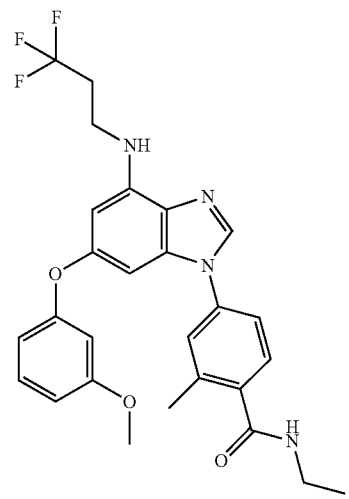

75 mg (165 μmol) 4-{6-bromo-4-[(3,3,3-trifluoropropyl)amino]-1H-benzimidazol-1-yl}-N,2-dimethylbenzamide which was prepared according to intermediate example 67a were transformed in analogy to example 4 using 3-methoxyphenol to give after working up and purification 27.1 mg (31%) of the title compound.

70 mg (149 μmol) 4-{6-bromo-4-[(3,3,3-trifluoropropyl)amino]-1H-benzimidazol-1-yl}-N-ethyl-2-methylbenzamide which was prepared according to intermediate example 66a were transformed in analogy to example 4 using 3-methoxyphenol to give after working up and purification 40.4 mg (50%) of the title compound.

¹H-NMR (DMSO-d6): δ=1.08 (3H), 2.36 (3H), 2.58 (2H), 3.22 (2H), 3.50 (2H), 3.67 (3H), 6.13 (1H), 6.18 (1H), 6.37 (1H), 6.49-6.54 (2H), 6.61 (1H), 7.18 (1H), 7.38-7.46 (3H), 8.27 (1H), 8.30 (1H) ppm.

Example 70

N-cyclopropyl-4-{6-(3-methoxyphenoxy)-4-[(3,3,3-trifluoropropyl)amino]-1H-benzimidazol-1-yl}-2-methylbenzamide

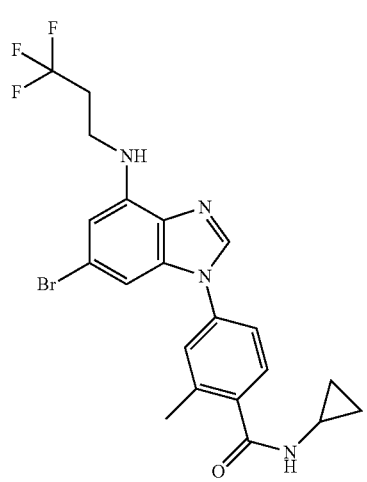

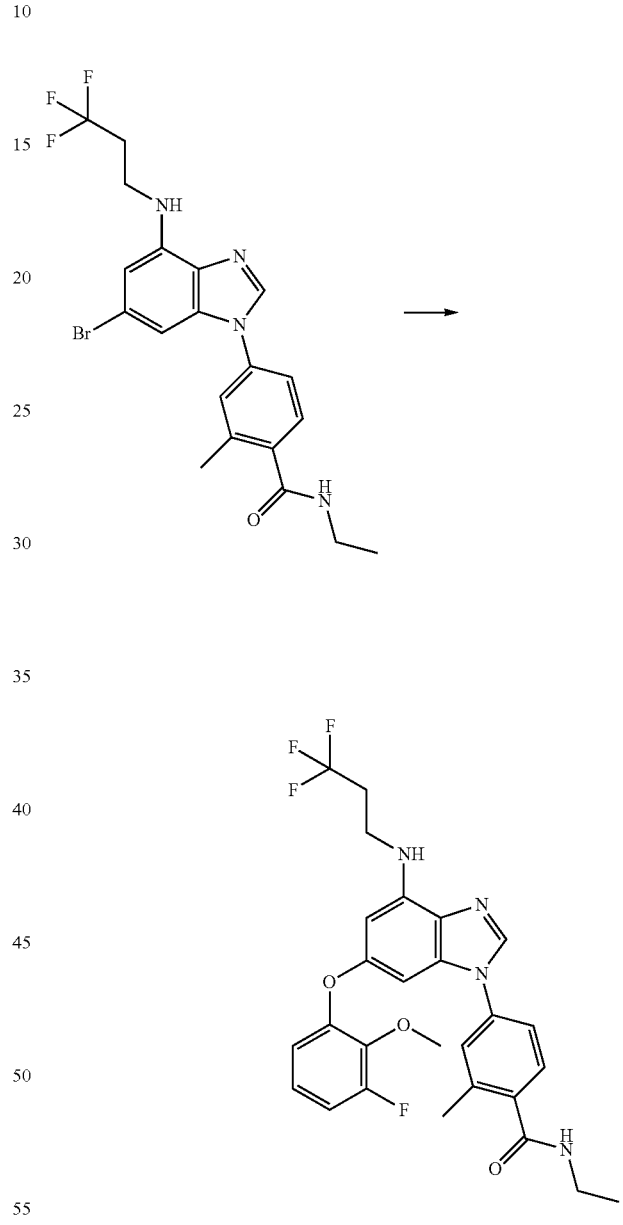

75 mg (156 μmol) 4-{6-bromo-4-[(3,3,3-trifluoropropyl)amino]-1H-benzimidazol-1-yl}-N-cyclopropyl-2-methyl-benzamide which was prepared according to intermediate example 11-1 were transformed in analogy to example 4 using 3-methoxyphenol to give after working up and purification 54.5 mg (67%) of the title compound.

¹H-NMR (DMSO-d6): δ=0.49 (2H), 0.65 (2H), 2.34 (3H), 2.58 (2H), 2.80 (1H), 3.50 (2H), 3.67 (3H), 6.13 (1H), 6.18 (1H), 6.35 (1H), 6.48-6.54 (2H), 6.61 (1H), 7.18 (1H), 7.41 (2H), 7.44 (1H), 8.29 (1H), 8.31 (1H) ppm.

Example 71

N-ethyl-4-{6-(3-fluoro-2-methoxyphenoxy)-4-[(3,3,3-trifluoropropyl)amino]-1H-benzimidazol-1-yl}-2-methylbenzamide 70 mg (149 μmol) 4-{6-bromo-4-[(3,3,3-trifluoropropyl)amino]-1H-benzimidazol-1-yl}-N-ethyl-2-methylbenzamide which was prepared according to intermediate example 66a were transformed in analogy to example 4 using 3-fluoro-2-methoxyphenol to give after working up and purification 34.2 mg (41%) of the title compound.

¹H-NMR (DMSO-d6): δ=1.08 (3H), 2.35 (3H), 2.58 (2H), 3.22 (2H), 3.50 (2H), 3.80 (3H), 6.12 (1H), 6.20 (1H), 6.31 (1H), 6.76 (1H), 6.96-7.03 (2H), 7.39 (1H), 7.41-7.46 (2H), 8.28 (1H), 8.29 (1H) ppm.

Example 72

4-{6-(3-fluoro-2-methoxyphenoxy)-4-[(3,3,3-trifluoropropyl)amino]-1H-benzimidazol-1-yl}-N,2-dimethylbenzamide ¹H-NMR (DMSO-d6): δ=2.35 (3H), 2.58 (2H), 2.73 (3H), 3.50 (2H), 3.80 (3H), 6.12 (1H), 6.20 (1H), 6.32 (1H), 6.76 (1H), 6.98 (1H), 7.00 (1H), 7.39 (1H), 7.43-7.48 (2H), 8.21 (1H), 8.29 (1H) ppm.

Example 73

4-{6-(4-cyano-2-methoxyphenoxy)-4-[(3,3,3-trifluoropropyl)amino]-1H-benzimidazol-1-yl}-N-cyclopropyl-2-methylbenzamide

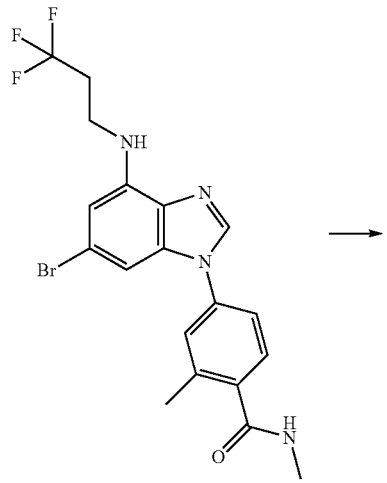

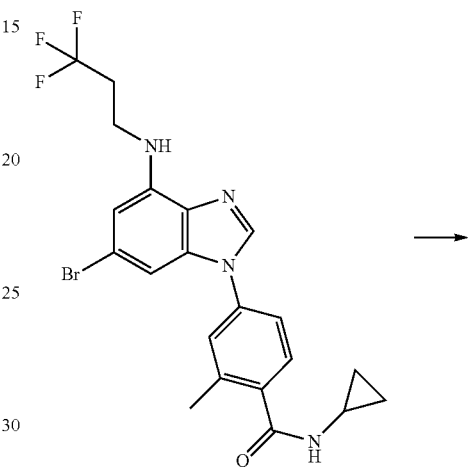

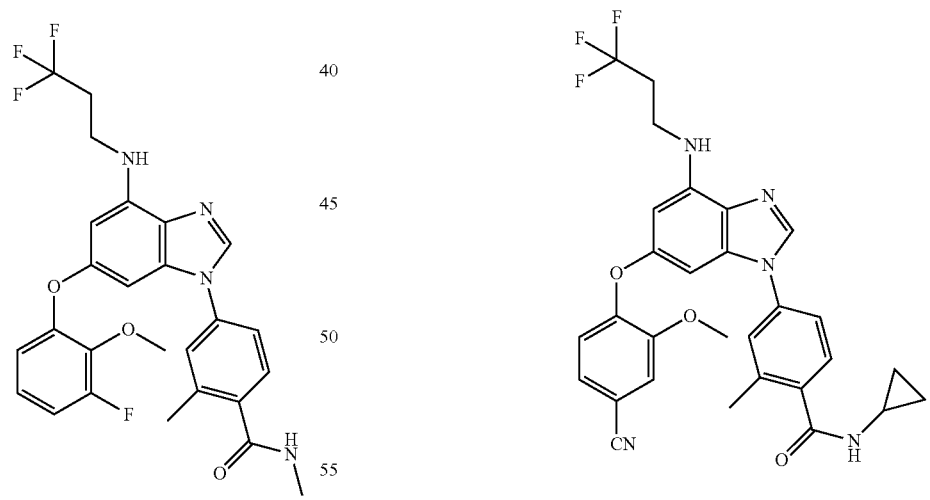

75 mg (165 μmol) 4-{6-bromo-4-[(3,3,3-trifluoropropyl)amino]-1H-benzimidazol-1-yl}-N,2-dimethylbenzamide which was prepared according to intermediate example 67a were transformed in analogy to example 4 using 3-fluoro-2-methoxyphenol to give after working up and purification 27.3 mg (30%) of the title compound.

40 mg (83 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using 4-hydroxy-3-methoxybenzonitrile to give after working up and purification 2.8 mg (6%) of the title compound.

¹H-NMR (CDCl₃): δ=0.63 (2H), 0.91 (2H), 2.45-2.58 (2H), 2.51 (3H), 2.93 (1H), 3.58 (2H), 3.94 (3H), 5.48 (1H), 5.88 (1H), 6.20 (1H), 6.49 (1H), 6.84 (1H), 7.17 (1H), 7.20 (1H), 7.30 (2H), 7.48 (1H), 7.99 (1H) ppm.

5.91 (1H), 6.20 (1H), 6.52 (1H), 7.08 (2H), 7.25-7.34 (2H), 7.49 (1H), 7.86 (2H), 7.98 (1H) ppm.

Example 74

N-cyclopropyl-2-methyl-4-{6-[4-(methylsulfonyl)phenoxy]-4-[(3,3,3-trifluoropropyl)amino]-1H-benzimidazol-1-yl}benzamide

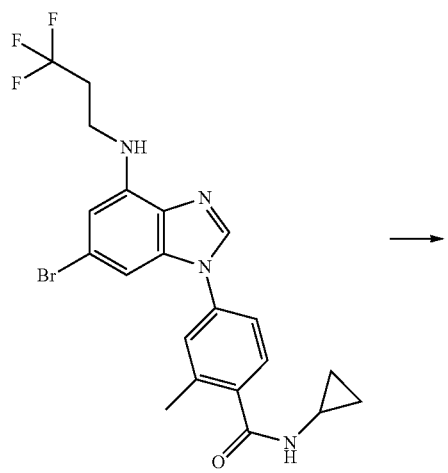

Example 75

N-cyclopropyl-2-methyl-4-{6-[4-(1,3-oxazol-2-yl)phenoxy]-4-[(3,3,3-trifluoropropyl)amino]-1H-benzimidazol-1-yl}benzamide

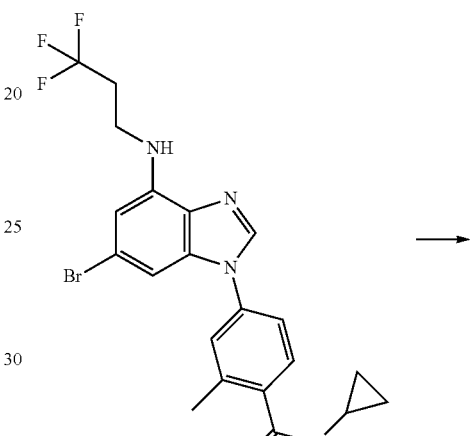

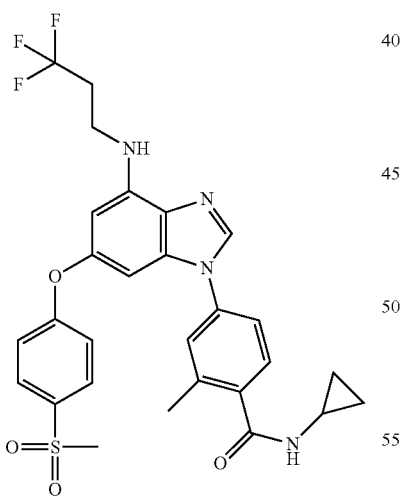

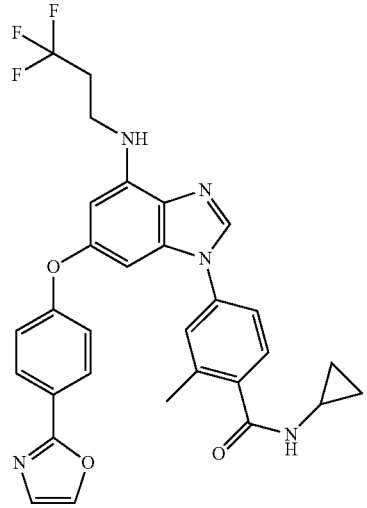

40 mg (83 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using 4-(methylsulfonyl)phenol to give after working up and purification 4.3 mg (8%) of the title compound.

$^1$H-NMR (CDCl$_3$): δ=0.63 (2H), 0.90 (2H), 2.45-2.60 (2H), 2.52 (3H), 2.92 (1H), 3.04 (3H), 3.59 (2H), 5.39 (1H), 40 mg (83 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using 4-(1,3-oxazol-2-yl)phenol to give after working up and purification 18.6 mg (38%) of the title compound.

¹H-NMR (CDCl₃): δ=0.62 (2H), 0.89 (2H), 2.43-2.62 (2H), 2.50 (3H), 2.91 (1H), 3.59 (2H), 5.33 (1H), 5.92 (1H), 6.23 (1H), 6.50 (1H), 7.02-7.36 (5H), 7.46 (1H), 7.68 (1H), 7.94 (1H), 7.98 (2H) ppm.

¹H-NMR (CDCl₃): δ=0.63 (2H), 0.91 (2H), 2.46-2.58 (2H), 2.51 (3H), 2.93 (1H), 3.59 (2H), 5.36 (1H), 5.90 (1H), 6.17 (1H), 6.42 (1H), 7.10-7.32 (5H), 7.48 (1H), 7.95 (1H) ppm.

Example 76

N-cyclopropyl-4-{6-[4-fluoro-3-(trifluoromethyl) phenoxy]-4-[(3,3,3-trifluoropropyl)amino]-1H-benzimidazol-1-yl}-2-methylbenzamide Example 77

4-{6-(3-cyanophenoxy)-4-[(3,3,3-trifluoropropyl) amino]-1H-benzimidazol-1-yl}-N-cyclopropyl-2-methylbenzamide

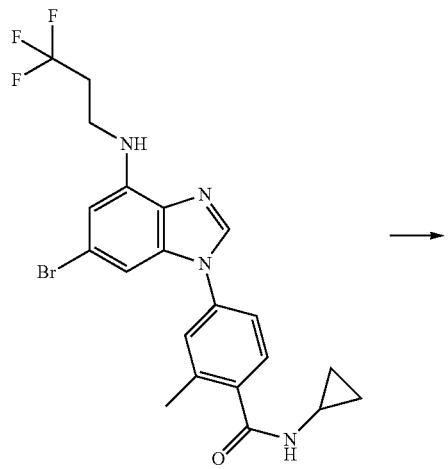

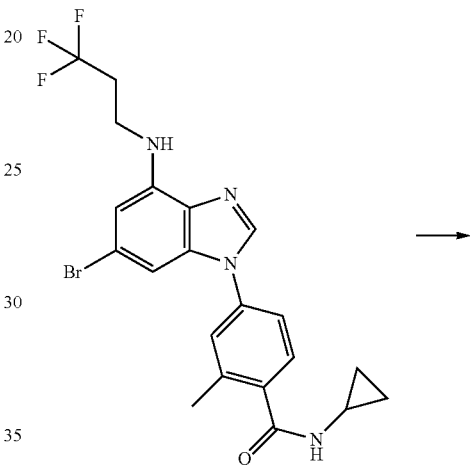

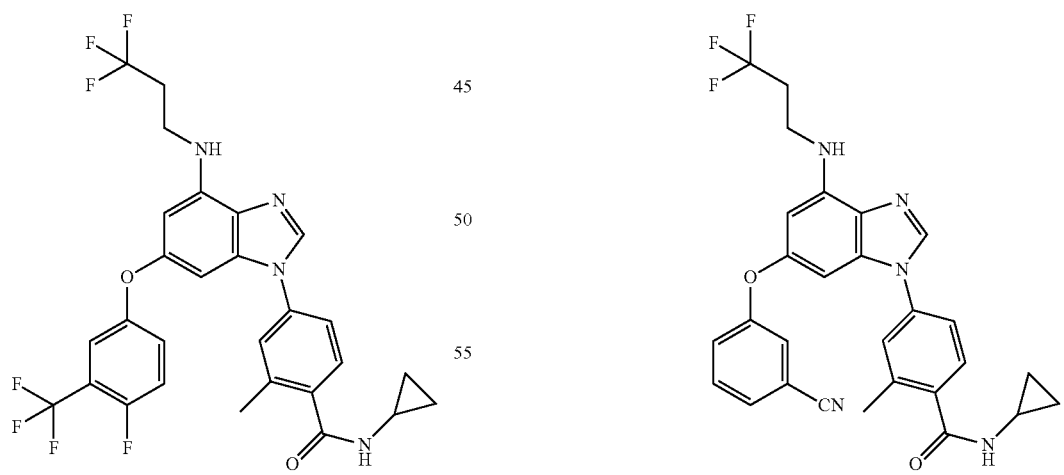

40 mg (83 µmol) 4-{6-bromo-4-[(3,3,3-trifluoropropyl) amino]-1H-benzimidazol-1-yl}-N-cyclopropyl-2-methylbenzamide which was prepared according to intermediate example 11-1 were transformed in analogy to example 4 using 4-fluoro-3-(trifluoromethyl)phenol to give after working up and purification 9.5 mg (19%) of the title compound.

150 mg (312 µmol) 4-{6-bromo-4-[(3,3,3-trifluoropropyl) amino]-1H-benzimidazol-1-yl}-N-cyclopropyl-2-methylbenzamide which was prepared according to intermediate example 11-1 were transformed in analogy to example 4 using 3-hydroxybenzonitrile to give after working up and purification 123 mg (76%) of the title compound.

¹H-NMR (DMSO-d6): δ=0.49 (2H), 0.66 (2H), 2.35 (3H), 2.58 (2H), 2.80 (1H), 3.50 (2H), 6.16 (1H), 6.26 (1H), 6.45 (1H), 7.28 (1H), 7.39 (1H), 7.41-7.50 (5H), 8.31 (1H), 8.34 (1H) ppm.

Example 78

N-cyclopropyl-2-methyl-4-{6-[4-(1H-1,2,4-triazol-1-yl)phenoxy]-4-[(3,3,3-trifluoropropyl)amino]-1H-benzimidazol-1-yl}benzamide

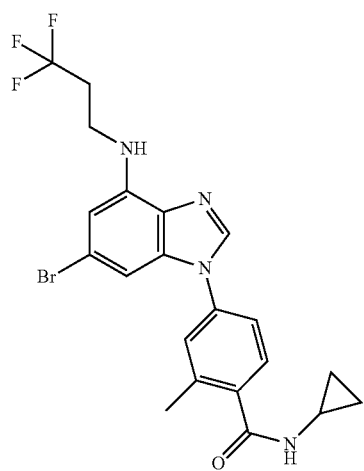

6.22 (1H), 6.48 (1H), 7.11 (2H), 7.28-7.34 (2H), 7.47 (1H), 7.58 (2H), 7.93 (1H), 8.08 (1H), 8.47 (1H) ppm.

Example 79

N-cyclopropyl-4-{6-[3-(cyclopropylcarbamoyl)phenoxy]-4-[(3,3,3-trifluoropropyl)amino]-1H-benzimidazol-1-yl}-2-methylbenzamide

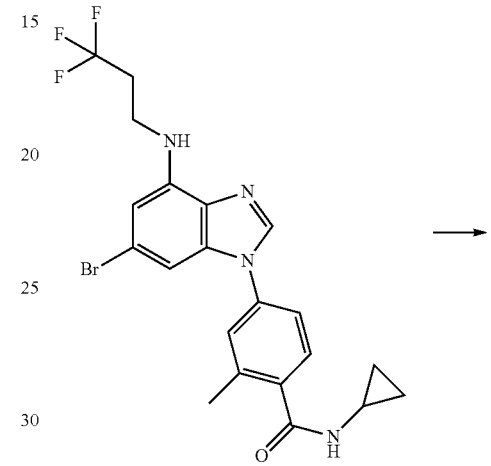

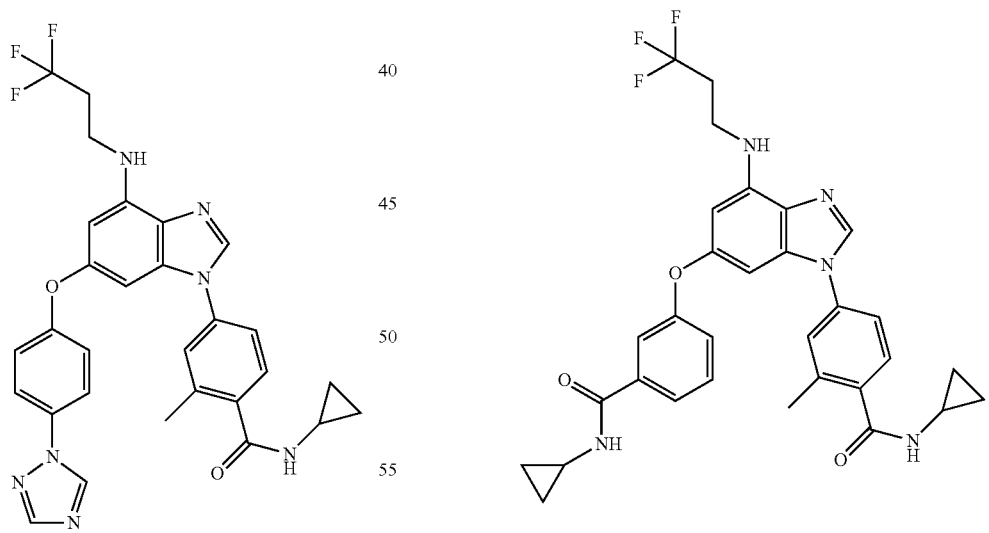

40 mg (83 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using 4-(1H-1,2,4-triazol-1-yl)phenol to give after working up and purification 11.0 mg (22%) of the title compound.

¹H-NMR (CDCl₃): δ=0.62 (2H), 0.90 (2H), 2.46-2.59 (2H), 2.51 (3H), 2.91 (1H), 3.60 (2H), 5.30 (1H), 5.92 (1H), 40 mg (83 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using N-cyclopropyl-3-hydroxybenzamide to give after working up and purification 4.9 mg (10%) of the title compound.

¹H-NMR (CDCl₃): δ=0.53-0.67 (4H), 0.79-0.94 (4H), 2.43-2.58 (2H), 2.49 (3H), 2.80-2.96 (2H), 3.57 (2H), 5.27

(1H), 6.01 (1H), 6.19 (2H), 6.41 (1H), 7.11 (1H), 7.23-7.38 (5H), 7.45 (1H), 7.91 (1H) ppm.

Example 82

N-cyclopropyl-4-{6-[(2-hydroxyphenyl)amino]-4-[(3,3,3-trifluoropropyl)amino]-1H-benzimidazol-1-yl}-2-methylbenzamide

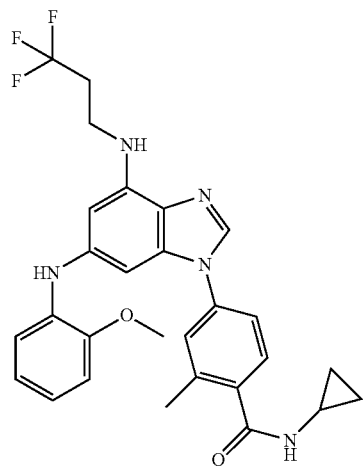

→

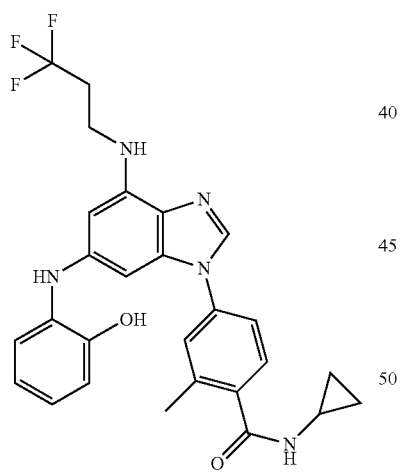

46 mg (88 µmol)N-cyclopropyl-4-{6-[(2-methoxyphenyl)amino]-4-[(3,3,3-trifluoropropyl)amino]-1H-benzimidazol-1-yl}-2-methylbenzamide which was prepared according to example 63 were transformed in analogy to example 54 to give after working up and purification 7.9 mg (17%) of the title compound.

$^1$H-NMR (DMSO-d6): δ=0.50 (2H), 0.66 (2H), 2.36 (3H), 2.53-2.71 (2H), 2.81 (1H), 3.47 (2H), 5.84 (1H), 6.22 (1H), 6.51 (1H), 6.60-6.71 (2H), 6.78 (1H), 6.98 (1H), 7.17 (1H), 7.40 (2H), 7.45 (1H), 8.11 (1H), 8.34 (1H), 9.36 (1H) ppm.

Example 83

N-cyclopropyl-4-{6-(3-fluoro-4-hydroxyphenoxy)-4-[(3,3,3-trifluoropropyl)amino]-1H-benzimidazol-1-yl}-2-methylbenzamide

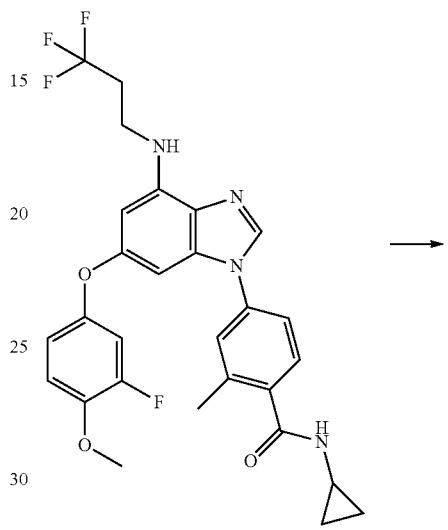

→

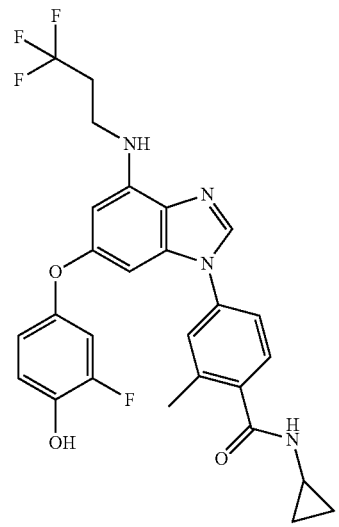

28 mg (52 µmol)N-cyclopropyl-4-{6-(3-fluoro-4-methoxyphenoxy)-4-[(3,3,3-trifluoropropyl)amino]-1H-benzimidazol-1-yl}-2-methylbenzamide which was prepared according to example 33 were transformed in analogy to example 54 to give after working up and purification 4.4 mg (15%) of the title compound.

$^1$H-NMR (DMSO-d6): δ=0.49 (2H), 0.565 (2H), 2.34 (3H), 2.49-2.65 (2H), 2.80 (1H), 3.49 (2H), 6.08 (1H), 6.15

(1H), 6.26 (1H), 6.65 (1H), 6.82-6.89 (2H), 7.35-7.45 (3H), 8.26 (1H), 8.32 (1H), 9.58 (1H) ppm.

Example 84

4-{6-(2,3-difluorophenoxy)-4-[(tetrahydro-2H-pyran-4-ylmethyl)amino]-1H-benzimidazol-1-yl}-N,2-dimethylbenzamide

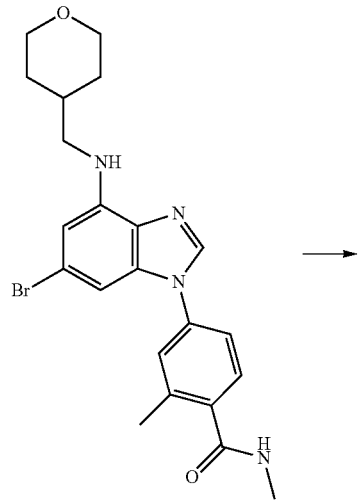

→

(1H), 5.81 (1H), 6.21 (1H), 6.39 (1H), 6.76 (1H), 6.85-7.01 (2H), 7.27-7.38 (2H), 7.50 (1H), 7.93 (1H) ppm.

Example 85

4-{6-(2,3-Difluorophenoxy)-4-[(tetrahydro-2H-pyran-4-ylmethyl)amino]-1H-benzimidazol-1-yl}-N-ethyl-2-methylbenzamide

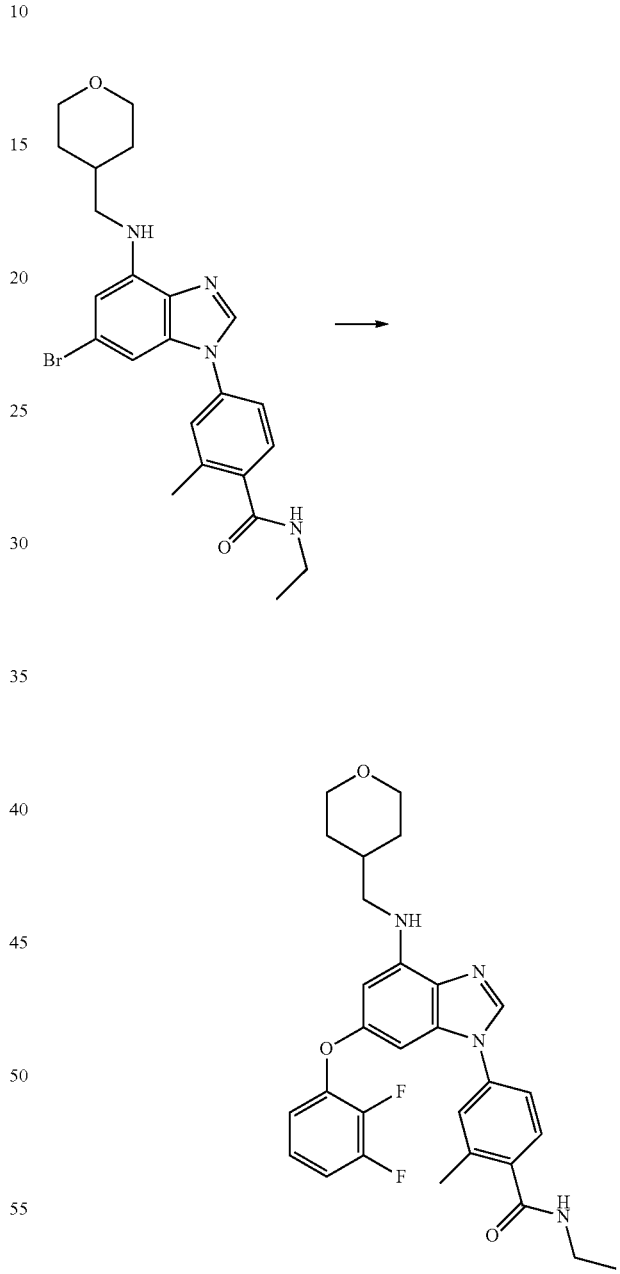

100 mg (219 μmol) 4-{6-bromo-4-[(tetrahydro-2H-pyran-4-ylmethyl)amino]-1H-benzimidazol-1-yl}-N,2-dimethylbenzamide which was prepared according to intermediate example 42a were transformed in analogy to example 14 using 2,3-difluorophenol to give after working up and purification 20.5 mg (18%) of the title compound.

$^1$H-NMR (CDCl$_3$): δ=1.40 (2H), 1.77 (2H), 1.96 (1H), 2.51 (3H), 3.03 (3H), 3.17 (2H), 3.40 (2H), 4.00 (2H), 5.30

100 mg (212 μmol) 4-{6-bromo-4-[(tetrahydro-2H-pyran-4-ylmethyl)amino]-1H-benzimidazol-1-yl}-N-ethyl-2-methylbenzamide which was prepared according to intermediate example 43a were transformed in analogy to example 14 using 2,3-difluorophenol to give after working up and purification 21.9 mg (19%) of the title compound.

$^1$H-NMR (CDCl$_3$): δ=1.27 (3H), 1.40 (2H), 1.77 (2H), 1.95 (1H), 2.51 (3H), 3.17 (2H), 3.40 (2H), 3.51 (2H), 4.00

(2H), 5.30 (1H), 5.77 (1H), 6.21 (1H), 6.39 (1H), 6.76 (1H), 6.86-7.01 (2H), 7.27-7.36 (2H), 7.50 (1H), 7.92 (1H) ppm.

Example 86

4-{6-(2-fluoro-4-methoxyphenoxy)-4-[(tetrahydro-2H-pyran-4-ylmethyl)amino]-1H-benzimidazol-1-yl}-N,2-dimethylbenzamide

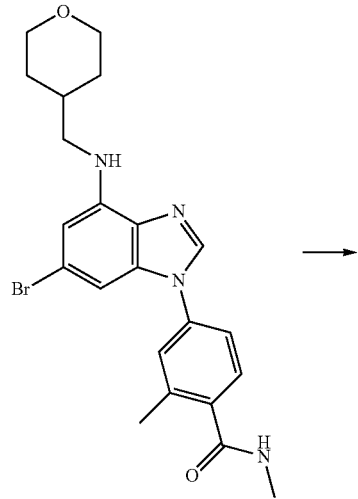

(2H), 5.30 (1H), 5.83 (1H), 6.19 (1H), 6.23 (1H), 6.63 (1H), 6.74 (1H), 7.02 (1H), 7.23-7.31 (2H), 7.48 (1H), 7.88 (1H) ppm.

Example 87

N-ethyl-4-{6-(2-fluoro-4-methoxyphenoxy)-4-[(tetrahydro-2H-pyran-4-ylmethyl)amino]-1H-benzimidazol-1-yl}-2-methylbenzamide

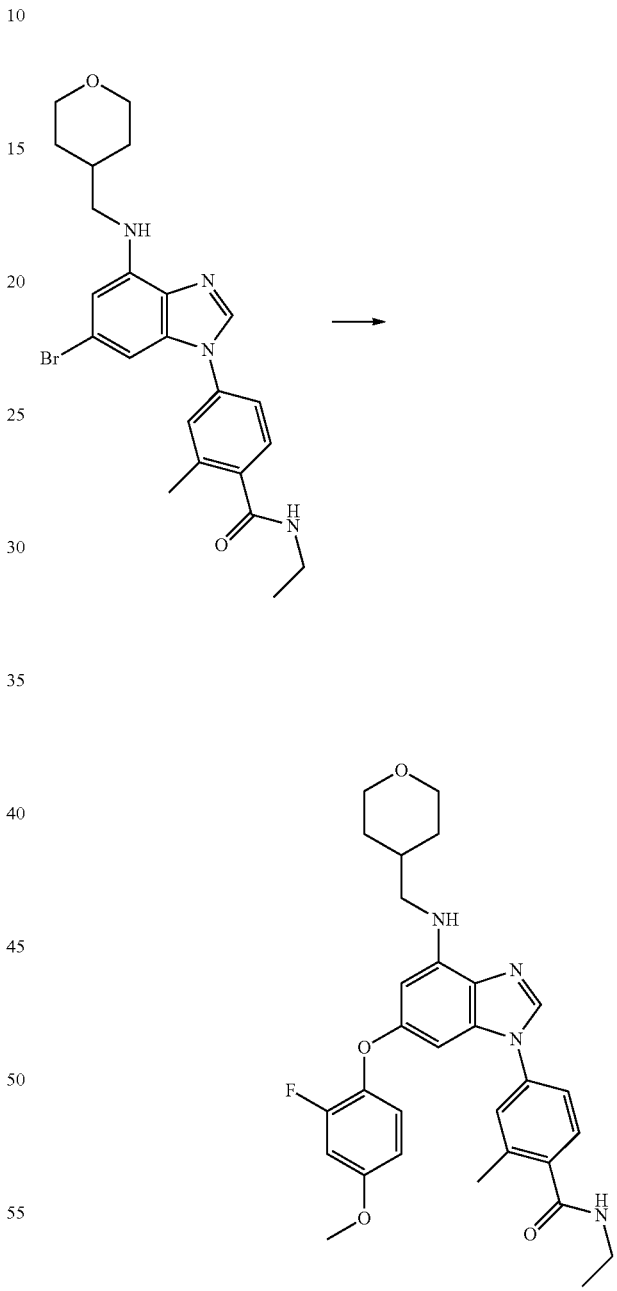

100 mg (219 µmol) 4-{6-bromo-4-[(tetrahydro-2H-pyran-4-ylmethyl)amino]-1H-benzimidazol-1-yl}-N,2-dimethylbenzamide which was prepared according to intermediate example 42a were transformed in analogy to example 14 using 2-fluoro-4-methoxyphenol to give after working up and purification 33.6 mg (28%) of the title compound.

$^1$H-NMR (CDCl$_3$): δ=1.40 (2H), 1.77 (2H), 1.96 (1H), 2.50 (3H), 3.03 (3H), 3.17 (2H), 3.40 (2H), 3.79 (3H), 4.00

100 mg (212 µmol) 4-{6-bromo-4-[(tetrahydro-2H-pyran-4-ylmethyl)amino]-1H-benzimidazol-1-yl}-N-ethyl-2-methylbenzamide which was prepared according to intermediate example 43a were transformed in analogy to example 14 using 2-fluoro-4-methoxyphenol to give after working up and purification 44.1 mg (37%) of the title compound.

$^1$H-NMR (CDCl$_3$): δ=1.27 (3H), 1.40 (2H), 1.77 (2H), 1.96 (1H), 2.50 (3H), 3.16 (2H), 3.40 (2H), 3.51 (2H), 3.80

(3H), 4.00 (2H), 5.30 (1H), 5.78 (1H), 6.21 (2H), 6.63 (1H), 6.74 (1H), 7.02 (1H), 7.24-7.30 (2H), 7.48 (1H), 7.89 (1H) ppm.

Example 88

4-{6-(2-fluoro-4-methoxyphenoxy)-4-[(3,3,3-trifluoropropyl)amino]-1H-benzimidazol-1-yl}-N,2-dimethylbenzamide

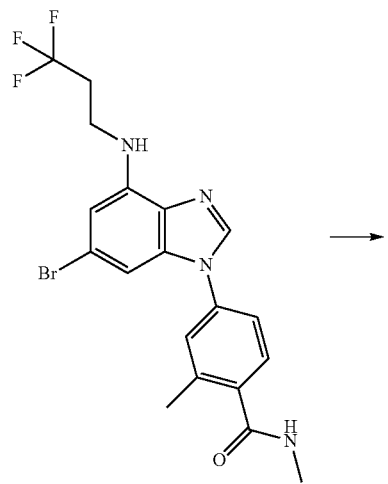

¹H-NMR (DMSO-d6): δ=2.35 (3H), 2.51-2.66 (2H), 2.73 (3H), 3.50 (2H), 3.72 (3H), 6.08 (1H), 6.13-6.22 (2H), 6.72 (1H), 6.96 (1H), 7.11 (1H), 7.33-7.47 (3H), 8.22 (1H), 8.25 (1H) ppm.

Example 89

N-ethyl-4-{6-(2-fluoro-4-methoxyphenoxy)-4-[(3,3,3-trifluoropropyl)amino]-1H-benzimidazol-1-yl}-2-methylbenzamide

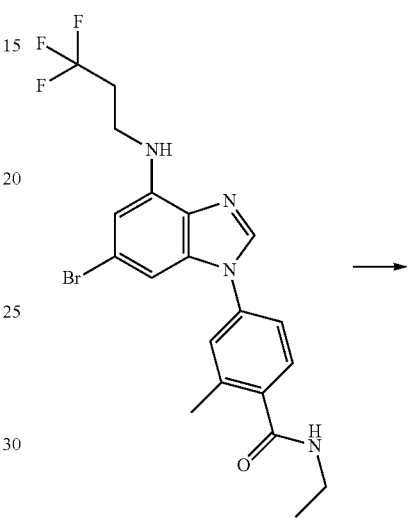

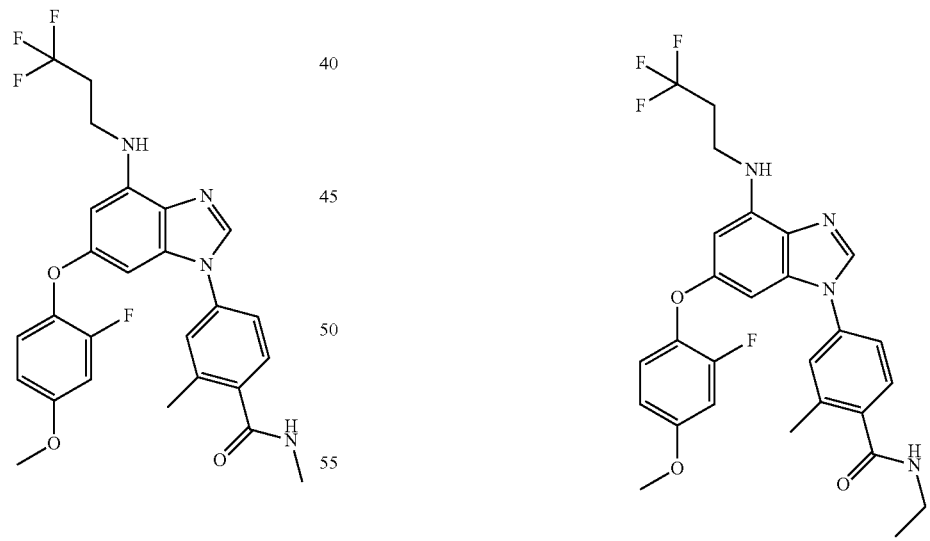

100 mg (220 µmol) 4-{6-bromo-4-[(3,3,3-trifluoropropyl)amino]-1H-benzimidazol-1-yl}-N,2-dimethylbenzamide which was prepared according to intermediate example 67a were transformed in analogy to example 4 using 2-fluoro-4-methoxyphenol to give after working up and purification 68 mg (57%) of the title compound.

100 mg (213 µmol) 4-{6-bromo-4-[(3,3,3-trifluoropropyl)amino]-1H-benzimidazol-1-yl}-N-ethyl-2-methylbenzamide which was prepared according to intermediate example 66a were transformed in analogy to example 4 using 2-fluoro-4-methoxyphenol to give after working up and purification 65 mg (55%) of the title compound.

¹H-NMR (DMSO-d6): δ=1.08 (3H), 2.35 (3H), 2.51-2.64 (2H), 3.22 (2H), 3.50 (2H), 3.72 (3H), 6.09 (1H), 6.17 (1H), 6.19 (1H), 6.72 (1H), 6.96 (1H), 7.11 (1H), 7.36 (1H), 7.40 (1H), 7.43 (1H), 8.25 (1H), 8.29 (1H) ppm.

Example 90

N-cyclopropyl-4-{6-(2-fluoro-4-hydroxyphenoxy)-4-[(3,3,3-trifluoropropyl)amino]-1H-benzimidazol-1-yl}-2-methylbenzamide

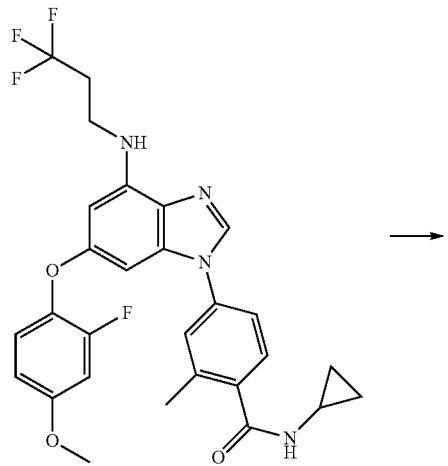

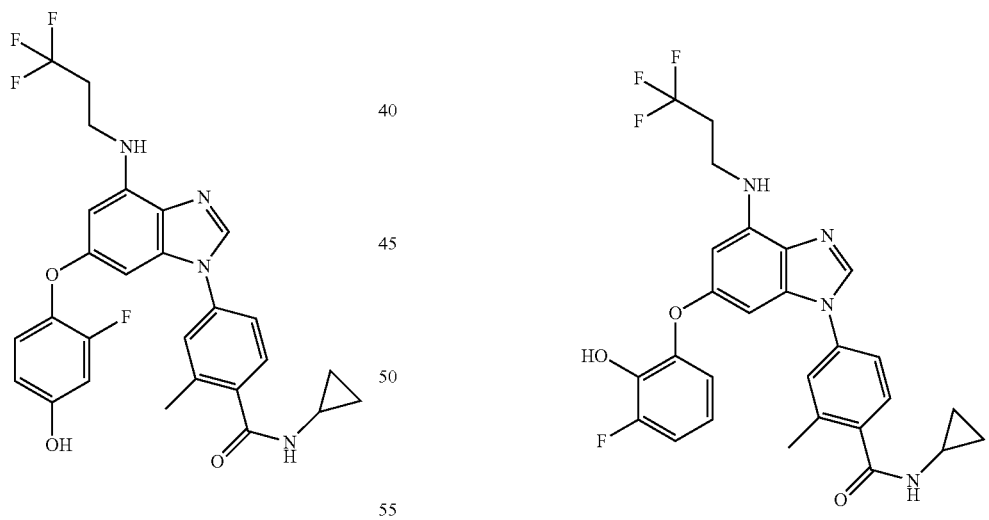

30 mg (55 µmol)N-cyclopropyl-4-{6-(2-fluoro-4-methoxyphenoxy)-4-[(3,3,3-trifluoropropyl)amino]-1H-benzimidazol-1-yl}-2-methylbenzamide which was prepared according to example 29 were transformed in analogy to example 54 to give after working up and purification 8.7 mg (28%) of the title compound.

$^1$H-NMR (DMSO-d6): δ=0.50 (2H), 0.65 (2H), 2.33 (3H), 2.57 (2H), 2.80 (1H), 3.49 (2H), 6.06 (1H), 6.11-6.17 (2H), 6.54 (2H), 6.66 (1H), 7.00 (1H), 7.31-7.43 (3H), 8.22 (1H), 8.34 (1H) ppm.

Example 91

N-cyclopropyl-4-{6-(3-fluoro-2-hydroxyphenoxy)-4-[(3,3,3-trifluoropropyl)amino]-1H-benzimidazol-1-yl}-2-methylbenzamide

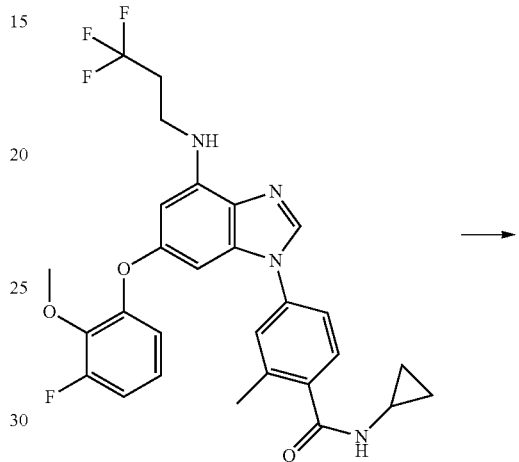

30 mg (55 µmol)N-cyclopropyl-4-{6-(3-fluoro-2-methoxyphenoxy)-4-[(3,3,3-trifluoropropyl)amino]-1H-benzimidazol-1-yl}-2-methylbenzamide which was prepared according to example 57 were transformed in analogy to example 54 to give after working up and purification 21.0 mg (68%) of the title compound.

$^1$H-NMR (DMSO-d6): δ=0.49 (2H), 0.65 (2H), 2.33 (3H), 2.49-2.66 (2H), 2.80 (1H), 3.50 (2H), 6.10 (1H), 6.15 (1H), 6.24 (1H), 6.65-6.74 (2H), 6.91 (1H), 7.33-7.44 (3H), 8.26 (1H), 8.32 (1H), 9.58 (1H) ppm.

Example 92

4-{6-(3-fluoro-2-hydroxyphenoxy)-4-[(3,3,3-trifluoropropyl)amino]-1H-benzimidazol-1-yl}-N,2-dimethylbenzamide

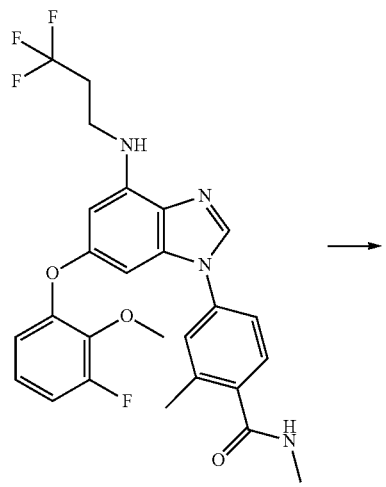

22 mg (43 µmol) 4-{6-(3-fluoro-2-methoxyphenoxy)-4-[(3,3,3-trifluoropropyl)amino]-1H-benzimidazol-1-yl}-N,2-dimethylbenzamide which was prepared according to example 72 were transformed in analogy to example 54 to give after working up and purification 8.6 mg (38%) of the title compound.

$^1$H-NMR (DMSO-d6): δ=2.35 (3H), 2.51-2.66 (2H), 2.73 (3H), 3.50 (2H), 6.11 (1H), 6.15 (1H), 6.26 (1H), 6.70 (2H), 6.91 (1H), 7.34-7.47 (3H), 8.22 (1H), 8.27 (1H), 9.61 (1H) ppm.

Example 93

N-ethyl-4-{6-(3-fluoro-2-hydroxyphenoxy)-4-[(3,3,3-trifluoropropyl)amino]-1H-benzimidazol-1-yl}-2-methylbenzamide

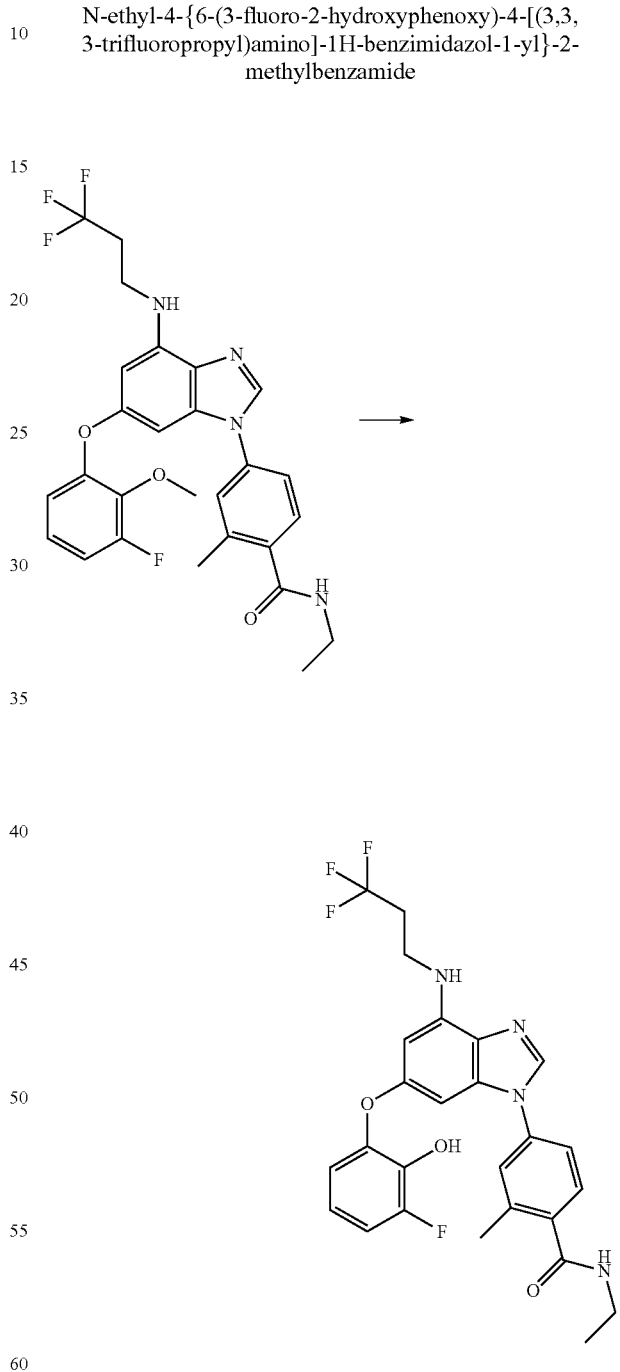

29 mg (55 µmol) N-ethyl-4-{6-(3-fluoro-2-methoxyphenoxy)-4-[(3,3,3-trifluoropropyl)amino]-1H-benzimidazol-1-yl}-2-methylbenzamide which was prepared according to example 71 were transformed in analogy to example 54 to give after working up and purification 11.5 mg (39%) of the title compound.

¹H-NMR (DMSO-d6): δ=1.08 (3H), 2.35 (3H), 2.49-2.66 (2H), 3.22 (2H), 3.50 (2H), 6.11 (1H), 6.16 (1H), 6.25 (1H), 6.66-6.75 (2H), 6.91 (1H), 7.34-7.45 (3H), 8.26 (1H), 8.28 (1H), 9.60 (1H) ppm.

Example 94

4-{6-(3-hydroxyphenoxy)-4-[(3,3,3-trifluoropropyl)amino]-1H-benzimidazol-1-yl}-N,2-dimethylbenzamide ¹H-NMR (DMSO-d6): δ=2.36 (3H), 2.49-2.67 (2H), 2.72 (3H), 3.50 (2H), 6.13 (1H), 6.16 (1H), 6.32 (1H), 6.34-6.44 (3H), 7.06 (1H), 7.35-7.48 (3H), 8.21 (1H), 8.30 (1H), 9.41 (1H) ppm.

Example 95

N-ethyl-4-{6-(3-hydroxyphenoxy)-4-[(3,3,3-trifluoropropyl)amino]-1H-benzimidazol-1-yl}-2-methylbenzamide

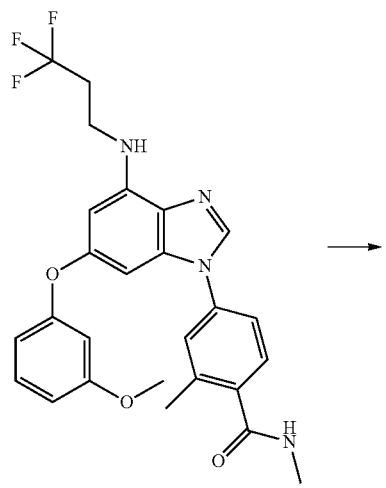

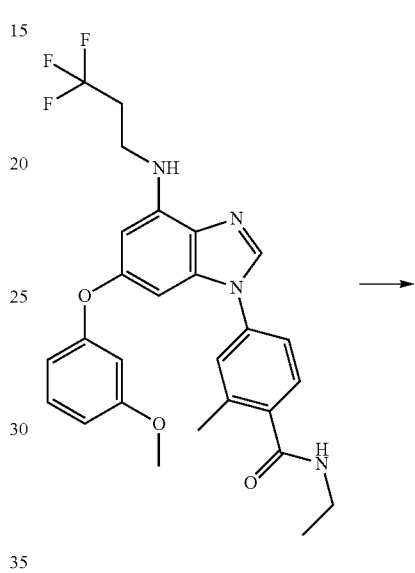

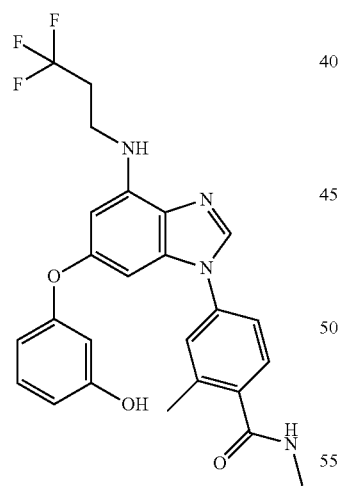

21.4 mg (43 µmol) 4-{6-(3-methoxyphenoxy)-4-[(3,3,3-trifluoropropyl)amino]-1H-benzimidazol-1-yl}-N,2-dimethylbenzamide which was prepared according to example 68 were transformed in analogy to example 54 to give after working up and purification 13.1 mg (60%) of the title compound.

36 mg (70 µmol) N-ethyl-4-{6-(3-methoxyphenoxy)-4-[(3,3,3-trifluoropropyl)amino]-1H-benzimidazol-1-yl}-2-methylbenzamide which was prepared according to example 69 were transformed in analogy to example 54 to give after working up and purification 20.0 mg (54%) of the title compound.

¹H-NMR (DMSO-d6): δ=1.08 (3H), 2.36 (3H), 2.49-2.67 (2H), 3.22 (2H), 3.50 (2H), 6.13 (1H), 6.17 (1H), 6.31-6.44 (4H), 7.06 (1H), 7.35-7.47 (3H), 8.27 (1H), 8.30 (1H), 9.42 (1H) ppm.

Example 96

N-cyclopropyl-2-methyl-4-{6-[3-(pentafluoro-lambda⁶-sulfanyl)phenoxy]-4-[(3,3,3-trifluoropropyl)amino]-1H-benzimidazol-1-yl}benzamide ¹H-NMR (DMSO-d6): δ=0.48 (2H), 0.65 (2H), 2.34 (3H), 2.49-2.64 (2H), 2.80 (1H), 3.49 (2H), 6.17 (1H), 6.31 (1H), 6.49 (1H), 7.24 (1H), 7.39-7.48 (4H), 7.50-7.57 (2H), 8.33 (1H), 8.35 (1H) ppm.

Example 97

4-{6-(2-fluoro-4-hydroxyphenoxy)-4-[(3,3,3-trifluoropropyl)amino]-1H-benzimidazol-1-yl}-N,2-dimethylbenzamide

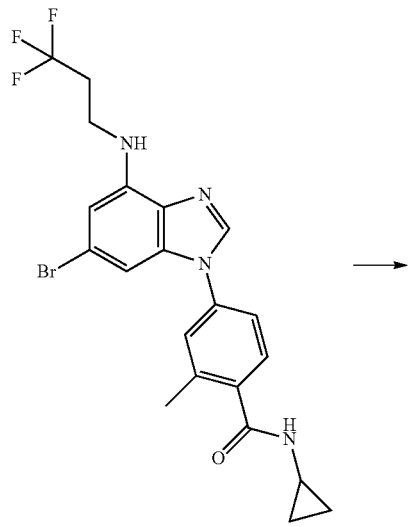
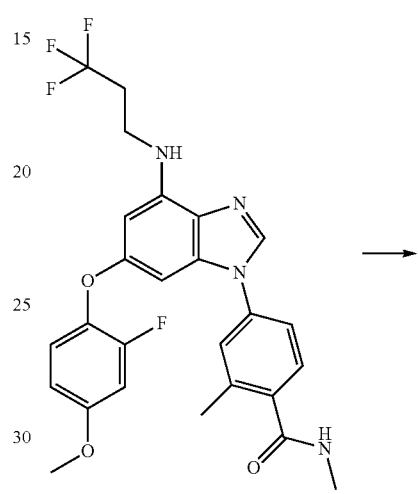

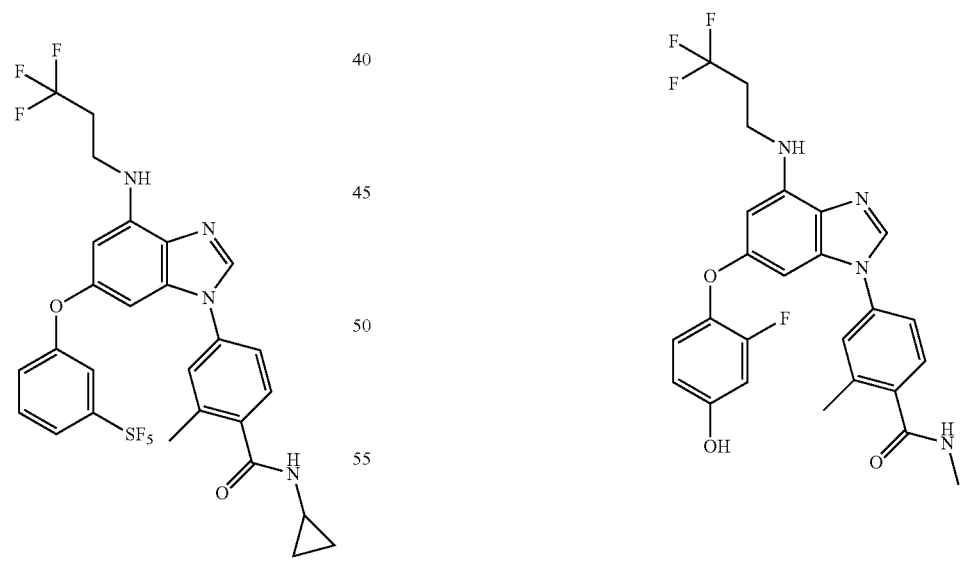

40 mg (83 µmol) 4-{6-bromo-4-[(3,3,3-trifluoropropyl)amino]-1H-benzimidazol-1-yl}-N-cyclopropyl-2-methyl-benzamide which was prepared according to intermediate example 11-1 were transformed in analogy to example 4 using 3-(pentafluoro-lambda⁶-sulfanyl)phenol to give after working up and purification 4.1 mg (8%) of the title compound.

30 mg (58 µmol) 4-{6-(2-fluoro-4-methoxyphenoxy)-4-[(3,3,3-trifluoropropyl)amino]-1H-benzimidazol-1-yl}-N,2-dimethylbenzamide which was prepared according to example 88 were transformed in analogy to example 54 to give after working up and purification 21.5 mg (70%) of the title compound.

$^1$H-NMR (DMSO-d6): δ=2.35 (3H), 2.58 (2H), 2.73 (3H), 3.49 (2H), 6.07 (1H), 6.15 (2H), 6.55 (1H), 6.67 (1H), 7.00 (1H), 7.35 (1H), 7.40 (1H), 7.44 (1H), 8.24 (2H), 9.73 (1H) ppm.

Example 98

N-ethyl-4-{6-(2-fluoro-4-hydroxyphenoxy)-4-[(3,3,3-trifluoropropyl)amino]-1H-benzimidazol-1-yl}-2-methylbenzamide

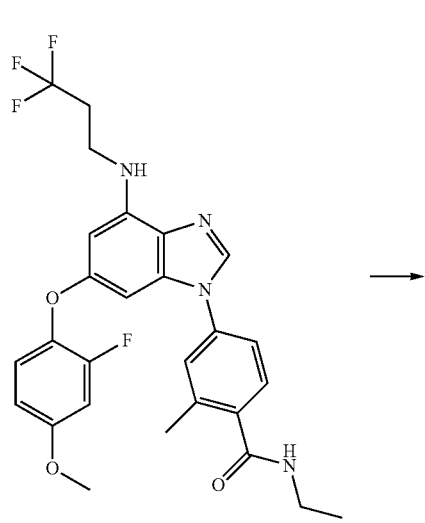

30 mg (58 µmol)N-ethyl-4-{6-(2-fluoro-4-methoxyphenoxy)-4-[(3,3,3-trifluoropropyl)amino]-1H-benzimidazol-1-yl}-2-methylbenzamide which was prepared according to example 89 were transformed in analogy to example 54 to give after working up and purification 20.3 mg (66%) of the title compound.

$^1$H-NMR (DMSO-d6): δ=1.08 (3H), 2.34 (3H), 2.51-2.62 (2H), 3.22 (2H), 3.49 (2H), 6.07 (1H), 6.12-6.17 (2H), 6.54 (1H), 6.66 (1H), 7.00 (1H), 7.34 (1H), 7.39 (1H), 7.42 (1H), 8.23 (1H), 8.30 (1H), 9.77 (1H) ppm.

Example 99

4-{6-(3-fluoro-4-hydroxyphenoxy)-4-[(3,3,3-trifluoropropyl)amino]-1H-benzimidazol-1-yl}-N,2-dimethylbenzamide

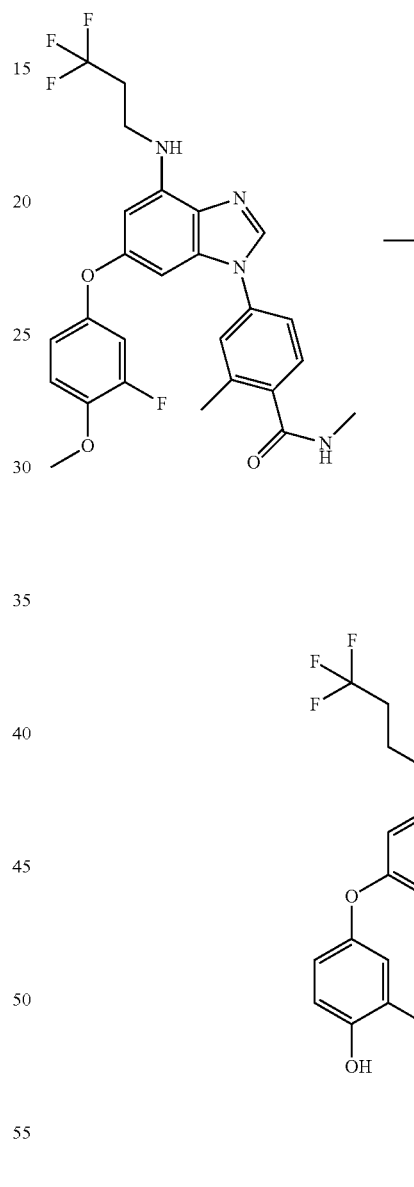

30 mg (58 µmol) 4-{6-(3-fluoro-4-methoxyphenoxy)-4-[(3,3,3-trifluoropropyl)amino]-1H-benzimidazol-1-yl}-N,2-dimethylbenzamide which was prepared according to example 35 were transformed in analogy to example 54 to give after working up and purification 15.7 mg (51%) of the title compound.

¹H-NMR (DMSO-d6): δ=2.36 (3H), 2.49-2.66 (2H), 2.73 (3H), 3.49 (2H), 6.08 (1H), 6.15 (1H), 6.28 (1H), 6.66 (1H), 6.81-6.91 (2H), 7.36-7.47 (3H), 8.22 (1H), 8.27 (1H), 9.57 (1H) ppm.

Example 100

N-ethyl-4-{6-(3-fluoro-4-hydroxyphenoxy)-4-[(3,3,3-trifluoropropyl)amino]-1H-benzimidazol-1-yl}-2-methylbenzamide ¹H-NMR (DMSO-d6): δ=1.08 (3H), 2.36 (3H), 2.52-2.64 (2H), 3.22 (2H), 3.50 (2H), 6.09 (1H), 6.16 (1H), 6.27 (1H), 6.66 (1H), 6.83-6.90 (2H), 7.39 (1H), 7.42-7.45 (2H), 8.26-8.32 (2H), 9.56 (1H) ppm.

Example 101

N-cyclopropyl-4-{6-(3-fluoro-4-methoxybenzoyl)-4-[(3,3,3-trifluoropropyl)amino]-1H-benzimidazol-1-yl}-2-methylbenzamide

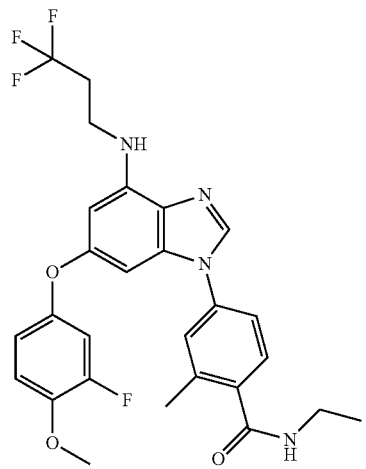

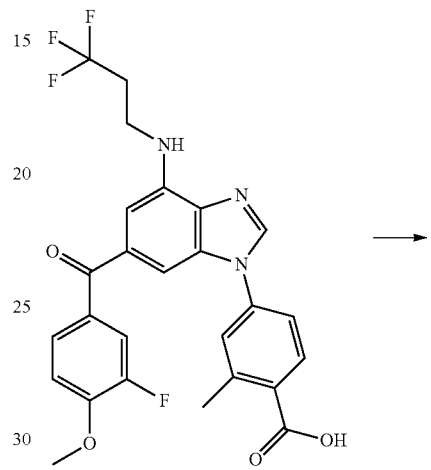

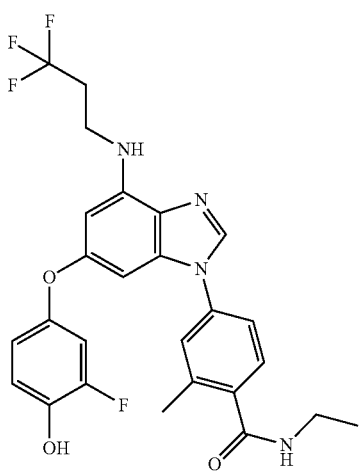

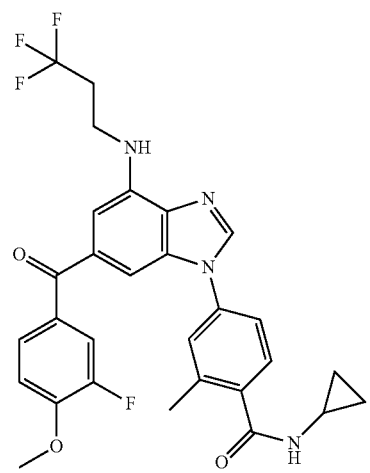

30 mg (58 µmol)N-ethyl-4-{6-(3-fluoro-4-methoxyphenoxy)-4-[(3,3,3-trifluoropropyl)amino]-1H-benzimidazol-1-yl}-2-methylbenzamide which was prepared according to example 34 were transformed in analogy to example 54 to give after working up and purification 18.0 mg (59%) of the title compound.

A mixture comprising 626 mg (1.21 mmol) 4-{6-(3-fluoro-4-methoxybenzoyl)-4-[(3,3,3-trifluoropropyl)amino]-1H-benzimidazol-1-yl}-2-methylbenzoic acid which was prepared according to intermediate example 101a, 252 µL cyclopropanamine, 554 mg N-[dimethylamino)(3H-[1,2,3]triazolo[4,5-b]pyridin-3-yloxy)methylene]-N-methylmethanaminium hexafluorophosphate, 178 mg N,N-dimethylpyridin-4-amine and 15 mL N,N-dimethylformamide was stirred at 23° C. overnight. The solvent was removed and the residue purified by chromatography to give 453 mg (67%) of the title compound.

¹H-NMR (DMSO-d6): δ=0.50 (2H), 0.66 (2H), 2.37 (3H), 2.55-2.71 (2H), 2.81 (1H), 3.58 (2H), 3.90 (3H), 6.29 (1H), 6.74 (1H), 7.08 (1H), 7.25 (1H), 7.43-7.64 (5H), 8.35 (1H), 8.54 (1H) ppm.

Example 101a

4-{6-(3-fluoro-4-methoxybenzoyl)-4-[(3,3,3-trifluoropropyl)amino]-1H-benzimidazol-1-yl}-2-methylbenzoic acid

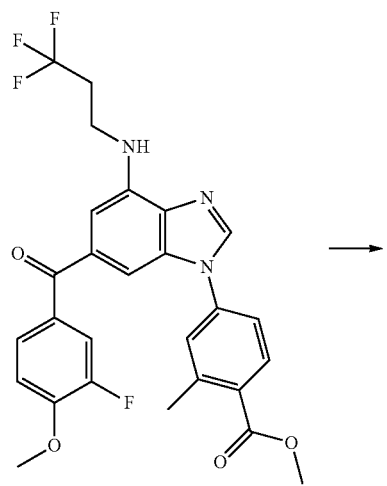

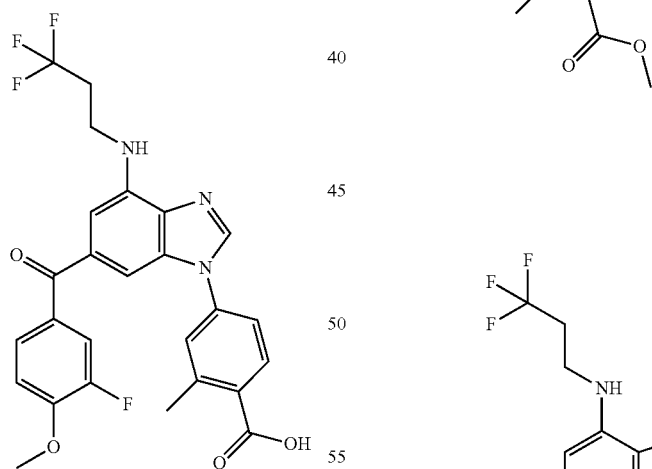

To a solution of 660 mg (1.25 mmol) methyl 4-{6-(3-fluoro-4-methoxybenzoyl)-4-[(3,3,3-trifluoropropyl)amino]-1H-benzimidazol-1-yl}-2-methylbenzoate which was prepared according to intermediate example 101b in 25 mL tetrahydrofurane and 8 mL methanol were added 6.2 mL of a 1M aqueous lithium hydroxide solution and the mixture was stirred at 23° C. overnight. Water was added, the mixture was acidified by the addition of a 1M hydrochloric acid and extracted with dichloromethane and methanol. The organic layer was washed with brine and dried over sodium sulfate.

After filtration and removal of solvent the residue was purified by chromatography to give 632 mg (98%) of the title compound.

Example 101b methyl 4-{6-(3-fluoro-4-methoxybenzoyl)-4-[(3,3,3-trifluoropropyl)amino]-1H-benzimidazol-1-yl}-2-methylbenzoate (A) and 1-[4-(methoxycarbonyl)-3-methylphenyl]-4-[(3,3,3-trifluoropropyl)amino]-1H-benzimidazole-6-carboxylic acid (B)

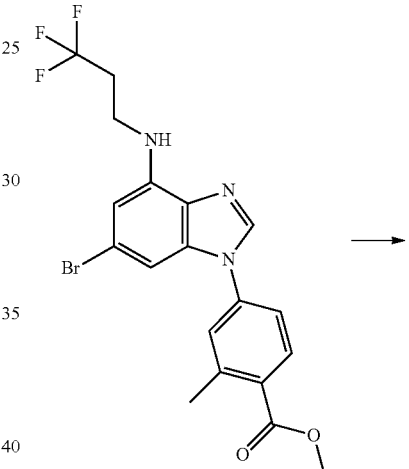

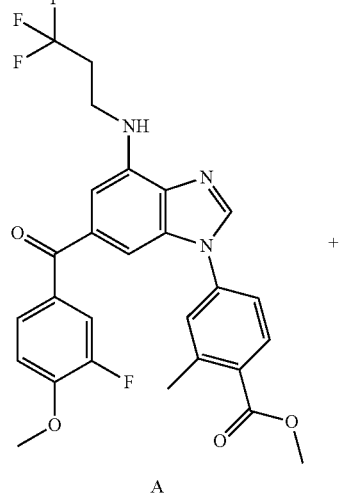

A

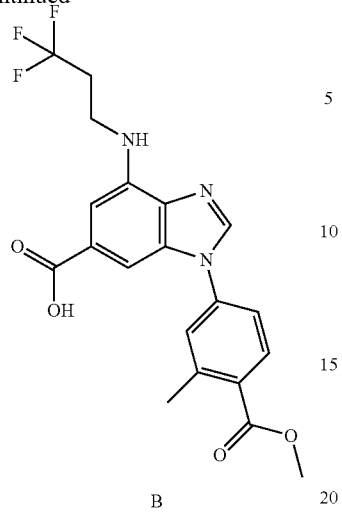

B

A mixture comprising 2.50 g (5.48 mmol) methyl 4-{6-bromo-4-[(3,3,3-trifluoropropyl)amino]-1H-benzimidazol-1-yl}-2-methylbenzoate which was prepared according to intermediate example 101c, 2.79 g (3-fluoro-4-methoxyphenyl)boronic acid, 6.15 mg palladium(II) diacetate, 31.0 mg butyldi-1-adamantylphosphine, 643 mg tetramethylethylenediamine and 100 mL toluene was reacted at 100° C. under a carbon monoxide pressure up to 14 bar. After filtration the residue was purified by chromatography to give 550 mg (19%) of title compound A and 956 mg (41%) of title compound B.

Example 101c

Methyl 4-{6-bromo-4-[(3,3,3-trifluoropropyl)amino]-1H-benzimidazol-1-yl}-2-methylbenzoate

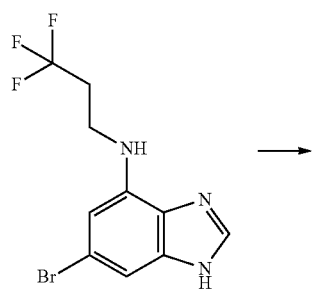

A mixture comprising 9.80 g (31.8 mmol) 6-bromo-N-(3,3,3-trifluoropropyl)-1H-benzimidazol-4-amine which was prepared according to intermediate example 101d, 18.5 g [4-(methoxycarbonyl)-3-methylphenyl]boronic acid, 390 mL dichloromethane, 9.08 g pyridine N-oxide, 11.55 copper (II)acetate and 10.3 mL pyridine was stirred for 1.5 days at 23° C. 9.08 g pyridine N-oxide, 8.6 g [4-(methoxycarbonyl)-3-methylphenyl]boronic acid and 10.3 mL pyridine were added and stirring continued for another day. Water was added and the mixture extracted with dichloromethane and methanol. The organic layer was washed with water and brine and dried over sodiumsulfate. After filtration and removal of the solvent the crude product was purified by chromatography to give 4.97 g (34%) of the title compound.

Example 101d

6-Bromo-N-(3,3,3-trifluoropropyl)-1H-benzimidazol-4-amine methyl

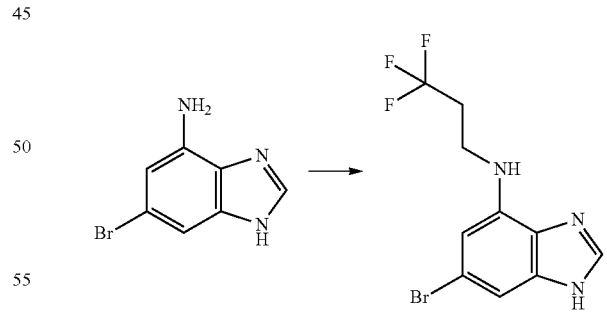

To a solution of 15.0 g (70.74 mmol) 6-bromo-1H-benzimidazol-4-amine which was prepared according to intermediate example 101e in 900 mL dichloromethane were added 11.89 g 3,3,3-trifluoropropanal and 12.55 mL acetic acid at 23° C. A total of 44.98 g sodium triacetoxy borohydride were added in three portions and the mixture was stirred overnight. The mixture was cooled to 3° C., 2M aqueous ammonia was added and extracted with dichloromethane. The organic layer was washed with brine and dried over sodiumsulfate. After

Example 101e

Preparation of 6-bromo-1H-benzimidazol-4-amine

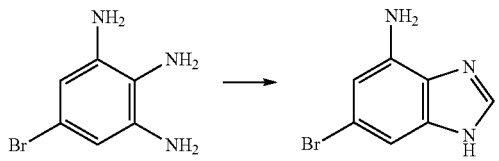 [SMILES: Nc1cc(Br)cc(N)c1N ; Nc1cc(Br)cc2[nH]cnc12]

To a stirred suspension of 5-bromobenzene-1,2,3-triamine (81.5 g, 403 mmol) in HCl conc (2400 mL) at rt was added formic acid (46 mL, 1210 mmol, 3 eq). After stirring at reflux for 90 min, water (500 mL) was added to the suspension, and the pH was adjusted to 8 using ammonia (33% aqueous solution). After extraction with ethyl acetate (3×1000 mL), the organic phase was washed with saturated sodium chloride solution, dried over sodium sulphate and evaporated in vaccuo. The crude product was trituarated with diethyl ether (200 mL), filtered and dried to yield 82.3 g (96.3%) of the title compound.

Example 102

N-cyclopropyl-4-{6-[(3-fluoro-4-methoxyphenyl)(hydroxy)methyl]-4-[(3,3,3-trifluoropropyl)amino]-1H-benzimidazol-1-yl}-2-methylbenzamide

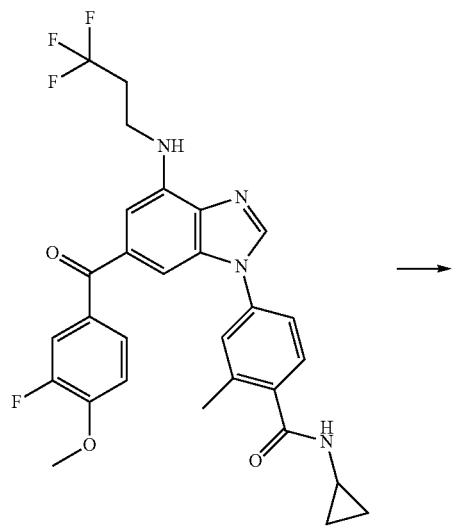

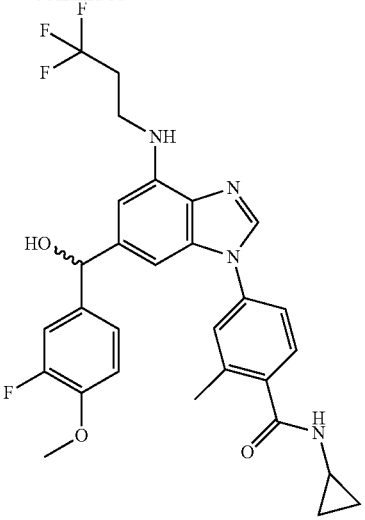

To a solution of 50 mg (90 μmol)N-cyclopropyl-4-{6-(3-fluoro-4-methoxybenzoyl)-4-[(3,3,3-trifluoropropyl)amino]-1H-benzimidazol-1-yl}-2-methylbenzamide which was prepared according to example 101 in 1 mL tetrahydrofuran and 0.1 mL methanol were added 6.82 mg sodium borohydride. The mixture was stirred at 23° C. for 1 hour, water was added and extracted with ethyl acetate. The organic layer was washed with saturated ammonium chloride solution and dried over sodium sulfate. After filtration and removal of the solvent, the residue was purified by chromatography to give 27.1 mg (51%) of the title compound.

$^1$H-NMR (DMSO-d6): δ=0.51 (2H), 0.67 (2H), 2.38 (3H), 2.48-2.62 (2H), 2.83 (1H), 3.49 (2H), 3.73 (3H), 5.63 (1H), 5.76 (1H), 5.87 (1H), 6.35 (1H), 6.85 (1H), 7.01 (1H), 7.07 (1H), 7.11 (1H), 7.41-7.49 (3H), 8.27 (1H), 8.36 (1H) ppm.

Example 103

N-cyclopropyl-4-{6-[(1RS)-1-(3-fluoro-4-methoxyphenyl)-1-hydroxyethyl]-4-[(3,3,3-trifluoropropyl)amino]-1H-benzimidazol-1-yl}-2-methylbenzamide (A) and N-cyclopropyl-4-{6-[(1RS)-1-(3-fluoro-4-methoxyphenyl)-1-hydroxyethyl]-4-[(3,3,3-trifluoropropyl)amino]-1H-benzimidazol-1-yl}-2-(hydroxymethyl)benzamide (B)

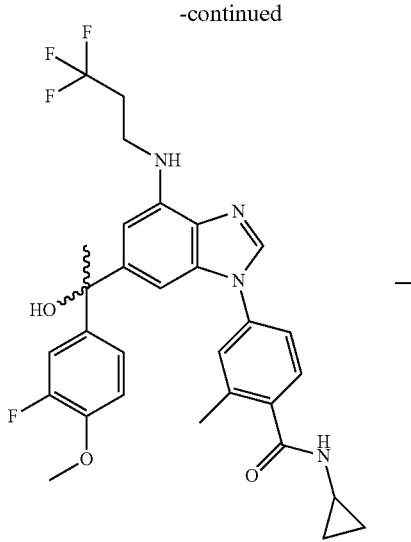

A

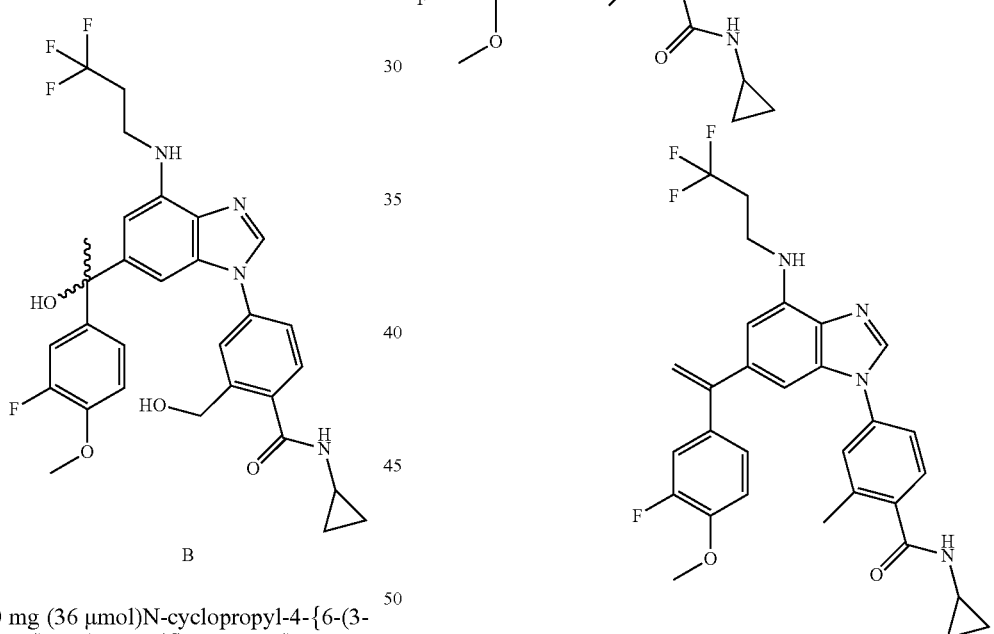

(2H), 5.36 (1H), 5.60 (1H), 5.83 (1H), 6.33 (1H), 6.95-7.02 (2H), 7.11 (1H), 7.15 (1H), 7.51 (1H), 7.57 (1H), 7.72 (1H), 8.28 (1H), 8.47 (1H) ppm.

Example 104

N-cyclopropyl-4-{6-[1-(3-fluoro-4-methoxyphenyl)vinyl]-4-[(3,3,3-trifluoropropyl)amino]-1H-benzimidazol-1-yl}-2-methylbenzamide To a solution of 20 mg (36 µmol)N-cyclopropyl-4-{6-(3-fluoro-4-methoxybenzoyl)-4-[(3,3,3-trifluoropropyl)amino]-1H-benzimidazol-1-yl}-2-methylbenzamide which was prepared according to example 101 in 1.0 mL tetrahydrofuran were added at 3° C. 90 µL of a 1.6 M solution of methyllithium in diethyl ether. The mixture was stirred at 3° C. for 1 hour, water was added and extraction was performed using ethyl acetate. The organic layer was washed with saturated ammonium chloride solution and dried over sodium sulfate. After filtration and removal of the solvent, the residue was purified by chromatography to give 4.5 mg (21%) of the title compound A and 3.5 mg (16%) of the title compound B.

$^1$H-NMR (DMSO-d6) of A: δ=0.51 (2H), 0.67 (2H), 1.77 (3H), 2.38 (3H), 2.48-2.57 (2H), 2.82 (1H), 3.48 (2H), 3.74 (3H), 5.60 (1H), 5.82 (1H), 6.32 (1H), 6.91 (1H), 6.99 (1H), 7.07-7.18 (2H), 7.41-7.50 (3H), 8.27 (1H), 8.37 (1H) ppm.

$^1$H-NMR (DMSO-d6) of B: δ=0.53 (2H), 0.68 (2H), 1.78 (3H), 2.48-2.57 (2H), 2.82 (1H), 3.48 (2H), 3.74 (3H), 4.66

A solution of 128.8 mg methyltriphenylphosphonium bromide in 2 mL tetrahydrofuran was cooled to −30° C., 140.6 µL n-butyl lithium (2.5 M in n-hexane) were added and the mixture was stirred for 0.5 hours at 23° C. A solution of 50 mg (90 µmol)N-cyclopropyl-4-{6-(3-fluoro-4-methoxybenzoyl)-4-[(3,3,3-trifluoropropyl)amino]-1H-benzimidazol-1-yl}-2-methylbenzamide which was prepared according to example 101 in 1 mL tetrahydrofuran were added and stirring was continued overnight. Water was added and the mixture extracted with ethyl acetate. The organic layer was washed with saturated ammonium chloride solution and dried over sodium sulfate. After filtration and removal of the solvent, the residue was purified by chromatography to give 20.1 mg (38%) of the title compound.

¹H-NMR (DMSO-d6): δ=0.49 (2H), 0.65 (2H), 2.35 (3H), 2.49-2.65 (2H), 2.80 (1H), 3.51 (2H), 3.80 (3H), 5.37 (1H), 5.41 (1H), 6.01 (1H), 6.28 (1H), 6.64 (1H), 7.03-7.18 (3H), 7.40-7.48 (3H), 8.32 (1H), 8.34 (1H) ppm.

Example 105

N-cyclopropyl-4-{6-[(1RS)-1-(3-fluoro-4-methoxyphenyl)ethyl]-4-[(3,3,3-trifluoropropyl)amino]-1H-benzimidazol-1-yl}-2-methylbenzamide

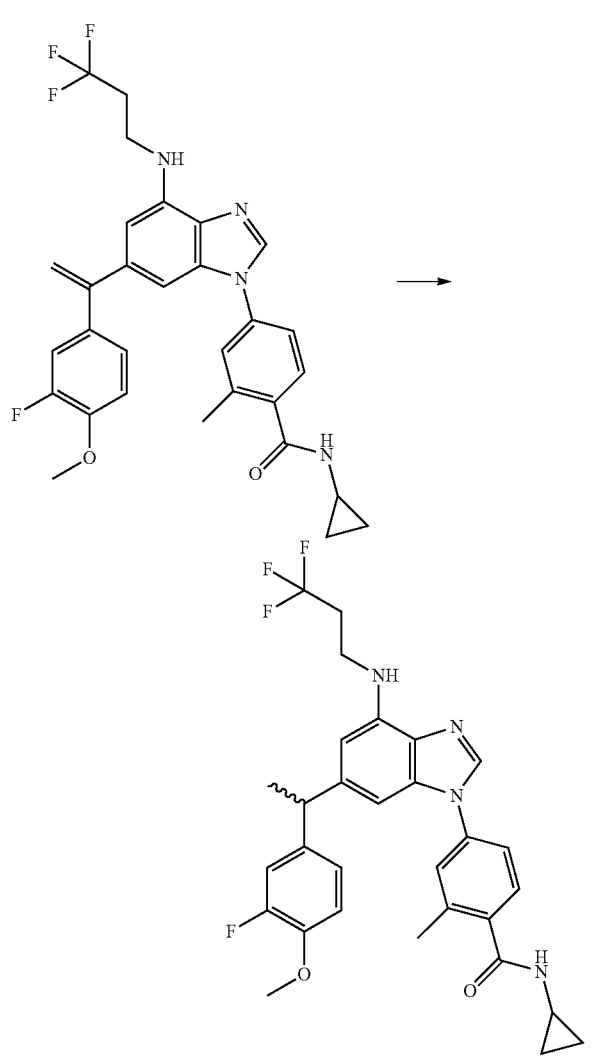

To a solution of 14.5 mg (26 μmol)N-cyclopropyl-4-{6-[1-(3-fluoro-4-methoxyphenyl)vinyl]-4-[(3,3,3-trifluoropropyl)amino]-1H-benzimidazol-1-yl}-2-methylbenzamide which was prepared according to example 104 in 0.7 mL ethanol were added 1.12 mg palladium on charcoal (10%) and the mixture was vigorously stirred under an atmosphere of hydrogen for 2 days at 23° C. After filtration and removal of the solvent the residue was purified by chromatography to give 7.1 mg (46%) of the title compound.

¹H-NMR (DMSO-d6): δ=0.51 (2H), 0.67 (2H), 1.52 (3H), 2.38 (3H), 2.50-2.61 (2H), 2.82 (1H), 3.50 (2H), 3.73 (3H), 4.10 (1H), 5.85 (1H), 6.25 (1H), 6.67 (1H), 6.97-7.02 (2H), 7.06 (1H), 7.42-7.47 (3H), 8.25 (1H), 8.36 (1H) ppm.

Example 106

N-cyclopropyl-4-{6-(3-fluoro-4-methoxybenzyl)-4-[(3,3,3-trifluoropropyl)amino]-1H-benzimidazol-1-yl}-2-methylbenzamide

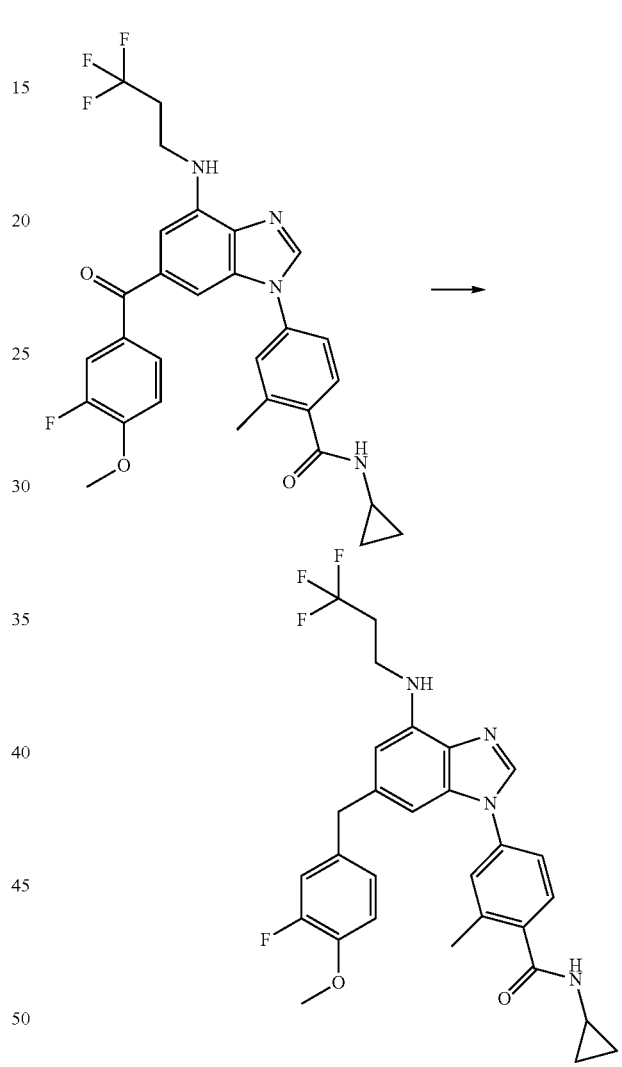

To a solution of 50 mg (90 μmol)N-cyclopropyl-4-{6-(3-fluoro-4-methoxybenzoyl)-4-[(3,3,3-trifluoropropyl)amino]-1H-benzimidazol-1-yl}-2-methylbenzamide which was prepared according to example 101 in 0.25 mL dichloromethane and 0.5 mL trifluoroacetic acid were added 40.9 mg sodium borohydride and the mixture was stirred at 3° C. for two hours. Saturated sodium hydrogencarbonate solution was added and the mixture extracted with dichloromethane. The organic layer was dried over sodium sulfate. After filtration and removal of the solvent, the residue was purified by chromatography to give 19.4 mg (38%) of the title compound.

¹H-NMR (DMSO-d6): δ=0.51 (2H), 0.67 (2H), 2.37 (3H), 2.49-2.65 (2H), 2.82 (1H), 3.50 (2H), 3.73 (3H), 3.85 (2H), 5.87 (1H), 6.26 (1H), 6.65 (1H), 6.93-7.06 (3H), 7.40-7.49 (3H), 8.25 (1H), 8.35 (1H) ppm.

6.22 (1H), 6.29 (1H), 6.60 (1H), 6.81 (1H), 7.25 (1H), 7.36-7.47 (3H), 8.30 (1H), 8.33 (1H) ppm.

Example 107

N-cyclopropyl-4-{6-(5-fluoro-2-methylphenoxy)-4-[(3,3,3-trifluoropropyl)amino]-1H-benzimidazol-1-yl}-2-methylbenzamide

Example 108

N-cyclopropyl-4-{6-(3-fluoro-4-hydroxybenzoyl)-4-[(3,3,3-trifluoropropyl)amino]-1H-benzimidazol-1-yl}-2-methylbenzamide

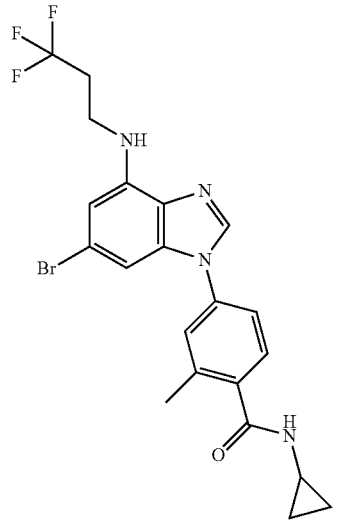

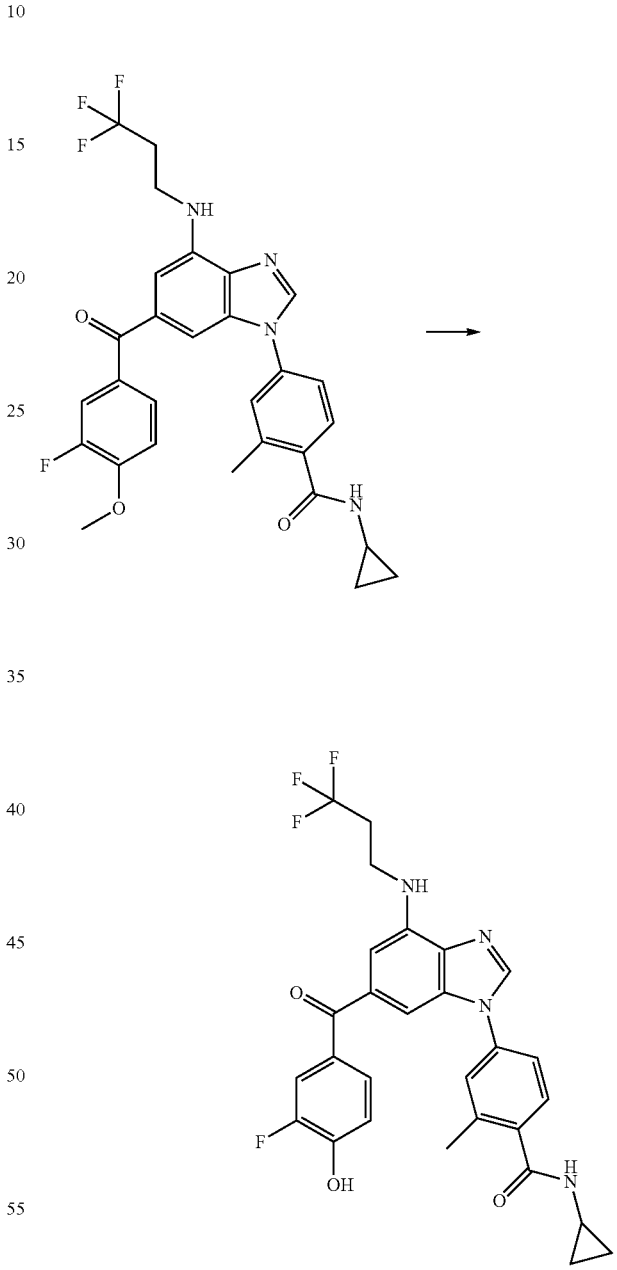

50 mg (104 µmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using 5-fluoro-2-methylphenol to give after working up and purification 32.2 mg (56%) of the title compound.

¹H-NMR (DMSO-d6): δ=0.49 (2H), 0.65 (2H), 2.16 (3H), 2.34 (3H), 2.49-2.66 (2H), 2.79 (1H), 3.49 (2H), 6.10 (1H), 25 mg (45 µmol)N-cyclopropyl-4-{6-(3-fluoro-4-methoxybenzoyl)-4-[(3,3,3-trifluoropropyl)amino]-1H-benzimidazol-1-yl}-2-methylbenzamide which was prepared according to example 101 were transformed in analogy to example 54 to give after working up and purification 2.7 mg (11%) of the title compound.

1H-NMR (DMSO-d6): δ=0.50 (2H), 0.65 (2H), 2.37 (3H), 2.56-2.70 (2H), 2.81 (1H), 3.58 (2H), 6.24 (1H), 6.70 (1H), 6.92 (1H), 7.04 (1H), 7.42-7.55 (5H), 8.35 (1H), 8.52 (1H) ppm.

Example 109

N-cyclopropyl-4-{6-[3-(difluoromethyl)phenoxy]-4-[(3,3,3-trifluoropropyl)amino]-1H-benzimidazol-1-yl}-2-methylbenzamide

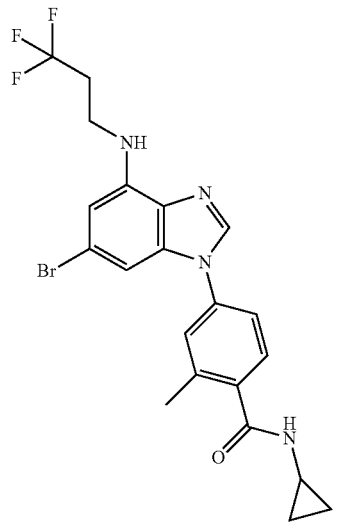

50 mg (104 μmol) 4-{6-bromo-4-[(3,3,3-trifluoropropyl)amino]-1H-benzimidazol-1-yl}-N-cyclopropyl-2-methylbenzamide which was prepared according to intermediate example 11-1 were transformed in analogy to example 4 using 3-(difluoromethyl)phenol to give after working up and purification 34.7 mg (58%) of the title compound.

1H-NMR (DMSO-d6): δ=0.48 (2H), 0.65 (2H), 2.34 (3H), 2.51-2.64 (2H), 2.79 (1H), 3.49 (2H), 6.16 (1H), 6.26 (1H), 6.42 (1H), 6.95 (1H), 7.10-7.24 (3H), 7.39-7.47 (4H), 8.31-8.35 (2H) ppm.

Example 110

N-cyclopropyl-4-{6-(2-methoxybenzoyl)-4-[(3,3,3-trifluoropropyl)amino]-1H-benzimidazol-1-yl}-2-methylbenzamide

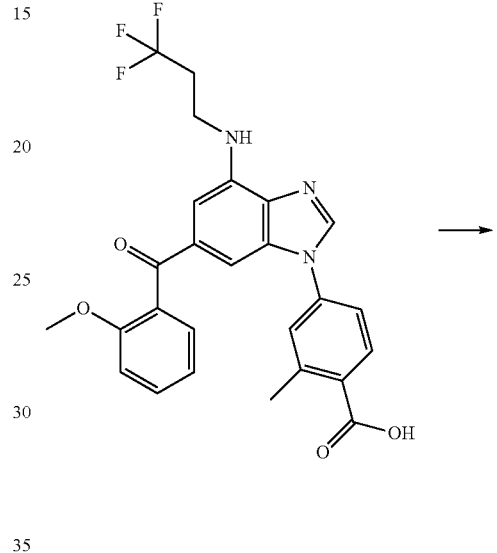

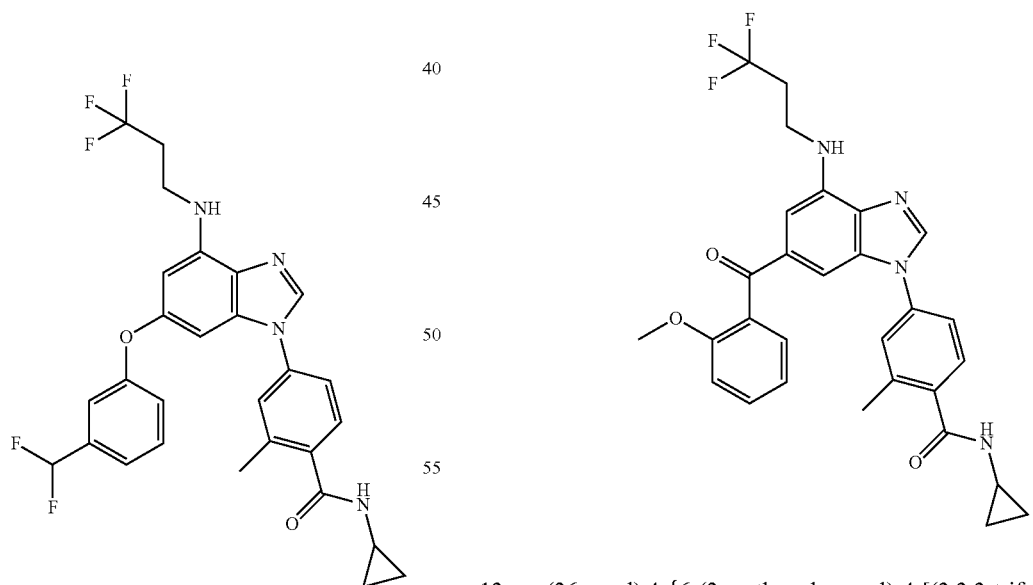

13 mg (26 μmol) 4-{6-(2-methoxybenzoyl)-4-[(3,3,3-trifluoropropyl)amino]-1H-benzimidazol-1-yl}-2-methylbenzoic acid which was prepared according to intermediate example 110a were transformed in analogy to example 10 using cyclopropanamine to give after working up and purification 10.5 mg (71%) of the title compound.

1H-NMR (DMSO-d6): δ=0.50 (2H), 0.66 (2H), 2.34 (3H), 2.53-2.65 (2H), 2.81 (1H), 3.53 (2H), 3.66 (3H), 6.25 (1H), 6.78 (1H), 7.01 (1H), 7.08 (1H), 7.13 (1H), 7.25 (1H), 7.39-7.49 (4H), 8.38 (1H), 8.53 (1H) ppm.

Example 110a

4-{6-(2-methoxybenzoyl)-4[(3,3,3-trifluoropropyl)amino]-1H-benzimidazol-1-yl}-2-methylbenzoic acid

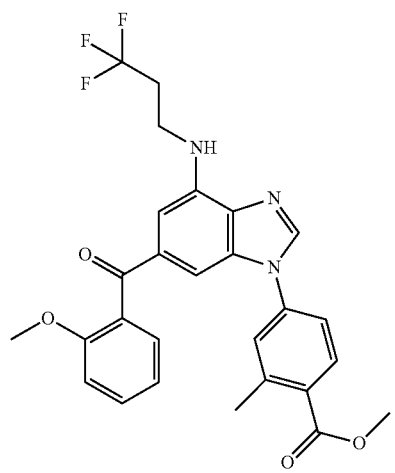

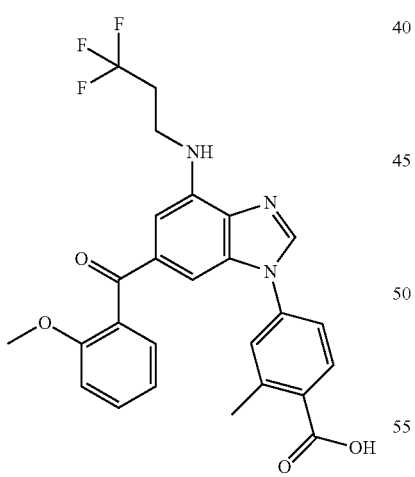

17 mg (33 μmol) methyl 4-{6-(2-methoxybenzoyl)-4-[(3,3,3-trifluoropropyl)amino]-1H-benzimidazol-1-yl}-2-methylbenzoate which was prepared according to intermediate example 110b were transformed in analogy to intermediate example 10a to give after working up and purification 13.5 mg (82%) of the title compound.

Example 110b methyl 4-{6-(2-methoxybenzoyl)-4-[(3,3,3-trifluoropropyl)amino]-1H-benzimidazol-1-yl}-2-methylbenzoate

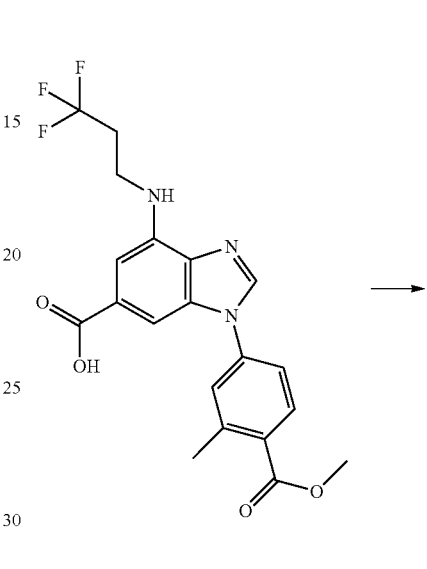

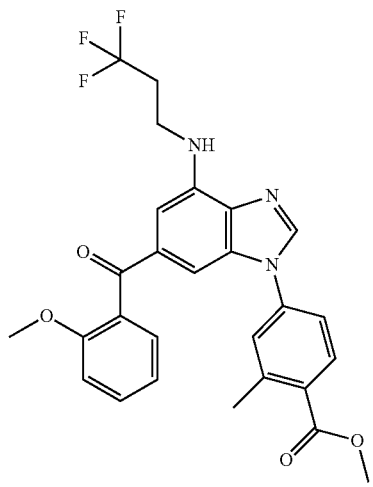

A mixture comprising 100 mg (237 μmol) 1-[4-(methoxycarbonyl)-3-methylphenyl]-4-[(3,3,3-trifluoropropyl)amino]-1H-benzimidazole-6-carboxylic acid which was prepared according to intermediate example 101b, compound B, 1.2 mL tetrahydrofuran, 10.7 μL water, 96.3 μL 2,2-dimethylpropanoic anhydride, 7.5 mg triphenylphosphine, and 3.2 mg palladium(II) diacetate was heated at 130° C. under microwave irradiation for 2 hours. The solvent was removed and the residue purified by chromatography to give 17.4 mg (14%) of the title compound.

¹H-NMR (DMSO-d6): δ=0.51 (2H), 0.67 (2H), 2.37 (3H), 2.55-2.67 (2H), 2.82 (1H), 3.53 (2H), 6.15 (1H), 6.19 (1H), 6.33-6.45 (4H), 7.08 (1H), 7.40-7.48 (3H), 8.32 (1H), 8.34 (1H), 9.45 (1H) ppm.

Example 111

N-cyclopropyl-4-{6-(3-hydroxyphenoxy)-4-[(3,3,3-trifluoropropyl)amino]-1H-benzimidazol-1-yl}-2-methylbenzamide Example 112

4-{6-(3-fluoro-4-hydroxyphenoxy)-4-[(tetrahydro-2H-pyran-4-ylmethyl)amino]-1H-benzimidazol-1-yl}-N,2-dimethylbenzamid

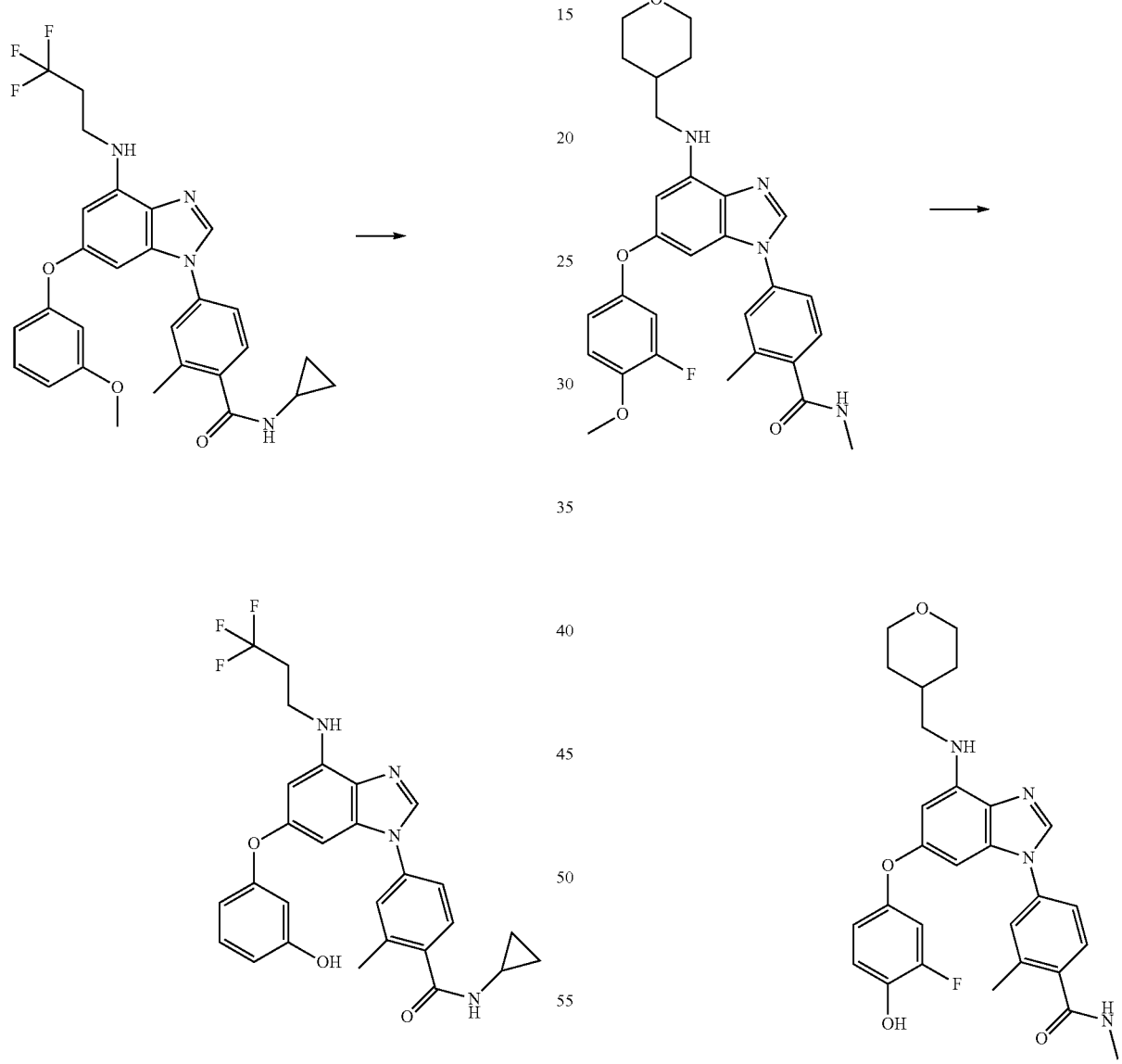

27 mg (51 μmol)N-cyclopropyl-4-{6-(3-methoxyphenoxy)-4-[(3,3,3-trifluoropropyl)amino]-1H-benzimidazol-1-yl}-2-methylbenzamide which was prepared according to example 70 were transformed in analogy to example 54 to give after working up and purification 4.3 mg (16%) of the title compound.

33.3 mg (64 μmol) 4-{6-(3-fluoro-4-methoxyphenoxy)-4-[(tetrahydro-2H-pyran-4-ylmethyl)amino]-1H-benzimidazol-1-yl}-N,2-dimethylbenzamide which was prepared according to example 42 were transformed in analogy to example 58 to give after working up and purification 10.3 mg (30%) of the title compound.

¹H-NMR (CD₃OD): δ=1.37 (2H), 1.75 (2H), 1.94 (1H), 2.45 (3H), 2.90 (3H), 3.13 (2H), 3.41 (2H), 3.95 (2H), 6.13

(1H), 6.27 (1H), 6.66 (1H), 6.74 (1H), 6.86 (1H), 7.07-7.22 (2H), 7.38 (1H), 7.41 (1H), 7.51 (1H), 8.15 (1H) ppm.

Example 113

N-ethyl-4-{6-(3-fluoro-4-hydroxyphenoxy)-4-[(tetrahydro-2H-pyran-4-ylmethyl)amino]-1H-benzimidazol-1-yl}-2-methylbenzamide A and N-ethyl-4-{6-[4-methoxy-3-(methylsulfanyl)phenoxy]-4-[(tetrahydro-2H-pyran-4-ylmethyl)amino]-1H-benzimidazol-1-yl}-2-methylbenzamide B

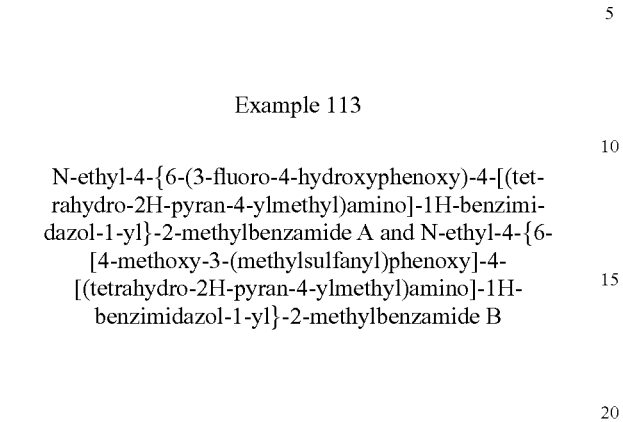

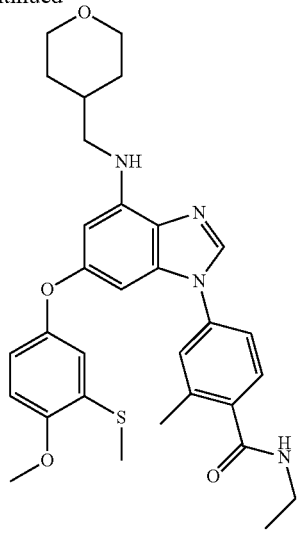

21.5 mg (40 µmol) N-ethyl-4-{6-(3-fluoro-4-methoxyphenoxy)-4-[(tetrahydro-2H-pyran-4-ylmethyl)amino]-1H-benzimidazol-1-yl}-2-methylbenzamide which was prepared according to example 43 were transformed in analogy to example 58 to give after working up and purification 5.9 mg (27%) of the title compound A and 2.0 mg (8%) of the title compound B.

$^1$H-NMR (CDCl$_3$) of A: δ=1.27 (3H), 1.39 (2H), 1.81 (2H), 1.99 (1H), 2.50 (3H), 3.12 (2H), 3.40 (2H), 3.50 (2H), 3.97 (2H), 5.98 (1H), 6.07-6.41 (3H), 6.71 (1H), 6.78 (1H), 6.96 (1H), 7.23-7.35 (3H), 7.51 (1H), 8.38 (1H) ppm.

$^1$H-NMR (CDCl$_3$) of B: δ=1.28 (3H), 1.41 (2H), 1.81 (2H), 2.00 (1H), 2.37 (3H), 2.51 (3H), 3.15 (2H), 3.42 (2H), 3.52 (2H), 3.88 (3H), 4.00 (2H), 5.79 (1H), 6.22 (2H), 6.77 (2H), 6.87 (1H), 7.25-7.34 (3H), 7.51 (1H), 8.09 (1H) ppm.

Example 114

N-cyclopropyl-4-{6-(3-fluoro-4-hydroxyphenoxy)-4-[(tetrahydro-2H-pyran-4-ylmethyl)amino]-1H-benzimidazol-1-yl}-2-methylbenzamide A and N-cyclopropyl-4-{6-[4-methoxy-3-(methylsulfanyl)phenoxy]-4-[(tetrahydro-2H-pyran-4-ylmethyl)amino]-1H-benzimidazol-1-yl}-2-methylbenzamide B

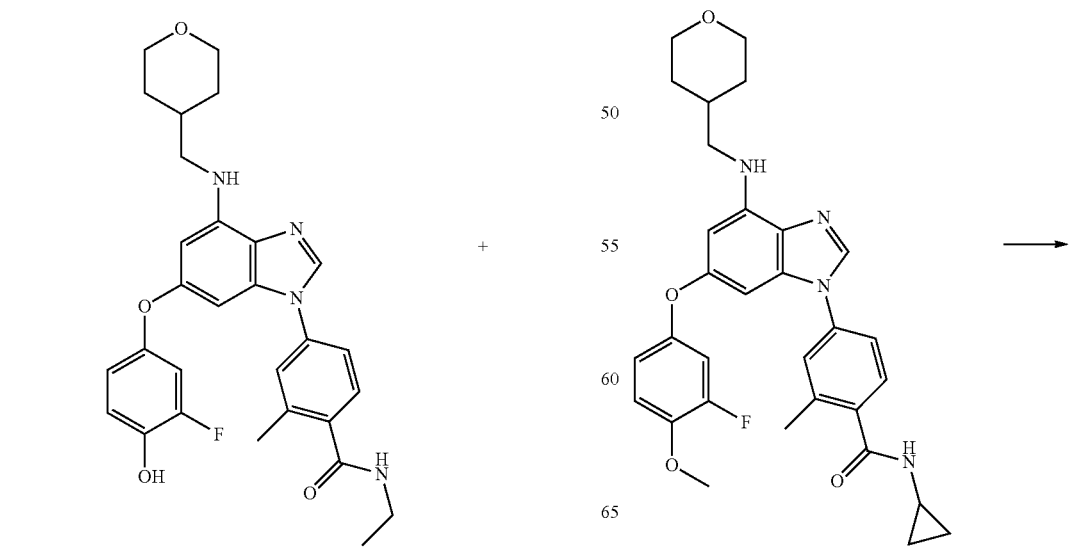

-continued

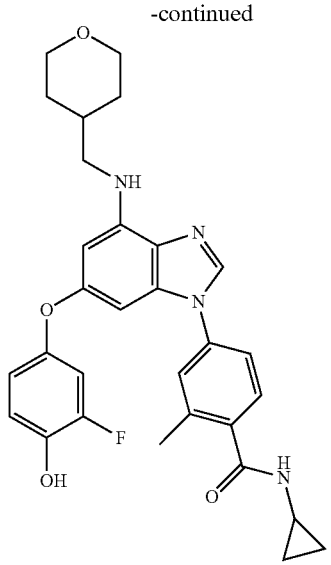

42.3 mg (μmol)N-cyclopropyl-4-{6-(3-fluoro-4-methoxyphenoxy)-4-[(tetrahydro-2H-pyran-4-ylmethyl)amino]-1H-benzimidazol-1-yl}-2-methylbenzamide which was prepared according to example 44 were transformed in analogy to example 58 to give after working up and purification 3.0 mg (21%) of the title compound A and 3.0 mg (23%) of the title compound B.

$^1$H-NMR (CDCl$_3$) of A: δ=0.63 (2H), 0.91 (2H), 1.40 (2H), 1.80 (2H), 1.98 (1H), 2.50 (3H), 2.93 (1H), 3.14 (2H), 3.40 (2H), 3.98 (2H), 5.87 (1H), 6.01 (1H), 6.19 (1H), 6.26 (1H), 6.72 (1H), 6.79 (1H), 6.95 (1H), 7.25-7.34 (3H), 7.48 (1H), 8.13 (1H) ppm.

$^1$H-NMR (CDCl$_3$) of B: δ=0.64 (2H), 0.91 (2H), 1.40 (2H), 1.81 (2H), 2.00 (1H), 2.37 (3H), 2.51 (3H), 2.94 (1H), 3.15 (2H), 3.41 (2H), 3.88 (3H), 4.00 (2H), 5.94 (1H), 6.21 (2H), 6.77 (2H), 6.87 (1H), 7.25-7.32 (3H), 7.48 (1H), 8.12 (1H) ppm.

Example 115

4-{6-(2-fluoro-4-hydroxyphenoxy)-4-[(tetrahydro-2H-pyran-4-ylmethyl)amino]-1H-benzimidazol-1-yl}-N,2-dimethylbenzamide A and 4-{6-[4-methoxy-2-(methylsulfanyl)phenoxy]-4-[(tetrahydro-2H-pyran-4-ylmethyl)amino]-1H-benzimidazol-1-yl}-N,2-dimethylbenzamide B

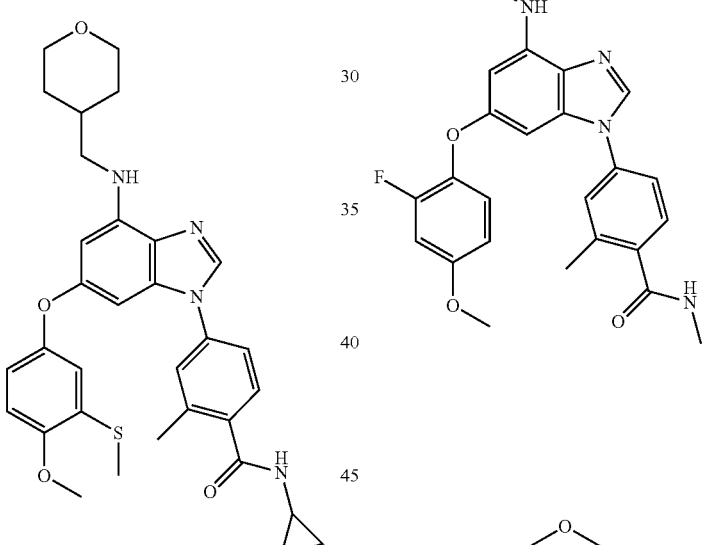

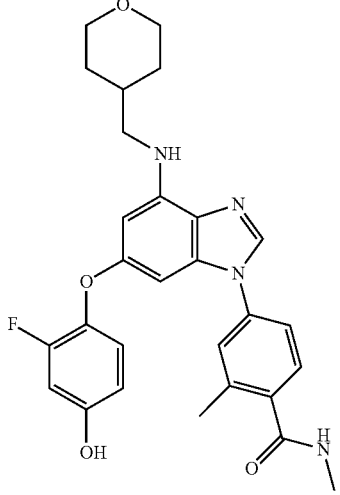

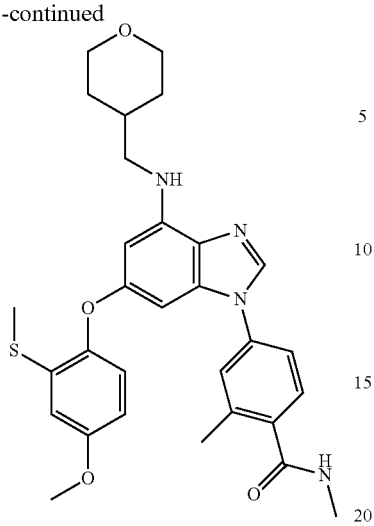

25.6 mg (49 μmol) 4-{6-(2-fluoro-4-methoxyphenoxy)-4-[(tetrahydro-2H-pyran-4-ylmethyl)amino]-1H-benzimidazol-1-yl}-N,2-dimethylbenzamide which was prepared according to example 86 were transformed in analogy to example 58 to give after working up and purification 3.0 mg (10%) of the title compound A and 3.7 mg (12%) of the title compound B.

$^1$H-NMR (DMSO-d6) of A: δ=1.18 (2H), 1.60 (2H), 1.83 (1H), 2.34 (3H), 2.72 (3H), 3.09 (2H), 3.22 (2H), 3.82 (2H), 6.07 (2H), 6.55 (1H), 6.67 (1H), 7.00 (1H), 7.36 (1H), 7.41 (1H), 7.45 (1H), 8.27 (1H), 8.49 (1H), 9.78 (1H) ppm.

$^1$H-NMR (CDCl$_3$) of B: δ=1.39 (2H), 1.77 (2H), 1.96 (1H), 2.43 (3H), 2.49 (3H), 3.02 (3H), 3.15 (2H), 3.40 (2H), 3.81 (3H), 3.99 (2H), 5.86 (1H), 6.19 (1H), 6.22 (1H), 6.62 (1H), 6.79 (1H), 6.88 (1H), 7.23-7.31 (3H), 7.48 (1H), 7.94 (1H) ppm.

Example 116

N-cyclopropyl-4-{6-(2-fluoro-4-hydroxyphenoxy)-4-[(tetrahydro-2H-pyran-4-ylmethyl)amino]-1H-benzimidazol-1-yl}-2-methylbenzamide A and N-cyclopropyl-4-{6-[4-methoxy-2-(methylsulfanyl)phenoxy]-4-[(tetrahydro-2H-pyran-4-ylmethyl)amino]-1H-benzimidazol-1-yl}-2-methylbenzamide B

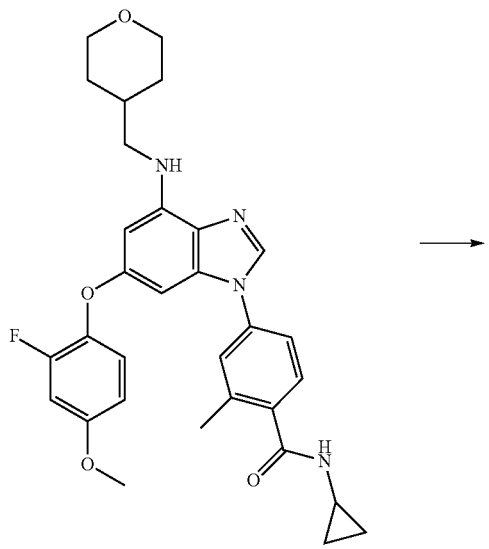

⟶

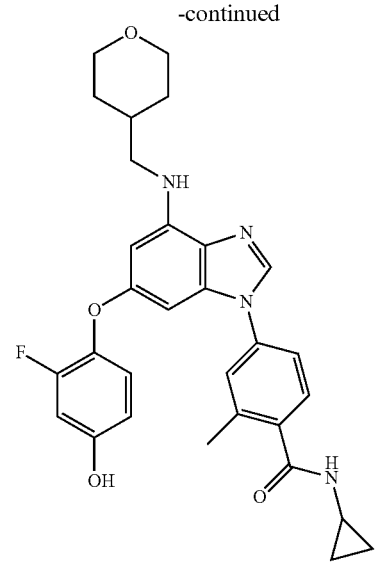

+

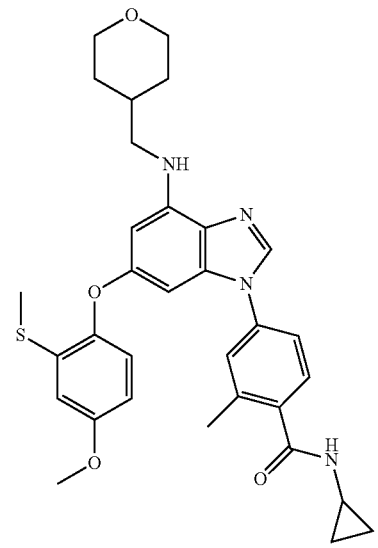

42.3 mg (78 μmol) N-cyclopropyl-4-{6-(2-fluoro-4-methoxyphenoxy)-4-[(tetrahydro-2H-pyran-4-ylmethyl)amino]-1H-benzimidazol-1-yl}-2-methylbenzamide which was prepared according to example 24 were transformed in analogy to example 58 to give after working up and purification 3.2 mg (7%) of the title compound A and 7.0 mg (16%) of the title compound B.

$^1$H-NMR (DMSO-d6) of A: δ=0.49 (2H), 0.65 (2H), 1.18 (2H), 1.59 (2H), 1.83 (1H), 2.32 (3H), 2.80 (2H), 3.09 (2H), 3.22 (2H), 3.81 (2H), 6.06 (2H), 6.55 (1H), 6.67 (1H), 7.00 (1H), 7.32-7.46 (3H), 8.37 (1H), 8.40 (1H), 9.77 (1H) ppm.

$^1$H-NMR (CDCl$_3$) of B: δ=0.63 (2H), 0.90 (2H), 1.39 (2H), 1.76 (2H), 1.95 (1H), 2.43 (3H), 2.48 (3H), 2.92 (1H), 3.15

(2H), 3.39 (2H), 3.81 (3H), 3.99 (2H), 5.97 (1H), 6.18 (1H), 6.23 (1H), 6.62 (1H), 6.79 (1H), 6.87 (1H), 7.22-7.34 (3H), 7.44 (1H), 7.87 (1H) ppm.

Example 117

N-ethyl-4-{6-(2-fluoro-4-hydroxyphenoxy)-4-[(tetrahydro-2H-pyran-4-ylmethyl)amino]-1H-benzimidazol-1-yl}-2-methylbenzamide A and N-ethyl-4-[6-{4-methoxy-2-(methylsulfanyl)phenoxy]-4-[(tetrahydro-2H-pyran-4-ylmethyl)amino]-1H-benzimidazol-1-yl}-2-methylbenzamide B

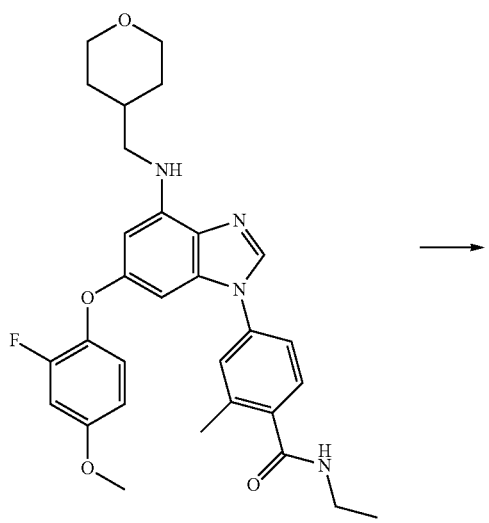

→

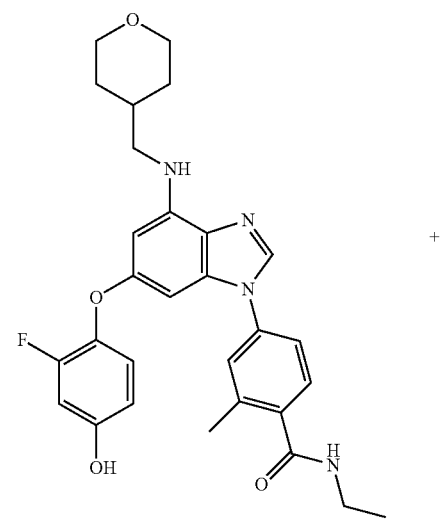

+

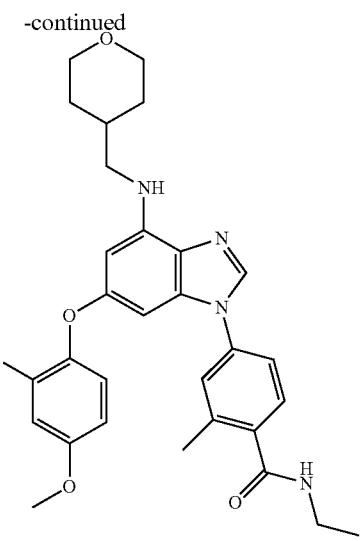

36 mg (68 μmol) N-ethyl-4-{6-(2-fluoro-4-methoxyphenoxy)-4-[(tetrahydro-2H-pyran-4-ylmethyl)amino]-1H-benzimidazol-1-yl}-2-methylbenzamide which was prepared according to example 87 were transformed in analogy to example 58 to give after working up and purification 4.9 mg (13%) of the title compound A and 6.6 mg (17%) of the title compound B.

$^1$H-NMR (CDCl$_3$) of A: δ=1.26 (3H), 1.36 (2H), 1.74 (2H), 1.93 (1H), 2.47 (3H), 3.12 (2H), 3.36 (2H), 3.50 (2H), 3.95 (2H), 5.41 (1H), 6.09 (1H), 6.19 (2H), 6.59 (1H), 6.70 (1H), 6.93 (1H), 7.19-7.34 (3H), 7.46 (1H), 7.97 (1H) ppm.

$^1$H-NMR (CDCl$_3$) of B: δ=1.27 (3H), 1.39 (2H), 1.77 (2H), 1.96 (1H), 2.43 (3H), 2.49 (3H), 3.15 (2H), 3.39 (2H), 3.51 (2H), 3.81 (3H), 3.99 (2H), 5.80 (1H), 6.21 (2H), 6.62 (1H), 6.79 (1H), 6.88 (1H), 7.23-7.34 (3H), 7.48 (1H), 7.92 (1H) ppm.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine); adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$) air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised Powder for IV Administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known antihyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The additional pharmaceutical agent can be 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

Preferable additional pharmaceutical agents are: afinitor, aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulfate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, RDEA 119, rebif, rhenium-186 etidronate, rituximab, roferon-A, romurtide, salagen, sandostatin, sargramostim, semustine, sizofiran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, sorafenib (BAY 43-9006), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, Libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyper-proliferative agents which can be added to the composition include but are not limited to compounds listed on the cancer chemotherapy drug regimens in the 11th Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, epothilone, an epothilone derivative, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in Goodman and Gilman's *The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-llinked lintuzumab, EM-1421, HyperAcute vaccine, tucotuzumab celmoleukin, galiximab, HPV-16-E7, Javelin-prostate cancer, Javelin-melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

The compounds of the invention may also be combined with biological therapeutic agents, such as antibodies (e.g. avastin, rituxan, erbitux, herceptin), or recombinant proteins.

The compounds of the invention may also be in combination with antiangiogenesis agents, such as, for example, with avastin, axitinib, DAST, recentin, sorafenib or sunitinib. Combinations with inhibitors of proteasomes or mTOR inhibitors, or anti-hormones or steroidal metabolic enzyme inhibitors are also possible.

Generally, the use of cytotoxic and/or cytostatic agents in combination with a compound or composition of the present invention will serve to:

(1) yield better efficacy in reducing the growth of a tumour or even eliminate the tumour as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumour progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit Mps-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haematological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assay: Proliferation Assay

Cultivated tumour cells (MCF7, hormone dependent human mammary carcinoma cells, ATCC HTB22; NCI-H460, human non-small cell lung carcinoma cells, ATCC HTB-177; DU 145, hormone-independent human prostate carcinoma cells, ATCC HTB-81; HeLa-MaTu, human cervical carcinoma cells, EPO-GmbH, Berlin; HeLa-MaTu-ADR, multidrug-resistant human cervical carcinoma cells, EPO-GmbH, Berlin; HeLa human cervical tumour cells, ATCC CCL-2; B16F10 mouse melanoma cells, ATCC CRL-6475) were plated at a density of 5000 cells/well (MCF7, DU145, HeLa-MaTu-ADR), 3000 cells/well (NCI-H460, HeLa-MaTu, HeLa), or 1000 cells/well (B16F10) in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.01-30 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The IC50 values were determined by means of a 4 parameter fit using the company's own software.

Mps-1 Kinase Assay

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity.

N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence PWDPDDADITEILG (C-terminus in amide form, purchased from Biosynthan GmbH, Berlin) was used.

For the assay 50 nL of a 100-fold concentrated solution of the test compound in DMSO was pipetted into a black low volume 384 well microtiter plate (Greiner Bio-One, Frickenhausen, Germany), 2 µl of a solution of Mps-1 in assay buffer [0.1 mM sodium-ortho-vanadate, 10 mM $MgCl_2$, 2 mM DTT, 25 mM Hepes pH 7.7, 0.05% BSA, 0.001% Pluronic F-127] were added and the mixture was incubated for 15 min at 22° C. to allow pre-binding of the test compounds to Mps-1 before the start of the kinase reaction. Then the kinase reaction was started by the addition of 3 µl of a solution of 16.7 adenosine-tri-phosphate (ATP, 16.7 µM=>final conc. in the 5 µl assay volume is 10 µM) and peptide substrate (1.67 µM=>final conc. in the 5 µl assay volume is 1 µM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 1 nM (final conc. in the 5 µl assay volume). The reaction was stopped by the addition of 3 µl of a solution of HTRF detection reagents (100 mM Hepes pH 7.4, 0.1% BSA, 40 mM EDTA, 140 nM Streptavidin-XLent [#61GSTXLB, Fa. Cis Biointernational, Marcoule, France], 1.5 nM anti-phospho (Ser/Thr)-Europium-antibody [#AD0180, Perkin Elmer LAS, Rodgau-Jügesheinn, Germany].

The resulting mixture was incubated 1 h at 22° C. to allow the binding of the phosphorylated peptide to the anti-phospho (Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Jügesheinn, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Test compounds were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an in-house software.

It was surprisingly found that the inhibitory activity of compounds of general formula (I) can be positively influenced by $R^3$ being an aryl-X— or heteroaryl-X-group. Therefore, compounds of general formula (I), supra, in which $R^3$ represents an aryl-X— or heteroaryl-X—group (X being selected from O, S, S(=O), S(=O)$_2$, NR, CR'R") are preferred.

TABLE

| Example | Mps1 IC$_{50}$ [nM] | Example | Mps1 IC$_{50}$ [nM] | Example | Mps1 IC$_{50}$ [nM] |
|---|---|---|---|---|---|
| 1 | 24.4 | 32 | 20.2 | 64 | 2.6 |
| 2 | 0.2 | 33 | 0.7 | 65 | 2.8 |
| 3 | 1.5 | 34 | 5.8 | 66 | 2.1 |
| 4 | 0.7 | 35 | 3.9 | 67 | 1 |
| 5 | 2.3 | 36 | 0.4 | 68 | 8.8 |
| 6 | 16.6 | 37 | 0.5 | 69 | 25.9 |
| 7 | 1.9 | 38 | 0.4 | 70 | 2 |
| 8 | 5.3 | 39 | 43.3 | 71 | 28.5 |
| 9 | 0.4 | 40 | 58.2 | 72 | 33 |
| 10 | 4.7 | 41 | 10.1 | 73 | 52.2 |
| 11 | 6.6 | 42 | 4.9 | 74 | 6.4 |
| 12 | 15.3 | 43 | 4 | 75 | 21.9 |
| 13 | 48.7 | 44 | 0.7 | 76 | 7.2 |
| 14 | 0.5 | 45 | 6.7 | 77 | 1 |
| 15 | 0.6 | 46 | 100 | 78 | 11 |
| 16 | 0.6 | 47 | 100 | 79 | 3.9 |
| 17 | 1.1 | 48 | 5.6 | 82 | 3.9 |
| 18 | 2.4 | 49 | 5.5 | 83 | 0.7 |
| 19 | 1.2 | 50 | 1.1 | 84 | 3.4 |
| 20 | 1.5 | 51 | 0.9 | 85 | 3.3 |
| 21 | 1.8 | 52 | 0.9 | 86 | 7 |
| 22 | 2.7 | 53 | 1.9 | 87 | 11.4 |
| 23 | 2.2 | 54 | 0.2 | 88 | 6.7 |
| 24 | 0.4 | 55 | 0.7 | 89 | 10.8 |
| 25 | 0.2 | 56 | 0.3 | 90 | 1.1 |
| 26 | 1.8 | 57 | 6.8 | 91 | 0.4 |
| 27 | 1.4 | 59 | 11.9 | 92 | 3 |
| 28 | 3.1 | 60 | 11.5 | 93 | 4.1 |
| 29 | 0.9 | 61 | 1.3 | 94 | 3.1 |
| 30 | 4.8 | 62 | 3.2 | 95 | 5.6 |
| 31 | 33 | 63 | 18.9 | 96 | 4.8 |
| 97 | 4.6 | 105 | 2.9 | 113B | 54 |
| 98 | 4.6 | 106 | 0.9 | 114A | 0.7 |
| 99 | 2.4 | 107 | 5.3 | 114B | 6.7 |
| 100 | 3.4 | 108 | 17 | 115A | 7.3 |
| 101 | 6.4 | 109 | 2.8 | 115B | 28.9 |
| 102 | 1.8 | 110 | 12 | 116A | 1 |
| 103A | 2.7 | 111 | 0.6 | 116B | 2.9 |
| 103B | 24.2 | 112 | 3.6 | 117A | 6.7 |
| 104 | 2.1 | 113A | 6.3 | 117B | 25.8 |

Spindle Assembly Checkpoint Assay

The spindle assembly checkpoint assures the proper segregation of chromosomes during mitosis. Upon entry into mitosis, chromosomes begin to condensate which is accompanied by the phosphorylation of histone H3 on serine 10. Dephosphorylation of histone H3 on serine 10 begins in anaphase and ends at early telophase. Accordingly, phosphorylation of histone H3 on serine 10 can be utilized as a marker of cells in mitosis. Nocodazole is a microtubule destabilizing substance. Thus, nocodazole interferes with microtubule dynamics and mobilises the spindle assembly checkpoint. The cells arrest in mitosis at G2/M transition and exhibit phosphorylated histone H3 on serine 10. An inhibition of the spindle assembly checkpoint by Mps-1 inhibitors overrides the mitotic blockage in the presence of nocodazole, and the cells complete mitosis prematurely. This alteration is detected by the decrease of cells with phosphorylation of histone H3 on serine 10. This decline is used as a marker to determine the capability of compounds of the present invention to induce a mitotic breakthrough.

Cultivated cells of the human cervical tumour cell line HeLa (ATCC CCL-2) were plated at a density of 2500 cells/well in a 384-well microtiter plate in 20 µl Dulbeco's Medium (w/o phenol red, w/o sodium pyruvate, w 1000 mg/ml glucose, w pyridoxine) supplemented with 1% (v/v) glutamine, 1% (v/v) penicillin, 1% (v/v) streptomycin and 10% (v/v) fetal calf serum. After incubation overnight at 37° C., 10 µl/well nocodazole at a final concentration of 0.1 µg/ml were added to cells. After 24 h incubation, cells were arrested at G2/M phase of the cell cycle progression. Test compounds solubilised in dimethyl sulfoxide (DMSO) were added at various concentrations (0 µM, as well as in the range of 0.005 µM-10 µM; the final concentration of the solvent DMSO was 0.5% (v/v)). Cells were incubated for 4 h at 37° C. in the presence of test compounds. Thereafter, cells were fixed in 4% (v/v) paraformaldehyde in phosphate buffered saline (PBS) at 4° C. overnight then permeabilised in 0.1% (v/v) Triton X™ 100 in PBS at room temperature for 20 min and blocked in 0.5% (v/v) bovine serum albumin (BSA) in PBS at room temperature for 15 min. After washing with PBS, 20 µl/well antibody solution (anti-phospho-histone H3 clone 3H10, FITC; Upstate, Cat#16-222; 1:200 dilution) was added to cells, which were incubated for 2 h at room temperature. Afterwards, cells were washed with PBS and 20 µl/well HOECHST 33342 dye solution (5 µg/ml) was added to cells and cells were incubated 12 min at room temperature in the dark. Cells were washed twice with PBS then covered with PBS and stored at 4° C. until analysis. Images were acquired with a Perkin Elmer OPERA™ High-Content Analysis reader. Images were analyzed with image analysis software MetaXpress™ from Molecular devices utilizing the Cell Cycle application module. In this assay both labels HOECHST 33342 and phosphorylated Histone H3 on serine 10 were measured. HOECHST 33342 labels DNA and is used to count cell number. The staining of phosphorylated Histone H3 on serine 10 determines the number of mitotic cells. Inhibition of Mps-1 decreases the number of mitotic cells in the presence of nocodazole indicating an inappropriate mitotic progression. The raw assay data were further analysed by four parameter logistic regression analysis to determine the IC50 value for each tested compound.

It will be apparent to persons skilled in the art that assays for other Mps kinases may be performed in analogy using the appropriate reagents.

Thus the compounds of the present invention effectively inhibit one or more Mps-1 kinases and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, more particularly in which the diseases of uncontrolled cell growth, proliferation and/or survival, inappropriate cellular immune responses, or inappropriate cellular inflammatory responses are haematological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Investigation of In Vitro Metabolic Stability in Rat Hepatocytes (Including Calculation of Hepatic In Vivo Blood Clearance (CL))

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold WME. The resulting cell suspension was filtered through sterile gaze in 50 ml falcon tubes and centrifuged at 50×g for 3 min at room temperature. The cell pellet was resuspended in 30 ml WME and centrifuged through a Percoll® gradient for 2 times at 100×g. The hepatocytes were washed again with Williams' medium E (WME) and resuspended in medium containing 5% FCS. Cell viability was determined by trypan blue exclusion.

For the metabolic stability assay liver cells were distributed in WME containing 5% FCS to glass vials at a density of $1.0 \times 10^6$ vital cells/ml. The test compound was added to a final concentration of 1 μM. During incubation, the hepatocyte suspensions were continuously shaken and aliquots were taken at 2, 8, 16, 30, 45 and 90 min, to which equal volumes of cold methanol were immediately added. Samples were frozen at −20° C. over night, after subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro.

The hepatic in vivo blood clearance (CL) and the maximal oral bioavailability ($F_{max}$) was calculated. The following parameter values were used: Liver blood flow—4.2 L/h/kg rat; specific liver weight—32 g/kg rat body weight; liver cells in vivo—$1.1 \times 10^8$ cells/g liver, liver cells in vitro—$0.5 \times 10^6$/ml.

It was surprisingly found that the metabolic stability of compounds of general formula (I) can be positively influenced by at least one of the groups $R^{4b}$ and $R^{4c}$ being different from a hydrogen atom. Therefore, $R^{4b}$ and/or $R^{4c}$ are selected from halo-, —CN, —OH, $C_1$-$C_6$-alkyl-, $C_1$-$C_6$-alkoxy-, halo-$C_1$-$C_6$-alkyl-, halo-$C_1$-$C_6$-alkoxy-, $R^{6a}(R^{6b})N$—$C_1$-$C_6$-alkyl-, HO—$C_1$-$C_6$-alkyl-, NC—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-. Preferably, $R^{4b}$ and/or $R^{4c}$ are selected from halo-, —CN, —OH, $C_1$-$C_6$-alkyl-, $C_1$-$C_6$-alkoxy-; more preferably, $R^{4b}$ and/or $R^{4c}$ are selected from halo-, $C_1$-$C_6$-alkyl-; most preferably, $R^{4b}$ and/or $R^{4c}$ are selected from halo-, $C_1$-$C_3$-alkyl-.

It was surprisingly found that the metabolic stability of compounds of general formula (I) can be positively influenced by $R^5$ being a 1,1,1-trifluoroethyl group. Compounds of formula (I) with $R^5$ being a 1,1,1-trifluoroethyl group are therefore preferred.

The invention claimed is:
1. A compound of general formula (I):

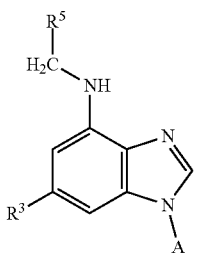

(I)

in which:
A represents

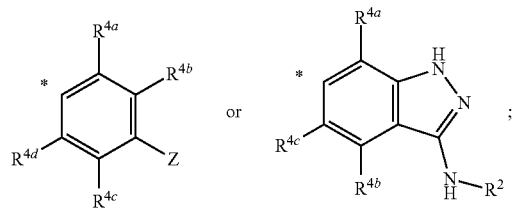

wherein * indicates the point of attachment of said groups with the rest of the molecule;

Z represents a —C(=O)N(H)$R^1$ or —C(=S)N(H)$R^1$ group;

$R^1$ represents a hydrogen atom or a $C_1$-$C_6$-alkyl- or $C_3$-$C_6$-cycloalkyl-group;
wherein said $C_1$-$C_6$-alkyl- or $C_3$-$C_6$-cycloalkyl-group is optionally substituted, identically or differently, with 1, 2, 3 or 4 groups selected from: halogen, —OH, —CN, $C_1$-$C_6$-alkyl-, $C_1$-$C_6$-alkoxy-;

$R^2$ represents a hydrogen atom or a $C_1$-$C_6$-alkyl- or $C_3$-$C_6$-cycloalkyl-group;
wherein said $C_1$-$C_6$-alkyl- or $C_3$-$C_6$-cycloalkyl-group is optionally substituted, identically or differently, with 1, 2, 3 or 4 groups selected from: halogen, OH, —CN, $C_1$-$C_6$-alkyl-, $C_1$-$C_6$-alkoxy-;

$R^3$ represents a hydrogen atom or a halogen atom or a —CN, $C_1$-$C_6$-alkyl-, —(CH$_2$)$_m$—$C_2$-$C_6$-alkenyl, —(CH$_2$)$_m$—$C_4$-$C_8$-cycloalkenyl, —(CH$_2$)$_m$—$C_2$-$C_6$-alkynyl, —(CH$_2$)$_m$—$C_3$-$C_6$-cycloalkyl, —(CH$_2$)$_m$-(3- to 7-membered heterocycloalkyl), —(CH$_2$)$_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, —$C_1$-$C_6$-alkyl-aryl, —$C_1$-$C_6$-alkyl-heteroaryl, heteroaryl-, $C_1$-$C_6$-alkyl-X—, —X—(CH$_2$)$_m$—$C_2$-$C_6$-alkenyl, —X—(CH$_2$)$_m$—$C_4$-$C_8$-cycloalkenyl, —X—(CH$_2$)$_m$—$C_2$-$C_6$-alkynyl, —X—(CH$_2$)$_m$—$C_3$-$C_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —O$R^6$, —S$R^6$, —S(=O)$R^6$, —S(=O)$_2R^6$, —S(=O)(=N$R^{6a}$)$R^{6b}$, —S(=O)$_2$N($R^{6b}$)$R^{6c}$, —S—(CH$_2$)$_n$—N($R^{6a}$)$R^{6b}$, or —S—(CH$_2$)$_n$-(3- to 7-membered heterocycloalkyl) group;
said
$C_1$-$C_6$-alkyl-, —(CH$_2$)$_m$—$C_2$-$C_6$-alkenyl, —(CH$_2$)$_m$—$C_2$-$C_6$-alkynyl, —(CH$_2$)$_m$—$C_3$-$C_6$-cycloalkyl, aryl-$C_1$-$C_6$-alkyl-, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—(CH$_2$)$_m$—$C_2$-$C_6$-alkenyl, —X—(CH$_2$)$_m$—$C_4$-$C_8$-cycloalkenyl, —X—(CH$_2$)$_m$—$C_2$-$C_6$-alkynyl, —X—(CH$_2$)$_m$—$C_3$-$C_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —$C_1$-$C_6$-alkyl-aryl, —$C_1$-$C_6$-alkyl-heteroaryl or heteroaryl-group being optionally substituted, identically or differently, with 1, 2, 3, 4 or 5 $R^7$ groups;

$R^{4a}$, $R^{4b}$, $R^{4c}$, $R^{4d}$
represent, independently from each other, a hydrogen or halogen atom, or a —CN, $C_1$-$C_6$-alkyl-, $C_1$-$C_6$-alkoxy-, halo-$C_1$-$C_6$-alkyl-, halo-$C_1$-$C_6$-alkoxy-, $R^{6a}(R^{6b})N$—$C_1$-$C_6$-alkyl-, HO—$C_1$-$C_6$-alkyl-, NC—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-group;

$R^5$ represents a hydrogen atom or a $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl- group;

said
$C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl- group being optionally substituted, identically or differently, with 1, 2, 3, 4 or 5 $R^8$ groups;

$R^6$, $R^{6a}$, $R^{6b}$, $R^{6c}$
represent, independently from each other, a hydrogen atom or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl- or heteroaryl-$C_1$-$C_6$-alkyl-group;

$R^7$ represents a hydrogen or halogen atom or a HO—, —CN, $C_1$-$C_6$-alkoxy-, halo-$C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —$NO_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$ $R^6$, —N($R^{6c}$)S(=O)$_2R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —$SR^6$, —$SF_5$, —S(=O)$R^6$, —S(=O)N(H)$R^6$, —S(=O)N($R^{6a}$)$R^{6b}$, —S(=O)$_2R^6$, —S(=O)$_2$ N(H)$R^6$, —S(=O)$_2$N($R^{6a}$)$R^{6b}$ or —S(=O)(=N$R^{6c}$)$R^6$ group;

wherein said aryl- or heteroaryl-group is optionally substituted, identically or differently, with 1, 2 or 3 $C_1$-$C_6$-alkyl-groups;

or
when 2 $R^7$ groups are present ortho- to each other on an aryl ring, said 2 $R^7$ groups together form a bridge: *O(CH$_2$)$_2$O*, *O(CH$_2$)O*, *NH(C(=O))NH*, wherein * represent the point of attachment to said aryl ring;

$R^8$ represents a hydrogen or halogen atom or a —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl, HO—$C_1$-$C_6$-alkyl, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O) O—$R^6$, —N($R^{6a}$)$R^{6b}$, —$NO_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —$SR^6$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$, —S(=O)(=N$R^{6c}$)$R^6$ or —S(=O)$_2$-(3- to 7-membered heterocycloalkyl) group;

wherein said 3- to 7-membered heterocycloalkyl- or heteroaryl-group, is optionally substituted, identically or differently, with 1, 2, 3 or 4 $C_1$-$C_6$-alkyl-groups;

m is an integer of 0, 1, 2, 3, 4, 5, or 6;
n is an integer of 0, 1, 2, 3, 4, or 5; and
X is S, S(=O), S(=O)$_2$, O, N$R^6$, C$R^{6a}R^{6b}$, C(=C$R^{6a}R^{6b}$), C(=O) or C(OH)($R^{6a}$);

or a stereoisomer, a tautomer, an N-oxide, a hydrate, a solvate, or a salt thereof, or a mixture of same.

2. A compound according to claim 1, wherein:
$R^{4a}$ and $R^{4d}$ represent hydrogen;
$R^{4b}$ and $R^{4c}$ are selected, independently from each other, from hydrogen, halogen, —CN, $C_1$-$C_6$-alkyl-, $C_1$-$C_6$-alkoxy-, halo-$C_1$-$C_6$-alkyl-, or halo-$C_1$-$C_6$-alkoxy-;
or a stereoisomer, a tautomer, an N-oxide, a hydrate, a solvate, or a salt thereof, or a mixture of same.

3. A compound according to claim 1, wherein:
A represents

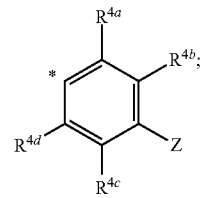

wherein * indicates the point of attachment of said group with the rest of the molecule;
Z represents a —C(=O)N(H)$R^1$ group;
$R^1$ represents a $C_1$-$C_6$-alkyl- or $C_3$-$C_6$-cycloalkyl-group;
wherein said $C_1$-$C_6$-alkyl- or $C_3$-$C_6$-cycloalkyl-group is optionally substituted, identically or differently, with 1, 2, 3 or 4 groups selected from: halogen, OH, —CN, $C_1$-$C_6$-alkyl-, $C_1$-$C_6$-alkoxy-;
or a stereoisomer, a tautomer, an N-oxide, a hydrate, a solvate, or a salt thereof, or a mixture of same.

4. A compound according to claim 1, wherein:
$R^3$ represents a hydrogen atom or a halogen atom or an aryl-, heteroaryl-, aryl-X— or heteroaryl-X— group;
said aryl-, heteroaryl-, aryl-X— or heteroaryl-X— group being optionally substituted, identically or differently, with 1, 2 or 3 $R^7$ groups;
or a stereoisomer, a tautomer, an N-oxide, a hydrate, a solvate, or a salt thereof, or a mixture of same.

5. A compound according to claim 1, wherein:
$R^7$ represents a halogen atom, or a HO—, —CN, $C_1$-$C_6$-alkoxy-, halo-$C_1$-$C_6$-alkoxy-, $C_1$-$C_6$-alkyl-, HO—$C_1$-$C_6$-alkyl-, 3- to 7-membered heterocycloalkyl-, heteroaryl-, —C(=O)N(H)$R^{6a}$, —O$R^6$, —$SR^6$, —$SF_5$ or —S(=O)$_2R^6$ group;

or a stereoisomer, a tautomer, an N-oxide, a hydrate, a solvate, or a salt thereof, or a mixture of same.

6. A compound according to claim 1, wherein:
$R^5$ represents a $C_1$-$C_6$-alkyl-, —$(CH_2)_m$-(3- to 7-membered heterocycloalkyl) or halo-$C_1$-$C_6$-alkyl-group; said $C_1$-$C_6$-alkyl-, —$(CH_2)_m$-(3- to 7-membered heterocycloalkyl) or halo-$C_1$-$C_6$-alkyl-group is optionally substituted, identically or differently, with 1, 2, 3, 4 or 5 $R^8$ groups;
or a stereoisomer, a tautomer, an N-oxide, a hydrate, a solvate, or a salt thereof, or a mixture of same.

7. A compound according to claim 1, wherein:
m is an integer of 0 or 1;
or a stereoisomer, a tautomer, an N-oxide, a hydrate, a solvate, or a salt thereof, or a mixture of same.

8. A compound according to claim 1, wherein:
X is O, $NR^6$, $CR^{6a}R^{6b}$, $C(=CR^{6a}R^{6b})$, $C(=O)$ or $C(OH)(R^{6a})$;
or a stereoisomer, a tautomer, an N-oxide, a hydrate, a solvate, or a salt thereof, or a mixture of same.

9. A compound according to claim 1, which is selected from the group consisting of:
N-cyclopropyl-4-{4-[(2-methylpropyl)amino]-1H-benzimidazol-1-yl}benzamide,
N-cyclopropyl-2-methyl-4-{6-(pyridin-4-yl)-4-[(3,3,3-trifluoropropyl)amino]-1H-benzimidazol-1-yl}benzamide,
N-cyclopropyl-4-{6-[(5-fluoro-2-methylphenyl)amino]-4-[(3,3,3-trifluoropropyl)amino]-1H-benzimidazol-1-yl}-2-methylbenzamide,
N-cyclopropyl-4-{6-(3-fluorophenoxy)-4-[(3,3,3-trifluoropropyl)amino]-1H-benzimidazol-1-yl}-2-methylbenzamide,
N-cyclopropyl-4-{6-[(2,3-difluorophenyl)amino]-4-[(3,3,3-trifluoropropyl)amino]-1H-benzimidazol-1-yl}-2-methylbenzamide,
4-{6-bromo-4-[(2-methylpropyl)amino]-1H-benzimidazol-1-yl}-N-cyclopropylbenzamide,
N-cyclopropyl-4-{6-(4-fluorophenyl)-4-[(2-methylpropyl)amino]-1H-benzimidazol-1-yl}benzamide,
N-cyclopropyl-4-{4-[(2-methylpropyl)amino]-6-phenyl-1H-benzimidazol-1-yl}benzamide,
N-cyclopropyl-4-{6-(3-fluorophenoxy)-4-[(tetrahydro-2H-pyran-4-ylmethyl)amino]-1H-benzimidazol-1-yl}-2-methylbenzamide,
4-{6-(3-fluorophenoxy)-4-[(3,3,3-trifluoropropyl)amino]-1H-benzimidazol-1-yl}-N,2-dimethylbenzamide,
N-ethyl-4-{6-(3-fluorophenoxy)-4-[(3,3,3-trifluoropropyl)amino]-1H-benzimidazol-1-yl}-2-methylbenzamide,
4-{6-(3-fluorophenoxy)-4-[(3,3,3-trifluoropropyl)amino]-1H-benzimidazol-1-yl}-2-methyl-N-(1-methylcyclopropyl)benzamide,
N-(1-cyanocyclopropyl)-4-{6-(3-fluorophenoxy)-4-[(3,3,3-trifluoropropyl)amino]-1H-benzimidazol-1-yl}-2-methylbenzamide,
N-cyclopropyl-4-{6-(2,3-difluorophenoxy)-4-[(3,3,3-trifluoropropyl)amino]-1H-benzimidazol-1-yl}-2-methylbenzamide,
N-cyclopropyl-4-{6-(3-fluoro-5-methylphenoxy)-4-[(tetrahydro-2H-pyran-4-ylmethyl)amino]-1H-benzimidazol-1-yl}-2-methylbenzamide,
N-cyclopropyl-4-{6-(5-fluoro-2-methylphenoxy)-4-[(tetrahydro-2H-pyran-4-ylmethyl)amino]-1H-benzimidazol-1-yl}-2-methylbenzamide,
N-cyclopropyl-4-{6-(3,4-difluorophenoxy)-4-[(tetrahydro-2H-pyran-4-ylmethyl)amino]-1H-benzimidazol-1-yl}-2-methylbenzamide,
4-{6-(4-chlorophenoxy)-4-[(3,3,3-trifluoropropyl)amino]-1H-benzimidazol-1-yl}-N-cyclopropyl-2-methylbenzamide,
N-cyclopropyl-4-{6-[(5-fluoro-2-methylphenyl)amino]-4-[(tetrahydro-2H-pyran-4-ylmethyl)amino]-1H-benzimidazol-1-yl}-2-methylbenzamide,
N-cyclopropyl-4-{6-[2-(hydroxymethyl)phenyl]-4-[(tetrahydro-2H-pyran-4-ylmethyl)amino]-1H-benzimidazol-1-yl}-2-methylbenzamide,
N-cyclopropyl-4-{6-[2-(hydroxymethyl)phenyl]-4-[(3,3,3-trifluoropropyl)amino]-1H-benzimidazol-1-yl}-2-methylbenzamide,
4-{6-(4-chloro-3-fluorophenoxy)-4-[(tetrahydro-2H-pyran-4-ylmethyl)amino]-1H-benzimidazol-1-yl}-N-cyclopropyl-2-methylbenzamide,
4-{6-(4-chlorophenoxy)-4-[(tetrahydro-2H-pyran-4-ylmethyl)amino]-1H-benzimidazol-1-yl}-N-cyclopropyl-2-methylbenzamide,
N-cyclopropyl-4-{6-(2-fluoro-4-methoxyphenoxy)-4-[(tetrahydro-2H-pyran-4-ylmethyl)amino]-1H-benzimidazol-1-yl}-2-methylbenzamide,
N-cyclopropyl-4-{6-(2,3-difluorophenoxy)-4-[(tetrahydro-2H-pyran-4-ylmethyl)amino]-1H-benzimidazol-1-yl}-2-methylbenzamide,
N-cyclopropyl-4-{6-(3-fluoro-5-methylphenoxy)-4-[(3,3,3-trifluoropropyl)amino]-1H-benzimidazol-1-yl}-2-methylbenzamide,
N-cyclopropyl-4-{6-(3,4-difluorophenoxy)-4-[(3,3,3-trifluoropropyl)amino]-1H-benzimidazol-1-yl}-2-methylbenzamide,
4-{6-(4-chloro-3-fluorophenoxy)-4-[(3,3,3-trifluoropropyl)amino]-1H-benzimidazol-1-yl}-N-cyclopropyl-2-methylbenzamide,
N-cyclopropyl-4-{6-(2-fluoro-4-methoxyphenoxy)-4-[(3,3,3-trifluoropropyl)amino]-1H-benzimidazol-1-yl}-2-methylbenzamide,
N-cyclopropyl-2-methyl-4-{6-(1-methyl-1H-pyrazol-5-yl)-4-[(3,3,3-trifluoropropyl)amino]-1H-benzimidazol-1-yl}benzamide,
N-ethyl-2-methyl-4-{6-(1-methyl-1H-pyrazol-5-yl)-4-[(3,3,3-trifluoropropyl)amino]-1H-benzimidazol-1-yl}benzamide,
N,2-dimethyl-4-{6-(1-methyl-1H-pyrazol-5-yl)-4-[(3,3,3-trifluoropropyl)amino]-1H-benzimidazol-1-yl}benzamide,
N-cyclopropyl-4-{6-(3-fluoro-4-methoxyphenoxy)-4-[(3,3,3-trifluoropropyl)amino]-1H-benzimidazol-1-yl}-2-methylbenzamide,
N-ethyl-4-{6-(3-fluoro-4-methoxyphenoxy)-4-[(3,3,3-trifluoropropyl)amino]-1H-benzimidazol-1-yl}-2-methylbenzamide,
4-{6-(3-fluoro-4-methoxyphenoxy)-4-[(3,3,3-trifluoropropyl)amino]-1H-benzimidazol-1-yl}-N,2-dimethylbenzamide,
N-cyclopropyl-4-{6-(2,3-difluorophenoxy)-4-[(3,3,3-trifluoropropyl)amino]-1H-benzimidazol-1-yl}benzamide,
N-cyclopropyl-4-{6-phenoxy-4-[(3,3,3-trifluoropropyl)amino]-1H-benzimidazol-1-yl}benzamide,
N-cyclopropyl-4-{6-(3-fluoro-4-methoxyphenoxy)-4-[(3,3,3-trifluoropropyl)amino]-1H-benzimidazol-1-yl}benzamide, 4-{6-(2-methoxyphenoxy)-4-[(3,3,3-trifluoropropyl)
amino]-1H-benzimidazol-1-yl}-N,2-dimethylbenzamide,
N-ethyl-4-{6-(2-methoxyphenoxy)-4-[(3,3,3-trifluoropropyl)amino]-1H-benzimidazol-1-yl}-2-methylbenzamide,
N-cyclopropyl-4-{6-(2-methoxyphenoxy)-4-[(3,3,3-trifluoropropyl)amino]-1H-benzimidazol-1-yl}-2-methylbenzamide,
4-{6-(3-fluoro-4-methoxyphenoxy)-4-[(tetrahydro-2H-pyran-4-ylmethyl)amino]-1H-benzimidazol-1-yl}-N,2-dimethylbenzamide,
N-ethyl-4-{6-(3-fluoro-4-methoxyphenoxy)-4-[(tetrahydro-2H-pyran-4-ylmethyl)amino]-1H-benzimidazol-1-yl}-2-methylbenzamide,
N-cyclopropyl-4-{6-(3-fluoro-4-methoxyphenoxy)-4-[(tetrahydro-2H-pyran-4-ylmethyl)amino]-1H-benzimidazol-1-yl}-2-methylbenzamide,
4-{6-[4-(benzyloxy)phenoxy]-4-[(3,3,3-trifluoropropyl)amino]-1H-benzimidazol-1-yl}-N-cyclopropyl-2-methylbenzamide,
4-{6-[4-(benzyloxy)phenoxy]-4-[(3,3,3-trifluoropropyl)amino]-1H-benzimidazol-1-yl}-N-ethyl-2-methylbenzamide,
4-{6-[4-(benzyloxy)phenoxy]-4-[(3,3,3-trifluoropropyl)amino]-1H-benzimidazol-1-yl}-N,2-dimethylbenzamide,
4-{6-(4-hydroxyphenoxy)-4-[(3,3,3-trifluoropropyl)amino]-1H-benzimidazol-1-yl}-N,2-dimethylbenzamide,
N-ethyl-4-{6-(4-hydroxyphenoxy)-4-[(3,3,3-trifluoropropyl)amino]-1H-benzimidazol-1-yl}-2-methylbenzamide,
N-cyclopropyl-4-{6-(4-hydroxyphenoxy)-4-[(3,3,3-trifluoropropyl)amino]-1H-benzimidazol-1-yl}-2-methylbenzamide,
4,4'-{4-[(3,3,3-trifluoropropyl)amino]-1H-benzimidazole-1,6-diyl}bis(N-cyclopropyl-2-methylbenzamide),
4-{1-[4-(cyclopropylcarbamoyl)-3-methylphenyl]-4-[(3,3,3-trifluoropropyl)amino]-1H-benzimidazol-6-yl}-N,2-dimethylbenzamide,
4-{1-[4-(cyclopropylcarbamoyl)-3-methylphenyl]-4-[(3,3,3-trifluoropropyl)amino]-1H-benzimidazol-6-yl}-N-ethyl-2-methylbenzamide,
N-cyclopropyl-4-{6-(2-hydroxyphenoxy)-4-[(3,3,3-trifluoropropyl)amino]-1H-benzimidazol-1-yl}-2-methylbenzamide,
N-ethyl-4-{6-(2-hydroxyphenoxy)-4-[(3,3,3-trifluoropropyl)amino]-1H-benzimidazol-1-yl}-2-methylbenzamide,
4-{6-(2-hydroxyphenoxy)-4-[(3,3,3-trifluoropropyl)amino]-1H-benzimidazol-1-yl}-N,2-dimethylbenzamide,
N-cyclopropyl-4-{6-(3-fluoro-2-methoxyphenoxy)-4-[(3,3,3-trifluoropropyl)amino]-1H-benzimidazol-1-yl}-2-methylbenzamide,
N-cyclopropyl-2-methyl-4-{6-[3-(trifluoromethoxy)phenoxy]-4-[(3,3,3-trifluoropropyl)amino]-1H-benzimidazol-1-yl}benzamide,
N-cyclopropyl-2-methyl-4-{6-[4-(morpholin-4-yl)phenoxy]-4-[(3,3,3-trifluoropropyl)amino]-1H-benzimidazol-1-yl}benzamide,
N-cyclopropyl-4-{6-[4-(difluoromethoxy)phenoxy]-4-[(3,3,3-trifluoropropyl)amino]-1H-benzimidazol-1-yl}-2-methylbenzamide,
N-cyclopropyl-4-{6-[3-(difluoromethoxy)phenoxy]-4-[(3,3,3-trifluoropropyl)amino]-1H-benzimidazol-1-yl}-2-methylbenzamide,
N-cyclopropyl-4-{6-[(2-methoxyphenyl)amino]-4-[(3,3,3-trifluoropropyl)amino]-1H-benzimidazol-1-yl}-2-methylbenzamide,
N-cyclopropyl-2-methyl-4-{6-[3-(methylsulfonyl)phenoxy]-4-[(3,3,3-trifluoropropyl)amino]-1H-benzimidazol-1-yl}benzamide,
N-cyclopropyl-4-{6-[(3-methoxy-2-methylphenyl)amino]-4-[(3,3,3-trifluoropropyl)amino]-1H-benzimidazol-1-yl}-2-methylbenzamide,
4-{6-(2,3-difluorophenoxy)-4-[(3,3,3-trifluoropropyl)amino]-1H-benzimidazol-1-yl}-N-ethyl-2-methylbenzamide,
4-{6-(2,3-difluorophenoxy)-4-[(3,3,3-trifluoropropyl)amino]-1H-benzimidazol-1-yl}-N,2-dimethylbenzamide,
4-{6-(3-methoxyphenoxy)-4-[(3,3,3-trifluoropropyl)amino]-1H-benzimidazol-1-yl}-N,2-dimethylbenzamide,
N-ethyl-4-{6-(3-methoxyphenoxy)-4-[(3,3,3-trifluoropropyl)amino]-1H-benzimidazol-1-yl}-2-methylbenzamide,
N-cyclopropyl-4-{6-(3-methoxyphenoxy)-4-[(3,3,3-trifluoropropyl)amino]-1H-benzimidazol-1-yl}-2-methylbenzamide,
N-ethyl-4-{6-(3-fluoro-2-methoxyphenoxy)-4-[(3,3,3-trifluoropropyl)amino]-1H-benzimidazol-1-yl}-2-methylbenzamide,
4-{6-(3-fluoro-2-methoxyphenoxy)-4-[(3,3,3-trifluoropropyl)amino]-1H-benzimidazol-1-yl}-N,2-dimethylbenzamide,
4-{6-(4-cyano-2-methoxyphenoxy)-4-[(3,3,3-trifluoropropyl)amino]-1H-benzimidazol-1-yl}-N-cyclopropyl-2-methylbenzamide,
N-cyclopropyl-2-methyl-4-{6-[4-(methylsulfonyl)phenoxy]-4-[(3,3,3-trifluoropropyl)amino]-1H-benzimidazol-1-yl}benzamide,
N-cyclopropyl-2-methyl-4-{6-[4-(1,3-oxazol-2-yl)phenoxy]-4-[(3,3,3-trifluoropropyl)amino]-1H-benzimidazol-1-yl}benzamide,
N-cyclopropyl-4-{6-[4-fluoro-3-(trifluoromethyl)phenoxy]-4-[(3,3,3-trifluoropropyl)amino]-1H-benzimidazol-1-yl}-2-methylbenzamide,
4-{6-(3-cyanophenoxy)-4-[(3,3,3-trifluoropropyl)amino]-1H-benzimidazol-1-yl}-N-cyclopropyl-2-methylbenzamide,
N-cyclopropyl-2-methyl-4-{6-[4-(1H-1,2,4-triazol-1-yl)phenoxy]-4-[(3,3,3-trifluoropropyl)amino]-1H-benzimidazol-1-yl}benzamide,
N-cyclopropyl-4-{6-[3-(cyclopropylcarbamoyl)phenoxy]-4-[(3,3,3-trifluoropropyl)amino]-1H-benzimidazol-1-yl}-2-methylbenzamide,
N-cyclopropyl-4-{6-[(2-hydroxyphenyl)amino]-4-[(3,3,3-trifluoropropyl)amino]-1H-benzimidazol-1-yl}-2-methylbenzamide,
N-cyclopropyl-4-{6-(3-fluoro-4-hydroxyphenoxy)-4-[(3,3,3-trifluoropropyl)amino]-1H-benzimidazol-1-yl}-2-methylbenzamide,
4-{6-(2,3-difluorophenoxy)-4-[(tetrahydro-2H-pyran-4-ylmethyl)amino]-1H-benzimidazol-1-yl}-N,2-dimethylbenzamide,
4-{6-(2,3-difluorophenoxy)-4-[(tetrahydro-2H-pyran-4-ylmethyl)amino]-1H-benzimidazol-1-yl}-N-ethyl-2-methylbenzamide, 4-{6-(2-fluoro-4-methoxyphenoxy)-4-[(tetrahydro-2H-pyran-4-ylmethyl)amino]-1H-benzimidazol-1-yl}-N,2-dimethylbenzamide, N-ethyl-4-{6-(2-fluoro-4-methoxyphenoxy)-4-[(tetrahydro-2H-pyran-4-ylmethyl)amino]-1H-benzimidazol-1-yl}-2-methylbenzamide, 4-{6-(2-fluoro-4-methoxyphenoxy)-4-[(3,3,3-trifluoropropyl)amino]-1H-benzimidazol-1-yl}-N,2-dimethylbenzamide, N-ethyl-4-{6-(2-fluoro-4-methoxyphenoxy)-4-[(3,3,3-trifluoropropyl)amino]-1H-benzimidazol-1-yl}-2-methylbenzamide, N-cyclopropyl-4-{6-(2-fluoro-4-hydroxyphenoxy)-4-[(3,3,3-trifluoropropyl)amino]-1H-benzimidazol-1-yl}-2-methylbenzamide, N-cyclopropyl-4-{6-(3-fluoro-2-hydroxyphenoxy)-4-[(3,3,3-trifluoropropyl)amino]-1H-benzimidazol-1-yl}-2-methylbenzamide, 4-{6-(3-fluoro-2-hydroxyphenoxy)-4-[(3,3,3-trifluoropropyl)amino]-1H-benzimidazol-1-yl}-N,2-dimethylbenzamide, N-ethyl-4-{6-(3-fluoro-2-hydroxyphenoxy)-4-[(3,3,3-trifluoropropyl)amino]-1H-benzimidazol-1-yl}-2-methylbenzamide, 4-{6-(3-hydroxyphenoxy)-4-[(3,3,3-trifluoropropyl)amino]-1H-benzimidazol-1-yl}-N,2-dimethylbenzamide, N-ethyl-4-{6-(3-hydroxyphenoxy)-4-[(3,3,3-trifluoropropyl)amino]-1H-benzimidazol-1-yl}-2-methylbenzamide, N-cyclopropyl-2-methyl-4-{6-[3-(pentafluoro-lambda6-sulfanyl)phenoxy]-4-[(3,3,3-trifluoropropyl)amino]-1H-benzimidazol-1-yl}benzamide, 4-{6-(2-fluoro-4-hydroxyphenoxy)-4-[(3,3,3-trifluoropropyl)amino]-1H-benzimidazol-1-yl}-N,2-dimethylbenzamide, N-ethyl-4-{6-(2-fluoro-4-hydroxyphenoxy)-4-[(3,3,3-trifluoropropyl)amino]-1H-benzimidazol-1-yl}-2-methylbenzamide, 4-{6-(3-fluoro-4-hydroxyphenoxy)-4-[(3,3,3-trifluoropropyl)amino]-1H-benzimidazol-1-yl}-N,2-dimethylbenzamide, N-ethyl-4-{6-(3-fluoro-4-hydroxyphenoxy)-4-[(3,3,3-trifluoropropyl)amino]-1H-benzimidazol-1-yl}-2-methylbenzamide, N-cyclopropyl-4-{6-(3-fluoro-4-methoxybenzoyl)-4-[(3,3,3-trifluoropropyl)amino]-1H-benzimidazol-1-yl}-2-methylbenzamide, N-cyclopropyl-4-{6-[(3-fluoro-4-methoxyphenyl)(hydroxy)methyl]-4-[(3,3,3-trifluoropropyl)amino]-1H-benzimidazol-1-yl}-2-methylbenzamide, N-cyclopropyl-4-{6-[(1RS)-1-(3-fluoro-4-methoxyphenyl)-1-hydroxyethyl]-4-[(3,3,3-trifluoropropyl)amino]-1H-benzimidazol-1-yl}-2-methylbenzamide, N-cyclopropyl-4-{6-[(1RS)-1-(3-fluoro-4-methoxyphenyl)-1-hydroxyethyl]-4-[(3,3,3-trifluoropropyl)amino]-1H-benzimidazol-1-yl}-2-(hydroxymethyl)benzamide, N-cyclopropyl-4-{6-[1-(3-fluoro-4-methoxyphenyl)vinyl]-4-[(3,3,3-trifluoropropyl)amino]-1H-benzimidazol-1-yl}-2-methylbenzamide, N-cyclopropyl-4-{6-[(1RS)-1-(3-fluoro-4-methoxyphenyl)ethyl]-4-[(3,3,3-trifluoropropyl)amino]-1H-benzimidazol-1-yl}-2-methylbenzamide, N-cyclopropyl-4-{6-(3-fluoro-4-methoxybenzyl)-4-[(3,3,3-trifluoropropyl)amino]-1H-benzimidazol-1-yl}-2-methylbenzamide, N-cyclopropyl-4-{6-(5-fluoro-2-methylphenoxy)-4-[(3,3,3-trifluoropropyl)amino]-1H-benzimidazol-1-yl}-2-methylbenzamide, N-cyclopropyl-4-{6-(3-fluoro-4-hydroxybenzoyl)-4-[(3,3,3-trifluoropropyl)amino]-1H-benzimidazol-1-yl}-2-methylbenzamide, N-cyclopropyl-4-{6-[3-(difluoromethyl)phenoxy]-4-[(3,3,3-trifluoropropyl)amino]-1H-benzimidazol-1-yl}-2-methylbenzamide, N-cyclopropyl-4-{6-(2-methoxybenzoyl)-4-[(3,3,3-trifluoropropyl)amino]-1H-benzimidazol-1-yl}-2-methylbenzamide, N-cyclopropyl-4-{6-(3-hydroxyphenoxy)-4-[(3,3,3-trifluoropropyl)amino]-1H-benzimidazol-1-yl}-2-methylbenzamide, 4-{6-(3-fluoro-4-hydroxyphenoxy)-4-[(tetrahydro-2H-pyran-4-ylmethyl)amino]-1H-benzimidazol-1-yl}-N,2-dimethylbenzamide, N-ethyl-4-{6-(3-fluoro-4-hydroxyphenoxy)-4-[(tetrahydro-2H-pyran-4-ylmethyl)amino]-1H-benzimidazol-1-yl}-2-methylbenzamide, N-ethyl-4-{6-[4-methoxy-3-(methylsulfanyl)phenoxy]-4-[(tetrahydro-2H-pyran-4-ylmethyl)amino]-1H-benzimidazol-1-yl}-2-methylbenzamide, N-cyclopropyl-4-{6-(3-fluoro-4-hydroxyphenoxy)-4-[(tetrahydro-2H-pyran-4-ylmethyl)amino]-1H-benzimidazol-1-yl}-2-methylbenzamide, N-cyclopropyl-4-{6-[4-methoxy-3-(methylsulfanyl)phenoxy]-4-[(tetrahydro-2H-pyran-4-ylmethyl)amino]-1H-benzimidazol-1-yl}-2-methylbenzamide, 4-{6-(2-fluoro-4-hydroxyphenoxy)-4-[(tetrahydro-2H-pyran-4-ylmethyl)amino]-1H-benzimidazol-1-yl}-N,2-dimethylbenzamide, 4-{6-[4-methoxy-2-(methylsulfanyl)phenoxy]-4-[(tetrahydro-2H-pyran-4-ylmethyl)amino]-1H-benzimidazol-1-yl}-N,2-dimethylbenzamide, N-cyclopropyl-4-{6-(2-fluoro-4-hydroxyphenoxy)-4-[(tetrahydro-2H-pyran-4-ylmethyl)amino]-1H-benzimidazol-1-yl}-2-methylbenzamide, N-cyclopropyl-4-{6-[4-methoxy-2-(methylsulfanyl)phenoxy]-4-[(tetrahydro-2H-pyran-4-ylmethyl)amino]-1H-benzimidazol-1-yl}-2-methylbenzamide, N-ethyl-4-{6-(2-fluoro-4-hydroxyphenoxy)-4-[(tetrahydro-2H-pyran-4-ylmethyl)amino]-1H-benzimidazol-1-yl}-2-methylbenzamide, N-ethyl-4-{6-[4-methoxy-2-(methylsulfanyl)phenoxy]-4-[(tetrahydro-2H-pyran-4-ylmethyl)amino]-1H-benzimidazol-1-yl}-2-methylbenzamide, or a stereoisomer, a tautomer, an N-oxide, a hydrate, a solvate, or a salt thereof, or a mixture of same.

10. A method of preparing a compound according to claim 1, said method comprising the step:

allowing an intermediate compound of general formula (II):

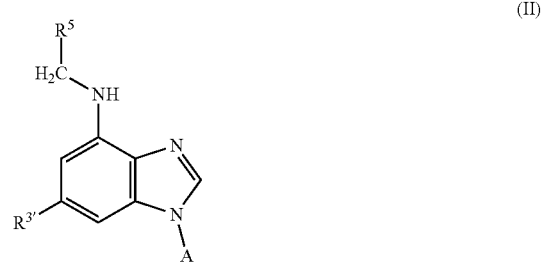

(II)

in which
R[5] and A are as defined in claim 1;
R[3'] is a halogen atom;
to react with a compound of general formula (IIa):

 (IIa)

in which
R[3] is as defined in claim 1;
Y is a substituent which is displaced in a coupling reaction;
thereby giving a compound of general formula (I):

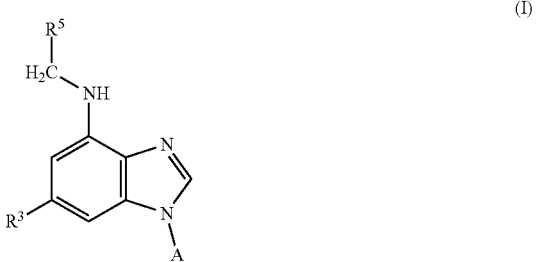 (I)

in which
R[3], R[5] and A are as defined in claim 1.

11. A method of preparing a compound according to claim 1, said method comprising the step:
allowing an intermediate compound of general formula (IV):

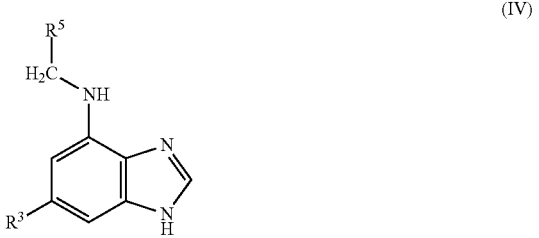 (IV)

in which
R[3] and R[5] are as defined in claim 1;
to react with a compound of general formula (IVa):

 (IVa)

in which
A is as defined in claim 1;
Y is a substituent which is displaced in a coupling reaction;
thereby giving a compound of general formula (I):

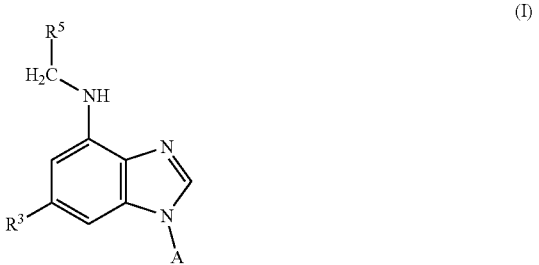 (I)

in which
R[3], R[5] and A are as defined in claim 1.

12. A pharmaceutical composition comprising a compound according to claim 1, or a stereoisomer, a tautomer, an N-oxide, a hydrate, a solvate, or a pharmaceutically acceptable salt thereof, or a mixture of same, and a pharmaceutically acceptable diluent or carrier.

13. A pharmaceutical composition comprising:
one or more compounds according to claim 1, or a stereoisomer, a tautomer, an N-oxide, a hydrate, a solvate, or a pharmaceutically acceptable salt thereof, or a mixture of same; and
one or more agents selected from: a taxane, Docetaxel, Paclitaxel, Taxol; an epothilone, Ixabepilone, Patupilone, Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2'-deoxyadenosine; Thioguanine; an anti-androgen, Flutamide, Cyproterone acetate, Bicalutamide; Bortezomib; a platinum derivative, Cisplatin, Carboplatin; Chlorambucil; Methotrexate; and Rituximab.

14. A method for inhibiting monopolar spindle 1 kinase activity in a patient in need thereof, comprising administering to the patient a therapeutically effective amount of a compound according to claim 1.

15. A compound of general formula (II):

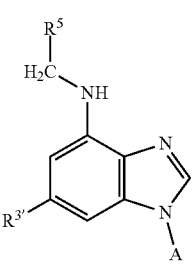 (II)

in which R[5] and A are as defined in claim 1 and R[3'] is a halogen atom.

16. The method of claim 14, wherein the uncontrolled cell growth, proliferation and/or survival, inappropriate cellular immune response, or inappropriate cellular inflammatory response is mediated by the mitogen-activated protein kinase (MEK-ERK) pathway.

17. The method of claim 14, wherein the disease of uncontrolled cell growth, proliferation and/or survival, inappropriate cellular immune response, or inappropriate cellular inflammatory response is a haematological tumour, a solid tumour and/or metastases thereof.

18. The method of claim 17, wherein the haematological tumour, solid tumour and/or metastases thereof, is selected from leukaemias and myelodysplastic syndrome, malignant lymphomas, head and neck tumours, brain tumours and brain metastases, tumours of the thorax, non-small cell and small cell lung tumours, gastrointestinal tumours, endocrine tumours, mammary and other gynaecological tumours, urological tumours, renal, bladder and prostate tumours, skin tumours, and sarcomas, and/or metastases thereof.

\* \* \* \* \*